US011633504B2

(12) United States Patent
Doering et al.

(10) Patent No.: US 11,633,504 B2
(45) Date of Patent: Apr. 25, 2023

(54) NUCLEIC ACIDS ENCODING CLOTTING FACTOR VARIANTS AND THEIR USE

(71) Applicants: EMORY UNIVERSITY, Atlanta, GA (US); CHILDREN'S HEALTHCARE OF ATLANTA, INC., Atlanta, GA (US); GEORGIA TECH RESEARCH CORPORATION, Atlanta, GA (US)

(72) Inventors: Christopher Doering, Atlanta, GA (US); Harold Trent Spencer, Atlanta, GA (US); Eric Gaucher, Atlanta, GA (US); Caelan Radford, Powder Springs, GA (US)

(73) Assignees: EMORY UNIVERSITY, Atlanta, GA (US); CHILDREN'S HEALTHCARE OF ATLANTA, INC., Atlanta, GA (US); GEORGIA TECH RESEARCH CORPORATION, Atlanta, GA (US)

( * ) Notice: Subject to any disclaimer, the term of this patent is extended or adjusted under 35 U.S.C. 154(b) by 393 days.

(21) Appl. No.: 16/612,167

(22) PCT Filed: May 9, 2018

(86) PCT No.: PCT/US2018/031881
§ 371 (c)(1),
(2) Date: Nov. 8, 2019

(87) PCT Pub. No.: WO2018/208973
PCT Pub. Date: Nov. 15, 2018

(65) Prior Publication Data
US 2021/0052740 A1 Feb. 25, 2021

Related U.S. Application Data

(60) Provisional application No. 62/503,766, filed on May 9, 2017.

(51) Int. Cl.
| | | |
|---|---|---|
| *A61K 48/00* | (2006.01) | |
| *A61P 7/04* | (2006.01) | |
| *A61K 38/00* | (2006.01) | |
| *C07K 14/755* | (2006.01) | |
| *C12N 9/64* | (2006.01) | |

(52) U.S. Cl.
CPC ............ *A61K 48/005* (2013.01); *A61K 38/00* (2013.01); *A61P 7/04* (2018.01); *C07K 14/755* (2013.01); *C12N 9/644* (2013.01); *C12N 9/6437* (2013.01); *C12N 2750/14143* (2013.01)

(58) Field of Classification Search
None
See application file for complete search history.

(56) References Cited

U.S. PATENT DOCUMENTS

2021/0052740 A1* 2/2021 Doering ............... C07K 14/755

FOREIGN PATENT DOCUMENTS

| | | |
|---|---|---|
| CN | 1416348 A | 5/2003 |
| JP | 2010523150 | 7/2010 |
| JP | 2016500519 | 1/2016 |
| WO | 2016123200 | 8/2016 |
| WO | 2016146757 | 9/2016 |

OTHER PUBLICATIONS

Application No. JP2019-561967, Office Action dated Jan. 7, 2022, 13 pages.
High-dose AAV Gene Therapy Deaths, Nature Biotechnology, vol. 38, No. 8, Aug. 2020, p. 910.
Human Factor IX (fIX) Sequence, SDQ ID 19 from International Patent Application Publication No. WO2016146757, Database Geneseq, EBI Accession No. GSP: BDH72337, Dec. 1, 2016.
Baranyi, Rapid Generation of Stable Cell Lines Expressing High Levels of Erythropoietin, Factor VIII, and an Antihuman CD20 Antibody using Lentiviral Vectors, Human Gene Therapy Methods, vol. 24, No. 4, Aug. 2013, pp. 214-227.
Bertina, Elevated Clotting Factor Levels and Venous Thrombosis, Pathophysiology of Haemostasis and Thrombosis, vol. 33, No. 5-6, 2003, pp. 395-400.
Brown et al., Development of a Clinical Candidate AAV3 Vector for Gene Therapy of Hemophilia B, Human Gene Therapy, vol. 31, Nos. 19-20, Oct. 2020, pp. 1114-1123.
Brown et al., Target-Cell-Directed Bioengineering Approaches for Gene Therapy of Hemophilia A, Molecular Therapy—Methods & Clinical Development, vol. 9, Jan. 31, 2018, pp. 57-69.
Buyue et al., The Heparin-binding Exosite of Factor IXa is a Critical Regulator of Plasma Thrombin Generation and Venous Thrombosis, Blood, vol. 112, No. 8, Oct. 15, 2008, pp. 3234-3241.
Dixon, Staircase Bioassay: The Up-and-down Method, Neuroscience & Biobehavioral Reviews, vol. 15, No. 1, 1991, pp. 47-50.
Dixon, The Up-and-down Method for Small Samples, Journal of the American Statistical Association, vol. 60, No. 312, Dec. 1965, pp. 967-978.
Doering, High Level Expression of Recombinant Porcine Coagulation Factor VIII, Journal of Biological Chemistry, vol. 277, No. 41, Oct. 11, 2002, pp. 38345-38349.
Doering et al., Identification of Porcine Coagulation Factor VIII Domains Responsible for High Level Expression via Enhanced Secretion, The Journal of Biological Chemistry, vol. 279, No. 8, Feb. 20, 2004, pp. 6546-6552.
Doering et al., Preclinical Development of a Hematopoietic Stem and Progenitor Cell Bioengineered Factor VIII Lentiviral Vector Gene Therapy for Hemophilia A, Human Gene Therapy, vol. 29, No. 10, Oct. 1, 2018, pp. 1183-1201.
Dooriss et al., Comparison of Factor VIII Transgenes Bioengineered for Improved Expression in Gene Therapy of Hemophilia A, Human Gene Therapy, vol. 20, No. 5, May 1, 2009, pp. 465-478.
George et al., Hemophilia B Gene Therapy with a High-Specific-Activity Factor IX Variant, The New England Journal of Medicine, vol. 377, No. 23, Dec. 7, 2017, pp. 2215-2227.

(Continued)

*Primary Examiner* — Hope A Robinson
(74) *Attorney, Agent, or Firm* — Kilpatrick Townsend & Stockton LLP

(57) ABSTRACT

Disclosed herein are novel variants of clotting factors VII, VIII, and IX and their use, for example, in methods of treating a subject with a clotting disorder, such as hemophilia A or hemophilia B.

11 Claims, 6 Drawing Sheets

Specification includes a Sequence Listing.

(56) References Cited

OTHER PUBLICATIONS

Iorio et al., Establishing the Prevalence and Prevalence at Birth of Hemophilia in Males: A Meta-Analytic Approach using National Registries, Annals of Internal Medicine, vol. 171, No. 8, Oct. 15, 2019, pp. 540-546.
Kao et al., Incorporation of the Factor IX Padua Mutation into FIX-Triple Improves Clotting Activity in Vitro and in Vivo, Thrombosis and Haemostasis, vol. 110, No. 2, 2013, pp. 244-256.
Kotin et al., Recombinant Adeno-Associated Virus Quality Control for Non-Clinical and Clinical Vectors: How an Unregulated Commercial Sector Can Compromise Development of New Gene Therapies, Human Gene Therapy, vol. 30, No. 12, Dec. 2019, pp. 1447-1448.
Kovnir et al., A Highly Productive CHO Cell Line Secreting Human Blood Clotting Factor IX, Acta Naturae, vol. 10, No. 1, Jan.-Mar. 2018, pp. 51-65.
Kratzer et al., Evolutionary History and Metabolic Insights of Ancient Mammalian Uricases, Proceedings of the National Academy of Sciences of U.S.A., vol. 111, No. 10, Mar. 11, 2014, pp. 3763-3768.
Mauro et al., A Critical Analysis of Codon Optimization in Human Therapeutics, Trends in Molecular Medicine, vol. 20, No. 11, Nov. 2014, pp. 604-613.
McIntosh et al., Comprehensive Characterization and Quantification of Adeno Associated Vectors by Size Exclusion Chromatography and Multi Angle Light Scattering, Scientific Reports, vol. 11, No. 3012, 2021, 12 pages.
McIntosh et al., Therapeutic Levels of FVIII Following a Single Peripheral Vein Administration of Raav Vector Encoding a Novel Human Factor VIII Variant, Blood, vol. 121, No. 17, Apr. 25, 2013, pp. 3335-3344.
Nair et al., Computationally Designed Liver-Specific Transcriptional Modules and Hyperactive Factor IX Improve Hepatic Gene Therapy, Blood, vol. 123, No. 20, May 15, 2014, pp. 3195-3199.
Nathwani et al., Self-complementary Adeno-associated Virus Vectors Containing a Novel Liver-specific Human Factor IX Expression Cassette Enable Highly Efficient Transduction of Murine and Non-human Primate Liver, Blood, vol. 107, No. 7, Apr. 1, 2006, pp. 2653-2661.
Nguyen et al., Novel Factor VIII Variants with a Modified Furin Cleavage Site Improve the Efficacy of Gene Therapy for Hemophilia A, Journal of Thrombosis and Haemostasis, vol. 15, No. 1, Jan. 2017, pp. 110-121.
Pastoft et al., A Sensitive Venous Bleeding Model in Haemophilia A Mice: Effects of Two Recombinant FVIII Products (N8 and Advate((R))), Haemophilia, vol. 18, No. 5, Sep. 2012.
International Application No. PCT/US2018/031881, International Preliminary Report on Patentability, dated Nov. 21, 2019, 11 pages.
International Application No. PCT/US2018/031881, International Search Report and Written Opinion, dated Oct. 8, 2019, 17 pages.
Quade-Lyssy et al., Next Generation FIX Muteins with FVIII-independent Activity for Alternative Treatment of Hemophilia A, Journal of Thrombosis and Haemostasis, vol. 12, No. 11, Nov. 2014, pp. 1861-1873.
Randall et al., An Experimental Phylogeny to Benchmark Ancestral Sequence Reconstruction, Nature Communications, vol. 7, No. 12847, 2016, 6 pages.
Samelson-Jones et al., Hyperactivity of Factor IX Padua (R338L) Depends on Factor VIIIa Cofactor Activity, JCI Insight, vol. 5, No. 14, Jun. 20, 2019, 15 pages.
Simioni et al., X-Linked Thrombophilia with a Mutant Factor IX (Factor IX Padua), The New England Journal of Medicine, vol. 361, No. 17, Oct. 22, 2009, pp. 1671-1675.
Spencer et al., Lentiviral Vector Platform for Production of Bioengineered Recombinant Coagulation Factor VIII, Molecular Therapy, vol. 19, No. 2, Feb. 2011, pp. 302-309.
Zakas et al., Development and Characterization of Recombinant Ovine Coagulation Factor VIII, PLoS One, vol. 7, No. 11, Nov. 9, 2012, pp. 1-9.
Zakas et al., Enhancing the Pharmaceutical Properties of Protein Drugs by Ancestral Sequence Reconstruction, Nature Biotechnology, vol. 35, No. 1, Jan. 2017, 13 pages.
Zhang et al., Optimized Human Factor IX Expression Cassettes for Hepatic-Directed Gene Therapy of Hemophilia B, Frontiers of Medicine, vol. 9, No. 1, 2015, pp. 90-99.
EP18730484.5, "Invitation to Pay Additional Search Fees", dated Jun. 13, 2022, 3 pages.
JP2019-561967, "Final Rejection", dated Jul. 5, 2022, 11 pages with English Translation.
Ohmori, "Blood Coagulation Factor IX", Japanese Journal of Thrombosis and Hemostasis, vol. 25, 2014, pp. 458-464.
CN Application No. 201880043373.3, Office Action, dated Sep. 5, 2022, 12 pages with English translation.
"Coagulation factor VIII (FVIII) mutant (B-domain del/E434V), SEQ ID 40", Database Accession No. BDC92847, Sep. 22, 2016, 2 pages.
Eaton, et al., "Construction and Characterization of an Active Factor VIII Variant Lacking The Central One-third of The Molecule", Biochemistry, vol. 25, No. 26, Dec. 30, 1986, pp. 8343-8347.
EP Application No. 18730484.5, Communication pursuant to Rule 164(2)(b) and Article 94(3) EPC dated Nov. 28, 2022, 9 pages.
Kessler, et al., "B-domain Deleted Recombinant Factor VIII Preparations are Bioequivalent to A Monoclonal Antibody Purified Plasma-derived Factor VIII Concentrate: A Randomized, Three-way Crossover Study", Haemophilia, vol. 11, No. 2, Apr. 2005, pp. 84-91.

\* cited by examiner

NUCLEIC ACIDS ENCODING CLOTTING FACTOR VARIANTS AND THEIR USE

RELATED APPLICATIONS

This application is a U.S. National Application, filed Under 35 U.S.C. § 371, of International Application No. PCT/US2018/031881, filed on May 9, 2018, which claims priority to U.S. Provisional Application No. 62/503,766, filed May 9, 2017. The provisional patent application is incorporated by reference in its entirety.

ACKNOWLEDGMENT OF GOVERNMENT SUPPORT

This invention was made with government support under Grant No. 1 R56 HL 131059 awarded by the National Institutes of Health. The government has certain rights in the invention.

FIELD OF THE DISCLOSURE

This relates to novel clotting factor proteins, such as clotting factor IX, clotting factor VIII, and clotting factor VII proteins, as well as recombinant nucleic acid molecules and vectors encoding the clotting factor proteins, and related methods of use to treat a clotting disorder, such as hemophilia, in a subject.

BACKGROUND

Mutations in the clotting factor VIII (fVIII) gene result in a decreased or defective clotting factor (fVIII) protein that gives rise to hemophilia A, which is characterized by uncontrolled bleeding. Hemophilia B is similarly associated with clotting factor IX (fIX). Proconvertin deficiency, a hemophilia-like disease, is similarly associated with clotting factor VII (fVII). Treatment of clotting disorders such as hemophilia A, hemophilia B, and proconvertin deficiency typically entails lifelong, multi-weekly intravenous infusion of either human plasma-derived or recombinant clotting factors to replace the missing clotting factor activity in the patient. Due to the high cost, less than 30% of the global hemophilia population receives this form of treatment. Furthermore, about 25% of patients treated with clotting factor replacement products develop neutralizing antibodies that render future treatment ineffective. Thus, there is a need to identify improved therapies.

SUMMARY

Disclosed herein are variants of the fVII, fVIII, and fIX clotting factors with increased clotting factor activity relative to the corresponding native human clotting factor proteins.

In some embodiments, an isolated nucleic acid molecule is provided that comprises a nucleic acid sequence encoding a fIX protein comprising an amino acid sequence at least 95% identical to residues 47-462 of SEQ ID NO: 1 (An96 fIX Padua) or residues 47-461 of SEQ ID NO: 2 (An97 fIX Padua). In some embodiments, an isolated nucleic acid molecule is provided that comprises a nucleic acid sequence encoding a fIX protein comprising an amino acid sequence set forth as residues 47-462 of SEQ ID NO: 1 (An96 fIX Padua) or residues 47-461 of SEQ ID NO: 2 (An97 fIX Padua). In some embodiments, an isolated nucleic acid molecule is provided that comprises a nucleic acid sequence encoding a fIX protein comprising an amino acid sequence at least 95% identical to SEQ ID NO: 1 (An96 fIX Padua) or SEQ ID NO: 2 (An97 fIX Padua). In some embodiments, an isolated nucleic acid molecule is provided that comprises a nucleic acid sequence encoding a fIX protein comprising an amino acid sequence set forth as SEQ ID NO: 1 (An96 fIX Padua) or SEQ ID NO: 2 (An97 fIX Padua). In some embodiments, the nucleic acid sequence comprises nucleotides 139-1389 of SEQ ID NO: 9 or nucleotides 139-1386 of SEQ ID NO: 10. In some embodiments, the nucleic acid sequence comprises the sequence set forth as SEQ ID NO: 9 or SEQ ID NO: 10.

In some embodiments, an isolated nucleic acid molecule is provided that comprises a nucleic acid sequence encoding a fVIII protein comprising an amino acid sequence at least 95% identical to residues 20-1458 of SEQ ID NO: 3 (An84 fVIII BDD), SEQ ID NO: 4 (An63 fVIII BDD), SEQ ID NO: 5 (An96 fVIII BDD), or SEQ ID NO: 6 (An97 fVIII BDD). In some embodiments, an isolated nucleic acid molecule is provided that comprises a nucleic acid sequence encoding a fVIII protein comprising an amino acid sequence set forth as residues 20-1458 of SEQ ID NO: 3 (An84 fVIII BDD), SEQ ID NO: 4 (An63 fVIII BDD), SEQ ID NO: 5 (An96 fVIII BDD), or SEQ ID NO: 6 (An97 fVIII BDD). In some embodiments, an isolated nucleic acid molecule is provided that comprises a nucleic acid sequence encoding a fVIII protein comprising an amino acid sequence at least 95% identical to SEQ ID NO: 3 (An84 fVIII BDD), SEQ ID NO: 4 (An63 fVIII BDD), SEQ ID NO: 5 (An96 fVIII BDD), or SEQ ID NO: 6 (An97 fVIII BDD). In some embodiments, an isolated nucleic acid molecule is provided that comprises a nucleic acid sequence encoding a fVIII protein comprising an amino acid sequence set forth as SEQ ID NO: 3 (An84 fVIII BDD), SEQ ID NO: 4 (An63 fVIII BDD), SEQ ID NO: 5 (An96 fVIII BDD), or SEQ ID NO: 6 (An97 fVIII BDD). In some embodiments, the nucleotide sequence comprises nucleotides 58-4377 of any one of SEQ ID NOs: 11-14. In some embodiments, the nucleotide sequence comprises the sequence set forth as any one of SEQ ID NOs: 11-14.

In some embodiments, an isolated nucleic acid molecule is provided that comprises a nucleic acid sequence encoding a fVII protein comprising an amino acid sequence at least 95% identical to residues 21-444 of SEQ ID NO: 7 (An81 fVII) or SEQ ID NO: 8 (An61 fVII). In some embodiments, an isolated nucleic acid molecule is provided that comprises a nucleic acid sequence encoding a fVII protein comprising an amino acid sequence set forth as residues 21-444 of SEQ ID NO: 7 (An81 fVII) or SEQ ID NO: 8 (An61 fVII). In some embodiments, an isolated nucleic acid molecule is provided that comprises a nucleic acid sequence encoding a fVII protein comprising an amino acid sequence at least 95% identical to SEQ ID NO: 7 (An81 fVII) or SEQ ID NO: 8 (An61 fVII). In some embodiments, an isolated nucleic acid molecule is provided that comprises a nucleic acid sequence encoding a fVII protein comprising an amino acid sequence set forth as SEQ ID NO: 7 (An81 fVII) or SEQ ID NO: 8 (An61 fVII). In some embodiments, the nucleotide sequence comprises nucleotides 61-1335 of SEQ ID NO: 15 or SEQ ID NO: 16. In some embodiments, the nucleotide sequence comprises the sequence set forth as SEQ ID NO: 15 or SEQ ID NO: 16.

Also provided are vectors, such as an adeno-associated virus (AAV) vector, containing the nucleic acid molecules, as well as isolated fVII, fVIII, and fIX proteins encoded by the nucleic acid molecules.

In some embodiments, a method of inducing blood clotting in a subject in need thereof is provided. The method comprises administering to the subject a therapeutically effective amount of a vector (such as an AAV vector) encoding a recombinant clotting factor as described herein. In some embodiments, the subject is a subject with a clotting disorder, such as hemophilia A or hemophilia B. In some embodiments, the clotting disorder is hemophilia A and the subject is administered a vector comprising a nucleic acid molecule encoding a recombinant fVIII protein. In other embodiments, the clotting disorder is hemophilia B and the subject is administered a vector comprising a nucleic acid molecule encoding a recombinant fIX protein. In some embodiments, the clotting disorder is congenital proconvertin deficiency and the subject is administered a vector comprising a nucleic acid molecule encoding a recombinant fVII protein.

The foregoing and other features and advantages of this disclosure will become more apparent from the following detailed description of several embodiments which proceeds with reference to the accompanying figures.

BRIEF DESCRIPTION OF THE FIGURES

FIGS. 1A and 1B illustrate a sequence alignment of the human fIX (SEQ ID NO: 42) and several variants thereof, including An102 fIX (SEQ ID NO: 25), An97 fIX (SEQ ID NO: 24), An96 fIX (SEQ ID NO: 23), An95 fIX (SEQ ID NO: 22), An84 fIX (SEQ ID NO: 20), An63 fIX (SEQ ID NO: 17), An88 fIX (SEQ ID NO: 21), An65 fIX (SEQ ID NO: 18), and An70 fIX (SEQ ID NO: 19) proteins.

SEQUENCE LISTING

Figure 2:
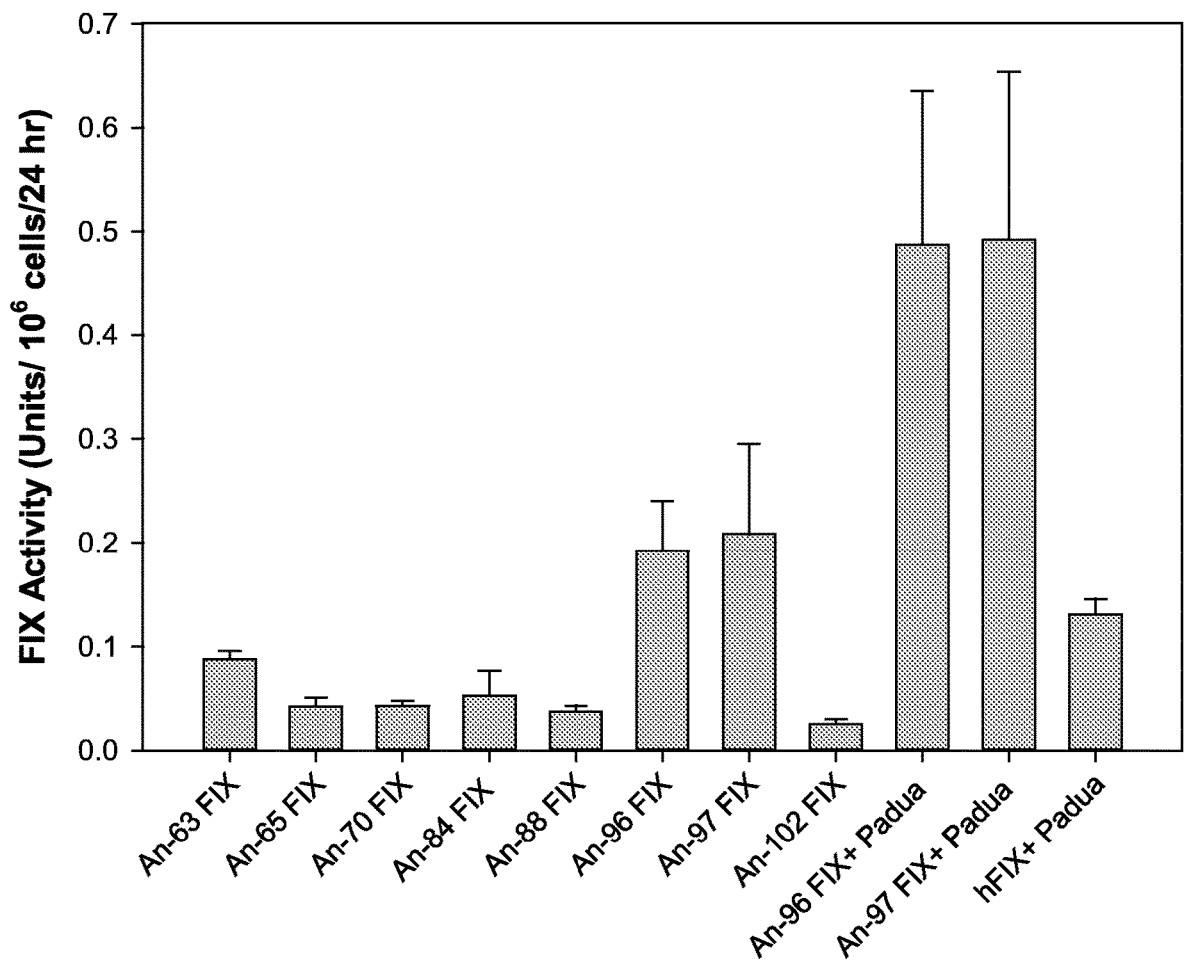
FIG. 2 shows fIX activity levels of various fIX variants expressed in HepG2 cells using AAV vectors encoding the indicated fIX variants.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~348 kb), which was created on May 2, 2018 which is incorporated by reference herein.

DETAILED DESCRIPTION

I. Terms

Unless otherwise noted, technical terms are used according to conventional usage. Definitions of common terms in molecular biology may be found in Krebs et al. (eds.), *Lewin's genes XII*, published by Jones & Bartlett Learning, 2017; Kendrew et al. (eds.), *The Encyclopedia of Molecular Biology*, published by Blackwell Science Ltd., 2009 (ISBN 9780632021826). The singular terms "a," "an," and "the" include plural referents unless context clearly indicates otherwise. "Comprising A or B" means including A, or B, or A and B. Although methods and materials similar or equivalent to those described herein can be used in the practice or testing of the present disclosure, suitable methods and materials are described below. In addition, the materials, methods, and examples are illustrative only and not intended to be limiting. In case of conflict, the present specification, including explanations of terms, will control. In order to facilitate review of the various embodiments of the disclosure, the following explanations of specific terms are provided:

5' and/or 3': Nucleic acid molecules (such as, DNA and RNA) are said to have "5' ends" and "3' ends" because mononucleotides are reacted to make polynucleotides in a manner such that the 5' phosphate of one mononucleotide pentose ring is attached to the 3' oxygen of its neighbor in one direction via a phosphodiester linkage. Therefore, one end of a linear polynucleotide is referred to as the "5' end" when its 5' phosphate is not linked to the 3' oxygen of a mononucleotide pentose ring. The other end of a polynucleotide is referred to as the "3' end" when its 3' oxygen is not linked to a 5' phosphate of another mononucleotide pentose ring. Notwithstanding that a 5' phosphate of one mononucleotide pentose ring is attached to the 3' oxygen of its neighbor, an internal nucleic acid sequence also may be said to have 5' and 3' ends.

In either a linear or circular nucleic acid molecule, discrete internal elements are referred to as being "upstream" or 5' of the "downstream" or 3' elements. With regard to DNA, this terminology reflects that transcription proceeds in a 5' to 3' direction along a DNA strand. Promoter and enhancer elements, which direct transcription of a linked gene, are generally located 5' or upstream of the coding region. However, enhancer elements can exert their effect even when located 3' of the promoter element and the coding region. Transcription termination and polyadenylation signals are located 3' or downstream of the coding region.

Adeno-associated virus (AAV): A small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. There are currently 11 recognized serotypes of AAV (AAV1-11).

Administration/Administer: To provide or give a subject an agent, such as a therapeutic agent (e.g. a recombinant AAV), by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Bleeding Time Assay: An assay used to measure the amount of time it takes for a subject's blood to clot. A blood pressure cuff is placed on the upper arm and inflated. Two incisions are made on the lower arm. These are about 10 mm (less than ½ inch) long and 1 mm deep (just deep enough to cause minimal bleeding). The blood pressure cuff is immediately deflated. Blotting paper is touched to the cuts every 30 seconds until the bleeding stops. The length of time it takes for the cuts to stop bleeding is recorded. In normal, non-hemophiliacs, bleeding stops within about one to ten minutes and may vary from lab to lab, depending on how the assay is measured. In contrast, severe hemophiliacs having less than 1% of normal levels of the appropriate clotting factor have a whole blood clotting time of greater than 60 minutes. In mice, the bleeding time is assayed by transecting the tip of the tail and periodically touching a blotting paper until a clot is formed at the tip of the tail. Normal bleeding time is between 2-4 minutes. In contrast, hemophiliac mice having less than 1% of normal levels of the appropriate clotting factor have a bleeding time of greater than 15 minutes.

cDNA (complementary DNA): A piece of DNA lacking internal, non-coding segments (introns) and regulatory sequences that determine transcription. cDNA is synthesized in the laboratory by reverse transcription from messenger RNA extracted from cells. cDNA can also contain untranslated regions (UTRs) that are responsible for translational control in the corresponding RNA molecule.

Clotting disorder: A general term for a wide range of medical problems that lead to poor blood clotting and continuous bleeding. Doctors also refer to clotting disorders by terms such as, for example, coagulopathy, abnormal bleeding and bleeding disorders. Clotting disorders include any congenital, acquired or induced defect that results in abnormal (or pathological) bleeding. Examples include, but are not limited to, disorders of insufficient clotting or hemostasis, such as hemophilia A (a deficiency in fVIII), hemophilia B (a deficiency in fIX), hemophilia C (a deficiency in Factor XI), proconvertin deficiency (a deficiency in fVII), abnormal levels of clotting factor inhibitors, platelet disorders, thrombocytopenia, vitamin K deficiency and von Willebrand's disease.

Some clotting disorders are present at birth and in some instances are inherited disorders. Specific examples include, but are not limited to: hemophilia A, hemophilia B, protein C deficiency, and Von Willebrand's disease. Some clotting disorders are developed during certain illnesses (such as vitamin K deficiency, severe liver disease), or treatments (such as use of anticoagulant drugs or prolonged use of antibiotics).

Clotting Factor VII (fVII): fVII is a vitamin K-dependent zymogen protein required for the efficient clotting of blood. When combined with tissue factor, fVII becomes proteolytically activated (fVIIa) and functions in coagulation as an activator of factor IX and factor X. At suprapyhsiologic levels, fVIIa can display tissue factor independent procoagulant activity as well. A concentration of about 0.5 μg/ml of fVII in the blood is considered normal. Deficiency of fVII is associated with congenital proconvertin deficiency, which presents as a hemophilia-like bleeding disorder. fVII is biosynthesized as a single-chain zymogen containing a domain structure with an N-terminal signal peptide (approximately residues −20 to −1), a γ-carboxyglutamic acid (Gla) rich domain (approximately residues 1-63), two epidermal growth factor (EGF)-like domains (approximately residues 64-100 [EGF1] and 101-170 [EGF2]), and a latent C-terminal serine protease domain (approximately residues 171-444). For activation, fVII requires a single peptide bond cleavage at Arg190-Iso191. This results in the formation of fVIIa consisting of a light chain composed of the Gla, EGF1, and EGF2 domains linked through a single disulphide bond to a heavy chain containing the protease domain. A substantial amount of information is available on the structure and function of fVII protein; see, e.g., Vadivel et al. "Structure and function of Vitamin K-dependent coagulant and anticoagulant proteins." in *Hemostasis and Thrombosis—Basic Principles and Clinical Practice*. 6$^{th}$ edition. Marder et al. (Eds.). Philadelphia: Lippincott Williams and Wilkens, 2013. Pages 208-232, which is incorporated by reference herein in its entirety. fVII nucleic acid and protein sequences are publicly available (for example see UniProtKB/Swiss-Prot Ref. No. P08709.1). fVII variants are provided herein that have increased fVII activity for blood clotting.

Clotting Factor VIII (fVIII): fVIII is a protein required for the efficient clotting of blood, and functions in coagulation as a cofactor in the activation of factor X by fIX. FVIII contains multiple domains (A1-A2-B-ap-A3-C1-C2) and circulates in blood in an inactivated form bound to von Willebrand factor (VWF). Thrombin cleaves fVIII causing dissociation with VWF ultimately leading to fibrin formation through fIX. Congenital hemophilia A is associated with genetic mutations in the fVIII gene and results in impaired clotting due to lower than normal levels of circulating fVIII. A concentration of about 100 ng/ml for fVIII in the blood is considered in the normal range. Severe forms of hemophilia A can result when a patient has less than about 1% of the normal amount of fVIII (i.e. less than about 1 ng of fVIII per ml of blood). fVIII is synthesized as an approximate 2351 amino acid single chain precursor protein, which is proteolytically processed. The human factor VIII gene (186,000 base-pairs) consists of 26 exons ranging in size from 69 to 3,106 bp and introns as large as 32.4 kilobases (kb). Examples of fVIII nucleic acid and protein sequences are publicly available (for example, see Genbank Accession Nos: K01740, M14113, and E00527). fVIII variants are provided herein that have increased fVIII activity for blood clotting but are reduced in size, such as fVIII variants that lack the fVIII B domain and also have one or more amino acid variations that provide for increased fVIII activity.

Clotting Factor IX (fIX): fIX is a vitamin K-dependent protein required for the efficient clotting of blood, and functions in coagulation as an activator of factor X. A concentration of about 1-5 μg/ml of fIX in the blood is considered in the normal range. Deficiency of fIX is associated with hemophilia B, and severe cases result when the concentration of fIX is less than about 1% of the normal concentration of fIX (i.e. less than about 0.01-0.05 μg fIX per ml of blood). fIX is biosynthesized as a single-chain zymogen containing a domain structure with an N-terminal signal peptide (approximately residues −28 to −1), a γ-carboxyglutamic acid (Gla) rich domain (approximately residues 1-40), a short hydrophobic segment (approximately residues 41-46), two epidermal growth factor (EGF)-like domains (approximately residues 47-84 [EGF1] and 85-127 [EGF2]), an activation peptide (approximately residues 146-180), and a latent C-terminal serine protease domain (approximately residues 181-415). For activation, fIX requires two peptide bond cleavages, one at Arg145-Ala146 and one at Arg180-Val 181, releasing a 35-residue activation peptide. This results in the formation of activated fIX (fIXa) consisting of a light chain composed of the Gla, EGF1, and EGF2 domains linked through a single disulphide bond to a heavy chain containing the protease domain (185-415). A substantial amount of information is available on the structure and function of fIX protein; see, e.g., Vadivel et al. "Structure and function of Vitamin K-dependent coagulant and anticoagulant proteins." in *Hemostasis and Thrombosis—Basic Principles and Clinical Practice*. 6$^{th}$ edition. Marder et al. (Eds.). Philadelphia: Lippincott Williams and Wilkens, 2013. Pages 208-232, which is incorporated by reference herein in its entirety. fIX nucleic acid and protein sequences are publicly available (see for example UniProtKB/Swiss-Prot Ref. No. P00740.2. fIX variants are provided herein that have increased fIX activity for blood clotting.

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells). Codon optimization does not alter the amino acid sequence of the encoded protein.

The term "liver specific amino acids codons" refers to codons that are differentially utilized-represented in genes highly expressed within the human liver compared to the codon usage of the entire coding region of the human genome. A liver-codon optimization strategy uses a maximum amount of liver specific amino acid codons seeks to avoid codons that are under-represented, e.g., because of low quantities of codon matching tRNA in liver cells resulting in slower protein translation.

Control: A reference standard. In some embodiments, the control is a negative control sample obtained from a healthy patient. In other embodiments, the control is a positive control sample obtained from a patient diagnosed with hemophilia. In still other embodiments, the control is a historical control or standard reference value or range of values (such as a previously tested control sample, such as a group of hemophilia A patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

Expression: Transcription or translation of a nucleic acid sequence. For example, an encoding nucleic acid sequence (such as a gene) can be expressed when its DNA is transcribed into RNA or an RNA fragment, which in some examples is processed to become mRNA. An encoding nucleic acid sequence (such as a gene) may also be expressed when its mRNA is translated into an amino acid sequence, such as a protein or a protein fragment. In a particular example, a heterologous gene is expressed when it is transcribed into RNA. In another example, a heterologous gene is expressed when its RNA is translated into an amino acid sequence. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcriptional terminators, a start codon (ATG) in front of a protein-encoding gene, splice signals for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

Gene: A nucleic acid sequence, typically a DNA sequence, that comprises control and coding sequences necessary for the transcription of an RNA, whether an mRNA or otherwise. For instance, a gene may comprise a promoter, one or more enhancers or silencers, a nucleic acid sequence that encodes a RNA and/or a polypeptide, downstream regulatory sequences and, possibly, other nucleic acid sequences involved in regulation of the expression of an mRNA.

As is well known in the art, most eukaryotic genes contain both exons and introns. The term "exon" refers to a nucleic acid sequence found in genomic DNA that is bioinformatically predicted and/or experimentally confirmed to contribute a contiguous sequence to a mature mRNA transcript. The term "intron" refers to a nucleic acid sequence found in genomic DNA that is predicted and/or confirmed not to contribute to a mature mRNA transcript, but rather to be "spliced out" during processing of the transcript.

Gene therapy: The introduction of a heterologous nucleic acid molecule into one or more recipient cells, wherein expression of the heterologous nucleic acid in the recipient cell affects the cell's function and results in a therapeutic effect in a subject. For example, the heterologous nucleic acid molecule may encode a protein, which affects a function of the recipient cell.

Hemophilia: A blood coagulation disorder caused by a deficient clotting factor activity, which decreases hemostasis. Severe forms result when the concentration of clotting factor is less than about 1% of the normal concentration of the clotting factor in a normal subject. In some subjects, hemophilia is due to a genetic mutation which results in impaired expression of a clotting factor. In others, hemophilia is an auto-immune disorder, referred to as acquired hemophilia, in which the antibodies which are generated against a clotting factor in a subject result in decreased hemostasis.

Hemophilia A results from a deficiency of functional clotting fVIII, while hemophilia B results from a deficiency of functional clotting fIX. These conditions which are due to a genetic mutation are caused by an inherited sex-linked recessive trait with the defective gene located on the X chromosome, and this disease is therefore generally found only in males. The severity of symptoms can vary with this disease, and the severe forms become apparent early on. Bleeding is the hallmark of the disease and typically occurs when a male infant is circumcised. Additional bleeding manifestations make their appearance when the infant becomes mobile. Mild cases may go unnoticed until later in life when they occur in response to surgery or trauma. Internal bleeding may happen anywhere, and bleeding into joints is common.

Hemostasis: Arrest of bleeding blood by blood clot formation. Blood clotting time is the length of time it takes for peripheral blood to clot using an activated partial thromboplastin time assay (APTT) or by measuring bleeding time. In a particular embodiment, the blood clotting time decreases by at least 50%, for example at least 60%, at least 70%, at least 75%, at least 80%, at least 90%, at least 95%, at least 98%, at least 99% or even about 100% (i.e. the blood clotting time is similar to what is observed for a normal subject) when compared to the blood clotting time of the subject prior to administration of a therapeutic vector encoding the appropriate clotting factor as described herein. In yet another embodiment, the blood clotting time in the affected subject is corrected to about 50% of a normal subject, to about 75% of a normal subject, to about 90% of a normal subject, for example to about 95%, for example about 100%, after oral administration of a therapeutically effective amount of the appropriate clotting factor. As used herein, "about" refers to plus or minus 5% from a reference value. Thus, about 50% refers to 47.5% to 52.5%.

Isolated: An "isolated" biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington: The Science and Practice of Pharmacy,* $22^{nd}$ ed., London, UK: Pharmaceutical Press, 2013, describes compositions and formulations suitable for pharmaceutical delivery of the disclosed vectors.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions (such as vector compositions) to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Purified: The term purified does not require absolute purity; rather, it is intended as a relative term. Thus, for example, a purified protein preparation is one in which the protein (such as a fVII, fVIII, or fIX protein) is more enriched than the peptide or protein is in its natural environment within a cell. In one embodiment, a preparation is purified such that the protein represents at least 50% of the total protein content of the preparation.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Preventing, treating or ameliorating a disease: "Preventing" a disease (such as hemophilia) refers to inhibiting the full development of a disease. "Treating" refers to a therapeutic intervention that ameliorates a sign or symptom of a disease or pathological condition after it has begun to develop.

"Ameliorating" refers to the reduction in the number or severity of signs or symptoms of a disease. Promoter: A region of DNA that directs/initiates transcription of a nucleic acid (e.g. a gene). A promoter includes necessary nucleic acid sequences near the start site of transcription. Typically, promoters are located near the genes they transcribe. A promoter also optionally includes distal enhancer or repressor elements which can be located as much as several thousand base pairs from the start site of transcription. A tissue-specific promoter is a promoter that directs/initiated transcription primarily in a single type of tissue or cell. For example, a liver-specific promoter is a promoter that directs/initiates transcription in liver tissue to a substantially greater extent than other tissue types.

Protein: A biological molecule expressed by a gene or other encoding nucleic acid (e.g., a cDNA) and comprised of amino acids.

Purified: The term "purified" does not require absolute purity; rather, it is intended as a relative term. Thus, for example, a purified peptide, protein, virus, or other active compound is one that is isolated in whole or in part from naturally associated proteins and other contaminants In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule is one that has a sequence that is not naturally occurring, for example, includes one or more nucleic acid substitutions, deletions or insertions, and/or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

A recombinant virus is one that includes a genome that includes a recombinant nucleic acid molecule. As used herein, "recombinant AAV" refers to an AAV particle in which a recombinant nucleic acid molecule (such as a recombinant nucleic acid molecule encoding a clotting factor) has been packaged.

A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell, or into the genome of a recombinant virus.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Comet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

As used herein, reference to "at least 90% identity" refers to "at least 90%, at least 91%, at least 92%, at least 93%, at least 94%, at least 95%, at least 96%, at least 97%, at least 98%, at least 99%, or even 100% identity" to a specified reference sequence.

Subject: Living multi-cellular vertebrate organisms, a category that includes human and non-human mammals.

Therapeutically effective amount: The amount of agent, such as a disclosed recombinant AAV vector encoding a clotting factor, that is sufficient to prevent, treat (including prophylaxis), reduce and/or ameliorate the symptoms and/or underlying causes of a disorder or disease, for example to prevent, inhibit, and/or treat hemophilia. For example, this can be the amount of a recombinant AAV vector encoding a novel clotting factor as described herein that produces sufficient amounts of the clotting factor to decrease the time it takes for the blood of a subject to clot.

In one example, a desired response is to reduce clotting time in a subject (such as a subject with hemophilia), for example as measured using a bleeding time assay. The clotting time does not need to be completely restored to that of normal healthy subjects without hemophilia for the method to be effective. For example, administration of a therapeutically effective amount of a vector (such as a fIX encoding vector) as disclosed herein can decrease the clotting time (or other symptom of the hemophilia) by a desired amount, for example by at least 20%, at least 30%, at least 40%, at least 50%, at least 60%, at least 70%, at least 80%, at least 90%, at least 95%, at least 98%, at least 100% or more, as compared to a suitable control.

It is understood that to obtain a therapeutic response to the disease or condition can require multiple administrations of a therapeutic agent. Thus, a therapeutically effective amount encompasses a fractional dose that contributes in combination with previous or subsequent administrations to attaining a therapeutic outcome in the patient. For example, a therapeutically effective amount of an agent can be administered in a single dose, or in several doses, for example daily, during a course of treatment. However, the therapeutically effective amount can depend on the subject being treated, the severity and type of the condition being treated, and the manner of administration. A unit dosage form of the agent can be packaged in a therapeutic amount, or in multiples of the therapeutic amount, for example, in a vial (e.g., with a pierceable lid) or syringe having sterile components.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is an adeno-associated virus (AAV) vector. In some embodiments, the vector is a gamma-retroviral vector, a lentiviral vector, or an adenoviral vector.

II. Novel Clotting Factors

The blood clotting system is a proteolytic cascade. Blood clotting factors are present in the plasma as a zymogen, in other words in an inactive form, which on activation undergoes proteolytic cleavage to release the active factor form the precursor molecule. The ultimate goal is to produce thrombin. Thrombin converts fibrinogen into fibrin, which forms a clot.

Factor X is the first molecule of the common pathway and is activated by a complex of molecules containing activated fIX, fVIII, calcium, and phospholipids which are on the platelet surface. FVIII is activated by thrombin, and it facilitates the activation of factor X by fIXa. Congenital hemophilia A is associated with genetic mutations in the fVIII gene and results in impaired clotting due to lower than normal levels of circulating fVIII. Hemophilia B is similarly associated with genetic mutations in the fIX gene. Proconvertin deficiency is similarly associated with mutations in the fVII gene.

As discussed in Examples 1-3, novel fVII, fVIII, and fIX sequences were identified from corresponding ancestral variants and assessed for clotting factor activity. Several sequences provide for increased clotting factor activity relative to the corresponding human clotting factor.

In some embodiments, a nucleic acid molecule is provided that encodes a protein with fIX activity comprising an amino acid sequence set forth as residues 47-462 SEQ ID NO: 1 (An96 fIX Padua without signal peptide and propeptide), or an amino acid sequence at least 95%, at least 96%, at least 97%, at least 98%, or at least 99% identical thereto. Residues 1-46 of SEQ ID NO: 1 are the fIX signal peptide and propeptide. In some embodiments, a nucleic acid molecule is provided that encodes a protein with fIX activity comprising an amino acid sequence set forth as SEQ ID NO: 1 (An96 fIX Padua with signal peptide and propeptide), or an amino acid sequence at least 95%, at least 96%, at least 97%, at least 98%, or at least 99% identical thereto. In alternative embodiments, a different signal peptide and/or propeptide can be used in place of the signal peptide and/or propeptide of SEQ ID NO: 1, such as an IL2 signal peptide and/or factor X propeptide.

As discussed in Example 1, the nucleotide sequence encoding An96 fIX Padua was codon-optimized for expression in human liver. An exemplary liver codon optimized An96 fIX Padua sequence is provided as SEQ ID NO: 9. In some embodiments, a recombinant nucleic acid molecule is provided comprising the nucleotide sequence set forth as nucleotides 139-1389 of SEQ ID NO: 9. In some embodiments, a recombinant nucleic acid molecule is provided comprising the nucleotide sequence set forth as SEQ ID NO: 9. In some embodiments, CpG motifs within the codon-optimized An96 fIX Padua sequence can be removed to provide a CpG deleted, liver codon optimized An96 fIX Padua sequence.

In some embodiments, a nucleic acid molecule is provided that encodes a protein with fIX activity comprising an amino acid sequence set forth as residues 47-461 SEQ ID NO: 2 (An97 fIX Padua without signal peptide and propeptide), or an amino acid sequence at least 95%, at least 96%, at least 97%, at least 98%, or at least 99% identical thereto. Residues 1-46 of SEQ ID NO: 2 are the fIX signal peptide and propeptide. In some embodiments, a nucleic acid molecule is provided that encodes a protein with fIX activity comprising an amino acid sequence set forth as SEQ ID NO: 2 (An97 fIX Padua with signal peptide and propeptide), or an amino acid sequence at least 95%, at least 96%, at least 97%, at least 98%, or at least 99% identical thereto. In alternative embodiments, a different signal peptide and/or propeptide can be used in place of the signal peptide and/or propeptide of SEQ ID NO: 2, such as an IL2 signal peptide and/or factor X propeptide.

As discussed in Example 1, the nucleotide sequence encoding An97 fIX Padua was codon-optimized for expression in human liver. An exemplary liver codon optimized An97 fIX Padua sequence is provided as SEQ ID NO: 10. In some embodiments, a recombinant nucleic acid molecule is provided comprising the nucleotide sequence set forth as nucleotides 139-1386 of SEQ ID NO: 10. In some embodiments, a recombinant nucleic acid molecule is provided comprising the nucleotide sequence set forth as SEQ ID NO: 10. In some embodiments, CpG motifs within the codon-optimized An96 fIX Padua sequence can be removed to provide a CpG deleted, liver codon optimized An96 fIX Padua sequence.

In some embodiments, a nucleic acid molecule is provided that encodes a protein with fVIII activity comprising an amino acid sequence set forth as residues 20-1458 of SEQ ID NO: 3 (An84 fVIII BDD without signal peptide), or an amino acid sequence at least 95%, at least 96%, at least 97%, at least 98%, or at least 99% identical thereto. Residues 1-19 of SEQ ID NO: 3 are the fVIII signal peptide. In some embodiments, a nucleic acid molecule is provided that encodes a protein with fVIII activity comprising an amino acid sequence set forth as SEQ ID NO: 3 (An84 fVIII BDD with signal peptide), or an amino acid sequence at least 95%, at least 96%, at least 97%, at least 98%, or at least 99% identical thereto. In alternative embodiments, a different signal peptide and/or propeptide can be used in place of the signal peptide and/or propeptide of SEQ ID NO: 3, such as an IL2 signal peptide and/or factor X propeptide.

As discussed in Example 2, the nucleotide sequence encoding An84 fVIII BDD was codon-optimized for expression in human liver. An exemplary liver codon optimized An84 fVIII BDD sequence is provided as SEQ ID NO: 11. In some embodiments, a recombinant nucleic acid molecule is provided comprising the nucleotide sequence set forth as nucleotides 58-4377 of SEQ ID NO: 11. In some embodiments, a recombinant nucleic acid molecule is provided comprising the nucleotide sequence set forth as SEQ ID NO: 11. In some embodiments, CpG motifs within the codon-optimized An84 fVIII BDD sequence can be removed to provide a CpG deleted, liver codon optimized An84 fVIII sequence.

In some embodiments, a nucleic acid molecule is provided that encodes a protein with fVIII activity comprising an amino acid sequence set forth as residues 20-1458 of SEQ ID NO: 4 (An63 fVIII BDD without signal peptide), or an amino acid sequence at least 95%, at least 96%, at least 97%, at least 98%, or at least 99% identical thereto. Residues 1-19 of SEQ ID NO: 4 are the fVIII signal peptide. In some embodiments, a nucleic acid molecule is provided that encodes a protein with fVIII activity comprising an amino acid sequence set forth as SEQ ID NO: 4 (An63 fVIII BDD with signal peptide), or an amino acid sequence at least 95%, at least 96%, at least 97%, at least 98%, or at least 99% identical thereto. In alternative embodiments, a different signal peptide and/or propeptide can be used in place of the signal peptide and/or propeptide of SEQ ID NO: 4, such as an IL2 signal peptide and/or factor X propeptide.

As discussed in Example 2, the nucleotide sequence encoding An63 fVIII BDD was codon-optimized for expression in human liver. An exemplary liver codon optimized An63 fVIII BDD sequence is provided as SEQ ID NO: 12. In some embodiments, a recombinant nucleic acid molecule is provided comprising the nucleotide sequence set forth as nucleotides 58-4377 of SEQ ID NO: 12. In some embodiments, a recombinant nucleic acid molecule is provided comprising the nucleotide sequence set forth as SEQ ID NO: 12. In some embodiments, CpG motifs within the codon-optimized An63 fVIII BDD sequence can be removed to provide a CpG deleted, liver codon optimized An63 fVIII sequence.

In some embodiments, a nucleic acid molecule is provided that encodes a protein with fVIII activity comprising an amino acid sequence set forth as residues 20-1458 of SEQ ID NO: 5 (An96 fVIII BDD without signal peptide), or an amino acid sequence at least 95%, at least 96%, at least 97%, at least 98%, or at least 99% identical thereto. Residues 1-19 of SEQ ID NO: 5 are the fVIII signal peptide. In some embodiments, a nucleic acid molecule is provided that encodes a protein with fVIII activity comprising an amino acid sequence set forth as SEQ ID NO: 5 (An96 fVIII BDD with signal peptide), or an amino acid sequence at least 95%, at least 96%, at least 97%, at least 98%, or at least 99% identical thereto. In alternative embodiments, a different signal peptide and/or propeptide can be used in place of the signal peptide and/or propeptide of SEQ ID NO: 5, such as an IL2 signal peptide and/or factor X propeptide.

As discussed in Example 2, the nucleotide sequence encoding An96 fVIII BDD was codon-optimized for expression in human liver. An exemplary liver codon optimized An96 fVIII BDD sequence is provided as SEQ ID NO: 13. In some embodiments, a recombinant nucleic acid molecule is provided comprising the nucleotide sequence set forth as nucleotides 58-4377 of SEQ ID NO: 13. In some embodiments, a recombinant nucleic acid molecule is provided comprising the nucleotide sequence set forth as SEQ ID NO: 13. In some embodiments, CpG motifs within the codon-optimized An96 fVIII BDD sequence can be removed to provide a CpG deleted, liver codon optimized An96 fVIII sequence.

In some embodiments, a nucleic acid molecule is provided that encodes a protein with fVIII activity comprising an amino acid sequence set forth as residues 20-1458 of SEQ ID NO: 6 (An97 fVIII BDD without signal peptide), or an amino acid sequence at least 95%, at least 96%, at least 97%, at least 98%, or at least 99% identical thereto. Residues 1-19 of SEQ ID NO: 6 are the fVIII signal peptide. In some embodiments, a nucleic acid molecule is provided that encodes a protein with fVIII activity comprising an amino acid sequence set forth as SEQ ID NO: 6 (An97 fVIII BDD with signal peptide), or an amino acid sequence at least 95%, at least 96%, at least 97%, at least 98%, or at least 99% identical thereto. In alternative embodiments, a different signal peptide and/or propeptide can be used in place of the signal peptide and/or propeptide of SEQ ID NO: 6, such as an IL2 signal peptide and/or factor X propeptide.

As discussed in Example 2, the nucleotide sequence encoding An97 fVIII BDD was codon-optimized for expression in human liver. An exemplary liver codon optimized An97 fVIII BDD sequence is provided as SEQ ID NO: 14. In some embodiments, a recombinant nucleic acid molecule is provided comprising the nucleotide sequence set forth as nucleotides 58-4377 of SEQ ID NO: 14. In some embodiments, a recombinant nucleic acid molecule is provided comprising the nucleotide sequence set forth as SEQ ID NO: 14. In some embodiments, CpG motifs within the codon-optimized An97 fVIII BDD sequence can be removed to provide a CpG deleted, liver codon optimized An97 fVIII sequence.

The An84 fVIII BDD, An63 fVIII BDD, An96 fVIII BDD, and An97 fVIII BDD proteins are a B-domain deleted fVIII proteins, where the A2 domain and activation peptide are fused by a linker set forth as SFSQNPPVLKRHQR (residues 761-774 of SEQ ID NO: 3). In some embodiments, an alternative linker sequence may be substituted, as long as the alternative linker sequence include RHQR (residues 770-774 of SEQ ID NO: 3) recognition sequence for PACE/furin processing sequence for the B-domain and does not disrupt the folding and function of the fVIII protein.

In some embodiments, a nucleic acid molecule is provided that encodes a protein with fVII activity comprising an amino acid sequence set forth as residues 21-444 of SEQ ID NO: 7 (An81 fVII without signal peptide), or an amino acid sequence at least 95%, at least 96%, at least 97%, at least 98%, or at least 99% identical thereto. Residues 1-20 of SEQ ID NO: 7 are the fVII signal peptide. In some embodiments, a nucleic acid molecule is provided that encodes a protein with fVII activity comprising an amino acid sequence set forth as SEQ ID NO: 7 (An81 fVII with signal peptide), or an amino acid sequence at least 95%, at least 96%, at least 97%, at least 98%, or at least 99% identical thereto. In alternative embodiments, a different signal peptide can be used in place of the signal peptide of SEQ ID NO: 7, such as an IL2 signal peptide.

As discussed in Example 3, the nucleotide sequence encoding An81 fVII was codon-optimized for expression in human liver. An exemplary liver codon optimized An81 fVII sequence is provided as SEQ ID NO: 15. In some embodiments, a recombinant nucleic acid molecule is provided comprising the nucleotide sequence set forth as nucleotides 61-1335 of SEQ ID NO: 15. In some embodiments, a recombinant nucleic acid molecule is provided comprising the nucleotide sequence set forth as SEQ ID NO: 15. In some embodiments, CpG motifs within the codon-optimized An81 fVII sequence can be removed to provide a CpG deleted, liver codon optimized An81 WIT sequence.

In some embodiments, a nucleic acid molecule is provided that encodes a protein with fVII activity comprising an amino acid sequence set forth as residues 21-444 of SEQ ID NO: 8 (An61 fVII without signal peptide), or an amino acid sequence at least 95%, at least 96%, at least 97%, at least 98%, or at least 99% identical thereto. Residues 1-20 of SEQ ID NO: 8 are the fVII signal peptide. In some embodiments, a nucleic acid molecule is provided that encodes a protein with fVII activity comprising an amino acid sequence set forth as SEQ ID NO: 8 (An61 fVII with signal peptide), or an amino acid sequence at least 95%, at least 96%, at least 97%, at least 98%, or at least 99% identical thereto. In alternative embodiments, a different signal peptide can be used in place of the signal peptide of SEQ ID NO: 8, such as an IL2 signal peptide.

As discussed in Example 3, the nucleotide sequence encoding An61 fVII was codon-optimized for expression in human liver. An exemplary liver codon optimized An61 fVII sequence is provided as SEQ ID NO: 16. In some embodiments, a recombinant nucleic acid molecule is provided comprising the nucleotide sequence set forth as nucleotides 61-1335 of SEQ ID NO: 16. In some embodiments, a recombinant nucleic acid molecule is provided comprising the nucleotide sequence set forth as SEQ ID NO: 16. In some embodiments, CpG motifs within the codon-optimized An61 fVII sequence can be removed to provide a CpG deleted, liver codon optimized An61 WIT sequence.

In further embodiments, an isolated mature fVII, fVIII, or fIX protein is provided that is encoded by any of the fVII, fVIII, or fIX sequences provided herein.

In some embodiments, an isolated protein is provided comprising an amino acid sequence set forth as residues 47-462 of SEQ ID NO: 1 (An96 fIX Padua), or an amino acid sequence at least 95%, at least 96%, at least 97%, at least 98%, or at least 99% identical thereto and having fIX activity. In some embodiments, an isolated protein is provided comprising an amino acid sequence set forth as SEQ ID NO: 1 (An96 fIX Padua), or an amino acid sequence at least 95%, at least 96%, at least 97%, at least 98%, or at least 99% identical thereto and having fIX activity.

In some embodiments, an isolated protein is provided comprising an amino acid sequence set forth as residues 47-461 of SEQ ID NO: 2 (An97 fIX Padua), or an amino acid sequence at least 95%, at least 96%, at least 97%, at least 98%, or at least 99% identical thereto and having fIX activity. In some embodiments, an isolated protein is provided comprising an amino acid sequence set forth as SEQ ID NO: 2 (An97 fIX Padua), or an amino acid sequence at least 95%, at least 96%, at least 97%, at least 98%, or at least 99% identical thereto and having fIX activity.

In some embodiments, an isolated protein is provided comprising an amino acid sequence set forth as residues 20-1458 of SEQ ID NO: 3 (An84 fVIII BDD), or an amino acid sequence at least 98% or at least 99% identical thereto and having fVIII activity. In some embodiments, an isolated protein is provided comprising an amino acid sequence set forth as SEQ ID NO: 3 (An84 fVIII BDD), or an amino acid sequence at least 98% or at least 99% identical thereto and having fVIII activity.

In some embodiments, an isolated protein is provided comprising an amino acid sequence set forth as residues 20-1458 of SEQ ID NO: 4 (An63 fVIII BDD), or an amino acid sequence at least 98% or at least 99% identical thereto and having fVIII activity. In some embodiments, an isolated protein is provided comprising an amino acid sequence set forth as SEQ ID NO: 4 (An63 fVIII BDD), or an amino acid sequence at least 98% or at least 99% identical thereto and having fVIII activity.

In some embodiments, an isolated protein is provided comprising an amino acid sequence set forth as residues 20-1458 of SEQ ID NO: 5 (An96 fVIII BDD), or an amino acid sequence at least 98% or at least 99% identical thereto and having fVIII activity. In some embodiments, an isolated protein is provided comprising an amino acid sequence set forth as SEQ ID NO: 5 (An96 fVIII BDD), or an amino acid sequence at least 98% or at least 99% identical thereto and having fVIII activity.

In some embodiments, an isolated protein is provided comprising an amino acid sequence set forth as residues 20-1458 of SEQ ID NO: 6 (An97 fVIII BDD), or an amino acid sequence at least 98% or at least 99% identical thereto and having fVIII activity. In some embodiments, an isolated protein is provided comprising an amino acid sequence set forth as SEQ ID NO: 6 (An97 fVIII BDD), or an amino acid sequence at least 98% or at least 99% identical thereto and having fVIII activity.

In some embodiments, an isolated protein is provided comprising an amino acid sequence set forth as residues 21-444 of SEQ ID NO: 7 (An81 fVII), or an amino acid sequence at least 98% or at least 99% identical thereto and having fVII activity. In some embodiments, an isolated protein is provided comprising an amino acid sequence set forth as SEQ ID NO: 7 (An81 fVII), or an amino acid sequence at least 98% or at least 99% identical thereto and having fVII activity.

In some embodiments, an isolated protein is provided comprising an amino acid sequence set forth as residues 21-444 of SEQ ID NO: 8 (An61 fVII), or an amino acid sequence at least 98% or at least 99% identical thereto and having fVII activity. In some embodiments, an isolated protein is provided comprising an amino acid sequence set forth as SEQ ID NO: 8 (An61 fVII), or an amino acid sequence at least 98% or at least 99% identical thereto and having fVII activity.

The isolated proteins described above a clotting factor proteins. In several embodiments, the clotting factor protein is a mature clotting factor protein having clotting factor activity.

Thus, nucleic acid molecules (for example, cDNA or RNA molecules) encoding the disclosed novel clotting factors, as well as purified forms of the clotting factors, are provided. Nucleic acids encoding these molecules can readily be produced using the amino acid sequences provided herein and the genetic code. In several embodiments, the nucleic acid molecules can be expressed in a host cell (such as a mammalian cell) to produce a disclosed clotting factor.

The genetic code can be used to construct a variety of functionally equivalent nucleic acid sequences, such as nucleic acids which differ in sequence but which encode the same polypeptide sequence.

Nucleic acid molecules encoding the novel clotting factors disclosed herein can be prepared by any suitable method including, for example, cloning of appropriate sequences or by direct chemical synthesis by standard methods. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques can be found, for example, in Green and Sambrook (*Molecular Cloning: A Laboratory Manual*, 4$^{th}$ ed., New York: Cold Spring Harbor Laboratory Press, 2012) and Ausubel et al. (Eds.) (*Current Protocols in Molecular Biology*, New York: John Wiley and Sons, including supplements, 2017).

Nucleic acids can also be prepared by amplification methods. Amplification methods include the polymerase chain reaction (PCR), the ligase chain reaction (LCR), the transcription-based amplification system (TAS), and the self-sustained sequence replication system (3SR).

The nucleic acid molecules can be expressed in a recombinantly engineered cell such as bacteria, plant, yeast, insect and mammalian cells. DNA sequences encoding the clotting factors can be expressed in vitro by DNA transfer into a suitable host cell. The cell may be prokaryotic or eukaryotic. Numerous expression systems available for expression of proteins including *E. coli*, other bacterial hosts, yeast, and various higher eukaryotic cells such as the COS, CHO, HeLa and myeloma cell lines, can be used to express the disclosed novel clotting factors. Methods of stable transfer, meaning that the foreign DNA is continuously maintained in the host, are known in the art.

The expression of nucleic acids encoding the disclosed novel clotting factors described herein can be achieved by operably linking the DNA or cDNA to a promoter (which is either constitutive or inducible), followed by incorporation into an expression cassette. The promoter can be any promoter of interest, including a liver-specific promoter, such as the HCB promoter. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signals for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, for example, a strong promoter to direct transcription, a ribosome binding site for translational initiation (e.g., internal ribosomal binding sequences), and a transcription/translation terminator. For *E. coli*, this can include a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, GPt, neo, and hyg genes.

Modifications can be made to a nucleic acid encoding a polypeptide described herein without diminishing its biological activity. Some modifications can be made to facilitate the cloning, expression, or incorporation of the targeting molecule into a fusion protein. Such modifications include, for example, termination codons, sequences to create conveniently located restriction sites, and sequences to add a methionine at the amino terminus to provide an initiation site, or additional amino acids (such as poly His) to aid in purification steps.

Once expressed, the disclosed novel clotting factors can be purified according to standard procedures in the art, including ammonium sulfate precipitation, affinity columns, column chromatography, and the like (see, generally, Simpson et al. (Eds.), *Basic methods in Protein Purification and Analysis: A Laboratory Manual*, New York: Cold Spring Harbor Laboratory Press, 2009). The disclosed novel clotting factors need not be 100% pure. Once purified, partially or to homogeneity as desired, if to be used therapeutically, the polypeptides should be substantially free of endotoxin.

III. Recombinant Vectors and Gene Therapy Applications

Any of the above discussed recombinant nucleic acid molecules encoding a fIX protein, a fVIII protein, a fVII protein, or variant thereof, can be included in an vector (such as a AAV vector) for expression in a cell or a subject.

The nucleic acid sequences disclosed herein are useful in production of vectors (such as rAAV vectors), and are also useful in antisense delivery vectors, gene therapy vectors, or vaccine vectors. In certain embodiments, the disclosure provides for gene delivery vectors, and host cells which contain the nucleic acid sequences disclosed herein. In some embodiments, the selected vector may be delivered to a subject by any suitable method, including intravenous injection, ex-vivo transduction, transfection, electroporation, liposome delivery, membrane fusion techniques, high velocity DNA-coated pellets, viral infection, or protoplast fusion, to introduce a transgene into the subject.

In certain embodiments, the disclosure relates to virus particle, e.g., capsids, containing the nucleic acid sequences encoding the fVII, fVIII, or fIX proteins disclosed herein. The virus particles, capsids, and recombinant vectors are useful in delivery of the nucleic acid sequences encoding the fVII, fVIII, or fIX proteins to a target cell. The nucleic acids may be readily utilized in a variety of vector systems, capsids, and host cells. In certain embodiments, the nucleic acids are in vectors contained within a capsid comprising cap proteins, including AAV capsid proteins vp1, vp2, vp3 and hypervariable regions.

In certain embodiments, the nucleic acid sequences encoding the fVII, fVIII, or fIX proteins may be a part of any genetic element (vector) which may be delivered to a host cell, e.g., naked DNA, a plasmid, phage, transposon, cosmid, episome, a protein in a non-viral delivery vehicle (e.g., a lipid-based carrier), virus, etc. which transfer the sequences carried thereon.

In certain embodiments, a vector may be a lentivirus based (containing lentiviral genes or sequences) vector, e.g., having nucleic acid sequences derived from VSVG or GP64 pseudotypes or both. In certain embodiments, the nucleic acid sequences derived from VSVG or GP64 pseudotypes may be at least one or two or more genes or gene fragments of more than 1000, 500, 400, 300, 200, 100, 50, or 25 continuous nucleotides or nucleotides sequences with greater than 50, 60, 70, 80, 90, 95 or 99% identity to the gene or fragment.

In some embodiments, the nucleic acid and promotor sequences disclosed herein are useful in production of AAV vectors. AAV belongs to the family Parvoviridae and the genus *Dependovirus*. AAV is a small, non-enveloped virus that packages a linear, single-stranded DNA genome. Both sense and antisense strands of AAV DNA are packaged into AAV capsids with equal frequency. The AAV genome is characterized by two inverted terminal repeats (ITRs) that flank two open reading frames (ORFs). In the AAV2 genome, for example, the first 125 nucleotides of the ITR are a palindrome, which folds upon itself to maximize base pairing and forms a T-shaped hairpin structure. The other 20 bases of the ITR, called the D sequence, remain unpaired. The ITRs are cis-acting sequences important for AAV DNA replication; the ITR is the origin of replication and serves as a primer for second-strand synthesis by DNA polymerase. The double-stranded DNA formed during this synthesis, which is called replicating-form monomer, is used for a second round of self-priming replication and forms a replicating-form dimer. These double-stranded intermediates are processed via a strand displacement mechanism, resulting in single-stranded DNA used for packaging and double-stranded DNA used for transcription. Located within the ITR are the Rep binding elements and a terminal resolution site (TRS). These features are used by the viral regulatory protein Rep during AAV replication to process the double-stranded intermediates. In addition to their role in AAV replication, the ITR is also essential for AAV genome packaging, transcription, negative regulation under non-permissive conditions, and site-specific integration (Daya and Berns, *Clin Microbial Rev* 21(4):583-593, 2008).

The left ORF of AAV contains the Rep gene, which encodes four proteins—Rep78, Rep 68, Rep52 and Rep40. The right ORF contains the Cap gene, which produces three viral capsid proteins (VP1, VP2 and VP3). The AAV capsid contains 60 viral capsid proteins arranged into an icosahedral symmetry. VP1, VP2 and VP3 are present in a 1:1:10 molar ratio (Daya and Berns, *Clin Microbiol Rev* 21(4):583-593, 2008).

AAV vectors typically contain a transgene expression cassette between the ITRs that replaces the rep and cap genes. Vector particles are produced by the co-transfection of cells with a plasmid containing the vector genome and a packaging/helper construct that expresses the rep and cap proteins in trans. During infection, AAV vector genomes enter the cell nucleus and can persist in multiple molecular states. One common outcome is the conversion of the AAV genome to a double-stranded circular episome by second-strand synthesis or complementary strand pairing.

In the context of AAV vectors, the disclosed vectors typically have a recombinant genome comprising the following structure:

(5'AAV ITR)-(promoter)-(transgene)-(3'AAV ITR)

As discussed above, these recombinant AAV vectors contain a transgene expression cassette between the ITRs that replaces the rep and cap genes. Vector particles are produced, for example, by the co-transfection of cells with a plasmid containing the recombinant vector genome and a packaging/helper construct that expresses the rep and cap proteins in trans.

The transgene can be flanked by regulatory sequences such as a 5' Kozak sequence and/or a 3' polyadenylation signal.

The AAV ITRs, and other selected AAV components described herein, may be readily selected from among any AAV serotype, including, without limitation, AAV1, AAV2, AAV3, AAV4, AAV5, AAV6, AAV7, AAV8, AAV9 and function variants thereof. These ITRs or other AAV components may be readily isolated using techniques available to those of skill in the art from an AAV serotype. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like.

In some embodiments, the recombinant AAV vector genome can have a liver-specific promoter, such as any one of the HCB, HSh-HCB, 5'HSh-HCB, 3'HSh-HCB, ABP-HP1-God-TSS, HSh-SynO-TSS, or sHS-SynO-TSS promoters set forth in WO 2016/168728, which is incorporated by reference herein in its entirety.

AAV is currently one of the most frequently used viruses for gene therapy. Although AAV infects humans and some other primate species, it is not known to cause disease and elicits a very mild immune response. Gene therapy vectors that utilize AAV can infect both dividing and quiescent cells and persist in an extrachromosomal state without integrating into the genome of the host cell. Because of the advantageous features of AAV, the present disclosure contemplates the use of AAV for the recombinant nucleic acid molecules and methods disclosed herein.

AAV possesses several desirable features for a gene therapy vector, including the ability to bind and enter target cells, enter the nucleus, the ability to be expressed in the nucleus for a prolonged period of time, and low toxicity. However, the small size of the AAV genome limits the size of heterologous DNA that can be incorporated. To minimize this problem, AAV vectors have been constructed that do not encode Rep and the integration efficiency element (IEE). The ITRs are retained as they are cis signals required for packaging (Daya and Berns, *Clin Microbiol Rev* 21(4):583-593, 2008).

Methods for producing rAAV suitable for gene therapy are known (see, for example, U.S. Patent Application Nos. 2012/0100606; 2012/0135515; 2011/0229971; and 2013/0072548; and Ghosh et al., *Gene Ther* 13(4):321-329, 2006), and can be utilized with the recombinant nucleic acid molecules and methods disclosed herein.

In some embodiments, the nucleic acids disclosed herein are part of an expression cassette or transgene. See e.g., US Pat. App. Pub. 20150139953. The expression cassette is composed of a transgene and regulatory sequences, e.g., promotor and 5' and 3' AAV inverted terminal repeats (ITRs). In one desirable embodiment, the ITRs of AAV serotype 2 or 8 are used. However, ITRs from other suitable serotypes may be selected. An expression cassette is typically packaged into a capsid protein and delivered to a selected host cell.

In some embodiments, the disclosure provides for a method of generating a recombinant adeno-associated virus (AAV) having an AAV serotype capsid, or a portion thereof. Such a method involves culturing a host cell which contains a nucleic acid sequence encoding an adeno-associated virus (AAV) serotype capsid protein; a functional rep gene; an expression cassette composed of AAV inverted terminal repeats (ITRs) and a transgene; and sufficient helper functions to permit packaging of the expression cassette into the AAV capsid protein. See e.g., US Pat. App. Pub. 20150139953.

The components for culturing in the host cell to package an AAV expression cassette in an AAV capsid may be provided to the host cell in trans. Alternatively, any one or more of the components (e.g., expression cassette, rep sequences, cap sequences, and/or helper functions) may be provided by a stable host cell which has been engineered to contain one or more of the required components using methods known to those of skill in the art. Most suitably, such a stable host cell will contain the component(s) under the control of an inducible promoter. However, the required component(s) may be under the control of a constitutive promoter. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

In some embodiments, the disclosure relates to recombinant vectors comprising a liver specific promotor nucleic acid sequence in operable combination with transgene. The transgene is a nucleic acid sequence, heterologous to the vector sequences flanking the transgene, which encodes a novel fVII, fVIII, or fIX protein as disclosed herein, and optionally one or more additional proteins of interest. The nucleic acid coding sequence is operatively linked to regulatory components in a manner which permits transgene transcription, translation, and/or expression in a host cell.

The expression cassette can be carried on any suitable vector, e.g., a plasmid, which is delivered to a host cell. The plasmids useful in this disclosure may be engineered such that they are suitable for replication and, optionally, integration in prokaryotic cells, mammalian cells, or both. These plasmids (or other vectors carrying the 5' AAV ITR-heterologous molecule-3' ITR) contain sequences permitting replication of the expression cassette in eukaryotes and/or prokaryotes and selection markers for these systems. Preferably, the molecule carrying the expression cassette is transfected into the cell, where it may exist transiently. Alternatively, the expression cassette (carrying the 5' AAV ITR-heterologous molecule-3' ITR) may be stably integrated into the genome of the host cell, either chromosomally or as an episome. In certain embodiments, the expression cassette may be present in multiple copies, optionally in head-to-head, head-to-tail, or tail-to-tail concatamers. Suitable transfection techniques are known and may readily be utilized to deliver the expression cassette to the host cell.

Generally, when delivering the vector comprising the expression cassette by transfection, the vector and the relative amounts of vector DNA to host cells may be adjusted, taking into consideration such factors as the selected vector, the delivery method and the host cells selected. In addition to the expression cassette, the host cell contains the sequences which drive expression of the AAV capsid protein in the host cell and rep sequences of the same serotype as the serotype of the AAV ITRs found in the expression cassette, or a cross-complementing serotype. Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell.

The packaging host cell also typically contains helper functions in order to package the rAAV of the disclosure. Optionally, these functions may be supplied by a herpesvirus. Most desirably, the necessary helper functions are each provided from a human or non-human primate adenovirus source, such as those described above and/or are available from a variety of sources, including the American Type Culture Collection (ATCC), Manassas, Va. (US). The desired helper functions, can be provided using any means that allows their expression in a cell.

Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously added factors, for example.

The AAV techniques can be adapted for use in these and other viral vector systems for in vitro, ex vivo or in vivo gene delivery. The in certain embodiments the disclosure contemplates the use of nucleic acids and vectors disclosed herein in a variety of rAAV and non-rAAV vector systems. Such vectors systems may include, e.g., lentiviruses, retroviruses, poxviruses, vaccinia viruses, and adenoviral systems, among others.

In some embodiments, it is contemplated that viral particles, nucleic acids and vectors disclosed herein are useful for a variety of purposes, including for delivery of therapeutic molecules for gene expression of therapeutic proteins.

Therapeutic proteins encoded by the nucleic acids (e.g., operably in combination with promoters) reported herein include those used for treatment of clotting disorders, including hemophilia B (e.g., using a fIX protein as provided herein), hemophilia A (e.g., using a fVIII protein as provided herein), and congenital proconvertin deficiency (e.g., using a fVII protein as provided herein)

In some embodiments, a method of inducing blood clotting in a subject in need thereof is provided. The method comprises administering to the subject a therapeutically effective amount of a vector (such as an AAV vector, a lentiviral vector, or a retroviral vector) encoding a nucleic acid sequences encoding the fVII, fVIII, or fIX proteins as described herein. In some embodiments, the subject is a subject with a clotting disorder, such as hemophilia A or hemophilia B. In some embodiments, the clotting disorder is hemophilia A and the subject is administered a vector comprising a nucleic acid molecule encoding a protein with fVIII activity. In other embodiments, the clotting disorder is hemophilia B and the subject is administered a vector comprising a nucleic acid molecule encoding a protein with fIX activity. In other embodiments, the clotting disorder is congenital proconvertin deficiency and the subject is administered a vector comprising a nucleic acid molecule encoding a protein with fVII activity.

A treatment option for a patient diagnosed with hemophilia A is the exogenous administration of recombinant fVIII sometimes referred to as fVIII replacement therapy. Similar replacement therapies are used for treatment of hemophilia B (using administration of exogenous fIX) and congenital proconvertin deficiency (using administration of exogenous fVII). In some embodiments, a patient with hemophilia A or be can be treated by administration of a recombinant fVIII or fIX protein as described herein. In some patients, these therapies can lead to the development of antibodies that bind to the administered clotting factor. Subsequently, the clotting factor-antibody bound conjugates, typically referred to as inhibitors, interfere with or retard the ability of the exogenous clotting factor to cause blood clotting. Inhibitory autoantibodies also sometimes occur spontaneously in a subject that is not genetically at risk of having a clotting disorder such as hemophilia, termed acquired hemophilia Inhibitory antibodies assays are typically performed prior to exogenous clotting factor treatment in order to determine whether the anti-coagulant therapy will be effective.

A "Bethesda assay" has historically been used to quantitate the inhibitory strength the concentration of fVIII binding antibodies. In the assay, serial dilutions of plasma from a patient, e.g., prior to having surgery, are prepared and each dilution is mixed with an equal volume of normal plasma as a source of fVIII. After incubating for a couple hours, the activities of fVIII in each of the diluted mixtures are measured. Having antibody inhibitor concentrations that prevent fVIII clotting activity after multiple repeated dilutions indicates a heightened risk of uncontrolled bleeding. Patients with inhibitor titers after about ten dilutions are felt to be unlikely to respond to exogenous fVIII infusions to stop bleeding. A Bethesda titer is defined as the reciprocal of the dilution that results in 50% inhibition of FVIII activity present in normal human plasma. A Bethesda titer greater than 10 is considered the threshold of response to FVIII replacement therapy.

In certain embodiments, the disclosure relates to methods of inducing blood clotting comprising administering an effective amount of a viral particle or capsid comprising a vector comprising a nucleic acid encoding a blood clotting factor as disclosed herein to a subject in need thereof.

In certain embodiments, the subject is diagnosed with hemophilia A or B or acquired hemophilia or unlikely to respond to exogenous clotting factor infusions (e.g., based on a Bethesda assay result).

In some embodiments, this disclosure relates to methods of gene transfer for the treatment of hemophilia B using an adeno-associated viral (AAV) vector encoding human fIX as the gene delivery vehicle. While several such AAV-based gene therapies for hemophilia B have entered into human clinical trials, they have been hampered by low expression of the therapeutic protein, clotting fix, after administration of the virus resulting on only partial correction of the disease. AAV vector toxicity limits the dose of the virus that may be safely administered. Typically, the vector provides efficacious expression of fIX at viral doses below the threshold of toxicity.

In some embodiments, this disclosure relates to methods of gene transfer for the treatment of hemophilia A using an adeno-associated viral (AAV) vector encoding human fVIII as the gene delivery vehicle. While several such AAV-based gene therapies for hemophilia A have entered into human clinical trials, they have been hampered by low expression of the therapeutic protein, clotting fVIII, after administration of the virus resulting on only partial correction of the disease. AAV vector toxicity limits the dose of the virus that may be safely administered. Typically, the vector provides efficacious expression of fVIII at viral doses below the threshold of toxicity.

In some embodiments, this disclosure relates to methods of gene transfer for the treatment of congenital proconvertin deficiency using an adeno-associated viral (AAV) vector encoding human fVII as the gene delivery vehicle. While AAV-based gene therapies for hemophilia A have entered into human clinical trials, they have been hampered by low expression of the therapeutic protein, clotting fVII, after administration of the virus resulting on only partial correction of the disease. AAV vector toxicity limits the dose of the virus that may be safely administered. Typically, the vector provides efficacious expression of fVII at viral doses below the threshold of toxicity.

In some embodiments, this disclosure relates to methods of gene transfer for the treatment of hemophilia B using a lentiviral vector encoding human fIX as the gene delivery vehicle. Delivery of the lentiviral vector encoding the transgene can be, for example, by direct administration to the subject, or by ex vivo transduction and transplantation of hematopoietic stem and progenitor cells with the vector. Typically, the vector provides efficacious expression of fVII at viral doses below the threshold of toxicity.

In some embodiments, this disclosure relates to methods of gene transfer for the treatment of hemophilia A using a lentiviral vector encoding human fVIII as the gene delivery vehicle. Delivery of the lentiviral vector encoding the transgene can be, for example, by direct administration to the subject, or by ex vivo transduction and transplantation of hematopoietic stem and progenitor cells with the vector. Typically, the vector provides efficacious expression of fVII at viral doses below the threshold of toxicity.

In some embodiments, this disclosure relates to methods of gene transfer for the treatment of congenital proconvertin deficiency using a lentiviral vector encoding human fVII as the gene delivery vehicle. Delivery of the lentiviral vector encoding the transgene can be, for example, by direct administration to the subject, or by ex vivo transduction and transplantation of hematopoietic stem and progenitor cells with the vector. Typically, the vector provides efficacious expression of fVII at viral doses below the threshold of toxicity.

In some embodiments, recombinant virus particles, capsids, or vectors comprising nucleic acids disclosed herein can be delivered to liver via the hepatic artery, the portal vein, or intravenously to yield therapeutic levels of therapeutic proteins or clotting factors in the blood. The capsid or vector is preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, sesame oil, and water.

Optionally, the compositions of the disclosure may contain other pharmaceutically acceptable excipients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The recombinant virus particles, capsids, or vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the liver (optionally via the hepatic artery) or lung), oral, inhalation, intranasal, intratracheal, intraarterial, intraocular, intravenous, intramuscular, subcutaneous, intradermal, and other parental routes of administration. Routes of administration may be combined, if desired.

Dosages of the recombinant virus particles, capsids, or vectors will depend primarily on factors such as the condition being treated, the age, weight and health of the patient, and may thus vary among patients. For example, a therapeutically effective human dosage of the viral vector is generally in the range of from about 0.1 ml to about 100 ml of solution containing concentrations of from about 1×10⁹ to 1×10¹⁶ genomes virus vector.

Recombinant viral vectors of the disclosure provide an efficient gene transfer vehicle which can deliver a selected protein to a selected host cell in vivo or ex vivo even where the organism has neutralizing antibodies to the protein. In one embodiment, the vectors disclosed herein and the cells are mixed ex vivo; the infected cells are cultured using conventional methodologies; and the transduced cells are re-infused into the patient.

EXAMPLES

The following examples are provided to illustrate certain particular features and/or embodiments. These examples should not be construed to limit the disclosure to the particular features or embodiments described.

Example 1

Bioengineering Coagulation Factor IX Through Ancestral Protein Reconstruction

This example illustrates the optimization of fIX sequences to improve clotting factor activity, utility for protein expression and therapeutic applications such as gene therapy.

The development of transformative hemophilia therapeutics has been hindered by the size, instability, immunogenicity and biosynthetic inefficiency of coagulation factors such as fIX for treatment of hemophilia B. Accordingly, it is desirable to find additional fIX sequences that have increased activity (for example, due to increased serum half-life or increased enzymatic activity) because it is possible that the frequency of infusion may be lessened while still achieving full prophylaxis.

To search for additional fIX sequences that may facilitate improved clotting factor replacement therapy for hemophilia B, a mammalian fIX phylogenetic tree with corresponding ancestral node (An) sequences was constructed through Bayesian inference using both DNA and amino acid-based models in PAML Version 4.1. Initially, nine An-fIX sequences were selected for reconstruction, as follows:

An63 fIX (SEQ ID NO: 17)

**MQCLNMIMAESPGLITICLLGYLLSAEC*TVFLDHENATKILNRPKR***YNS

GKLEEFVQGNLERECIEEKCSFEEAREVFENTEKTTEFWKQYVDGDQCE

SNPCLNGGMCKDDINSYECWCQVGFEGKNCELDATCSIKNGRCKQFCKK

GADNKVVCSCTTGYRLAEDQKSCEPAVPFPCGRVSVSHTSKKLTRAETI

FSNMDYENSTEAETILDNVTQSTQSFNDFTRVVGGENAKPGQFPWQVLL

NGKIDAFCGGSIINEKWVVTAAHCIEPGVKITVVAGEHNTEETEHTEQK

RNVIRVIPHHSYNATINKYSHDIALLELDKPLTLNSYVTPICIANREYT

NIFLKFGSGYVSGWGKVFNRGRSASILQYLKVPLVDRATCLRSTKFTIY

NNMFCAGYHEGGKDSCQGDSGGPHVTEVEGTSFLTGIISWGEECAMKGK

YGIYTKVSRYVNWIKEKTKLT

-continued

An65 fIX (SEQ ID NO: 18)

**MQCLNMIMAESPGLITICLLGYLLSAEC*TVFLDHENATKILNRPKR***YNS

GKLEEFVQGNLERECIEEKCSFEEAREVFENTEKTTEFWKQYVDGDQCE

SNPCLNGGLCKDDINSYECWCQVGFEGKNCELDATCSIKNGRCKQFCKK

GADNKVVCSCTTGYRLAEDQKSCEPAVPFPCGRVSVSHTSTKLTRAETI

FSNMDYENSTEAETILDNVTQSTQSFNDFTRVVGGENAKPGQFPWQVLL

NGKIDAFCGGSIINEKWVVTAAHCIEPGVKITVVAGEHNTEETEHTEQK

RNVIRVIPHHSYNATINKYSHDIALLELDKPLTLNSYVTPICIADREYT

NIFLKFGSGYVSGWGKVFNRGRSASILQYLKVPLVDRATCLRSTKFTIY

NNMFCAGFHEGGKDSCQGDSGGPHVTEVEGTSFLTGIISWGEECAMKGK

YGIYTKVSRYVNWIKEKTKLT

An70 fIX (SEQ ID NO: 19)

**MQCLNMIMAESPGLVTICLLGYLLSAEC*TVFLDRENATKILNRPKR***YNS

GKLEEFVRGNLERECIEEKCSFEEAREVFENTEKTTEFWKQYVDGDQCE

SNPCLNGGLCKDDINSYECWCQVGFEGKNCELDATCSIKNGRCKQFCKK

GADNKVVCSCTTGYRLAEDQKSCEPAVPFPCGRVSVSHTSTKLTRAETI

FSNMDYENSTEAEIILDNVTQSNQSFNDFTRIVGGENAKPGQFPWQVLL

NGKIDAFCGGSIINEKWVVTAAHCIEPGVKITVVAGEHNTEETEPTEQK

RNVIRAIPHHSYNATVNKYSHDIALLELDEPLTLNSYVTPICIADREYT

NIFLKFGSGYVSGWGKVFNRGRSASILQYLKVPLVDRATCLRSTKFTIY

NNMFCAGFHEGGKDSCQGDSGGPHVTEVEGTSFLTGIISWGEECAVKGK

YGIYTKVSRYVNWIKEKTKLT

An84 fIX (SEQ ID NO: 20)

**MQCLNMIMAESPGLITICLLGYLLSAEC*TVFLDHENATKILNRPKR***YNS

GKLEEFVQGNLERECIEEKCSFEEAREVFENTEKTTEFWKQYVDGDQCE

SNPCLNGGSCKDDINSYECWCQVGFEGKNCELDATCSIKNGRCKQFCKK

GADNKVVCSCTEGYRLAEDQKSCEPAVPFPCGRVSVSHTSKKLTRAETI

FSNMDYENSTEAETILDNVTQSTQSFNDFTRVVGGENAKPGQFPWQVLL

NGKIDAFCGGSIINEKWVVTAAHCIEPGVKITVVAGEHNIEETEHTEQK

RNVIRVIPHHNYNATINKYSHDIALLELDKPLTLNSYVTPICIANREYT

NIFLKFGSGYVSGWGRVFNRGRSASILQYLRVPLVDRATCLRSTKFTIY

NNMFCAGYHEGGKDSCQGDSGGPHVTEVEGTSFLTGIISWGEECAMKGK

YGIYTKVSRYVNWIKEKTKLT

An88 fIX (SEQ ID NO: 21)

**MQHLNTIMAESPGLITIFLLGYLLSAEC*AVFLDRENATKILTRPKR***YNS

GKLEEFVQGNLERECIEERCSFEEAREVFENTEKTTEFWKQYVDGDQCE

SNPCLNGGKCKDDINSYECWCQVGFEGRNCELDATCNIKNGRCKQFCKN

GADNKVICSCTEGYQLAEDQKSCEPAVPFPCGRVSVSYSSKKLTRAETI

FSNMDYENSTEAETILDNVTENSESLNDFTRVVGGENAKPGQIPWQVIL

NGEIEAFCGGAIINEKWVVTAAHCLKPGDKIEVVAGEYNIDEKEDTEQR

RNVIRTIPHHHYNATINKYSHDIALLELDKPLILNSYVTPICVANREYT

NIFLKFGSGYVSGWGKVFNKGRQASILQYLRVPLVDRATCLRSTTFTIY

NNMFCAGYREGGKDSCEGDSGGPHVTEVEGTSFLTGIISWGEECAMKGK

YGIYTKVSRYVNWIKEKTKLT

An95 fIX
(SEQ ID NO: 22)
MQCLNMIMAESPGLITICLLGYLLSAEC*TVFLDHENATKILNRPKR*YNS

GKLEEFVQGNLERECIEEKCSFEEAREVFENTEKTTEFWKQYVDGDQCE

SNPCLNGGSCKDDINSYECWCQVGFEGKNCELDATCSIKNGRCKQFCKK

GADNKVVCSCTEGYRLAEDQKSCEPAVPFPCGRVSVSHTSKKLTRAETI

FSNMDYENSTEAETILDNVTQSTQSFNDFTRVVGGENAKPGQFPWQVLL

NGKIDAFCGGSIINEKWVVTAAHCIEPGVKITVVAGEHNIEETEHTEQK

RNVIRVIPHHNYNATINKYSHDIALLELDKPLTLNSYVTPICIANREYT

NIFLKFGSGYVSGWGRVFNRGRSASILQYLRVPLVDRATCLRSTKFTIY

NNMFCAGYHEGGKDSCQGDSGGPHVTEVEGTSFLTGIISWGEECAMKGK

YGIYTKVSRYVNWIKEKTKLT

An96 fIX
(SEQ ID NO: 23)
MQCLNMIMAESPGLITICLLGYLLSAEC*TVFLDHENATKILNRPKR*YNS

GKLEEFVRGNLERECIEEKCSFEEAREVFENTEKTTEFWKQYVDGDQCE

SNPCLNGGSCKDDINSYECWCRFGFEGKNCELDATCSIKNGRCKQFCKK

SADNKVVCSCTEGYRLAEDQKSCEPAVPFPCGRVSVSHTSKKLTRAETI

FSNMDYENSTEAETILDNVTQSTQSFNDFTRVVGGENAKPGQFPWQVLL

NGKIDAFCGGSIINEKWVVTAAHCIEPGVKITVVAGEHNIEKTEPTEQK

RNVIRVIPHHNYNATINKYSHDIALLELDKPLTLNSYVTPICIANREYT

NIFLKFGSGYVSGWGRVFNRGRSASILQYLRVPLVDRATCLRSTKFTIY

NNMFCAGYHEGGKDSCQGDSGGPHVTEVEGTSFLTGIISWGEECAMKGK

YGIYTKVSRYVNWIKEKTKLT

An97 fIX
(SEQ ID NO: 24)
MQCLNMIMAESPGLITICLLGYLLSAEC*TVFLDHENANKILNRPKR*YNS

GKLEEFVRGNLERECIEEKCSFEEAREVFENTEKTTEFWKQYVDGDQCE

SNPCLNGGSCKDDINSYECWCRFGFEGKNCELDATCSIKNGRCKQFCKK

SADNKVVCSCTEGYRLAEDQKSCEPAVPFPCGRVSVSHTSKLTRAETIF

SNMDYENSTEAETILDNVTQSTQSFNDFTRVVGGENAKPGQFPWQVLLN

GKIDAFCGGSIINEKWVVTAAHCIEPGVKITVVAGEHNIEKTEPTEQKR

NVIRVIPHHNYNATINKYSHDIALLELDKPLTLNSYVTPICIADREYTN

IFLKFGSGYVSGWGRVFNRGRSASILQYLRVPLVDRATCLRSTKFTIYN

NMFCAGYHEGGKDSCQGDSGGPHVTEVEGTSFLTGIISWGEECAMKGKY

GIYTKVSRYVNWIKEKTKLT

An102 fIX
(SEQ ID NO: 25)
MQRVNMIMAESPGLITICLLGYLLSAEC*TVFLDHENANKILNRPKR*YNS

GKLEEFVQGNLERECMEEKCSFEEAREVFENTEKTTEFWKQYVDGDQCE

SNPCLNGGSCKDDINSYECWCPFGFEGKNCELDVTCNIKNGRCKQFCKN

SADNKVVCSCTEGYRLAENQKSCEPAVPFPCGRVSVSQTSKLTRAETVF

PDVDYVNSTEAETILDNITQSTQSFNDFTRVVGGEDAKPGQFPWQVVLN

GKVDAFCGGSIVNEKWVVTAAHCIETGVKITVVAGEHNIEETEHTEQKR

NVIRIIPHHNYNATINKYNHDIALLELDEPLVLNSYVTPICIADKEYTN

IFLKFGSGYVSGWGRVFNKGRSASVLQYLRVPLVDRATCLRSTKFTIYN

NMFCAGFHEGGRDSCQGDSGGPHVTEVEGTSFLTGIISWGEECAMKGKY

GIYTKVSRYVNWIKEKTKLT

Figure 1A:
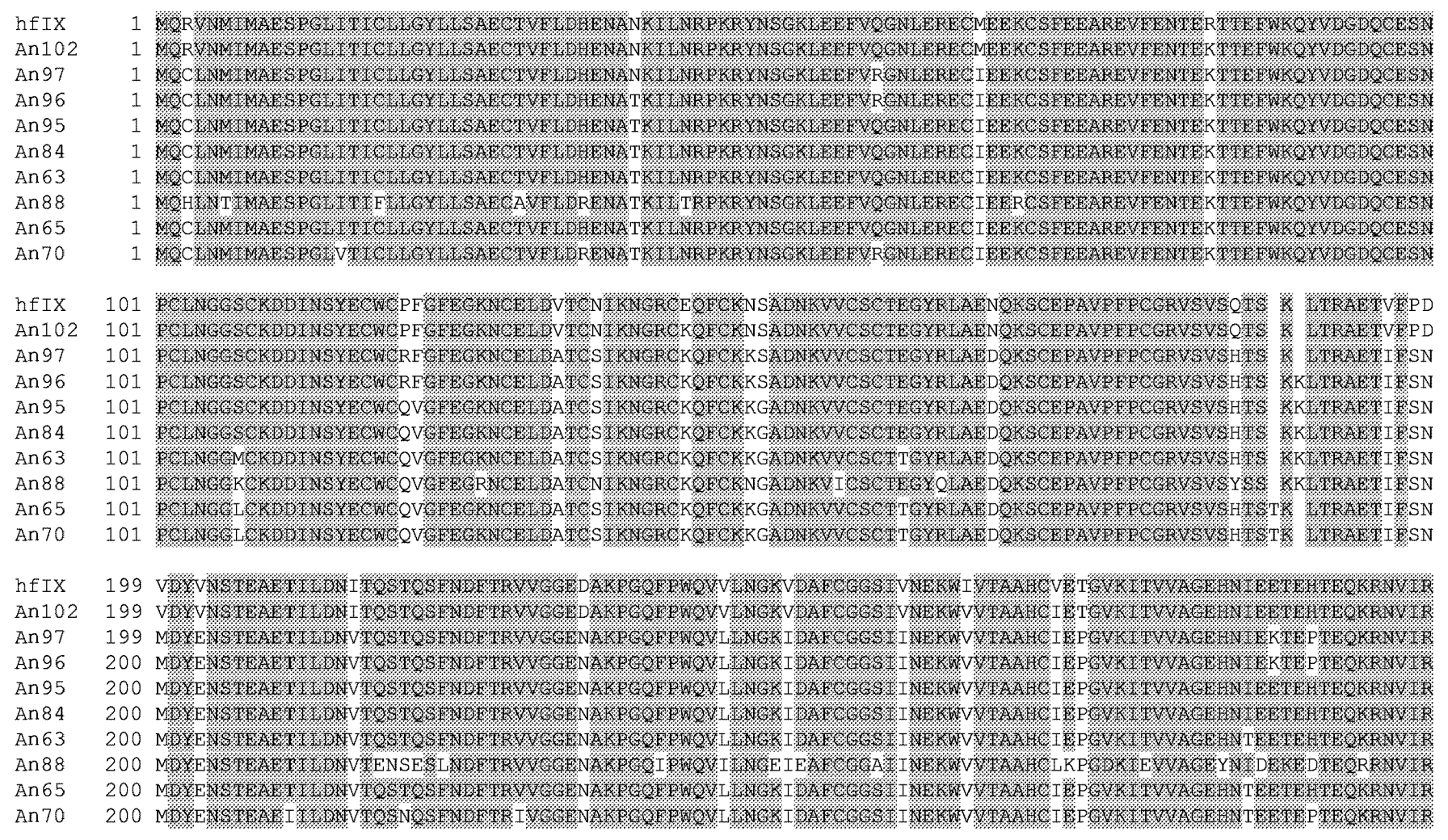
Figure 1B:
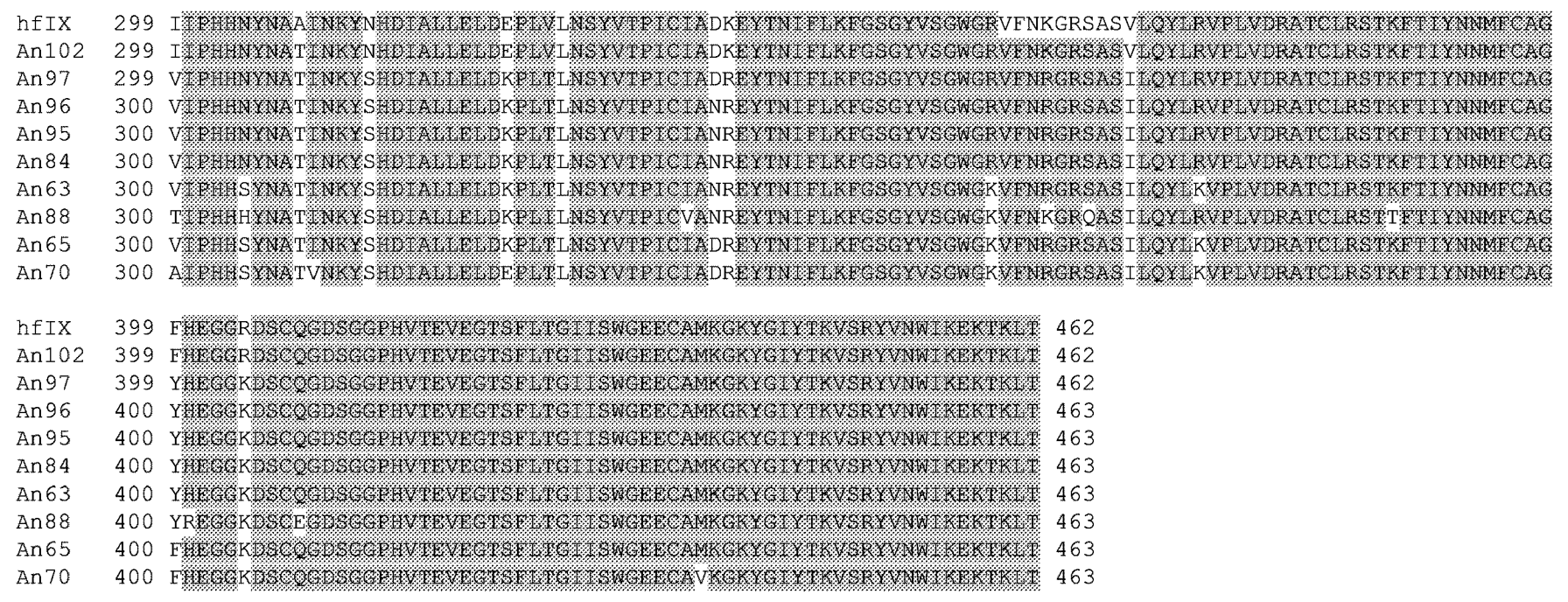

FIG. 1 shows a sequence alignment of the above fIX proteins with hfIX sequence, which is provided as SEQ ID NO: 42:

MQRVNMIMAESPGLITICLLGYLLSAECTVFLDHENANKILNRPKRYNS

GKLEEFVQGNLERECMEEKCSFEEAREVFENTERTTEFWKQYVDGDQCE

SNPCLNGGSCKDDINSYECWCPFGFEGKNCELDVTCNIKNGRCEQFCKN

SADNKVVCSCTEGYRLAENQKSCEPAVPFPCGRVSVSQTSKLTRAETVF

PDVDYVNSTEAETILDNITQSTQSFNDFTRVVGGEDAKPGQFPWQVVLN

GKVDAFCGGSIVNEKWIVTAAHCVETGVKITVVAGEHNIEETEHTEQKR

NVIRIIPHHNYNAAINKYNHDIALLELDEPLVLNSYVTPICIADKEYTN

IFLKFGSGYVSGWGRVFNKGRSASVLQYLRVPLVDRATCLRSTKFTIYN

MFCAGFHEGGRDSCQGDSGGPHVTEVEGTSFLTGIISWGEECAMKGKY

GIYTKVSRYVNWIKEKTKLT

Additionally, the "Padua" mutation was introduced into the An96 and An97 fIX proteins to determine if addition of this mutation might increase the factor IX activity. The Padua mutation is a R338L substitution in the mature fIX amino sequence that increases fIX activity ("fIX Padua," see Paolo et al, "X-Linked Thrombophilia with a Mutant Factor IX" N Engl J Med; 361:1671-1675, 2009). The sequences of the An96 and An97 fIX proteins with the Padua mutation (shown in bold underline) are as follows:

An96 fIX Padua
(SEQ ID NO: 1)
MQCLNMIMAESPGLITICLLGYLLSAEC*TVFLDHENATKILNRPKR*YNS

GKLEEFVRGNLERECIEEKCSFEEAREVFENTEKTTEFWKQYVDGDQCE

SNPCLNGGSCKDDINSYECWCRFGFEGKNCELDATCSIKNGRCKQFCKK

SADNKVVCSCTEGYRLAEDQKSCEPAVPFPCGRVSVSHTSKKLTRAETI

FSNMDYENSTEAETILDNVTQSTQSFNDFTRVVGGENAKPGQFPWQVLL

NGKIDAFCGGSIINEKWVVTAAHCIEPGVKITVVAGEHNIEKTEPTEQK

RNVIRVIPHHNYNATINKYSHDIALLELDKPLTLNSYVTPICIANREYT

NIFLKFGSGYVSGWGRVFNRGRSASILQYLRVPLVDRATCLLSTKFTIY

NNMFCAGYHEGGKDSCQGDSGGPHVTEVEGTSFLTGIISWGEECAMKGK

YGIYTKVSRYVNWIKEKTKLT

An97 fIX Padua
(SEQ ID NO: 2)
MQCLNMIMAESPGLITICLLGYLLSAEC*TVFLDHENANKILNRPKR*RYN

SGKLEEFVRGNLERECIEEKCSFEEAREVFENTEKTTEFWKQYVDGDQC

ESNPCLNGGSCKDDINSYECWCRFGFEGKNCELDATCSIKNGRCKQFCK

KSADNKVVCSCTEGYRLAEDQKSCEPAVPFPCGRVSVSHTSKLTRAETI

FSNMDYENSTEAETILDNVTQSTQSFNDFTRVVGGENAKPGQFPWQVLL

NGKIDAFCGGSIINEKWVVTAAHCIEPGVKITVVAGEHNIEKTEPTEQK

RNVIRVIPHHNYNATINKYSHDIALLELDKPLTLNSYVTPICIADREYT

NIFLKFGSGYVSGWGRVFNRGRSASILQYLRVPLVDRATCLLSTKFTIY

NNMFCAGYHEGGKDSCQGDSGGPHVTEVEGTSFLTGIISWGEECAMKGK

YGIYTKVSRYVNWIKEKTKLT

In SEQ ID NO: 1, residues 1-28 are the signal peptide (bold, referred to as fIX residues −46 to −18), residues 29-46 are the propeptide (italics, referred to as fIX residues −18 to −1), and residues 47-462 are the mature fIX sequence (referred to as mature fIX residues +1 to 415). In SEQ ID NO: 2, residues 1-28 are the signal peptide (bold ital., referred to as mature fIX residues −46 to −18), residues 29-46 are the propeptide (ital, referred to as fIX residues −18 to −1), and residues 47-461 are the mature fIX sequence (referred to as mature fIX residues +1 to 415). With reference to SEQ ID NO: 1, residues 47-92 are the GLA domain, residues 93-129 are the first EGF-like domain, residues 130-192 are the second EGF-like domain, residues 193-227 are the activation peptide, and residues 228-462 are the catalytic domain. Corresponding domains are also present in SEQ ID NO: 2.

The cDNA nucleotide sequence coding for these fIX proteins was optimized by implementing a codon usage bias specific for the human liver cell as compared to naturally occurring nucleotide sequence coding for the corresponding non-codon optimized sequence for a human, for example, using the liver-codon-optimization protocol described in WO 2016/168728. Nucleic acid sequences encoding SEQ ID NO: 1 and SEQ ID NO: 2 that are codon-optimized for expression in liver tissue were generated, and are provided as follows:

An96 fIX Padua (SEQ ID NO: 9)
ATGCAGTGCCTGAACATGATCATGGCCGAGTCCCCCGGCCTGATCACCA

TCTGCCTGCTGGGGTACCTGCTGAGCGCCGAGTGC*ACCGTGTTCCT*

*GGACCACGAGAACGCCACCAAGATCCTGAACAGGCCCAAGAGA*

TACAACTCCGGCAAGCTGGAGGAGTTCGTGAGGGGGAACCTGGAGAGAG

AGTGCATCGAGGAGAAGTGCAGCTTCGAGGAGGCCAGGGAGGTGTTCGA

GAACACCGAGAAGACCACCGAGTTCTGGAAGCAGTACGTGGACGGCGAC

CAGTGCGAGTCCAACCCCTGCCTGAACGGCGGGTCCTGCAAGGACGACA

TCAACAGCTACGAGTGCTGGTGCAGGTTCGGCTTCGAGGGGAAGAACTG

CGAGCTGGACGCCACCTGCAGCATCAAGAACGGCAGATGCAAGCAGTTC

TGCAAGAAGTCCGCCGACAACAAGGTGGTGTGCAGCTGCACCGAGGGAT

ACAGACTGGCTGAGGACCAGAAGTCCTGCGAGCCAGCTGTGCCATTCCC

ATGCGGGAGGGTGTCCGTGAGCCACACCAGCAAGAAGCTGACCAGAGCC

GAAACCATCTTCTCCAACATGGACTACGAGAACAGCACCGAGGCCGAAA

CCATCCTGGACAACGTGACCCAGTCCACCCAGAGCTTCAACGACTTCAC

CCGGGTGGTGGGAGGAGAGAACGCTAAGCCAGGACAGTTCCCATGGCAG

GTGCTGCTGAACGGGAAGATCGACGCCTTCTGCGGCGGGTCCATCATCA

ACGAGAAGTGGGTGGTGACCGCTGCTCACTGCATCGAGCCAGGAGTGAA

GATCACCGTGGTGGCTGGGGAGCACAACATCGAGAAGACCGAGCCCACC

GAGCAGAAGCGCAACGTGATCCGCGTGATCCCCCACCACAACTACAACG

CCACCATCAACAAGTACTCCCACGACATCGCCCTGCTGGAGCTGGACAA

GCCCCTGACCCTGAACAGCTACGTGACCCCCATCTGCATCGCCAACAGG

GAGTACACCAACATCTTCCTGAAGTTCGGATCCGGATACGTGAGCGGAT

GGGGACGCGTGTTCAACCGCGGCCGGTCCGCCAGCATCCTGCAGTACCT

GAGAGTGCCACTGGTGGACAGAGCTACCTGCCTGCTGTCCACCAAGTTC

ACCATCTACAACAACATGTTCTGCGCTGGATACCACGAGGGAGGGAAGG

ACTCCTGCCAGGGGGACAGCGGAGGACCACACGTGACCGAGGTGGAGGG

CACCTCCTTCCTGACCGGCATCATCAGCTGGGGGGAGGAGTGCGCCATG

AAGGGCAAGTACGGGATCTACACCAAGGTGAGCAGATACGTGAACTGGA

TCAAGGAGAAGACCAAGCTGACCTGA

An97 fIX Padua (SEQ ID NO: 10)
ATGCAGTGCCTGAACATGATCATGGCCGAGTCCCCCGGCCTGATCACCA

TCTGCCTGCTGGGGTACCTGCTGAGCGCCGAGTGC*ACCGTGTTCCT*

*GGACCACGAGAACGCCAACAAGATCCTGAACAGGCCCAAGAGA*

TACAACTCCGGCAAGCTGGAGGAGTTCGTGAGGGGGAACCTGGAGAGAG

AGTGCATCGAGGAGAAGTGCAGCTTCGAGGAGGCCAGGGAGGTGTTCGA

GAACACCGAGAAGACCACCGAGTTCTGGAAGCAGTACGTGGACGGCGAC

CAGTGCGAGTCCAACCCCTGCCTGAACGGCGGGTCCTGCAAGGACGACA

TCAACAGCTACGAGTGCTGGTGCAGGTTCGGCTTCGAGGGGAAGAACTG

CGAGCTGGACGCCACCTGCAGCATCAAGAACGGCAGATGCAAGCAGTTC

TGCAAGAAGTCCGCCGACAACAAGGTGGTGTGCAGCTGCACCGAGGGAT

ACAGACTGGCTGAGGACCAGAAGTCCTGCGAGCCAGCTGTGCCATTCCC

ATGCGGGAGGGTGTCCGTGAGCCACACCAGCAAGCTGACCAGAGCCGAA

ACCATCTTCTCCAACATGGACTACGAGAACAGCACCGAGGCCGAAACCA

TCCTGGACAACGTGACCCAGTCCACCCAGAGCTTCAACGACTTCACCCG

GGTGGTGGGAGGAGAGAACGCTAAGCCAGGACAGTTCCCATGGCAGGTG

CTGCTGAACGGGAAGATCGACGCCTTCTGCGGCGGGTCCATCATCAACG

AGAAGTGGGTGGTGACCGCTGCTCACTGCATCGAGCCAGGAGTGAAGAT

CACCGTGGTGGCTGGGGAGCACAACATCGAGAAGACCGAGCCCACCGAG

CAGAAGCGCAACGTGATCCGCGTGATCCCCCACCACAACTACAACGCCA

CCATCAACAAGTACTCCCACGACATCGCCCTGCTGGAGCTGGACAAGCC

CCTGACCCTGAACAGCTACGTGACCCCCATCTGCATCGCCGACAGGGAG

TACACCAACATCTTCCTGAAGTTCGGATCCGGATACGTGAGCGGATGGG

GACGCGTGTTCAACCGCGGCCGGTCCGCCAGCATCCTGCAGTACCTGAG

AGTGCCACTGGTGGACAGAGCTACCTGCCTGCTGTCCACCAAGTTCACC

ATCTACAACAACATGTTCTGCGCTGGATACCACGAGGGAGGGAAGGACT

CCTGCCAGGGGGACAGCGGAGGACCACACGTGACCGAGGTGGAGGGCAC

CTCCTTCCTGACCGGCATCATCAGCTGGGGGGAGGAGTGCGCCATGAAG

-continued

GGCAAGTACGGGATCTACACCAAGGTGAGCAGATACGTGAACTGGATCA

AGGAGAAGACCAAGCTGACCTGA

In SEQ ID NOs: 9 and 10, the signal peptide is shown in bold, the propeptide is shown in bold italics, and the mutated nucleotide of the Padua mutation is shown in bold underline. The liver codon-optimized fIX Padua sequences can be included in a vector (such as an AAV vector) and operably linked to a promoter (such as a liver specific promoter, for example, the HCB promoter) for administration to a subject, for example, to treat hemophilia B in the subject.

In vitro expression of the optimized fIX sequences was assessed in HepG2 cells transiently transfected with corresponding fIX expression vectors (see FIG. 2). HepG2 cells were seeded at 300,000 cells per well in a 24-well plate containing DMEM supplemented with 10% FBS and 1% Pen/Strep. The cells were approximately 70-80% confluent on the day of transfection. Transfection complex mixtures were prepared at a final concentration of: 0.5 µg plasmid DNA, 1.5 µl TransIT-X2 transfection reagent and OptiMEM supplemented up to a final volume of 50 µL. All of the An-fIX transgenes were cloned into a self-inactivating lentiviral vector expression cassette containing an internal EF1α promoter driving An-fIX expression. The human fIX-Padua (R338L) construct was expressed from a scAAV3 ITR cassette containing the HHS4 enhancer-transthyretin promoter and minute virus of mice intron prior to the human fIX transgene. Transfection complexes were pipetted up and down to mix and allowed to incubate for 15-30 min at room temperature prior to addition dropwise onto the plated cells and gently rocking for even distribution. Media change to DMEM supplemented with 10% FBS and 1% Pen/Strep was performed 24 hr later and the conditioned media was assayed for fX activity using a one-stage coagulation assay. Each An-fIX protein displayed activity in coagulation assays utilizing human hemophilia B plasma as a substrate thus demonstrating evolutionary mammalian compatibility. As shown in FIG. 2, incorporating the Padua mutation into the An96 and An97 sequences substantially increased the fIX activity relative to corresponding unmodified An96 and An97 proteins. Additionally, the An96 Padua and An97 Padua proteins provided substantially more fIX activity than the human fIX protein (hfIX), which was also encoded by a liver-codon-optimized sequence (~3.7 fold increase).

Figure 3:
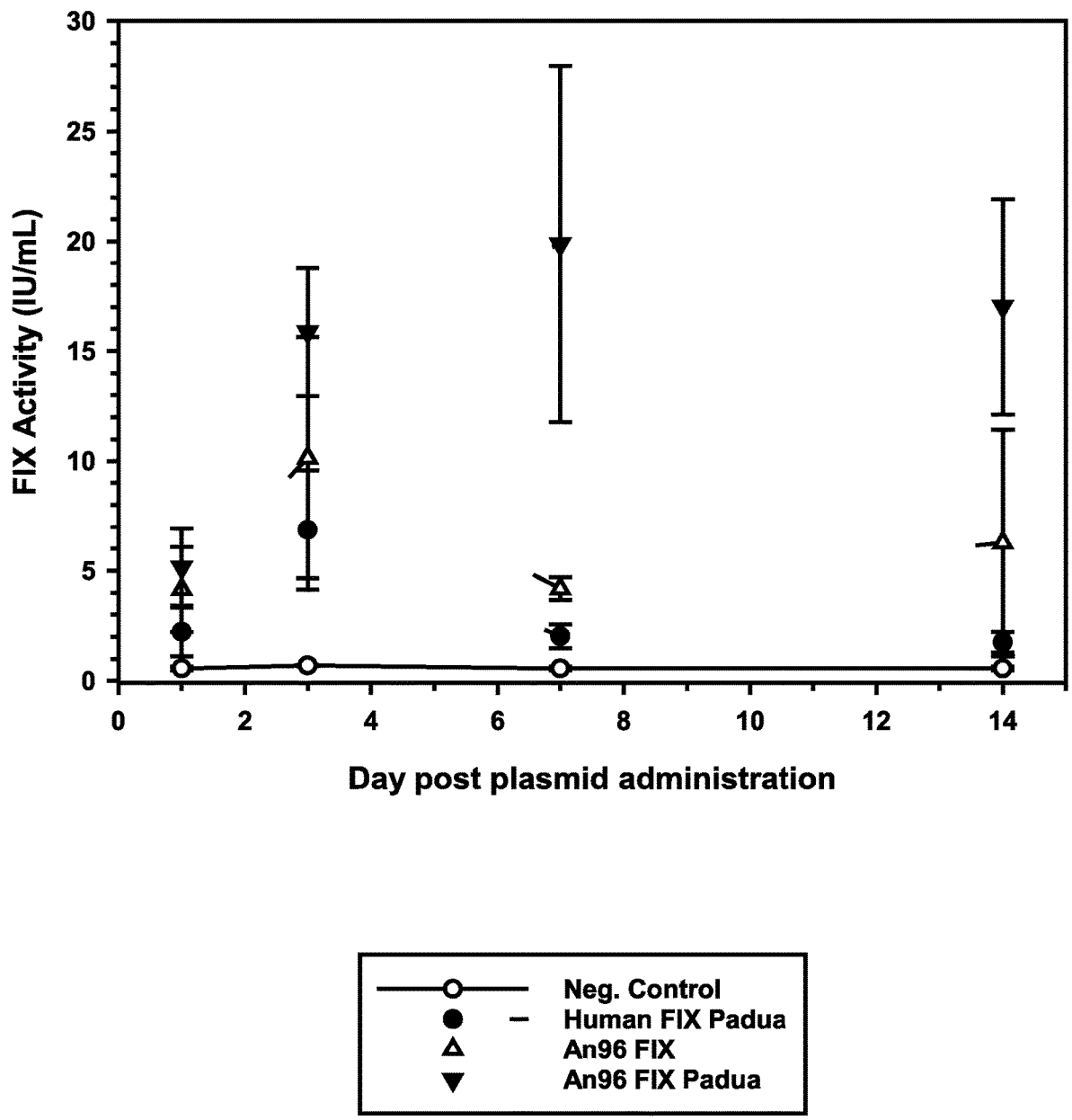
FIG. 3 shows in vivo data for fIX activity levels in serum of fIX deficient mice treated with AAV vectors encoding the indicated fIX variants.

Additionally, in vivo expression of the optimized fIX sequences was assessed in hemophilia B mice (FIG. 3). Liver codon optimized human fIX Padua (R338L), An96 fIX, and An96 fIX Padua (R338L, SEQ ID NO: 9) transgenes were cloned into a scAAV3-ITR-HHS4-TTR-MVM-FIX-sPa recombinant AAV expression cassette containing plasmid. The plasmids were linearized with enzymes that preserved ITRS flanking transgene and heat inactivated at 65° C. for 20 minutes. Each digest was screened for DNA quality comparison and shown to be acceptable prior to injection. Mice randomized and plasmid DNA dilutions were made at 5 µg/mL, using TransIT®-EE Delivery Solution warmed to 37° C. Each experimental animal received 0.5 µg/g linearized plasmid DNA delivered in hydrodynamic fashion in ≤8 s. The injections were performed in a blinded fashion for the 3 treatment groups: 1) scAAV3-HHS4-TTR-MVM-fIX_An96-LCO-sPa, 2) scAAV3-HHS4-TTR-MVM-fIX_An96-Padua-LCO-sPa, 3) scAAV3-HHS4-TTR-MVM-fIX-148T-Padua-LCO-NCO-sPA, as well as a forth control saline-only injection group. A total of 15 experimental mice was used ranging from 9-11 weeks old. Each treatment group received 5 mice. Three 12 week old hemophilia A E16 mice were selected as controls. Mice were ear punched and weighed the day before. Mice were bled 1, 3, 7, and 14 days post plasmid administration. Plasma processed and analyzed for fIX activity using a one-stage coagulation assay. Animals treated with the An96 fIX Padua vector, but not An96 fIX or hfIX treated animals, achieved sustained, supraphysiologic plasma fIX activity levels over two weeks (~15-20 IU/ml fIX activity versus 0-10 IU/ml fIX activity, respectively).

Figure 4:
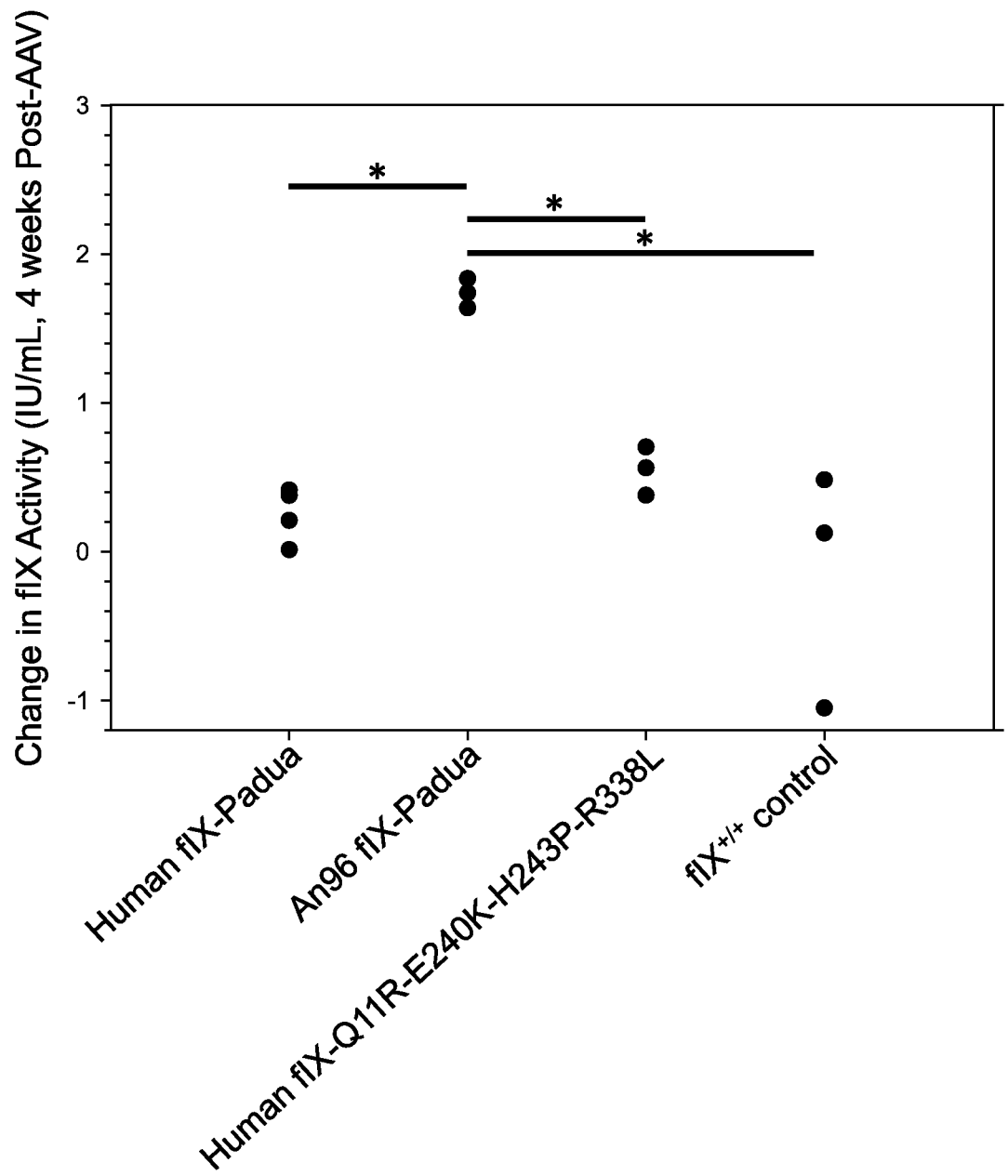
FIG. 4 shows in vivo data for fIX activity levels in serum of fIX$^{+/+}$ mice treated with AAV2/8 vectors containing a liver-directed promoter (HCB) and encoding the indicated fIX variants. The change in fIX activity level pre- and post-AAV administration is plotted. Statistical comparisons were made by one-way ANOVA and Holm-Sidak post-hoc analysis. Asterisks denote P<0.05.

Additionally, in vivo expression of the optimized fIX sequences was assessed in fIX$^{+/+}$ mice (FIG. 4). AAV2/8 vectors containing a liver-directed promoter (HCB), minute virus of mouse intron and one of three fIX transgenes (human fIX-Padua), An96-fIX-Padua (SEQ ID NO: 9) or hfIX Q11R-E240K-H243P-R338L were produced. The assay was conducted in a blinded fashion on randomized wt fIX$^{+/+}$ mice. Male, 9-11 week old wt fIX$^{+/+}$ mice were injected via tail vein with $5\times10^{11}$ vector genomes/kg of recombinant AAV (n=3/group). At baseline, prior to AAV administration, and at 4 weeks post-AAV administration, the mice were bled and plasma fIX activity levels were assessed by one-stage coagulation assay. The change in fIX activity level pre- and post-AAV administration is plotted in FIG. 4. Statistical comparisons were made by one-way ANOVA and Holm-Sidak post-hoc analysis. Asterisks denote P<0.05. Mice treated with AAV-2/8-AN96-fIX-PAgua displayed significantly greater increases in fIX activity than control, hfIX-Padua or hfIX Q11R-E240K-H243P-R338L mice. No other groups were significantly different form each other.

Example 2

Bioengineering Coagulation Factor VIII Through Ancestral Protein Reconstruction

This example illustrates the optimization of fVIII sequences to improve clotting factor activity, protein expression and therapeutic applications such as gene therapy.

The development of transformative hemophilia therapeutics has been hindered by the size, instability, immunogenicity and biosynthetic inefficiency of coagulation factors such as fVIII for treatment of hemophilia A. Through the study of fVIII orthologs from existing vertebrate species, unique molecular, cellular and biochemical properties that can overcome some of the limitations of human fVIII were discovered. Although this approach facilitated the development of recombinant porcine FVIII for acquired hemophilia A, improvements are still needed. For example, it is desirable to find additional fVIII sequences that have increased activity (for example, due to increased serum half-life or increased enzymatic activity) because it is possible that the frequency of infusion may be lessened while still achieving full prophylaxis.

To search for additional fVIII sequences that may facilitate improved clotting factor replacement therapy for hemophilia A, a mammalian fVIII phylogenetic tree with corresponding ancestral node (An) sequences was constructed through Bayesian inference using both DNA and amino acid-based models in PAML Version 4.1. Initially, nine An-fVIII sequences were selected for reconstruction, as follows:

An63 fVIII
(SEQ ID NO: 26)
MQIELSTCFFLCLLPFSFSATRRYYLGAVELSWDYMQSDLLSELHVDTRFPPRVPRSFPFNTSVMYKKTVFVEFTDHLFN
IAKPRPPWMGLLGPTIRAEVYDTVVITLKNMASHPVSLHAVGVSYWKASEGAEYDDQTSQREKEDDKVIPGESHTYVWQV
LKENGPMASDPPCLTYSYLSHVDLVKDLNSGLIGALLVCREGSLAKERTQTLHEFVLLFAVFDEGKSWHSEANESLTQAM
DSASARPWPKMHTVNGYVNRSLPGLIGCHRKSVYWHVIGMGTTPEVHSIFLEGHTFLVRNHRQASLEISPITFLTAQTLL
MDLGQFLLFCHIPSHQHDGMEAYVKVDSCPEEPQLRMKNNEEEEDYDDDLYDSDMDVLRFDDDNSPPFIQIRSVAKKHPK
TWIHYIAAEEEDWDYAPSVLTPTDRSYKSQYLNNGPQRIGRKYKKVRFMAYTDETFKTREAIQYESGILGPLLYGEVGDT
LLIIFKNQASRPYNIYPHGITNVSPLHSGRLPKGVKHLKDMPIMPGEIFKYKWTVTLEDGPTKSDPRCLTRYYSSFINLE
RDLASGLIGPLLICYKESVDQRGNQMMSDKRNVILFSVFDENRSWYLTENMQRFLPNAAGVQPQDPEFQASNIMHSINGY
VFDSLQLSVCLHEVAYWYILSVGAQTDFLSVFFSGYTFKHKMVFEDTLTLFPPFSGETVFMSMENPGLWVLGCHNSDFRNR
GMTALLKVSSCDRNTDDYYEDTYEDIPTYLLNENNVIEPRSFSQNSRHPSPRQKQFKATTTPENDIEKIDPQFGERTQLL
KAQSVSSSDLLMLLGQSPTPHGLSLSDLQEATYEAIPDDHSPGAIESNEGPSEVAHLRPELHHSGDTVFTPEPGLQRLN
ENLETTITVELKKLDLKVSSSSNNVMTSPTIPSDNLAAGTEKTGSLGPLNMPVHFSSQLGTILFGKKSSPLIGSGVPLHL
SERDNDSKLLEAALMNSQESSLGENVSSMESDRLFKEKRVHGPASLTKDNALFKVNISLVKTNKAPNNSTTNGKTHIDGP
TLLNENSTSVWQDIILENDTEFQEVTSLIHNEMFMDKNTTALGLNHVSNKTTSSKNMEMVHQKKEDPVPLDAENPDMSFF
KMLFLPDSANWIKRTHGKNSLSSEQGPSPKQLISLGSEKSVKDQNFLSEKSKVAVGEDEFTKDTGLKEMIFPNSKSIFLT
NLANVQENDTHNQEKKFQEEIERKETLIQENVVLPQVYTVTGTKNFLKNLFLLSTRQNVEGLDEGTYAPVLQDTRSLNDS
ANRAGIHMAHFSKRREEANLEGLRNQTKQMVEKYPSTTRMSFNPSQQNVITQRGKRALKQFGLPLEEIELERGLIVNDTS
TQWSKNMKYLTQGTLTQIDYNEKEKRAITQSPLSDCSMRNHGITQTNDSALPIAKVSAFPSIRPTDLTKIPSQDNSSHLL
ASACNYTFRERSSGVQESSHFLQGAKRNNLSSAILTLEMIRGQEKVGSLGTSATNSLMYKKLENTVLLKPGLPEASGKVE
LLPKVHVHQEDSFPTETSNGSPGHLDLMEEILLQKTQGAIKLNKVNRPGKVPFLKGATESSEKTLPKLLGPLAWDNQYAT
QIPREEWKSQEKSPKNTAFKTKDTILPLNPCESNHAIAAINEGQDRPQREATWAKQGGTGRLCSQNPPVLKHHQREITLT
TLQPEQEKIDYDDTLSIEMKREDFDIYGEDENQGPRSFQKRTRHYFIAAVERLWDYGMSRSPHALRNRAQSGSVPQFKKV
VFQEFTDGSFTQPLYRGELNEHLGLLGPYIRAEVEDNIMVTFKNQASRPYSFYSSLISYEEDQRQGAEPRKNFVKPNETK
TYFWKVQHHMAPTKDEFDCKAWAYFSDVDLEKDLHSGLIGPLLICRTNTLNPAHGRQLTVQEFALFFTIFDETKSWYFTE
NMERNCRAPCNIQMEDPTFKKNYRFHAINGYVMDTLPGLVMAQDQRIRWYLLSMGSNENIHSIHFSGHVFTVRKKEEYKM
AVYNLYPGVFETVEMLPSKAGIWRVECLIGEHLQAGMSTLFLVYSKECQTPLGMASGRIRDSQITASGQYGQWAPKLARL
HYSGSINAWSTKDPFSWIKVDLLAPMIIHGIKTQGARQKFSSLYISQFIIMYSLDGKKWQSYRGNSTGTLMVFFGNVDSS
GIKHNIFNPPIIARYIRLHPTHYSIRSTLRMELMGCDLNSCSMPLGMESKAISDAQITASSYFTNMFATWSPSQARLHLQ
GRTNAWRPQVNNPKEWLQVDFQKTMKVTGITTQGAKSLLTSMYVKEFLISSSQDGHHWTLFLQNGKVKVFQGNQDSFTPV
VNSLDPPLLTRYLRIHPQSWVHHIALRLEVLGCEAQQLY

An65 fVIII
(SEQ ID NO: 27)
MQIELSTCFFLCLLPFSFSATRRYYLGAVELSWDYMQSELLSELHVDTRFPPRVPRSFPFNTSVMYKKTVFVEFTDHLFN
IAKPRPPWMGLLGPTIRAEVYDTVVITLKNMASHPVSLHAVGVSYWKASEGAEYEDQTSQREKEDDKVIPGESHTYVWQV
LKENGPMASDPPCLTYSYLSHVDLVKDLNSGLIGALLVCREGSLAKERTQTLHEFVLLFAVFDEGKSWHSETNESLTQAM
DPASAQAQPEMHTVNGYVNRSLPGLIGCHKKSVYWHVIGMGTTPEVHSIFLEGHTFLVRNHRQASLEISPITFLTAQTLL
MDLGQFLLFCHISSHQHDGMEAYVKVDSCPEEPQLRMKNNEEEEDYDDDLYDSDMDVVRFDDDNSPPFIQIRSVAKKHPK
TWVHYIAAEEEDWDYAPSVLTPNDRSYKSLYLNNGPQRIGRKYKKVRFMAYTDETFKTREAIQYESGILGPLLYGEVGDT
LLIIFKNQASRPYNIYPHGITDVSPLHSGRLPKGVKHLKDMPILPGEIFKYKWTVTVEDGPTKSDPRCLTRYYSSFINLE
RDLASGLIGPLLICYKESVDQRGNQMMSDKRNVILFSVFDENRSWYLTENMQRFLPNADGVQPQDPEFQVSNIMHSINGY
VFDSLQLSVCLHEVAYWYILSVGAQTDFLSVFFSGYTFKHKMVYEDTLTLFPPFSGETVFMSMENPGLWVLGCHNSDFRNR

-continued

```
GMTALLKVSSCNRNTGDYYEDTYEDIPTSLLNENNVIEPRSFSQNSRHPSTRQKQFKATTTPENDIEKIDPQSGERTQLL
KVQSVSSSDLLMLLGQNPTPHGLSLSDLQEATYEAIPDDHLPGAIERNKGPSEVAHLRPELHHSGDRVFTPEPELQLRLN
ENLGTTITVELKKLDLKISSSSNNLMTSPTIPSDKLAAGTEKTGSLGPPNMPVHFSSQLGTIVFGKNSSHLIGSGVPLGL
SEGDNDSKLLEAALMNSQESSLGENVLSMESDRLFKEERVHGPASLTKDNALFKVNISLVKTNKAPINSTTNRKTHIDGP
TLLIENSTSVWQDIILESNTEFQEVTSLIHDETFMDKNTTALGLNHVSNKTTSSKNMEMVHQKKEGPVPLGAENPDMSFF
KMLFLPDSANWIKRTHGKNSLSSGQRPSPKQLTSLGSEKSVKDQNFLSEKNKVVVGEDEFTKDTGLKEMIFPNSKSIFLT
NLANVQENDTHNQEKKSQEEIERKEKLIQENVVLPQVYTVTGTKNFLKNLFLLSTKQNVEGLDEGTYTPILQDTRSLNDS
ANRAGIHMAHFSKIREEANLEGLGNQTKQMVEKYPSTTRMSPNPSQQNVITQRGKRALKQFRLPLEEIKLERGVILNDTS
TQWSKNMKYLTQGTLTQIEYNEKEKRAITQSLLSDCSMRNHGIIQTNDSALPIAKVSAFPSIRPTDLTKIPSQDNSSHLL
ASACNYTFRERSSGVQESSHFLQGAKRNNLSLAFLTLEMIRGQGKISSLGKSATNSLMYKKLENTVLLKPGLSEASGKVE
LLPKVHVHQEDSFPTKTSNGSPGHLDLMEEIFLQKTQGPVKLNKVNRPGKVPFLKWATESSEKTPSKLLGPLAWDNQYAT
QIPREEWKSQEKSQKNTAFKTKDTILPLDPCENNHSIAAINEGQDKPQREATWAKQGGTGRLCSQNPPVLKRHQREITLT
TLQPEEDKIDYDDTFSIEMKREDFDIYGEDENQGPRSFQKRTRHYFIAAVERLWDYGMSRSPHALRNRAQSGDVPQFKKV
VFQEFTDGSFTQPLYRGELNEHLGLLGPYIRAEVEDNIMVTFKNQASRPYSFYSSLISYEEDQRQGAEPRKKFVKPNETK
IYFWKVQHHMAPTKDEFDCKAWAYFSDVDLEKDVHSGLIGPLLICRANTLNPAHGRQVTVQEFALFFTIFDETKSWYFTE
NMERNCRAPCNIQMEDPTFKENYRFHAINGYVMDTLPGLVMAQDQRIRWYLLSMGSNENIHSIHFSGHVFTVRKKEEYKM
AVYNLYPGVFETVEMLPSKVGIWRIECLIGEHLQAGMSTLFLVYSKQCQTPLGMASGRIRDFQITASGQYGQWAPKLARL
HYSGSINAWSTKDPFSWIKVDLLAPMIIHSIMTQGARQKFSSLYISQFIIMYSLDGKKWQSYRGNSTGTLMVFFGNVDSS
GIKHNIFNPPIIARYIRLHPTHYSIRSTLRMELMGCDLNSCSMPLGMESKAISDAQITASSYLNNMFATWSPSQARLHLQ
GRTNAWRPQVNNPKEWLQVDFQKTMKVTGITTQGVKSLLTSMYVKEFLISSSQDGHNWTLFLQNGKVKVFQGNQDSFTPV
VNSLDPPLLTRYLRIHPQSWAHHIALRLEVLGCEAQQLY
An70 fVIII
                                                                 (SEQ ID NO: 28)
MQIELSTCFFLCLLPFSFSAIRRYYLGAVELSWDYMQSELLSELHVDTRFPPRVPRSFPFNTSVMYKKTVFVEFTDQLFN
IAKPRPPWMGLLGPTIQAEVYDTVVITLKNMASHPVSLHAVGVSYWKSSEGAEYEDQTSQREKEDDKVIPGKSHTYVWQV
LKENGPTASDPPCLTYSYLSHVDLVKDLNSGLIGALLVCREGSLTKERTQTLHEFVLLFAVFDEGKSWHSGKNESLTQAM
DPASARAQPAMHTINGYINRSLPGLIGCHKKSVYWHVIGMGTTPEVHSIFLEGHTFLVRNHRQASLEISPITFLTAQTLL
MDLGQFLLFCHISSHQHDGMEAYVKVDSCPEEPQLRMKNNEEEEDYDDDLYDSDMDVVRFDGDNAPPFIQIRSVAKKHPK
TWVHYIAAEEEDWDYAPSVLTSNDRSYKSLYLNNGPQRIGRKYKKVRFIAYTDETFKTREAIQYESGILGPLLYGEVGDT
LLIIFKNQASRPYNIYPHGITDVSPLHSGRFPKGVKHLKDMPILPGEIFKYKWTVTVEDGPTKSDPRCLTRYYSSFVNLE
RDLASGLIGPLLICYKESVDQRGNQMMSDKRNVILFSVFDENQSWYLTENIQRFLPNADGVQPQDPEFQVSNIMHSINGY
VFDSLQLSVCLHEVAYWYILSVGAQTDFLSVFFSGYTFKHKMVYEDTLTLFPPFSGETVFMSMENPGLWVLGCHNSDFRNR
GMTALLKVYSCDRNTGDYYEDTYEDIPTFLLNENNVIEPRSFSQNSRHPSTRQKQFKATTTPENDIEKIDPQSGERTQLL
KEQSVSSSDLLMLLGQNPTPHGLSLSDLQEARNEAIPDDHLPGAIERNKGPSEVAHLRPELHHSGERVFTPEPELPLRLN
ENLGTTITVELKKLDFKISSSSNNLMTSPTIPSDKLSAGTEKTGSLGPPNMPVNFSSQLGTIVFGKNSSHFIGSGVPLGL
SEEDNDSKLLEAALMNSQESSLGENVLSMESDRLFKEERVHGPASLTKDDALFKVNISLVKTNKAPINSTTNRKTHIDDP
TLLIENSTSVWQDIILESNTEFQEVTSLIHDETFMDKNTTALGLNHVSNKTTSSKNMEMVHQKKEGPVPLDAEYPDTSFF
KTLFLPDSTNWIKRTHGKNSLSSGQRPSPKQLTSSGSEKSVKDQNFLSEKNKVVVGEDEFSKDTGLKEMIFPNSKSIFLT
NLANVQENDTHNQEKKSQEEIERKEKLIQENVVLPQVYTVTGTKNFLKNLFLLSTKQNVEGLDEGTYTPVLQDTRSLNDS
AKRAGIHMAHFSKIREEANLEGLGNQTKQMVEKYPSTTRMSPNPSQQNVIPQRGKRDLKQFRLPLEEIKLERGVILNDTS
TQWSKNMKYLTQGTFTQIEYNKKEKRAITQSFLSDCSMRSHGIIQTNGSALPIAKVSAFPSIRPTDLTKIPSQDNSSHLP
```

-continued

ASACSYTFGERSSGVQESSHFLQGAKRNNLSLAFLTLEMIRGQGKISTLGKSATNPLMYKKLENTVLLKPGLSEASGKVE

FLPKVHVHQEDFFPTKTSNGSPAHLDLREEIFLQKTQGLVKLNKVNRPGKVPFLKWATESSEKTPSKLLGPLAWDNQYAT

LIPREEWKSLEKSQKSTALKTKDTILPLDPCENNHSIAAINEGQDKPQREATWVKQGGTGRLCSQNPPVLKRHQREITLT

TFQPEEDKIDYDDTFSIETKREDFDIYGEDENQDPRSFQKRTRHYFIAAVERLWDYGMSRSPHALRNRAQNGDVPQFKKV

VFQEFTDGSFTQPLYRGELNEHLGLLGPYIRAEVEDNIMVTFKNQASRPYSFYSSLISYEEDQRQGAEPRKKFVKPNETK

IYFWKVQHHMAPTKDEFDCKAWAYFSDVDLEKDVHSGLIGPLLICRTNTLNAAHGRQVTVQEFALFFTIFDETKSWYFTE

NMERNCRAPCNIQMEDPTFKENYRFHAINGYVMDTLPGLVMAQDQRIRWYLLSMGSNENIHSIHFSGHVFTVRKKEEYKM

AVYNLYPGVFETVEMLPSKVGIWRIECLIGEHLQAGMSTLFLVYSKQCQTPLGMASGRIRDFQITASGQYGQWAPKLARL

HYSGSINAWSTKDPFSWIKVDLLAPMIIHSIMTQGARQKFSSLYISQFIIMYSLDGKKWQSYRGNSTGTLMVFFGNVDSS

GIKHNIFNPPIIARYIRLHPTHYSIRSTLRMELMGCDLNSCSMPLGMENKAISDAQITASSHLSNMFATWSPSQARLHLQ

GRTNAWRPQVNNPKEWLQVDFQKTMKVTGITTQGVKSLLTSMYVKEFLISSSQDGHNWTLFLQNGKVKVFQGNQDSFTPV

VNALDPPLFTRYLRIHPQSWAHHIALRLELLGCEAQQLY

An84 fVIII (SEQ ID NO: 29)

MQIELSTCFFLCLLRFSFSATRRYYLGAVELSWDYMQSDLLSELHVDTRFPPRVPRSFPFNTSVMYKKTVFVEFTDHLFN

IAKPRPPWMGLLGPTIWAEVYDTVVITLKNMASHPVSLHAVGVSYWKASEGAEYDDQTSQREKEDDKVFPGESHTYVWQV

LKENGPMASDPPCLTYSYLSHVDLVKDLNSGLIGALLVCREGSLAKERTQTLHEFVLLFAVFDEGKSWHSETKDSLTQAM

DSASAQAWPKMHTVNGYVNRSLPGLIGCHRKSVYWHVIGMGTTPEVHSIFLEGHTFLVRNHRQASLEISPITFLTAQTLL

MDLGQFLLFCHISSHQHDGMEAYVKVDSCPEEPQLRMKNNEEEEDYDDDLDDSEMDVLRFDDDNSPSFIQIRSVAKKHPK

TWVHYIAAEEEDWDYAPSVLTPDDRSYKSQYLNNGPQRIGRKYKKVRFMAYTDETFKTREAIQYESGILGPLLYGEVGDT

LLIIFKNQASRPYNIYPHGITDVSPLHSGRLPKGVKHLKDLPILPGEIFKYKWTVTVEDGPTKSDPRCLTRYYSSFINLE

RDLASGLIGPLLICYKESVDQRGNQMMSDKRNVILFSVFDENQSWYLTENMQRFLPNAAGVQPQDPEFQASNIMHSINGY

VFDSLQLSVCLHEVAYWYILSVGAQTDFLSVFFSGYTFKHKMVYEDTLTLFPFSGETVFMSMENPGLWVLGCHNSDFRNR

GMTALLKVSSCDRNTGDYYEDTYEDIPTYLLSENNVIEPRSFSQNSRHPSTRQKQFKATTIPENDIEKIDPQFGERTQML

KVQSVSSSDLLMLLGQSPTPHGLSLSDLQEATYEAIPDDHSPGAIDSNEGPSEVAHLRPELHHSGDIVFTPEPGLQLRLN

ENLGTTIAVELKKLDLKVSSSSNNLMTSPTIPSDNLAAGTEKTGSLGPPNMPVHFSSQLGTTVFGKKSSPLIGSGVPLSL

SERNNDSKLLEAALMNSQESSLGKNVSSMESDRLFKEKRVHGPALLTKDNALFKVNISLVKTNKASNNSTTNGKTHIDGP

TLLIENSTSVWQDIILESDTEFQEVTSLIHDEMFMDKNTTALRLNHVSNKTTSSKNMEMVHQKKEGPVPPDAENPDMSFF

KMLFLPESANWIKRTHGKNSLNSGQGPSPKQLISLGSEKSVKDQNFLSEKNKVVVGEDEFTKDTGLKEMIFPSSRSIFLT

NLANVQENDTHNQEKKFQEEIERKETLIQENVVLPQVYTVTGTKNFLKNLFLLSTRQNVEGLDEGTYAPVLQDTRSLNDS

ANRAEIHMAHFSKRREEENLEGLRNQTKQMVEKYPSTTRMSPNPSQQNVITQRGKRALKQFRLPLEEIELERGLIVDDTS

TQWSKNMKYLTQGTLTQIDYNEKEKKAITQSPLSDCPMRNHGITQMNSSALPIAKVSAFPSIRPTDLTKIPSQDNSSHLL

ASACNYTFRERSSGVQESSHFLQGAKRNNLSLAILTLEMIRNQGKVGSLGTSATNSVMYKKLENTVLLKPGLPEASGKVE

LLPKVHIHQEDLFPTETSNGSPGHLDLMEEILLQKTQGAIKWNKANRPGKVPFLKGATESSEKTPSKLLGPLAWDNQYAT

QIPKEEWKSQEKSPKNTAFKTKDTILSLNPCESNHAIAAINEGQDRPQREATWAKQGGTGRLCSQNPPVLKRHQREITLT

TLQSEQEEIDYDDTISIEMKREDFDIYGEDENQGPRSFQKRTRHYFIAAVERLWDYGMSSSPHVLRNRAQSGSVPQFKKV

VFQEFTDGSFTQPLYRGELNEHLGLLGPYIRAEVEDNIMVTFKNQASRPYSFYSSLISYEEDQRQGAEPRKNFVKPNETK

TYFWKVQHHMAPTKDEFDCKAWAYFSDVDLEKDMHSGLIGPLLICHTNTLNPAHGRQVTVQEFALFFTIFDETKSWYFTE

NMERNCRAPCNIQMEDPTFKENYRFHAINGYVMDTLPGLVMAQDQRIRWYLLSMGSNENIHSIHFSGHVFTVRKKEEYKM

AVYNLYPGVFETVEMLPSKAGIWRVECLIGEHLHAGMSTLFLVYSKQCQTPLGMASGHIRDFQITASGQYGQWAPKLARL

HYSGSINAWSTKEPFSWIKVDLLAPMIIHGIKTQGARQKFSSLYISQFIIMYSLDGKKWQTYRGNSTGTLMVFFGNVDSS

GIKHNIFNPPIIARYIRLHPTHYSIRSTLRMELMGCDLNSCSMPLGMESKAISDAQITASSYFTNMFATWSPSQARLHLQ

-continued

GRTNAWRPQVNNPKEWLQVDFQKTMKVTGITTQGVKSLLTSMYVKEFLISSSQDGHHWTLFLQNGKVKVFQGNQDSFTPV

VNSLDPPLLTRYLRIHPQSWVHQIALRLEVLGCEAQQLY

An88 fVIII (SEQ ID NO: 30)

MQIALFTCFELSLENFCSSATRRYYLGAVELSWNYMQSDLLSVLHTDTRFLPRMPTSFPFNTSIMYKKTVFVEYMDHLFN

IAKPRPPWMGLLGPTIWTEVHDTVVITLKNMASHPVSLHAVGVSYWKASEGAEYEDQTSQREKEDDKVFPGESHTYVWQV

LKENGPMASDPPCLTYSYLSHVDLVKDLNSGLIGALLVCKEGSLSKERTQMLHQFVLLFAVFDEGKSWHSETKDSFTQAM

DSASTRAWPKMHTVNGYVNRSLPGLIGCHRKSVYWHVIGMGTTPEVHSIFLEGHTFLVRNHRQASLEISPITFLTAQTLL

IDLGQFLLFCHISSHKHDGMEAYVKVDSCPEEPQWQKKNNEEMEDYDDDLLDSEMDMFTLDDDNSPSFIQIRSVAKKYPK

TWIHYISAEEEDWDYAPSVLTSDDGSYKSQYLSNGPHRIGRKYKKVRFIAYTDETFKTRETIQHESGILGPLLYGEVGDT

LLIIFKNQASRPYNIYPHGITDVSPLHSRRLPRGIKHVKDLPIRPGEIFKYKWTVTVEDGPTKSDPRCLTRYYSSFINPE

RDLASGLIGPLLICYKESVDQRGNQMMSDKRNVILFSVFDENQSWYITENMQRFLPNAADTQPQDPEFQASNIMHSINGY

VFDSLQLTVCLHEVAYWYILSVGAQTDFLSIFFSGYTFKHKMVYEDTLTLFPFSGETVFMSMENPGLWVLGCHNSDFRKR

GMTALLKVSSCDKSTSDYYEEIYEDIPTQLVNDNNVIEPRSFFQNSNHPNTRKKKFKATTIPENDIEKIEPQFGETAEML

KVQSVSSSDLLMLLGQSPTPHGLSLSDNQEAIYEAIPDDHSPDAIDSNEGPSKVTQLRPELHHSGKIVFTPEPGLQRSN

KNLETTIEVKWKKLDLQVSSLPNNLMTTPTILSDNLTATSEKTDSSGSPDMPVHFSSKLSTTAFGKKSYPLIGSHVPLSI

SERNSDSNLLDATLMNSQESSLGDNISSMENDRLLKEKRFHGIALLTKDNTLFKDNISLMKTNKTYNHSTTNGKAHIDSP

TSLIENSTAVLQDTILKINSEIQEVTSLIHDGTLSGKNTTYLRLNHMLNRTTSSKNKEIFHQKDEDPVPQDAENTIMPFF

KMLFLPESANWMKRTNGNNSLNSEQGPSPKQLVYLMLEKSVKNQNFLSEKNKVIVEQDEFTKDTGLKDMVFPSNMSIFLT

TLANVQENDMHNQEKNIQEEIEKKEALIEEKVVLPQVHIATGSKNFLKDIFFLGTRQNVVSLDEEIYVPVLQDIRSINNS

TNTVEIHMAHFFKRREDENSEGLVNKTREMVKNYPSTTRMSPNPSQKNIITQRSKRALGQFRLPLEETELEKQQIVNNAS

TQWPQTMNYLTQSIITQIDHSKEGEKSITQSSLSDSSMIKKSTTQTNSSGLHIVKTSAFPPIRPTDLKRIPFQDKFFHVL

ASSYTYDFKTKSSRIQESSHFLKETKINNSSLAILPWEMIINQGKFASPGTSNTNSVTYKKLENIVLLKPVLPEESGKVE

LLPQVSIHEEELLPTETSHESPGHLDLMKEVFLQKTQGPIKWNKAKRHGESPFLKGTTESSEKTPSKLLDPLAWDNHYAA

QIPKDKWKSKEKSPEITSIKREDTILSLNPHENNHSIVAINEKQNWPQREATWVKQGQTQRLCSQNPPVLKRHQRELSAL

QSEQEATDYDDAITIETNEDFDIYGEDIKQGPRSFQQKTRHYFIAAVERLWDYGMSTSPHVLRNRDQSGNAPQFKKVVFQ

EFTDGSFSQPLYRGELNEHLGLLGPYIRAEVEDNIMVTFKNQASRPYSFYSSLISYKEDQRQGEEPRRNFVKPNETKIYF

WKVQHHMAPTEDEFDCKAWAYFSDVDLERDMHSGLIGPLLICHTNTLNPAHGRQVAVQEFALFFTIFDETKSWYFTENVE

RNCKTPCNIQMEDPTLKENYRFHAINGYVMDTLPGLVMAQDQRIRWYLLSMGSNENIQSIHFSGHVFTVRKKEEYKMAVY

NLYPGVFETVEMLPSRAGIWRVECLIGEHLQAGMSTLFLVYSKQCQIPLGMASGSIRDFQITASGHYGQWAPNLARLHHS

GSINAWSTKEPFSWIKVDLLTPMIIHGIKTQGARQKFSSLYISQFIIMYSLDGKKWLSYRGNSTGTLMVFFGNVDSSGIK

HNSFNPPIIARYIRLHPTHSSIRSTLRMELMGCDLNSCSIPLGMENKVISDTQITASSYFTNMFATWSPSQARLHLQGRT

NAWRPQVNDPKEWLQVDLQKTMKVTGIITQGVKSLFTSMFVKEFLISSSQDGHHWTHILHNGKVKVFQGNQDSSTPMVNS

LDPPLLTRYLRIHPQIWEHQIALRLEILGCEAQQLY

An95 fVIII (SEQ ID NO: 31)

MQIELSTCFFLCLLRFSFSATRRYYLGAVELSWDYMQSDLLGELHVDTRFPPRVPRSFPFNTSVMYKKTVFVEFTDHLFN

IAKPRPPWMGLLGPTIWAEVYDTVVITLKNMASHPVSLHAVGVSYWKASEGAEYDDQTSQREKEDDKVFPGESHTYVWQV

LKENGPMASDPPCLTYSYLSHVDLVKDLNSGLIGALLVCREGSLAKERTQTLHEFVLLFAVFDEGKSWHSETKDSLTQAM

DSASAQAWPKMHTVNGYVNRSLPGLIGCHRKSVYWHVIGMGTTPEVHSIFLEGHTFLVRNHRQASLEISPITFLTAQTLL

MDLGQFLLFCHISSHQHDGMEAYVKVDSCPEEPQLRMKNNEEEEDYDDDLDDSEMDVLRFDDDNSPSFIQIRSVAKKHPK

TWVHYIAAEEEDWDYAPSVLTPDDRSYKSQYLNNGPQRIGRKYKKVRFMAYTDETFKTREAIQYESGILGPLLYGEVGDT

-continued

```
LLIIFKNQASRPYNIYPHGITDVSPLHSGRLPKGVKHLKDLPILPGEIFKYKWTVTVEDGPTKSDPRCLTRYYSSFINLE
RDLASGLIGPLLICYKESVDQRGNQMMSDKRNVILFSVFDENQSWYLTENMQRFLPNAAGVQPQDPEFQASNIMHSINGY
VFDSLQLSVCLHEVAYWYILSVGAQTDFLSVFFSGYTFKHKMVYEDTLTLFPFSGETVFMSMENPGLWVLGCHNSDFRNR
GMTALLKVSSCDRNTGDYYEDTYEDIPTYLLSENNVIEPRSFSQNSRHPSTRQKQFKATTIPENDIEKIDPQFGERTQML
KVQSVSSSDLLMLLGQSPTPHGLSLSDLQEATYEAIPDDHSPGAIDSNEGPSEVAHLRPELHHSGDIVFTPEPGLQLRLN
ENLGTTIAVELKKLDLKVSSSSNNLMTSPTIPSDNLAAGTEKTGSLGPPNMPVHFSSQLGTTVFGKKSSPLIGSGVPLSL
SERNNDSKLLEAALMNSQESSLGKNVSSMESDRLFKEKRVHGPALLTKDNALFKVNISLVKTNKASNNSTTNGKTHIDGP
TLLIENSTSVWQDIILESDTEFQEVTSLIHDEMFMDKNTTALRLNHVSNKTTSSKNMEMVHQKKEGPVPPDAENPDMSFF
KMLFLPESANWIKRTHGKNSLNSGQGPSPKQLISLGSEKSVKDQNFLSEKNKVVGEDEFTKDTGLKEMIFPSSRSIFLT
NLANVQENDTHNQEKKFQEEIERKETLIQENVVLPQVYTVTGTKNFLKNLFLLSTRQNVEGLDEGAYAPVLQDTRSLNDS
ANRAEIHMAHFSKRREEENLEGLRNQTKQMVEKYPSTTRMSPNPSQQNVITQRGKRALKQFRLPLEEIELERGLIVDDTS
TQWSKNMKYLTQGTLTQIDYNKKEKKAITQSPLSDCPMRNHGITQMNSSALPIAKVSAFPSIRPTDLTRIPSQDNSSHLL
ASACNYTFRERSSGVQESSHFLQGAKRNNLSLAILTLEMIRNQGKVGSLGTSATNSVMYKKLENTVLLKPGLPEASGKVE
LLPKVHIHQEDLFPTETSNGSPGHLDLMEEILLQKTQGAIKWNKANRPGKVPFLKGATESSEKTPSKLLGPLAWDNQYAT
QIPKEEWKSQEKSPKNTAFKTKDTILSLNPCESNHAIAAINEGQDRPQREATWAKQGGTGRLCSQNPPVLKRHQREITLT
TLQSEQEEIDYDDTISIEMKREDFDIYGEDENQGPRSFQKRTRHYFIAAVERLWDYGMSSSPHVLRNRAQSGSVPQFKKV
VFQEFTDGSFTQPLYRGELNEHLGLLGPYIRAEVEDNIMVTFKNQASRPYSFYSSLISYEEDQRQGAEPRKNFVKPNETK
TYFWKVQHHMAPTKDEFDCKAWAYFSDVDLEKDMHSGLIGPLLICHTNTLNPAHGRQVTVQEFALFFTIFDETKSWYFTE
NMERNCRAPCNIQMEDPTFKENYRFHAINGYVMDTLPGLVMAQDQRIRWYLLSMGSNENIHSIHFSGHVFTVRKKEEYKM
AVYNLYPGVFETVEMLPSKAGIWRVECLIGEHLHAGMSTLFLVYSKQCQTPLGMASGHIRDFQITASGQYGQWAPKLARL
HYSGSINAWSTKEPFSWIKVDLLAPMIIHGIKTQGARQKFSSLYISQFIIMYSLDGKKWQTYRGNSTGTLMVFFGNVDSS
GIKHNIFNPPIIARYIRLHPTHYSIRSTLRMELMGCDLNSCSMPLGMESKAISDAQITASSYFTNMFATWSPSQARLHLQ
GRTNAWRPQVNNPKEWLQVDFQKTMKVTGITTQGVKSLLTSMYVKEFLISSSQDGHHWTLFFQNGKVKVFQGNQDSFTPV
VNSLDPPLLTRYLRIHPQSWVHQIALRLEVLGCEAQQLY
```

An96 fVIII
(SEQ ID NO: 32)

```
MQIELSTCFFLCLLRFSFSATRRYYLGAVELSWDYMQSDLLGELHVDTRFPPRVPRSFPFNTSVMYKKTVFVEFTDHLFN
IAKPRPPWMGLLGPTIWAEVYDTVVITLKNMASHPVSLHAVGVSYWKASEGAEYDDQTSQREKEDDKVFPGESHTYVWQV
LKENGPMASDPPCLTYSYLSHVDLVKDLNSGLIGALLVCREGSLAKERTQTLHEFVLLFAVFDEGKSWHSETKDSLTQAM
DSASAQAWPKMHTVNGYVNRSLPGLIGCHRKSVYWHVIGMGTTPEVHSIFLEGHTFLVRNHRQASLEISPITFLTAQTLL
MDLGQFLLFCHISSHQHDGMEAYVKVDSCPEEPQLRMKNNEEEEDYDDDLDDSEMDVLRFDDDNSPSFIQIRSVAKKHPK
TWVHYIAAEEEDWDYAPSVLTPDDRSYKSQYLNNGPQRIGRKYKKVRFMAYTDETFKTREAIQYESGILPGLLYGEVGDT
LLIIFKNQASRPYNIYPHGITDVSPLHSGRLPKGVKHLKDLPILPGEIFKYKWTVTVEDGPTKSDPRCLTRYYSSFINLE
RDLASGLIGPLLICYKESVDQRGNQMMSDKRNVILFSVFDENQSWYLTENMQRFLPNAAGVQPQDPEFQASNIMHSINGY
VFDSLQLSVCLHEVAYWYILSVGAQTDFLSVFFSGYTFKHKMVYEDTLTLFPFSGETVFMSMENPGLWVLGCHNSDFRNR
GMTALLKVSSCDRNTGDYYEDTYEDIPTYLLSENNVIEPRSFSQNSRHPSTRQKQFKATTIPENDIEKIDPQFGERTQML
KVQSVSSSDLLMLLGQSPTPHGLSLSDLQEATYEAIPDDHSPGAIDSNEGPSEVAHLRPELHHSGDIVFTPEPGLQLRLN
ENLGTTIAVELKKLDLKVSSSSNNLMTSPTIPSDNLAAGTEKTGSLGPPNMPVHFSSQLGTTVFGKKSSPLIGSGVPLSL
SERNNDSKLLEAALMNSQESSLGKNVSSMESDRLFKEKRAHGPALLTKDNALFKVNISLVKTNKASNNSTTNGKTHIDGP
TLLIENSTSVWQDTILESDTEFQEVTSLIHDEMFMDKNTTALRLNHVSNKTTSSKNMEMVHQKKEGPVPPDAENPDMSFF
KMLFLPESANWIKRTHGKNSLNSGQGPSPKQLISLGSEKSVKDQNFLSEKNKVVGEDEFTKDTGLKEMIFPSSRNIFLT
NLANVQENDTHNQEKKFQEEIERKETLIQENVVLPQVYTVTGTKNFLKNLFLLSTRQNVEGLDEGAYAPVLQDTRSLNDS
```

-continued

ANRAEIHMAHFSKRREEENLEGLRNQTKQMVEKYPSTTRMSPNPSQQNVITQRGKRALKQFRLPLEEIELEKGLIVDDTS
TQWSKNMKYLTQGTLTQIDYNKKEKKAITQSPLSDCPMRSHGITQMNSSALPIAKVSAFPSIRPTDLTRIPSQDNSSHLL
ASACNYTFRERSSGVQESSHFLQGAKRNNLSLAILTLEMIRNQRKVGSLGTSATNSVMYKKLENTVLLKPGLPEASGKVE
LLPKVHIHQEDLFPTETSNGSPGHLDLMEEILLQKTQGAIKWNKANRPGKVPFLKGATESSEKTPSKLLGPLAWDNQYAT
QIPKEEWKSQEKSPKNTAFKTKDTILSLNPCESNHAIAAINEGQDRPQREATWAKQGGTGRLCSQNPPVLKRHQREITLT
TLQSEQEEIDYDDTISIEMKREDFDIYGEDENQGPRSFQKRTRHYFIAAVERLWDYGMSSSPHVLRNRAQSGSVPQFKKV
VFQEFTDGSFTQPLYRGELNEHLGLLGPYIRAEVEDNIMVTFKNQASRPYSFYSSLISYEEDQRQGAEPRKNFVKPNETK
TYFWKVQHHMAPTKDEFDCKAWAYFSDVDLEKDMHSGLIGPLLICHTNTLNPAHGRQVTVQEFALFFTIFDETKSWYFTE
NMERNCRAPCNIQMEDPTFKENYRFHAINGYVMDTLPGLVMAQDQRIRWYLLSMGSNENIHSIHFSGHVFTVRKKEEYKM
AVYNLYPGVFETVEMLPSKAGIWRVECLIGEHLHAGMSTLFLVYSKQCQTPLGMASGHIRDFQITASGQYGQWAPKLARL
HYSGSINAWSTKEPFSWIKVDLLAPMIIHGIKTQGARQKFSSLYISQFIIMYSLDGKKWQTYRGNSTGTLMVFFGNVDSS
GIKHNIFNPPIIARYIRLHPTHYSIRSTLRMELMGCDLNSCSMPLGMESKAISDAQITASSYFTNMFATWSPSQARLHLQ
GRTNAWRPQVNNPKEWLQVDFQKTMKVTGITTQGVKSLLTSMYVKEFLISSSQDGHHWTLFFQNGKVKVFQGNQDSFTPV
VNSLDPPLLTRYLRIHPQSWVHQIALRLEVLGCEAQQLY

An97 fVIII
(SEQ ID NO: 33)
MQIELSTCFELCLLRFSFSATRRYYLGAVELSWDYMQSDLLGELHVDTRFPPRVPRSFPFNTSVMYKKTVFVEFTDHLFN
IAKPRPPWMGLLGPTIQAEVYDTVVITLKNMASHPVSLHAVGVSYWKASEGAEYDDQTSQREKEDDKVFPGESHTYVWQV
LKENGPMASDPPCLTYSYLSHVDLVKDLNSGLIGALLVCREGSLAKERTQTLHEFVLLFAVFDEGKSWHSETKDSLMQDT
DSASARQAWPKMHTVNGYVNRSLPGLIGCHRKSVYWHVIGMGTTPEVHSIFLEGHTFLVRNHRQASLEISPITFLTAQTLL
MDLGQFLLFCHISSHQHDGMEAYVKVDSCPEEPQLRMKNNEEEEDYDNDLDDSEMDVLRFDDDNSPSFIQIRSVAKKHPK
TWVHYIAAEEEDWDYAPSVLTPDDRSYKSQYLNNGPQRIGRKYKKVRFMAYTDETFKTREAIQYESGILGPLLYGEVGDT
LLIIFKNQASRPYNIYPHGITDVSPLHSGRLPKGVKHLKDLPILPGEIFKYKWTVTVEDGPTKSDPRCLTRYYSSFINLE
RDLASGLIGPLLICYKESVDQRGNQMMSDKRNVILFSVFDENQSWYLTENMQRFLPNAAGVQPQDPEFQASNIMHSINGY
VFDSLQLSVCLHEVAYWYILSIGAQTDFLSVFFSGYTFKHKMVYEDTLTLFPFSGETVFMSMENPGLWVLGCHNSDFRNR
GMTALLKVSSCDRNTGDYYEDTYEDISTYLLSENNVIEPRSFSQNSRHPSTRQKQFKATTIPENDIEKIDPQFGERTQML
KVQSVSSSDLLMLLGQSPTPHGLSLSDLQEATYEAIPDDHSPGAIDSNEGPSEVAHLRPELHHSGDIVFTPEPGLQLRLN
ENLGTTIAVELKKLDLKVSSSSNNLMTSPTIPSDNLAAGTEKTGSLGPPNMPVHFDSQLDTTVFGKKSSPLIGSGVPLSL
SEGNNDSKLLEAALMNSQESSLGKNVSSMESDRLFKEKRAHGPALLTKDNALFKVNISLVKTNKASNNSTTNRKTHIDGP
TLLIENSTSVWQDTILESDTEFQEVTSLIHDKMFMDKNTTALRLNHVSNKTTSSKNMEMVHQKKEGPVPPDAENPDMSFF
KMLFLPESANWIKRTHGKNSLNSGQGPSPKQLISLGSEKSVKDQNFLSEKNKVVVGEDEFTKDTGLKEMIFPSSRNIFLT
NLANVHENDTHNQEKKIQEEIERKETLIQENVVLPQVYTVTGTKNFMKNLFLLSTRQNVEGLDEGAYAPVLQDTRSLNDS
ANRTEIHMAHFSKKREEENLEGLRNQTKQMVEKYPSTTRMSPNPSQQNVITQRGKRALKQFRLPLEEIELEKGLIVDDTS
TQWSKNMKYLTQGTLTQIDYNKKEKKAITQSPLSDCLMRSHGITQMNSSALPIAKVSAFPSIRPTDLTRIPSQDNSSHLL
ASACRKKSSGVQESSHFLQGAKRNNLSLAILTLEMIGNQRKVGSLGTSATNSVMYKKLENTVLLKPGLPEASGKVELLPK
VHIHQEDLFPTETSNGSPGHLDLMEEILLQKTQGAIKWNKANRPGKVPFLKGATESSEKTPSKLLGPLAWDNQYATQIPK
EEWKSQEKSPENTAFKTKDTILSLNPCESNHAIAAINEGQDRPQREATWAKQGGTGRLCSQNPPVLKRHQREITLTTLQS
DQEEIDYDDTISTEMKREDFDIYGEDENQGPRSFQKKTRHYFIAAVERLWDYGMSSSPHVLRNRAQSGSVPQFKKVVFQE
FTDGSFTQPLYRGELNEHLGLLGPYIRAEVEDNIMVTFKNQASRPYSFYSSLISYEEDQRQGAEPRKNFVKPNETKTYFW
KVQHHMAPTKDEFDCKAWAYFSDVDLEKDMHSGLIGPLLICHTNTLNPAHGRQVTVQEFALFFTIFDETKSWYFTENMER
NCRAPCNIQMEDPTFKENYRFHAINGYVMDTLPGLVMAQDQRIRWYLLSMGSNENIHSIHFSGHVFTVRKKEEYKMAVYN

-continued

LYPGVFETVEMLPSKAGIWRVECLIGEHLHAGMSTLFLVYSKQCQTPLGMASGHIRDFQITASGQYGQWAPKLARLHYSG

SINAWSTKEPFSWIKVDLLAPMIIHGIKTQGARQKFSSLYISQFIIMYSLDGKKWQTYRGNSTGTLMVFFGNVDSSGIKH

NIFNPPIIARYIRLHPTHYSIRSTLRMELMGCDLNSCSMPLGMESKAISDAQITASSYFTNMFATWSPSQARLHLQGRTN

AWRPQVNNPKEWLQVDFQKTMKVTGITTQGVKSLLTSMYVKEFLISSSQDGHHWTLFFQNGKVKVFQGNQDSFTPVVNSL

DPPLLTRYLRIHPQSWVHQIALRLEVLGCEAQQLY

An102 fVIII
(SEQ ID NO: 34)

MQIELSTCFFLCLLRFCFSATRRYYLGAVELSWDYMQSDLLGELPVDTRFPPRVPRSFPENTSVMYKKTVFVEFTDHLFN

IAKPRPPWMGLLGPTIQAEVYDTVVITLKNMASHPVSLHAVGVSYWKASEGAEYDDQTSQREKEDDKVFPGGSHTYVWQV

LKENGPMASDPLCLTYSYLSHVDLVKDLNSGLIGALLVCREGSLAKEKTQTLHKFVLLFAVFDEGKSWHSETKNSLMQDR

DAASARAWPKMHTVNGYVNRSLPGLIGCHRKSVYWHVIGMGTTPEVHSIFLEGHTFLVRNHRQASLEISPITFLTAQTLL

MDLGQFLLFCHISSSHQHDGMEAYVKVDSCPEEPQLRMKNNEEAEDYDDDLADSEMDVVRFDDDNSPSFIQIRSVAKKHPK

TWVHYIAAEEEDWDYAPSVLAPDDRSYKSQYLNNGPQRIGRKYKKVRFMAYTDETFKTREAIQYESGILGPLLYGEVGDT

LLIIFKNQASRPYNIYPHGITDVRPLYSRRLPKGVKHLKDFPILPGEIFKYKWTVTVEDGPTKSDPRCLTRYYSSFINME

RDLASGLIGPLLICYKESVDQRGNQIMSDKRNVILFSVFDENQSWYLTENIQRFLPNPAGVQLEDPEFQASNIMHSINGY

VFDSLQLSVCLHEVAYWYILSIGAQTDFLSVFFSGYTFKHKMVYEDTLTLFPFSGETVFMSMENPGLWILGCHNSDFRNR

GMTALLKVSSCDKNTGDYYEDSYEDISTYLLSKNNAIEPRSFSQNSRHPSTRQKQFNATTIPENDIEKTDPWFAHRTPMP

KVQNVSSSDLLMLLRQSPTPHGLSLSDLQEAKYETFSDDPSPGAIDSNNSLSEMTHLRPQLHHSGDMVFTPEPGLQLRLN

EKLGTTVATELKKLDFKVSSSSNNLISSPTIPSDNLAAGTDNTSSLGPPNMPVHYDSQLDTTLFGKKSSPLIESGGPLSL

SEENNDSKLLESGLMNSQESSWGKNVSSTESGRLFKEKRAHGPALLTKDNALFKVSISLLKTNKTSNNSATNRKTHIDGP

SLLIENSPSVWQNTILESDTEFQKVTPLIHDRMLMDKNTTALRLNHMSNKTTSSKNMEMVQQKKEGPIPPDAENPDMSFF

KMLFLPESANWIQRTHGKNSLNSGQGPSPKQLVSLGPEKSVEGQNFLSEKNKVVVGKGEFTKDVGLKEMVFPSSRNLFLT

NLDNLHENNTHNQEKKIQEEIERKETLIQENVVLPQIHTVTGTKNFMKNLFLLSTRQNVEGSYEGAYAPVLQDFRSLNDS

TNRTKKHMAHFSKKGEEENLEGLGNQTKQIVEKYPHTTRISPNPSQQNFVTQRGKRALKQFRLPLEETELEKRLIVDDTS

TQWSKNMKHLTPSTLTQIDYNEKEKGAITQSPLSDCLTRSHSITQANRSPLPIAKVSSFPSIRPIDLTRVLFQDNSSHLP

APSYRKKDSGVQESSHFLQGAKKNNLSLAILTLEMIGDQREVGSLGTSATNSVTYKKVENTVLLKPGLPKTSGKVELLPK

VHIYQKDLFPTETSNGSPGHLDLMEGSLLQETEGAIKWNEANRPGKIPFLRGATESSAKTPSKLLGPLAWDNHYGTQIPK

EEWKSQEKSPENTAFKKKDTILSLNPCESNHAIAAINEGQNKPQIEVTWAKQGGTERLCSQNPPVLKRHQREITLTTLQS

DQEEIDYDDTISVEMKKEDFDIYGEDENQSPRSFQKKTRHYFIAAVERLWDYGMSSSPHVLRNRAQSGSVPQFKKVVFQE

FTDGSFTQPLYRGELNEHLGLLGPYIRAEVEDNIMVTFKNQASRPYSFYSSLISYEEDQRQGAEPRKNFVKPNETKTYFW

KVQHHMAPTKDEFDCKAWAYFSDVDLEKDVHSGLIGPLLVCHTNTLNPAHGRQVTVQEFALFFTIFDETKSWYFTENMER

NCRAPCNIQMEDPTFKENYRFHAINGYIMDTLPGLVMAQDQRIRWYLLSMGSNENIHSIHFSGHVFTVRKKEEYKMAVYN

LYPGVFETVEMLPSKAGIWRVECLIGEHLHAGMSTLFLVYSNKCQTPLGMASGRIRDFQITASGQYGQWAPKLARLHYSG

SINAWSTKEPFSWIKVDLLAPMIIHGIKTQGARQKFSSLYISQFIIMYSLDGKKWQTYRGNSTGTLMVFFGNVDSSGIKH

NIFNPPIIARYIRLHPTHYSIRSTLRMELMGCDLNSCSMPLGMESKAISDAQITASSYFTNMFATWSPSKARLHLQGRSN

AWRPQVNNPKEWLQVDFQKTMKVTGITTQGVKSLLTSMYVKEFLISSSQDGHHWTLFFQNGKVKVFQGNQDSFTPVVNSL

DPPLLTRYLRIHPQSWVHQIALRMEVLGCEAQELY

The sequences of the An84, An63, An96, and An97 fVIII proteins were modified to remove the B-domain and link the A2 domain with the activation peptide by a peptide linker (B Domain Deleted or "BDD" fVIII proteins). The modified amino acid sequences are as follows:

An84 fVIII BDD
(SEQ ID NO: 3)
MQIELSTCFFLCLLRFSFSATRRYYLGAVELSWDYMQSDLLSELHVDTRF
PPRVPRSFPFNTSVMYKKTVFVEFTDHLFNIAKPRPPWMGLLGPTIWAEV
YDTVVITLKNMASHPVSLHAVGVSYWKASEGAEYDDQTSQREKEDDKVFP
GESHTYVWQVLKENGPMASDPPCLTYSYLSHVDLVKDLNSGLIGALLVCR
EGSLAKERTQTLHEFVLLFAVFDEGKSWHSETKDSLTQAMDSASAQAWPK
MHTVNGYVNRSLPGLIGCHRKSVYWHVIGMGTTPEVHSIFLEGHTFLVRN
HRQASLEISPITFLTAQTLLMDLGQFLLFCHISSHQHDGMEAYVKVDSCP
EEPQLRMKNNEEEEDYDDDLDDSEMDVLRFDDDNSPSFIQIRSVAKKHPK
TWVHYIAAEEEDWDYAPSVLTPDDRSYKSQYLNNGPQRIGRKYKKVRFMA
YTDETFKTREAIQYESGILGPLLYGEVGDTLLIIFKNQASRPYNIYPHGI
TDVSPLHSGRLPKGVKHLKDLPILPGEIFKYKWTVTVEDGPTKSDPRCLT
RYYSSFINLERDLASGLIGPLLICYKESVDQRGNQMMSDKRNVILFSVFD
ENQSWYLTENMQRFLPNAAGVQPQDPEFQASNIMHSINGYVFDSLQLSVC
LHEVAYWYILSVGAQTDFLSVFFSGYTFKHKMVYEDTLTLFPPFSGETVFM
SMENPGLWVLGCHNSDFRNRGMTALLKVSSCDRNTGDYYEDTYEDIPTYL
LSENNVIEPRSFSQNPPVLKRHQREITLTTLQSEQEEIDYDDTISIEMKR
EDFDIYGEDENQGPRSFQKRTRHYFIAAVERLWDYGMSSSPHVLRNRAQS
GSVPQFKKVVFQEFTDGSFTQPLYRGELNEHLGLLGPYIRAEVEDNIMVT
FKNQASRPYSFYSSLISYEEDQRQGAEPRKNFVKPNETKTYFWKVQHHMA
PTKDEFDCKAWAYFSDVDLEKDMHSGLIGPLLICHTNTLNPAHGRQVTVQ
EFALFFTIFDETKSWYFTENMERNCRAPCNIQMEDPTFKENYRFHAINGY
VMDTLPGLVMAQDQRIRWYLLSMGSNENIHSIHFSGHVFTVRKKEEYKMA
VYNLYPGVFETVEMLPSKAGIWRVECLIGEHLHAGMSTLFLVYSKQCQTP
LGMASGHIRDFQITASGQYGQWAPKLARLHYSGSINAWSTKEPFSWIKVD
LLAPMIIHGIKTQGARQKFSSLYISQFIIMYSLDGKKWQTYRGNSTGTLM
VFFGNVDSSGIKHNIFNPPIIARYIRLHPTHYSIRSTLRMELMGCDLNSC
SMPLGMESKAISDAQITASSYFTNMFATWSPSQARLHLQGRTNAWRPQVN
NPKEWLQVDFQKTMKVTGITTQGVKSLLTSMYVKEFLISSSQDGHHWTLF
LQNGKVKVFQGNQDSFTPVVNSLDPPLLTRYLRIHPQSWVHQIALRLEVL
GCEAQQLY

An63 fVIII BDD
(SEQ ID NO: 4)
MQIELSTCFFLCLLPFSFSATRRYYLGAVELSWDYMQSDLLSELHVDTRF
PPRVPRSFPFNTSVMYKKTVFVEFTDHLFNIAKPRPPWMGLLGPTIRAEV
YDTVVITLKNMASHPVSLHAVGVSYWKASEGAEYDDQTSQREKEDDKVIP
GESHTYVWQVLKENGPMASDPPCLTYSYLSHVDLVKDLNSGLIGALLVCR
EGSLAKERTQTLHEFVLLFAVFDEGKSWHSEANESLTQAMDSASARPWPK
MHTVNGYVNRSLPGLIGCHRKSVYWHVIGMTTPEVHSIFLEGHTFLVRN
HRQASLEISPITFLTAQTLLMDLGQFLLFCHIPSHQHDGMEAYVKVDSCP
EEPQLRMKNNEEEEDYDDDLYDSDMDVLRFDDDNSPPFIQIRSVAKKHPK
TWIHYIAAEEEDWDYAPSVLTPTDRSYKSQYLNNGPQRIGRKYKKVRFMA
YTDETFKTREAIQYESGILGPLLYGEVGDTLLIIFKNQASRPYNIYPHGI
TNVSPLHSGRLPKGVKHLKDMPIMPGEIFKYKWTVTLEDGPTKSDPRCLT
RYYSSFINLERDLASGLIGPLLICYKESVDQRGNQMMSDKRNVILFSVFD
ENRSWYLTENMQRFLPNAAGVQPQDPEFQASNIMHSINGYVFDSLQLSVC
LHEVAYWYILSVGAQTDFLSVFFSGYTFKHKMVFEDTLTLFPPFSGETVFM
SMENPGLWVLGCHNSDFRNRGMTALLKVSSCDRNTDDYYEDTYEDIPTYL
LNENNVIEPRSFSQNPPVLKHHQREITLTTLQPEQEKIDYDDTLSIEMKR
EDFDIYGEDENQGPRSFQKRTRHYFIAAVERLWDYGMSRSPHALRNRAQS
GSVPQFKKVVFQEFTDGSFTQPLYRGELNEHLGLLGPYIRAEVEDNIMVT
FKNQASRPYSFYSSLISYEEDQRQGAEPRKNFVKPNETKTYFWKVQHHMA
PTKDEFDCKAWAYFSDVDLEKDLHSGLIGPLLICRTNTLNPAHGRQLTVQ
EFALFFTIFDETKSWYFTENMERNCRAPCNIQMEDPTFKKNYRFHAINGY
VMDTLPGLVMAQDQRIRWYLLSMGSNENIHSIHFSGHVFTVRKKEEYKMA
VYNLYPGVFETVEMLPSKAGIWRVECLIGEHLQAGMSTLFLVYSKECQTP
LGMASGRIRDSQITASGQYGQWAPKLARLHYSGSINAWSTKDPFSWIKVD
LLAPMIIHGIKTQGARQKFSSLYISQFIIMYSLDGKKWQSYRGNSTGTLM
VFFGNVDSSGIKHNIFNPPIIARYIRLHPTHYSIRSTLRMELMGCDLNSC
SMPLGMESKAISDAQITASSYFTNMFATWSPSQARLHLQGRTNAWRPQVN
NPKEWLQVDFQKTMKVTGITTQGAKSLLTSMYVKEFLISSSQDGHHWTLF
LQNGKVKVFQGNQDSFTPVVNSLDPPLLTRYLRIHPQSWVHHIALRLEVL
GCEAQQLY

An96 fVIII BDD
(SEQ ID NO: 5)
MQIELSTCFFLCLLRFSFSATRRYYLGAVELSWDYMQSDLLGELHVDTRF
PPRVPRSFPFNTSVMYKKTVFVEFTDHLFNIAKPRPPWMGLLGPTIWAEV
YDTVVITLKNMASHPVSLHAVGVSYWKASEGAEYDDQTSQREKEDDKVFP
GESHTYVWQVLKENGPMASDPPCLTYSYLSHVDLVKDLNSGLIGALLVCR
EGSLAKERTQTLHEFVLLFAVFDEGKSWHSETKDSLTQAMDSASAQAWPK
MHTVNGYVNRSLPGLIGCHRKSVYWHVIGMGTTPEVHSIFLEGHTFLVRN
HRQASLEISPITFLTAQTLLMDLGQFLLFCHISSHQHDGMEAYVKVDSCP
EEPQLRMKNNEEEEDYDDDLDDSEMDVLRFDDDNSPSFIQIRSVAKKHPK
TWVHYIAAEEEDWDYAPSVLTPDDRSYKSQYLNNGPQRIGRKYKKVREMA
YTDETFKTREAIQYESGILGPLLYGEVGDTLLIIFKNQASRPYNIYPHGI
TDVSPLHSGRLPKGVKHLKDLPILPGEIFKYKWTVTVEDGPTKSDPRCLT
RYYSSFINLERDLASGLIGPLLICYKESVDQRGNQMMSDKRNVILFSVFD
ENQSWYLTENMQRFLPNAAGVQPQDPEFQASNIMHSINGYVFDSLQLSVC
LHEVAYWYILSVGAQTDFLSVFFSGYTFKHKMVYEDTLTLFPPFSGETVFM
SMENPGLWVLGCHNSDFRNRGMTALLKVSSCDRNTGDYYEDTYEDIPTYL

-continued

LSENNVIEPRSFSQNPPVLKHRQREITLTTLQSEQEEIDYDDTISIEMKR

EDFDIYGEDENQGPRSFQKRTRHYFIAAVERLWDYGMSSSPHVLRNRAQS

GSVPQFKKVVFQEFTDGSFTQPLYRGELNEHLGLLGPYIRAEVEDNIMVT

FKNQASRPYSFYSSLISYEEDQRQGAEPRKNFVKPNETKTYFWKVQHHMA

PTKDEFDCKAWAYFSDVDLEKDMHSGLIGPLLICHTNTLNPAHGRQVTVQ

EFALFFTIFDETKSWYFTENMERNCRAPCNIQMEDPTFKENYRFHAINGY

VMDTLPGLVMAQDQRIRWYLLSMGSNENIHSIHFSGHVFTVRKKEEYKMA

VYNLYPGVFETVEMLPSKAGIWRVECLIGEHLHAGMSTLFLVYSKQCQTP

LGMASGHIRDFQITASGQYGQWAPKLARLHYSGSINAWSTKEPFSWIKVD

LLAPMIIHGIKTQGARQKFSSLYISQFIIMYSLDGKKWQTYRGNSTGTLM

VFFGNVDSSGIKHNIFNPPIIARYIRLHPTHYSIRSTLRMELMGCDLNSC

SMPLGMESKAISDAQITASSYFTNMFATWSPSQARLHLQGRTNAWRPQVN

NPKEWLQVDFQKTMKVTGITTQGVKSLLTSMYVKEFLISSSQDGHHWTLF

FQNGKVKVFQGNQDSFTPVVNSLDPPLLTRYLRIHPQSWVHQIALRLEVL

GCEAQQLY

An97 fVIII BDD (SEQ ID NO: 6)
MQIELSTCFFLCLLRFSFSATRRYYLGAVELSWDYMQSDLLGELHVDTRF

PPRVPRSFPFNTSVMYKKTVFVEFTDHLFNIAKPRPPWMGLLGPTIQAEV

YDTVVITLKNMASHPVSLHAVGVSYWKASEGAEYDDQTSQREKEDDKVFP

GESHTYVWQVLKENGPMASDPPCLTYSYLSHVDLVKDLNSGLIGALLVCR

EGSLAKERTQTLHEFVLLFAVFDEGKSWHSETKDSLMQDTDSASAQAWPK

MHTVNGYVNRSLPGLIGCHRKSVYWHVIGMGTTPEVHSIFLEGHTFLVRN

HRQASLEISPITFLTAQTLLMDLGQFLLFCHISSHQHDGMEAYVKVDSCP

EEPQLRMKNNEEEEDYDNDLDDSEMDVLRFDDDNSPSFIQIRSVAKKHPK

TWVHYIAAEEEDWDYAPSVLTPDDRSYKSQYLNNGPQRIGRKYKKVRFMA

YTDETFKTREAIQYESGILGPLLYGEVGDTLLIIFKNQASRPYNIYPHGI

TDVSPLHSGRLPKGVKHLKDLPILPGEIFKYKWTVTVEDGPTKSDPRCLT

RYYSSFINLEEDLASGLIGPLLICYKESVDQRGNQMMSDKRNVILFSVFD

ENQSWYLTENMQRFLPNAAGVQPQDPEFQASNIMHSINGYVFDSLQLSVC

LHEVAYWYILSIGAQTDFLSVFFSGYTFKHKMVYEDTLTLFPFSGETVFM

SMENPGLWVLGCHNSDFRNRGMTALLKVSSCDRNTGDYYEDTYEDISTYL

LSENNVIEPRSFSQNPPVLKRHQREITLTTLQSDQEEIDYDDTISTEMKR

EDFDIYGEDENQGPRSFQKKTRHYFIAAVERLWDYGMSSSPHVLRNRAQS

GSVPQFKKVVFQEFTDGSFTQPLYRGELNEHLGLLGPYIRAEVEDNIMVT

FKNQASRPYSFYSSLISYEEDQRQGAEPRKNFVKPNETKTYFWKVQHHMA

PTKDEFDCKAWAYFSDVDLEKDMHSGLIGPLLICHTNTLNPAHGRQVTVQ

EFALFFTIFDETKSWYFTENMERNCRAPCNIQMEDPTFKENYRFHAINGY

VMDTLPGLVMAQDQRIRWYLLSMGSNENIHSIHFSGHVFTVRKKEEYKMA

VYNLYPGVFETVEMLPSKAGIWRVECLIGEHLHAGMSTLFLVYSKQCQTP

LGMASGHIRDFQITASGQYGQWAPKLARLHYSGSINAWSTKEPFSWIKVD

LLAPMIIHGIKTQGARQKFSSLYISQFIIMYSLDGKKWQTYRGNSTGTLM

VFFGNVDSSGIKHNIFNPPIIARYIRLHPTHYSIRSTLRMELMGCDLNSC

SMPLGMESKAISDAQITASSYFTNMFATWSPSQARLHLQGRTNAWRPQVN

NPKEWLQVDFQKTMKVTGITTQGVKSLLTSMYVKEFLISSSQDGHHWTLF

FQNGKVKVFQGNQDSFTPVVNSLDPPLLTRYLRIHPQSWVHQIALRLEVL

GCEAQQLY

The An84 fVIII sequence provided as SEQ ID NO: 3 includes a signal peptide (residues 1-19 of SEQ ID NO: 3, shown in bold), the A1 domain (residues 20-393 of SEQ ID NO: 3), a A2 domain (residues 394-760 of SEQ ID NO: 3), a B-domain deletion with the A2 domain and activation peptide linked by a linker (residues 761-774 of SEQ ID NO: 3, shown in bold underline), an activation peptide (residues 775-815 of SEQ ID NO: 3), a A3 domain (residues 816-1145 of SEQ ID NO: 3), a C1 domain (residues 1146-1298 of SEQ ID NO: 3), and a C2 domain (residues 1298-1458 of SEQ ID NO: 3). Corresponding domains are also present in SEQ ID NOs: 4-6.

The cDNA nucleotide sequence coding for these fIX proteins was optimized by implementing a codon usage bias specific for the human liver cell as compared to naturally occurring nucleotide sequence coding for the corresponding non-codon optimized sequence for a human, for example, using the liver-codon-optimization protocol described in WO 2016/168728. Nucleic acid sequences encoding SEQ ID NO: 3-6 that are codon-optimized for expression in liver tissue were generated, and are provided as follows:

An84 fVIII BDD (SEQ ID NO: 11)
*ATGCAGATCGAGCTGTCCACCTGCTTCTTCCTGTGCCTGCTGCGCTTCTCCTTCAGC*GCCACCCGCCGGTACTACCTGGG

AGCTGTGGAGCTGAGCTGGGACTACATGCAGTCCGACCTGCTGAGCGAGCTGCACGTGGACACCAGATTCCCACCCAGGG

TGCCAAGATCCTTCCCCTTCAACACCAGCGTGATGTACAAGAAGACCGTGTTCGTGGAGTTCACCGACCACCTGTTCAAC

ATCGCCAAGCCCAGGCCCCCCTGGATGGGCCTGCTGGGACCAACCATCTGGGCTGAGGTGTACGACACCGTCGTCATCAC

CCTGAAGAACATGGCCTCCCACCCCGTGAGCCTGCACGCTGTGGGCGTGTCCTACTGGAAGGCTAGCGAGGGAGCTGAGT

ACGACGACCAGACCTCCCAGAGAGAAGGAGGACGACAAGGTGTTCCCCGGCGAGAGCCACACCTACGTGTGGCAGGTG

CTGAAGGAGAACGGACCAATGGCTTCCGACCCACCATGCCTGACCTACTCCTACCTGAGCCACGTGGACCTGGTGAAGGA

CCTGAACTCCGGCCTGATCGGGGCCCTGCTGGTGTGCAGAGAGGGCAGCCTGGCTAAGGAGAGAACCCAGACCCTGCACG

-continued

```
AGTTCGTGCTGCTGTTCGCCGTGTTCGACGAGGGGAAGTCCTGGCACAGCGAAACCAAGGACTCCCTGACCCAGGCTATG

GACTCCGCCAGCGCCCAGGCTTGGCCAAAGATGCACACCGTGAACGGATACGTGAACCGCTCCCTGCCAGGCCTGATCGG

ATGCCACAGAAAGAGCGTGTACTGGCACGTGATCGGAATGGGAACCACCCCAGAGGTGCACAGCATCTTCCTGGAGGGGC

ACACCTTCCTGGTGCGCAACCACAGACAGGCTTCCCTGGAGATCAGCCCCATCACCTTCCTGACCGCTCAGACCCTGCTG

ATGGACCTGGGACAGTTCCTGCTGTTCTGCCACATCTCCAGCCACCAGCACGACGGGATGGAGGCCTACGTGAAGGTGGA

CTCCTGCCCAGAGGAGCCACAGCTGCGGATGAAGAACAACGAGGAGGAGGAGGACTACGACGACGACCTGGACGACTCCG

AGATGGACGTGCTGCGCTTCGACGACGACAACTCCCCCAGCTTCATCCAGATCCGGAGCGTGGCCAAGAAGCACCCCAAG

ACCTGGGTGCACTACATCGCTGCTGAGGAGGAGGACTGGGACTACGCTCCAAGCGTGCTGACCCCAGACGACAGGTCCTA

CAAGAGCCAGTACCTGAACAACGGCCCCCAGAGGATCGGGAGAAAGTACAAGAAGGTGAGGTTCATGGCCTACACCGACG

AAACCTTCAAGACCAGAGAGGCCATCCAGTACGAGTCCGAATCCTGGGACCACTGCTGTACGGAGAAGTGGGGGACACC

CTGCTGATCATCTTCAAGAACCAGGCCAGCAGGCCCTACAACATCTACCCACACGGAATCACCGACGTGTCCCCACTGCA

CAGCGGCAGACTGCCAAAGGGGGTGAAGCACCTGAAGGACCTGCCCATCCTGCCCGGCGAGATCTTCAAGTACAAGTGGA

CCGTGACCGTGGAGGACGGACCAACCAAGTCCGACCCACGCTGCCTGACCCGGTACTACTCCAGCTTCATCAACCTGGAG

CGCGACCTGGCTAGCGGCCTGATCGGACCCCTGCTGATCTGCTACAAGGAGTCCGTGGACCAGAGGGGCAACCAGATGAT

GAGCGACAAGAGAAACGTGATCCTGTTCTCCGTGTTCGACGAGAACCAGAGCTGGTACCTGACCGAAAACATGCAGCGGT

TCCTGCCCAACGCTGCTGGAGTGCAGCCACAGGACCCAGAGTTCCAGGCTTCCAACATCATGCACAGCATCAACGGCTAC

GTGTTCGACTCCCTGCAGCTGAGCGTGTGCCTGCACGAGGTGGCCTACTGGTACATCCTGTCCGTGGGAGCTCAAACCGA

CTTCCTGTCCGTGTTCTTCAGCGGGTACACCTTCAAGCACAAGATGGTGTACGAGGACACCCTGACCCTGTTCCCCTTCT

CCGGCGAAACCGTGTTCATGAGCATGGAGAACCCAGGCCTGTGGGTGCTGGGATGCCACAACTCCGACTTCAGGAACAGA

GGCATGACCGCCCTGCTGAAGGTGTCCAGCTGCGACCGCAACACCGGGGACTACTACGAGGACACCTACGAGGACATCCC

CACCTACCTGCTGAGCGAGAACAACGTGATCGAGCCACGGTCCTTCAGCCAGAACCCACCCGTGCTGAAGAGACACCAGA

GAGAGATCACCCTGACCACCCTGCAGTCCGAGCAGGAGGAGATCGACTACGACGACACCATCAGCATCGAGATGAAGAGG

GAGGACTTCGACATCTACGGCGAGGACGAGAACCAGGGGCCCAGATCCTTCCAGAAGCGCACCCGGCACTACTTCATCGC

TGCTGTGGAGCGCCTGTGGGACTACGGCATGTCCAGCTCCCCCCACGTGCTGAGGAACAGAGCTCAGTCCGGAAGCGTGC

CACAGTTCAAGAAGGTGGTGTTCCAGGAGTTCACCGACGGATCCTTCACCCAGCCACTGTACAGAGGAGAGCTGAACGAG

CACCTGGGCCTGCTGGGACCATACATCAGAGCCGAGGTGGAGGACAACATCATGGTGACCTTCAAGAACCAGGCCTCCCG

GCCCTACAGCTTCTACAGCTCCCTGATCAGCTACGAGGAGGACCAGAGGCAGGGAGCTGAGCCCAGAAAGAACTTCGTGA

AGCCCAACGAAACCAAGACCTACTTCTGGAAGGTGCAGCACCACATGGCCCCCACCAAGGACGAGTTCGACTGCAAGGCC

TGGGCCTACTTCTCCGACGTGGACCTGGAGAAGGACATGCACAGCGGCCTGATCGGACCACTGCTGATCTGCCACACCAA

CACCCTGAACCCAGCTCACGGCAGGCAGGTGACCGTGCAGGAGTTCGCCCTGTTCTTCACCATCTTCGACGAAACCAAGT

CCTGGTACTTCACCGAGAACATGGAGAGGAACTGCAGAGCCCCCTGCAACATCCAGATGGAGGACCCCACCTTCAAGGAG

AACTACAGATTCCACGCCATCAACGGCTACGTGATGGACACCCTGCCAGGCCTGGTCATGGCTCAGGACCAGCGCATCCG

GTGGTACCTGCTGTCCATGGGCAGCAACGAGAACATCCACTCCATCCACTTCAGCGGGCACGTGTTCACCGTGAGGAAGA

AGGAGGAGTACAAGATGGCCGTGTACAACCTGTACCCCGGCGTGTTCGAAACCGTGGAGATGCTGCCCAGCAAGGCCGGG

ATCTGGAGAGTGGAGTGCCTGATCGGAGAGCACCTGCACGCTGGAATGTCCACCCTGTTCCTGGTGTACAGCAAGCAGTG

CCAGACCCCACTGGGAATGGCTTCCGGACACATCCGCGACTTCCAGATCACCGCTAGCGGACAGTACGGACAGTGGGCTC

CCAAGCTGGCCCGGCTGCACTACTCCGGCAGCATCAACGCCTGGTCCACCAAGGAGCCCTTCAGCTGGATCAAGGTGGAC

CTGCTGGCCCCCATGATCATCCACGGCATCAAGACCCAGGGGGCCAGGCAGAAGTTCAGCTCCCTGTACATCTCCCAGTT

CATCATCATGTACAGCCTGGACGGCAAGAAGTGGCAGACCTACAGAGGCAACTCCACCGGGACCCTGATGGTGTTCTTCG

GCAACGTGGACAGCTCCGGGATCAAGCACAACATCTTCAACCCCCCCATCATCGCTAGATACATCAGACTGCACCCAACC

CACTACTCCATCAGGAGCACCCTGAGAATGGAGCTGATGGGCTGCGACCTGAACTCCTGCAGCATGCCCCTGGGGATGGA
```

-continued

GTCCAAGGCCATCAGCGACGCCCAGATCACCGCCAGCTCCTACTTCACCAACATGTTCGCTACCTGGTCCCCCAGCCAGG

CTAGACTGCACCTGCAGGGCCGCACCAACGCCTGGCGGCCCCAGGTGAACAACCCCAAGGAGTGGCTGCAGGTGGACTTC

CAGAAGACCATGAAGGTGACCGGCATCACCACCCAGGGCGTGAAGTCCCTGCTGACCAGCATGTACGTGAAGGAGTTCCT

GATCAGCTCCAGCCAGGACGGACACCACTGGACCCTGTTCCTGCAGAACGGCAAGGTGAAGGTGTTCCAGGGGAACCAGG

ACTCCTTCACCCCAGTGGTGAACAGCCTGGATCCACCACTGCTGACCAGGTACCTGAGAATCCACCCCCAGTCCTGGGTG

CACCAGATCGCCCTGAGACTGGAGGTGCTGGGATGCGAGGCCCAGCAGCTGTACTGA

An63 fVIII BDD (SEQ ID NO: 12)

ATGCAGATCGAGCTGAGCACCTGCTTCTTCCTGTGCCTGCTGCCCTTCAGCTTCTCCGCCACCCGCCGGTACTACCTGGG

AGCTGTGGAGCTGTCCTGGGACTACATGCAGAGCGACCTGCTGTCCGAGCTGCACGTGGACACCAGATTCCCACCCCGCG

TGCCACGGAGCTTCCCCTTCAACACCTCCGTGATGTACAAGAAGACCGTGTTCGTGGAGTTCACCGACCACCTGTTCAAC

ATCGCCAAGCCTCGCCCGCCCTGGATGGGCCTGCTGGGACCAACCATCCGGGCCGAGGTGTACGACACCGTCGTCATCAC

CCTGAAGAACATGGCCAGCCACCCCGTGTCCCTGCACGCTGTGGGCGTGAGCTACTGGAAGGCTTCCGAGGGAGCTGAGT

ACGACGACCAGACCAGCCAGCGGGAGAAGGAGGACGACAAGGTCATCCCCGGCGAGTCCCACACCTACGTGTGGCAGGTG

CTGAAGGAGAACGGACCAATGGCTTCCGACCCACCATGCCTGACCTACAGCTACCTGTCCCACGTGGACCTGGTGAAGGA

CCTGAACAGCGGCCTGATCGGGCCCTGCTGGTGTGCAGAGAGGGCTCCCTGGCTAAGGAGAGAACCCAGACCCTGCACG

AGTTCGTGCTGCTGTTCGCCGTGTTCGACGAGGGGAAGAGCTGGCACTCCGAGGCCAACGAGAGCCTGACCCAGGCTATG

GACAGCGCCTCCGCCCGCCCCTGGCCCAAGATGCACACCGTGAACGGCTACGTGAACAGGAGCCTGCCAGGCCTGATCGG

ATGCCACAGAAAGTCCGTGTACTGGCACGTGATCGGAATGGGAACCACCCCAGAGGTGCACTCCATCTTCCTGGAGGGGC

ACACCTTCCTGGTGAGGAACCACAGACAGGCCAGCCTGGAGATCTCCCCCATCACCTTCCTGACCGCTCAGACCCTGCTG

ATGGACCTGGGACAGTTCCTGCTGTTCTGCCACATCCCAAGCCACCAGCACGACGGAATGGAGGCCTACGTGAAGGTGGA

CTCCTGCCCAGAGGAGCCACAGCTGAGGATGAAGAACAACGAGGAGGAGGAGGACTACGACGACGACCTGTACGACAGCG

ACATGGACGTGCTGCGCTTCGACGACGACAACAGCCCCCCCTTCATCCAGATCCGGTCCGTGGCCAAGAAGCACCCCAAG

ACCTGGATCCACTACATCGCTGCTGAGGAGGAGGACTGGGACTACGCTCCATCCGTGCTGACCCCAACCGACAGAAGCTA

CAAGTCCCAGTACCTGAACAACGGACCACAGAGAATCGGACGGAAGTACAAGAAGGTGAGGTTCATGGCCTACACCGACG

AAACCTTCAAGACCAGAGAGGCCATCCAGTACGAGAGCGGAATCCTGGGACCACTGCTGTACGGAGAAGTGGGGGACACC

CTGCTGATCATCTTCAAGAACCAGGCCTCCCGCCCCTACAACATCTACCCCCACGGCATCACCAACGTGAGCCCACTGCA

CTCCGGCCGGCTGCCCAAGGGGGTGAAGCACCTGAAGGACATGCCCATCATGCCCGGCGAGATCTTCAAGTACAAGTGGA

CCGTGACCCTGGAGGACGGACCAACCAAGAGCGACCCACGCTGCCTGACCCGGTACTACTCCAGCTTCATCAACCTGGAG

CGCGACCTGGCTTCCGGCCTGATCGGACCCCTGCTGATCTGCTACAAGGAGAGCGTGGACCAGCGCGGCAACCAGATGAT

GTCCGACAAGCGGAACGTGATCCTGTTCAGCGTGTTCGACGAGAACCGCTCCTGGTACCTGACCGAGAACATGCAGCGGT

TCCTGCCCAACGCTGCTGGAGTGCAGCCACAGGACCCAGAGTTCCAGGCTAGCAACATCATGCACTCCATCAACGGCTAC

GTGTTCGACAGCCTGCAGCTGTCCGTGTGCCTGCACGAGGTGGCCTACTGGTACATCCTGTCCGTGGGAGCTCAGACCGA

CTTCCTGAGCGTGTTCTTCTCCGGGTACACCTTCAAGCACAAGATGGTGTTCGAGGACACCCTGACCCTGTTCCCCTTCA

GCGGCGAAACCGTGTTCATGTCCATGGAGAACCCAGGCCTGTGGGTGCTGGGATGCCACAACTCCGACTTCAGGAACAGA

GGGATGACCGCCCTGCTGAAGGTGTCCAGCTGCGACCGGAACACCGACGACTACTACGAGGACACCTACGAGGACATCCC

CACCTACCTGCTGAACGAGAACAACGTGATCGAGCCCAGGAGCTTCTCCCAGAACCCCCCCGTGCTGAAGCACCACCAGA

GAGAGATCACCCTGACCACCCTGCAGCCCGAGCAGGAGAAGATCGACTACGACGACACCCTGAGCATCGAGATGAAGCGC

GAGGACTTCGACATCTACGGAGAGGACGAGAACCAGGGACCACGGTCCTTCCAGAAGAGAACCCGGCACTACTTCATCGC

TGCTGTGGAGAGGCTGTGGGACTACGGCATGAGCAGATCCCCCCACGCCCTGAGGAACAGAGCTCAGAGCGGATCCGTGC

CACAGTTCAAGAAGGTGGTGTTCCAGGAGTTCACCGACGGCAGCTTCACCCAGCCCCTGTACAGGGGAGAGCTGAACGAG

-continued

```
CACCTGGGCCTGCTGGGACCCTACATCAGAGCCGAGGTGGAGGACAACATCATGGTGACCTTCAAGAACCAGGCCAGCCG
CCCCTACTCCTTCTACTCCAGCCTGATCTCCTACGAGGAGGACCAGAGGCAGGGAGCTGAGCCCAGAAAGAACTTCGTGA
AGCCCAACGAAACCAAGACCTACTTCTGGAAGGTGCAGCACCACATGGCCCCCACCAAGGACGAGTTCGACTGCAAGGCC
TGGGCCTACTTCAGCGACGTGGACCTGGAGAAGGACCTGCACTCCGCCTGATCGGACCACTGCTGATCTGCAGGACCAA
CACCCTGAACCCAGCTCACGGCAGACAGCTGACCGTGCAGGAGTTCGCCCTGTTCTTCACCATCTTCGACGAAACCAAGT
CCTGGTACTTCACCGAGAACATGGAGAGGAACTGCAGAGCCCCCTGCAACATCCAGATGGAGGACCCCACCTTCAAGAAG
AACTACAGGTTCCACGCCATCAACGGCTACGTGATGGACACCCTGCCAGGCCTGGTCATGGCTCAGGACCAGCGCATCCG
GTGGTACCTGCTGAGCATGGGCTCCAACGAGAACATCCACAGCATCCACTTCTCCGGGCACGTGTTCACCGTGCGCAAGA
AGGAGGAGTACAAGATGGCCGTGTACAACCTGTACCCCGGCGTGTTCGAAACCGTGGAGATGCTGCCAAGCAAGGCTGGA
ATCTGGAGAGTGGAGTGCCTGATCGGAGAGCACCTGCAGGCTGGAATGAGCACCCTGTTCCTGGTGTACTCCAAGGAGTG
CCAGACCCCACTGGGAATGGCTTCCGGGAGGATCAGAGACAGCCAGATCACCGCTTCCGGACAGTACGGACAGTGGGCTC
CCAAGCTGGCCCGGCTGCACTACAGCGGCTCCATCAACGCCTGGAGCACCAAGGACCCCTTCTCCTGGATCAAGGTGGAC
CTGCTGGCCCCCATGATCATCCACGGCATCAAGACCCAGGGGCCAGGCAGAAGTTCTCCAGCCTGTACATCAGCCAGTT
CATCATCATGTACTCCCTGGACGGCAAGAAGTGGCAGAGCTACAGAGGCAACTCCACCGGGACCCTGATGGTGTTCTTCG
GCAACGTGGACTCCAGCGGGATCAAGCACAACATCTTCAACCCCCCCATCATCGCTAGATACATCAGACTGCACCCAACC
CACTACAGCATCAGGTCCACCCTGAGAATGGAGCTGATGGGCTGCGACCTGAACAGCTGCTCCATGCCCCTGGGGATGGA
GAGCAAGGCCATCTCCGACGCCCAGATCACCGCCTCCAGCTACTTCACCAACATGTTCGCCACCTGGAGCCCCTCCCAGG
CCAGGCTGCACCTGCAGGGAAGAACCAACGCTTGGCGGCCCCAGGTGAACAACCCCAAGGAGTGGCTGCAGGTGGACTTC
CAGAAGACCATGAAGGTGACCGGAATCACCACCCAGGGAGCTAAGAGCCTGCTGACCTCCATGTACGTGAAGGAGTTCCT
GATCTCCAGCTCCAGGACGGACACCACTGGACCCTGTTCCTGCAGAACGGCAAGGTGAAGGTGTTCCAGGGGAACCAGG
ACAGCTTCACCCCAGTGGTGAACTCCCTGGATCCACCACTGCTGACCAGGTACCTGAGAATCCACCCCCAGTCCTGGGTG
CACCACATCGCCCTGAGACTGGAGGTGCTGGGATGCGAGGCTCAGCAGCTGTACTGAGCGGCCGCTGA
```

An96 fVIII BDD (SEQ ID NO: 13)
```
ATGCAGATCGAGCTGTCCACCTGCTTCTTCCTGTGCCTGCTGCGCTTCTGCTTCAGCGCCACCCGCCGGTACTACCTGGG
AGCTGTGGAGCTGTCCTGGGACTACATGCAGAGCGACCTGCTGGGAGAGCTGCACGTGGACACCAGATTCCCACCCAGGG
TGCCAAGATCCTTCCCCTTCAACACCAGCGTGATGTACAAGAAGACCGTGTTCGTGGAGTTCACCGACCACCTGTTCAAC
ATCGCCAAGCCCAGGCCCCCCTGGATGGGCCTGCTGGGACCAACCATCTGGGCTGAGGTGTACGACACCGTCGTCATCAC
CCTGAAGAACATGGCCTCCCACCCCGTGAGCCTGCACGCTGTGGGCGTGTCCTACTGGAAGGCTAGCGAGGGAGCTGAGT
ACGACGACCAGACCTCCCAGAGAGAGAAGGAGGACGACAAGGTGTTCCCCGGCGAGAGCCACACCTACGTGTGGCAGGTG
CTGAAGGAGAACGGACCAATGGCTTCCGACCCACCATGCCTGACCTACTCCTACCTGAGCCACGTGGACCTGGTGAAGGA
CCTGAACTCCGGCCTGATCGGGGCCCTGCTGGTGTGCAGAGAGGGCAGCCTGGCTAAGGAGAGAACCCAGACCCTGCACG
AGTTCGTGCTGCTGTTCGCCGTGTTCGACGAGGGGAAGTCCTGGCACAGCGAAACCAAGGACTCCCTGACCCAGGCTATG
GACTCCGCCAGCGCCCAGGCTTGGCCAAAGATGCACACCGTGAACGGATACGTGAACCGCTCCCTGCCAGGCCTGATCGG
ATGCCACAGAAAGAGCGTGTACTGGCACGTGATCGGAATGGGAACCACCCCAGAGGTGCACAGCATCTTCCTGGAGGGGC
ACACCTTCCTGGTGCGCAACCACAGACAGGCTTCCCTGGAGATCAGCCCCATCACCTTCCTGACCGCTCAGACCCTGCTG
ATGGACCTGGGACAGTTCCTGCTGTTCTGCCACATCTCCAGCCACCAGCACGACGGGATGGAGGCCTACGTGAAGGTGGA
CTCCTGCCCAGAGGAGCCACAGCTGCGGATGAAGAACAACGAGGAGGAGGAGGACTACGACGACGACCTGGACGACTCCG
AGATGGACGTGCTGCGCTTCGACGACGACAACTCCCCCCAGCTTCATCCAGATCCGGAGCGTGGCCAAGAAGCACCCCAAG
ACCTGGGTGCACTACATCGCTGCTGAGGAGGAGGACTGGGACTACGCTCCAAGCGTGCTGACCCCAGACGACAGGTCCTA
CAAGAGCCAGTACCTGAACAACGGCCCCCAGAGGATCGGGAGAAAGTACAAGAAGGTGAGGTTCATGGCCTACACCGACG
AAACCTTCAAGACCAGAGAGGCCATCCAGTACGAGTCCGGAATCCTGGGACCACTGCTGTACGGAGAAGTGGGGGACACC
```

-continued

```
CTGCTGATCATCTTCAAGAACCAGGCCAGCAGGCCCTACAACATCTACCCACACGGAATCACCGACGTGTCCCCACTGCA
CAGCGGCAGACTGCCAAAGGGGGTGAAGCACCTGAAGGACCTGCCCATCCTGCCCGGCGAGATCTTCAAGTACAAGTGGA
CCGTGACCGTGGAGGACGGACCAACCAAGTCCGACCCACGCTGCCTGACCCGGTACTACTCCAGCTTCATCAACCTGGAG
CGCGACCTGGCTAGCGGCCTGATCGGACCCCTGCTGATCTGCTACAAGGAGTCCGTGGACCAGAGGGGCAACCAGATGAT
GAGCGACAAGAGAAACGTGATCCTGTTCTCCGTGTTCGACGAGAACCAGAGCTGGTACCTGACCGAAAACATGCAGCGGT
TCCTGCCCAACGCTGCTGGAGTGCAGCCACAGGACCCAGAGTTCCAGGCTTCCAACATCATGCACAGCATCAACGGCTAC
GTGTTCGACTCCCTGCAGCTGAGCGTGTGCCTGCACGAGGTGGCCTACTGGTACATCCTGTCCGTGGGAGCTCAAACCGA
CTTCCTGTCCGTGTTCTTCAGCGGGTACACCTTCAAGCACAAGATGGTGTACGAGGACACCCTGACCCTGTTCCCCTTCT
CCGGCGAAACCGTGTTCATGAGCATGGAGAACCCAGGCCTGTGGGTGCTGGGATGCCACAACTCCGACTTCAGGAACAGA
GGCATGACCGCCCTGCTGAAGGTGTCCAGCTGCGACCGCAACACCGGGGACTACTACGAGGACACCTACGAGGACATCCC
CACCTACCTGCTGAGCGAGAACAACGTGATCGAGCCACGGTCCTTCAGCCAGAACCCACCCGTGCTGAAGAGACACCAGA
GAGAGATCACCCTGACCACCCTGCAGTCCGAGCAGGAGGAGATCGACTACGACGACACCATCAGCATCGAGATGAAGAGG
GAGGACTTCGACATCTACGGCGAGGACGAGAACCAGGGGCCCAGATCCTTCCAGAAGCGCACCCGGCACTACTTCATCGC
TGCTGTGGAGCGCCTGTGGGACTACGGCATGTCCAGCTCCCCCACGTGCTGAGGAACAGAGCTCAGTCCGGAAGCGTGC
CACAGTTCAAGAAGGTGGTGTTCCAGGAGTTCACCGACGGATCCTTCACCCAGCCACTGTACAGAGGAGAGCTGAACGAG
CACCTGGGCCTGCTGGGACCATACATCAGAGCCGAGGTGGAGGACAACATCATGGTGACCTTCAAGAACCAGGCCTCCCG
GCCCTACAGCTTCTACAGCTCCCTGATCAGCTACGAGGAGGACCAGAGGCAGGGAGCTGAGCCCAGAAAGAACTTCGTGA
AGCCCAACGAAACCAAGACCTACTTCTGGAAGGTGCAGCACCACATGGCCCCCACCAAGGACGAGTTCGACTGCAAGGCC
TGGGCCTACTTCTCCGACGTGGACCTGGAGAAGGACATGCACAGCGGCCTGATCGGACCACTGCTGATCTGCCACACCAA
CACCCTGAACCCAGCTCACGGCAGGCAGGTGACCGTGCAGGAGTTCGCCCTGTTCTTCACCATCTTCGACGAAACCAAGT
CCTGGTACTTCACCGAGAACATGGAGAGGAACTGCAGAGCCCCTGCAACATCCAGATGGAGGACCCCACCTTCAAGGAG
AACTACAGATTCCACGCCATCAACGGCTACGTGATGGACACCCTGCCAGGCCTGGTCATGGCTCAGGACCAGCGCATCCG
GTGGTACCTGCTGTCCATGGGCAGCAACGAGAACATCCACTCCATCCACTTCAGCGGGCACGTGTTCACCGTGAGGAAGA
AGGAGGAGTACAAGATGGCCGTGTACAACCTGTACCCCGGCGTGTTCGAAACCGTGGAGATGCTGCCCAGCAAGGCCGGG
ATCTGGAGAGTGGAGTGCCTGATCGGAGAGCACCTGCACGCTGGAATGTCCACCCTGTTCCTGGTGTACAGCAAGCAGTG
CCAGACCCCACTGGGAATGGCTTCCGGACACATCCGCGACTTCCAGATCACCGCTAGCGGACAGTACGGACAGTGGGCTC
CCAAGCTGGCCCGGCTGCACTACTCCGGCAGCATCAACGCCTGGTCCACCAAGGAGCCCTTCAGCTGGATCAAGGTGGAC
CTGCTGGCCCCCATGATCATCCACGGCATCAAGACCCAGGGGGCCAGGCAGAAGTTCAGCTCCCTGTACATCTCCCAGTT
CATCATCATGTACAGCCTGGACGGCAAGAAGTGGCAGACCTACAGAGGCAACTCCACCGGGACCCTGATGGTGTTCTTCG
GCAACGTGGACAGCTCCGGGATCAAGCACAACATCTTCAACCCCCCCATCATCGCTAGATACATCAGACTGCACCCAACC
CACTACTCCATCAGGAGCACCCTGAGAATGGAGCTGATGGGCTGCGACCTGAACTCCTGCAGCATGCCCCTGGGGATGGA
GTCCAAGGCCATCAGCGACGCCCAGATCACCGCCAGCTCCTACTTCACCAACATGTTCGCTACCTGGTCCCCAGCCAGG
CTAGACTGCACCTGCAGGGCCGCACCAACGCCTGGCGGCCCCAGGTGAACAACCCCAAGGAGTGGCTGCAGGTGGACTTC
CAGAAGACCATGAAGGTGACCGGCATCACCACCCAGGGCGTGAAGTCCCTGCTGACCAGCATGTACGTGAAGGAGTTCCT
GATCAGCTCCAGCCAGGACGGACACCACTGGACCCTGTTCTTCCAGAACGGCAAGGTGAAGGTGTTCCAGGGGAACCAGG
ACTCCTTCACCCCAGTGGTGAACAGCCTGGATCCACCACTGCTGACCAGGTACCTGAGAATCCACCCCCAGTCCTGGGTG
CACCAGATCGCCCTGAGACTGGAGGTGCTGGGATGCGAGGCCCAGCAGCTGTACTGA
```

An97 fVIII BDD (SEQ ID NO: 14)

*ATGCAGATCGAGCTGTCCACCTGCTTCTTCCTGTGCCTGCTGCGCTTCTCCTTCAGC*GCCACCCGCCGGTACTACCTGGG

AGCTGTGGAGCTGTCCTGGGACTACATGCAGAGCGACCTGCTGGGAGAGCTGCACGTGGACACCAGATTCCCACCCCGCG

-continued

```
TGCCACGGTCCTTCCCCTTCAACACCAGCGTGATGTACAAGAAGACCGTGTTCGTGGAGTTCACCGACCACCTGTTCAAC
ATCGCCAAGCCCAGGCCCCCCTGGATGGGCCTGCTGGGACCAACCATCCAGGCTGAGGTGTACGACACCGTCGTCATCAC
CCTGAAGAACATGGCCTCCCACCCCGTGAGCCTGCACGCTGTGGGCGTGTCCTACTGGAAGGCTAGCGAGGGAGCTGAGT
ACGACGACCAGACCTCCCAGCGCGAGAAGGAGGACGACAAGGTGTTCCCCGGCGAGAGCCACACCTACGTGTGGCAGGTG
CTGAAGGAGAACGGACCAATGGCTTCCGACCCACCATGCCTGACCTACTCCTACCTGAGCCACGTGGACCTGGTGAAGGA
CCTGAACTCCGCCTGATCGGGGCCCTGCTGGTGTGCAGAGAGGGCAGCCTGGCTAAGGAGAGAACCCAGACCCTGCACG
AGTTCGTGCTGCTGTTCGCCGTGTTCGACGAGGGGAAGTCCTGGCACAGCGAAACCAAGGACTCCCTGATGCAGGATACC
GACTCCGCCAGCGCCCAGGCTTGGCCAAAGATGCACACCGTGAACGGATACGTGAACCGCTCCCTGCCAGGCCTGATCGG
ATGCCACAGAAAGAGCGTGTACTGGCACGTGATCGGAATGGGAACCACCCCAGAGGTGCACAGCATCTTCCTGGAGGGGC
ACACCTTCCTGGTGAGGAACCACAGACAGGCCTCCCTGGAGATCAGCCCCATCACCTTCCTGACCGCTCAGACCCTGCTG
ATGGACCTGGGACAGTTCCTGCTGTTCTGCCACATCTCCAGCCACCAGCACGACGGGATGGAGGCCTACGTGAAGGTGGA
CTCCTGCCCAGAGGAGCCACAGCTGCGGATGAAGAACAACGAGGAGGAGGAGGACTACGACAACGACCTGGACGACTCCG
AGATGGACGTGCTGCGCTTCGACGACGACAACTCCCCCAGCTTCATCCAGATCCGGAGCGTGGCCAAGAAGCACCCCAAG
ACCTGGGTGCACTACATCGCTGCTGAGGAGGAGGACTGGGACTACGCTCCAAGCGTGCTGACCCCAGACGACAGGTCCTA
CAAGAGCCAGTACCTGAACAACGGACCACAGAGAATCGGACGGAAGTACAAGAAGGTGAGGTTCATGGCCTACACCGACG
AAACCTTCAAGACCAGAGAGGCCATCCAGTACGAGTCCGGAATCCTGGGACCACTGCTGTACGGAGAAGTGGGGGACACC
CTGCTGATCATCTTCAAGAACCAGGCCAGCCGCCCCTACAACATCTACCCACACGGAATCACCGACGTGTCCCCACTGCA
CAGCGGCCGGCTGCCCAAGGGGGTGAAGCACCTGAAGGACCTGCCCATCCTGCCCGGCGAGATCTTCAAGTACAAGTGGA
CCGTGACCGTGGAGGACGGACCAACCAAGTCCGACCCAAGGTGCCTGACCAGATACTACTCCAGCTTCATCAACCTGGAG
CGCGACCTGGCTAGCGGCCTGATCGGACCCCTGCTGATCTGCTACAAGGAGTCCGTGGACCAGAGGGGCAACCAGATGAT
GAGCGACAAGAGAAACGTGATCCTGTTCTCCGTGTTCGACGAGAACCAGAGCTGGTACCTGACCGAAAACATGCAGCGGT
TCCTGCCCAACGCTGCTGGAGTGCAGCCACAGGACCCAGAGTTCCAGGCTTCCAACATCATGCACAGCATCAACGGCTAC
GTGTTCGACTCCCTGCAGCTGAGCGTGTGCCTGCACGAGGTGGCCTACTGGTACATCCTGTCCATCGGCGCCCAGACCGA
CTTCCTGTCCGTGTTCTTCAGCGGGTACACCTTCAAGCACAAGATGGTGTACGAGGACACCCTGACCCTGTTCCCCTTCT
CCGGCGAAACCGTGTTCATGAGCATGGAGAACCCAGGCCTGTGGGTGCTGGGATGCCACAACAGCGACTTCAGGAACAGA
GGCATGACCGCCCTGCTGAAGGTGTCCAGCTGCGACAGGAACACCGGGGACTACTACGAGGACACCTACGAGGACATCTC
CACCTACCTGCTGAGCGAGAACAACGTGATCGAGCCCAGATCCTTCAGCCAGAATCCCCCCGTGCTGAAGAGGCACCAGA
GAGAGATCACCCTGACCACCCTGCAGTCCGATCAGGAGGAGATCGACTACGACGACACCATCAGCACCGAGATGAAGCGC
GAGGACTTCGACATCTACGGAGAGGACGAGAACCAGGGACCAAGGTCCTTCCAGAAGAAGACCAGACACTACTTCATCGC
TGCTGTGGAGCGGCTGTGGGACTACGGAATGTCCAGCTCCCCACACGTGCTGAGAAACAGAGCTCAGTCCGGGAGCGTGC
CCCAGTTCAAGAAGGTGGTGTTCCAGGAGTTCACCGACGGCTCCTTCACCCAGCCCCTGTACAGGGGAGAGCTGAACGAG
CACCTGGGCCTGCTGGGACCCTACATCAGAGCCGAGGTGGAGGACAACATCATGGTGACCTTCAAGAACCAGGCCTCCCG
CCCCTACAGCTTCTACAGCTCCCTGATCAGCTACGAGGAGGACCAGAGACAGGGAGCTGAGCCACGGAAGAACTTCGTGA
AGCCCAACGAAACCAAGACCTACTTCTGGAAGGTGCAGCACCACATGGCCCCCACCAAGGACGAGTTCGACTGCAAGGCC
TGGGCCTACTTCTCCGACGTGGACCTGGAGAAGGACATGCACAGCGGCCTGATCGGACCACTGCTGATCTGCCACACCAA
CACCCTGAACCCAGCTCACGGCAGGCAGGTGACCGTGCAGGAGTTCGCCCTGTTCTTCACCATCTTCGACGAAACCAAGT
CCTGGTACTTCACCGAGAACATGGAGCGCAACTGCCGGGCCCCCTGCAACATCCAGATGGAGGACCCCACCTTCAAGGAG
AACTACAGATTCCACGCCATCAACGGCTACGTGATGGACACCCTGCCAGGCCTGGTCATGGCTCAGGACCAGAGGATCAG
ATGGTACCTGCTGTCCATGGGCAGCAACGAGAACATCCACTCCATCCACTTCAGCGGGCACGTGTTCACCGTGAGGAAGA
AGGAGGAGTACAAGATGGCCGTGTACAACCTGTACCCCGGCGTGTTCGAAACCGTGGAGATGCTGCCCAGCAAGGCCGGG
ATCTGGAGAGTGGAGTGCCTGATCGGAGAGCACCTGCACGCTGGAATGTCCACCCTGTTCCTGGTGTACAGCAAGCAGTG
```

```
CCAGACCCCACTGGGAATGGCTTCCGGACACATCAGGGACTTCCAGATCACCGCTAGCGGACAGTACGGACAGTGGGCTC

CAAAGCTGGCTAGACTGCACTACTCCGGCAGCATCAACGCCTGGTCCACCAAGGAGCCCTTCAGCTGGATCAAGGTGGAC

CTGCTGGCCCCCATGATCATCCACGGCATCAAGACCCAGGGAGCTAGACAGAAGTTCAGCTCCCTGTACATCTCCCAGTT

CATCATCATGTACAGCCTGGACGGCAAGAAGTGGCAGACCTACCGGGGCAACTCCACCGGGACCCTGATGGTGTTCTTCG

GCAACGTGGACAGCTCCGGGATCAAGCACAACATCTTCAACCCCCCCATCATCGCCAGGTACATCAGACTGCACCCCACC

CACTACTCCATCCGCAGCACCCTGCGGATGGAGCTGATGGGCTGCGACCTGAACTCCTGCAGCATGCCCCTGGGGATGGA

GTCCAAGGCCATCAGCGACGCCCAGATCACCGCCAGCTCCTACTTCACCAACATGTTCGCTACCTGGTCCCCCAGCCAGG

CTAGACTGCACCTGCAGGGAAGGACCAACGCTTGGCGCCCCCAGGTGAACAACCCCAAGGAGTGGCTGCAGGTGGACTTC

CAGAAGACCATGAAGGTGACCGGCATCACCACCCAGGGCGTGAAGTCCCTGCTGACCAGCATGTACGTGAAGGAGTTCCT

GATCAGCTCCAGCCAGGACGGACACCACTGGACCCTGTTCTTCCAGAACGGCAAGGTGAAGGTGTTCCAGGGGAACCAGG

ACTCCTTCACCCCAGTGGTGAACAGCCTGGATCCACCACTGCTGACCAGATACCTGCGGATCCACCCCCAGTCCTGGGTG

CACCAGATCGCCCTGAGACTGGAGGTGCTGGGATGCGAGGCCCAGCAGCTGTACTGAGCGGCCGCTGA
```

In SEQ ID NOs: 12-14, the signal peptide is shown in bold. The liver codon-optimized fVIII BDD sequences can be included in a vector (such as an AAV vector) and operably linked to a promoter (such as a liver specific promoter, for example, the HCB promoter) for administration to a subject, for example, to treat hemophilia A in the subject.

Figure 5:
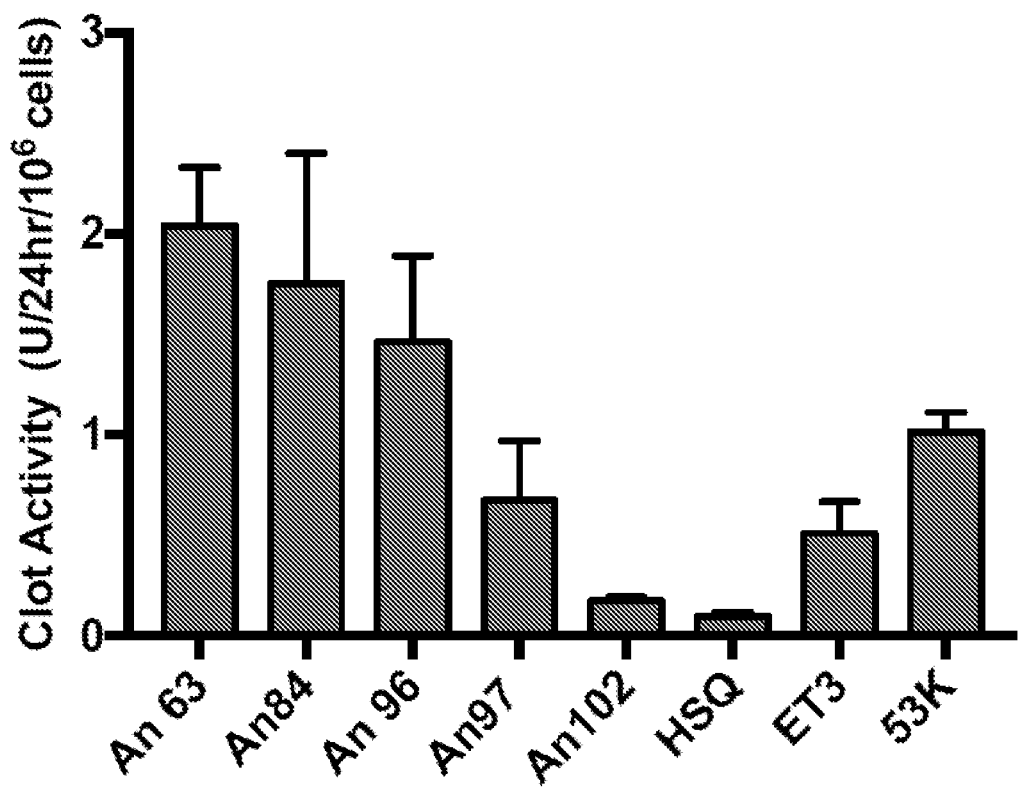
FIG. 5 shows fVIII activity levels of various fVIII variants expressed in HEK293T17 cells using plasmid DNA expression vectors encoding the indicated fVIII variants.

In vitro clotting activity of the optimized fVIII sequences was assessed (see FIG. 5). The AN63, An84, AN96, An97, An102, HSQ, Et3 and 53K fVIII proteins were expressed in HEK293T17 cells using transiently transfected expression vectors. The HEK293T17 cells were transiently transfected with 500 ng of plasmid DNA encoding the indicated fVIII proteins using PEI in a 2:1 (w:w) ratio in 24 well plates. Media was changed to serum-free SFM4CHO media 24-hours prior to supernatant collection. Each construct transfected in triplicate, and fVIII activity was measured via one-stage coagulation assay. All constructs were liver-codon-optimized and the transgenes were driven by an EF1α promoter.

Example 3

Bioengineering Coagulation Factor VIII Through Ancestral Protein Reconstruction This example illustrates the optimization of fVII sequences to improve clotting factor activity, protein expression and therapeutic applications such as gene therapy.

The development of transformative hemophilia therapeutics has been hindered by the size, instability, immunogenicity and biosynthetic inefficiency of coagulation factors such as fVII for treatment of congenital proconvertin deficiency. Accordingly, it is desirable to find additional fVII sequences that have increased activity (for example, due to increased serum half-life or increased enzymatic activity) because it is possible that the frequency of infusion may be lessened while still achieving full prophylaxis.

To search for additional fVII sequences that may facilitate improved therapy, such as clotting factor replacement therapy, a mammalian fVII phylogenetic tree with corresponding ancestral node (An) sequences was constructed through Bayesian inference using both DNA and amino acid-based models in PAML Version 4.1. Initially, nine An-fVII sequences were selected for reconstruction, as follows:

An61 fVII (SEQ ID NO: 8)

*MHSRRLAFLCFLLGLQQSLT*AVFINQEEANSVLHRQRRANSFLEELRSG

SLERECKEEQCSFEEAREIFKSTERTKQFWITYNDGNQCASNPCQNGGS

CVDQLQSYICFCLEDFEGRNCETNKNSQLICMNENGGCEQYCSDNPETK

RSCRCHEGYTLMADGVSCTPTVEYPCGKIPVLEKRNDSNPQGRIVGGKV

CPKGECPWQAVIKLNGELLCGGTLLDATWVVSAAHCFDKLRNWKNLTVV

LGEHDLSEEDGDEQERQVAQIIIPDKYIPGKTDHDIALLRLRTPVNFTD

YVVPLCLPEKAFSEQTLAYIRFSSVSGWGQLLDRGATALELMTIDVPRL

MTQDCLEQTKRTANSPAITENMFCAGYLDGTKDACKGDSGGPHATKYQG

TWYLTGIVSWGEGCAAVGHFGVYTRVSQYIEWLNRLMDSKPSPGVLLRA

PFP

An63 fVII (SEQ ID NO: 35)

*MVSQPRGLALICFLLGLQGSLA*AVFITQEEAHSVLHRQRRANSFLEELR

PGSLERECREEQCSFEEAREIFKNTERTKQFWISYNDGDQCASNPCQNG

GSCEDQLQSYICFCPEDFEGRNCETNKNDQLICMNENGGCEQYCSDHAE

ARRSCRCHEGYTLQADGVSCTPTVEYPCGKIPVLEKRNDSNPQGRIVGG

KVCPKGECPWQAALKLNGELLCGGTLLDTTWVVSAAHCFDRIRSWKNLT

VVLGEHDLSEEDGDEQERQVAQIIIPDKYVPRKTDHDIALLRLRRPVAF

TDHVVPLCLPEKAFSERTLAFIRFSSVSGWGQLLDRGATALELMAIDVP

RLMTQDCLEQSRRRAGSPAITENMFCAGYLDGSKDACKGDSGGPHATKF

QGTWYLTGWSWGEGCAAEGHFGVYTRVSQYIEWLHRLMSSEPHSGGLLR

APLP

An68 fVII (SEQ ID NO: 36)

*MASRGLALLCLLLGLQGSLA*AVFITQEQAHSVLHRQRRANSFLEELWPG

SLERECREEQCSFEEAREIFKNEERTKQFWISYNDGDQCASNPCQNGGS

CEDQLQSYICFCPEGFEGRNCETNKKSQLICMNDNGGCEQYCSDHAEAG

RSCWCHEGYALQADGVSCTPTVEYPCGKIPVLEKRNDSNPQGRIVGGKV

-continued

CPKGECPWQAMLKLNGALLCGGTLLDTTWVVSAAHCFDRIRSWRNLTVV
LGEHDLSQDEGDEQERQVAQVIVPDKYVPGKTDHDLALLRLARPVALSD
HVVPLCLPERAFSERTLAFVRFSAVSGWGQLLDRGATARVLMAIQVPRL
MTQDCLEQSRRRPGSPAITDNMFCAGYLDGSKDACKGDSGGPHATRFRG
TWYLTGVVSWGEGCAAAGHFGVYTRVSRYTAWLHRLMGSPPSSGGLLRA
PLP

An81 fVII (SEQ ID NO: 7)

*MAPRALALLCFLLGLQGSLA*AVFITQEEAHSVLHRQRRANSFLEELRPG
SLERECKEEQCSFEEAREIFRSTERTKQFWISYNDGDQCASNPCQNGGS
CEDQLQSYICFCLPDFEGRNCETNKNDQLICMNENGGCEQYCSDHAEAK
RSCRCHEGYTLQADGVSCTPTVEYPCGKIPVLEKRNASNPQGRIVGGKV
CPKGECPWQAVLKLNGALLCGGTLLDTSWVVSAAHCFDKIRSWRNLTVV
LGEHDLSEEDGDEQERQVAQVIIPDKYVPGKTDHDIALLRLRRPVALTD
HVVPLCLPERAFSERTLAYIRFSRVSGWGQLLDRGATALELMAIDVPRL
MTQDCLEQSKRRADSPAITENMFCAGYLDGSKDACKGDSGGPHATRYRG
TWYLTGVVSWGEGCAAVGHFGVYTRVSQYTEWLSRLMDSEPHPGVLLRA
PFP

An85 fVII (SEQ ID NO: 37)

*MQARGLLLLCFLLQLQGPLG*AVFITQEEAHSVLHRQRRANSFLEELWPG
SLERECLEEQCSFEEAREIFKSTERTKQFWIVYTDGDQCASNPCQNGGT
CQDHLQSYICFCLLDFEGRNCEKNKNEQLICANENGGCDQYCTDHPGTK
RTCRCHEDYVLQPDEVSCKPKVEYPCGKIPVLEKRNSSSPQGRIVGGKV
CPKGECPWQAVLKINGALLCGAVLLDTTWIVSAAHCFDNIRSWRNITVV
MGEHDFSEKDGTEQVRRVTQVIIPDKYIPGKIDHDIALLRLHRPVTFTD
YVVPLCLPERAFSENTLARIRFSRVSGWGQLLDRGATALELMAIEVPRL
MTQDCLEHAKHSPNTPKITENMFCAGYMDGTKDACKGDSGGPHATHYRG
TWYLTGVVSWGEGCAAVGHVGVYTRVSQYTDWLIRLMDSKLQVGVIFRV
PLL

An91 fVII (SEQ ID NO: 38)

*MAPRALSLLCLLLGLQGSLA*AVFITQEERHGVLHRQRRANSFLEELRPG
SLERECKEEQCSFEEAREIFRSTERTKQFWISYNDGDQCASNPCQNGGS
CEDQLQSYICFCLPDFEGRNCETNKNDQLICVNENGGCEQYCSDHAEAK
RSCRCHEGYTLLADGVSCTPTVEYPCGKIPVLEKRNASNPQGRIVGGKV
CPKGECPWQALLTLNGALLCGGTLLDTSWVVSAAHCFDKIRSWRNLTVV
LGEHDLSEEDGDEQERQVAQVIIPDKYVPGKTDHDIALLRLRRPVALTD
HVVPLCLPERAFSERTLAYIRFSRVSGWGQLLDRGATALELMAIDVPRL
MTQDCLEQSRRRADSPRITENMFCAGYLDGSKDACKGDSGGPHATRYRG
TWYLTGVVSWGEGCAAVGHFGVYTRVSQYTEWLSRLMHSEPRPGVLLRA
PFP

-continued

An92 fVII (SEQ ID NO: 39)

*MAPRALSLLCLLLGLQGSLA*AVEITQEEAHGVLHRQRRANSFLEELRPG
SLERECKEEQCSFEEAREIFRNTERTKQFWISYNDGDQCASNPCQNGGS
CEDQLQSYICFCLPDFEGRNCETNKNDQLICVNENGGCEQYCSDHAEAK
RSCRCHEGYTLLADGVSCAPTVEYPCGKIPILEKRNASNPQGRIVGGKV
CPKGECPWQALLTLNGALLCGGTLLDTSWVVSAAHCFDKIKSWRNLTVV
LGEHDLSEEDGDEQERQVAQVIIPDKYVPGKTDHDIALLRLRRPVALTD
HVVPLCLPERAFSERTLAYIRFSRVSGWGQLLDRGATALELMAIDVPRL
MTQDCLEQSRRRADSPRITENMFCAGYLDGSKDACKGDSGGPHATRYRG
TWYLTGVVSWGEGCAAVGHFGVYTRVSQYTEWLSRLMHSEPRPGVLLRA
PFP

An93 fVII (SEQ ID NO: 40)

*MASQALRLLCLLLGLQGSLA*AVFITQEEAHGVLHRQRRANSFLEELRPG
SLERECKEEQCSFEEAREIFRNTERTKQFWISYNDGDQCASNPCQNGGS
CEDQLQSYICFCLPDFEGRNCETNKNDQLICVNENGGCEQYCSDHAEAK
RSCRCHEGYSLLADGVSCAPTVEYPCGKIPILEKRNASNPQGRIVGGKV
CPKGECPWQALLTLNGALLCGGTLIDTSWVVSAAHCFDKIKSWRNLTVV
LGEHDLSEEDGDEQERRVAQVIIPDTYVPGTTDHDIALLRLRRPVALTD
HVVPLCLPERAFSERTLAYVRFSRVSGWGQLLDRGATALELMAIDVPRL
MTQDCLQQSRRRADSPRITENMFCAGYLDGSKDACKGDSGGPHATRYRG
TWYLTGVVSWGEGCAAVGHFGVYTRVSQYTEWLSRLMHSEPRPGVLLRA
PFP

An98 fVII (SEQ ID NO: 41)

*MVSQALRLICLLLGLQGCLA*AVEITQEEAHGVLHRQRRANSFLEELRPG
SLERECKEEQCSFEEAREIFKDLERTKLFWISYSDGDQCASSPCQNGGS
CKDQLQSYICFCLPAFEGRNCETNKDDQLICVNENGGCEQYCSDHAGAK
RSCRCHEGYSLLADGVSCMPTVEYPCGKIPILEKRNASKPQGRIVGGRV
CPKGECPWQVLLLVNGAQLCGGTLINTIWVVSAAHCFDKIKNWRNLTAV
LGEHDLSEHDGDEQSRRVAQVIIPSTYVPGTTNHDIALLRLHRPVVLTD
HVVPLCLPERTFSERTLAFVRFSLVSGWGQLLDRGATALELMALNVPRL
MTQDCLQQSRKVGDSPNITEYMFCAGYSDGSKDSCKGDSGGPHATRYRG
TWYLTGIVSWGQGCAAVGHFGVYTRVSQYIEWLQKLMHSEPRPGVLLRA
PFP

With reference to the fVII sequence of SEQ ID NO: 7, residues 1-20 are the signal peptide, residues 21-83 are the GLA domain, residues 84-120 are the first EGF-like domain, residues 121-190 are the second EGF-like domain, residues 191-444 are the catalytic domain. Corresponding domains are also present in SEQ ID NOs: 8 and 35-41.

The cDNA nucleotide sequence coding for these fVII proteins was optimized by implementing the codon usage bias specific for the human liver cell as compared to naturally occurring nucleotide sequence coding for the corresponding non-codon optimized sequence for a human as discussed above. Nucleic acid sequences encoding SEQ ID NO: 3-6 that are codon-optimized for expression in liver tissue were generated, and are provided as follows:

Am81 fvii (SEQ ID NO: 15)
*ATGGCTCCCCGGGCCCTGGCCCTGCTGTGCTTCCTGCT*

*GGGCCTGCAGGGGTCCCTGGCT*GCCGTGTTCATCACCCAGGAGGAGGCT

CACAGCGTGCTGCACAGGCAGAGAAGAGCTAACTCCTTCCTGGAGGAGC

TGCGCCCCGGCAGCCTGGAGCGCGAGTGCAAGGAGGAGCAGTGCTCCTT

CGAGGAGGCCAGGGAGATCTTCAAGAAGCACCGAGCGCACCAAGCAGTTC

TGGATCTCCTACAACGACGGCGACCAGTGCGCTAGCAACCCATGCCAGA

ACGGAGGATCCTGCGAGGACCAGCTGCAGAGCTACATCTGCTTCTGCCT

GCCAGACTTCGAGGGAAGAAACTGCGAAACCAACAAGAACGACCAGCTG

ATCTGCATGAACGAGAACGGCGGGTGCGAGCAGTACTGCTCCGACCACG

CTGAGGCTAAGCGCAGCTGCAGATGCCACGAGGGATACACCCTGCAGGC

TGACGGGGTGTCCTGCACCCCAACCGTGGAGTACCCATGCGGCAAGATC

CCCGTGCTGGAGAAGCGGAACGCTAGCAACCCACAGGGAAGGATCGTGG

GAGGGAAGGTGTGCCCAAAGGGAGAGTGCCCATGGCAGGCCGTGCTGAA

GCTGAACGGGGCCCTGCTGTGCGGAGGGACCCTGCTGGACACCTCCTGG

GTGGTGAGCGCCGCTCACTGCTTCGACAAGATCAGGTCCTGGAGAAACC

TGACCGTGGTGCTGGGAGAGCACGACCTGAGCGAGGAGGACGGGGACGA

GCAGGAGAGACAGGTGGCCCAGGTCATCATCCCCGACAAGTACGTGCCC

GGCAAGACCGACCACGACATCGCCCTGCTGAGACTGCGCAGGCCCGTGG

CCCTGACCGACCACGTGGTGCCACTGTGCCTGCCAGAGAGAGCCTTCTC

CGAGAGGACCCTGGCCTACATCCGCTTCTCCCGGGTGAGCGGATGGGGA

CAGCTGCTGGACAGAGGAGCCACCGCCCTGGAGCTGATGGCCATCGACG

TGCCCAGGCTGATGACCCAGGACTGCCTGGAGCAGTCCAAGAGAAGAGC

TGACAGCCCAGCCATCACCGAGAACATGTTCTGCGCTGGATACCTGGAC

GGATCCAAGGACGCCTGCAAGGGCGACAGCGGAGGACCACACGCTACCA

GGTACAGAGGCACCTGGTACCTGACCGGAGTGGTGTCCTGGGGAGAGGG

ATGCGCTGCTGTGGGACACTTCGGGGTGTACACCAGAGTGAGCCAGTAC

ACCGAGTGGCTGTCCCGCCTGATGGACAGCGAGCCACACCCCGGCGTGC

TGCTGCGCGCCCCCTTCCCCTGA

An61 fVII (SEQ ID NO: 16)
*ATGCACTCCCGCCGGCTGGCCTTCCTGTGCTTCCTGCTGGGCCT*

*GCAGCAGAGCCTGACC*GCCGTGTTCATCAACCAGGAGGAGCC

AACTCCGTGCTGCACAGGCAGAGGAGAGCCAACAGCTTCCTGGAGGAGC

TGCGCTCCGGGAGCCTGGAGAGAGAGTGCAAGGAGGAGCAGTGCTCCTT

CGAGGAGGCCAGGGAGATCTTCAAGAGCACCGAGAGAACCAAGCAGTTC

TGGATCACCTACAACGACGGCAACCAGTGCGCTTCCAACCCATGCCAGA

ACGGAGGATCCTGCGTGGACCAGCTGCAGAGCTACATCTGCTTCTGCCT

GGAGGACTTCGAGGGAGAAACTGCGAAACCAACAAGAACAGCCAGCTG

ATCTGCATGAACGAGAACGGCGGGTGCGAGCAGTACTGCTCCGACAACC

CCGAAACCAAGAGGAGCTGCAGATGCCACGAGGGCTACACCCTGATGGC

TGACGGGGTGTCCTGCACCCCAACCGTGGAGTACCCATGCGGCAAGATC

CCCGTGCTGGAGAAGCGCAACGACAGCAACCCACAGGGAAGAATCGTGG

GAGGGAAGGTGTGCCCAAAGGGAGAGTGCCCATGGCAGGCCGTGATCAA

GCTGAACGGGGAGCTGCTGTGCGGAGGGACCCTGCTGGACGCTACCTGG

GTGGTGTCCGCCGCTCACTGCTTCGACAAGCTGCGCAACTGGAAGAACC

TGACCGTGGTGCTGGGAGAGCACGACCTGAGCGAGGAGGACGGGGACGA

GCAGGAGAGACAGGTGGCCCAGATCATCATCCCCGACAAGTACATCCCC

GGCAAGACCGACCACGACATCGCCCTGCTGAGACTGAGAACCCCCGTGA

ACTTCACCGACTACGTGGTGCCACTGTGCCTGCCAGAGAAGGCCTTCTC

CGAGCAGACCCTGGCCTACATCAGGTTCTCCAGCGTGAGCGGATGGGGA

CAGCTGCTGGACAGAGGAGCCACCGCCCTGGAGCTGATGACCATCGACG

TGCCCCGCCTGATGACCCAGGACTGCCTGGAGCAGACCAAGAGAACCGC

TAACTCCCCAGCTATCACCGAGAACATGTTCTGCGCTGGATACCTGGAC

GGAACCAAGGACGCTTGCAAGGGCGACAGCGGAGGACCCCACGCCACCA

AGTACCAGGGCACCTGGTACCTGACCGGAATCGTGTCCTGGGGAGAGGG

ATGCGCTGCTGTGGGACACTTCGGGGTGTACACCAGGGTGAGCCAGTAC

ATCGAGTGGCTGAACAGACTGATGGACTCCAAGCCCAGCCCCGGCGTGC

TGCTGCGCGCCCCCTTCCCCTGA

In SEQ ID NOs: 15 and 16, the signal peptide is shown in bold. The liver codon-optimized fVII sequences can be included in a vector (such as an AAV vector) and operably linked to a promoter (such as a liver specific promoter, for example, the HCB promoter) for administration to a subject, for example, to treat hemophilia B in the subject.

Example 4

Treatment of Human Hemophilia A Using AAV-Based Gene Therapy

This example describes an exemplary method for the clinical use of AAV vectors encoding fVIII for the treatment of hemophilia A.

A patient diagnosed with hemophilia A is selected for treatment. The patient is administered a therapeutically effective amount of a recombinant AAV encoding the An84 BDD fVIII variant (e.g., SEQ ID NO: 11) under control of a HCB promoter. The recombinant AAV can be administered intravenously. An appropriate therapeutic dose can be selected by a medical practitioner. In some cases, the therapeutically effective dose is in the range of $1 \times 10^{11}$ to $1 \times 10^{14}$ viral particles (vp)/kg, such as about $1 \times 10^{12}$ vp/kg. In most instances, the patient is administered a single dose. The health of the subject can be monitored over time to determine the effectiveness of the treatment.

Example 5

Treatment of Human Hemophilia B Using AAV-Based Gene Therapy

This example describes an exemplary method for the clinical use of AAV vectors encoding fIX for the treatment of hemophilia B.

A patient diagnosed with hemophilia B is selected for treatment. The patient is administered a therapeutically effective amount of a recombinant AAV encoding the An96 fIX Padua variant (e.g., SEQ ID NO: 9) under control of a HCB promoter. The recombinant AAV can be administered intravenously. An appropriate therapeutic dose can be selected by a medical practitioner. In some cases, the therapeutically effective dose is in the range of $1\times10^{11}$ to $1\times10^{14}$ viral particles (vp)/kg, such as about $1\times10^{12}$ vp/kg. In most instances, the patient is administered a single dose. The health of the subject can be monitored over time to determine the effectiveness of the treatment.

It will be apparent that the precise details of the methods or compositions described may be varied or modified without departing from the spirit of the described embodiments. We claim all such modifications and variations that fall within the scope and spirit of the claims below.

We claim:

1. An isolated nucleic acid molecule, comprising:
a nucleic acid sequence encoding a Factor IX (fIX) protein comprising an amino acid sequence at least 95% identical to residues 47-462 of SEQ ID NO: 23 (An96 fIX);
wherein the fIX protein has increased blood clotting activity relative to human fIX.

2. The isolated nucleic acid molecule of claim 1, wherein: the fIX protein comprises the amino acid sequence set forth as residues 47-462 of SEQ ID NO: 23 (An96 fIX).

3. The isolated nucleic acid molecule of claim 1, wherein: the nucleic acid sequence encodes a fIX protein linked to a signal peptide and propeptide comprising an amino acid sequence at least 95% identical to SEQ ID NO: 23 (An96 fIX).

4. The isolated nucleic acid molecule of claim 1, wherein: the fIX protein linked to the signal peptide and propeptide comprises the amino acid sequence set forth as SEQ ID NO: 23 (An96 fIX).

5. The isolated nucleic acid molecule of claim 1, wherein the nucleic acid sequence is a cDNA sequence.

6. A vector comprising the nucleic acid molecule of claim 1 operably linked to a promoter.

7. The vector of claim 6, wherein the vector is a viral vector.

8. The vector of claim 7, wherein the viral vector is an AAV vector, a lentiviral vector, or a retroviral vector.

9. A host cell comprising the nucleic acid molecule of claim 1.

10. A composition comprising the nucleic acid molecule, of claim 1 in a pharmaceutically acceptable carrier.

11. The nucleic acid molecule of claim 1, wherein the nucleic acid sequence encodes a fIX protein comprising an amino acid sequence at least 95% identical to residues 47-462 of SEQ ID NO: 23 (An96 fIX), and wherein the amino acid sequence comprises a R338L mutation.

* * * * *

SEQUENCE LISTING

```
<160> NUMBER OF SEQ ID NOS: 42

<210> SEQ ID NO 1
<211> LENGTH: 462
<212> TYPE: PRT
<213> ORGANISM: Artificial sequence
<220> FEATURE:
<223> OTHER INFORMATION: recombinant clotting factor sequence

<400> SEQUENCE: 1

Met Gln Cys Leu Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Thr Lys Ile Leu Asn Arg Pro Lys Arg Tyr Asn
            35                  40                  45

Ser Gly Lys Leu Glu Glu Phe Val Arg Gly Asn Leu Glu Arg Glu Cys
        50                  55                  60

Ile Glu Glu Lys Cys Ser Phe Glu Glu Ala Arg Glu Val Phe Glu Asn
65                  70                  75                  80

Thr Glu Lys Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Arg Phe Gly Phe Glu Gly Lys Asn Cys
        115                 120                 125

Glu Leu Asp Ala Thr Cys Ser Ile Lys Asn Gly Arg Cys Lys Gln Phe
    130                 135                 140

Cys Lys Lys Ser Ala Asp Asn Lys Val Val Cys Ser Cys Thr Glu Gly
145                 150                 155                 160

Tyr Arg Leu Ala Glu Asp Gln Lys Ser Cys Glu Pro Ala Val Pro Phe
                165                 170                 175

Pro Cys Gly Arg Val Ser Val Ser His Thr Ser Lys Lys Leu Thr Arg
            180                 185                 190

Ala Glu Thr Ile Phe Ser Asn Met Asp Tyr Glu Asn Ser Thr Glu Ala
        195                 200                 205

Glu Thr Ile Leu Asp Asn Val Thr Gln Ser Thr Gln Ser Phe Asn Asp
    210                 215                 220

Phe Thr Arg Val Val Gly Gly Glu Asn Ala Lys Pro Gly Gln Phe Pro
225                 230                 235                 240

Trp Gln Val Leu Leu Asn Gly Lys Ile Asp Ala Phe Cys Gly Gly Ser
                245                 250                 255

Ile Ile Asn Glu Lys Trp Val Val Thr Ala Ala His Cys Ile Glu Pro
            260                 265                 270

Gly Val Lys Ile Thr Val Val Ala Gly Glu His Asn Ile Glu Lys Thr
        275                 280                 285

Glu Pro Thr Glu Gln Lys Arg Asn Val Ile Arg Val Ile Pro His His
    290                 295                 300
```

-continued

Asn Tyr Asn Ala Thr Ile Asn Lys Tyr Ser His Asp Ile Ala Leu Leu
305                 310                 315                 320

Glu Leu Asp Lys Pro Leu Thr Leu Asn Ser Tyr Val Thr Pro Ile Cys
            325                 330                 335

Ile Ala Asn Arg Glu Tyr Thr Asn Ile Phe Leu Lys Phe Gly Ser Gly
            340                 345                 350

Tyr Val Ser Gly Trp Gly Arg Val Phe Asn Arg Gly Arg Ser Ala Ser
        355                 360                 365

Ile Leu Gln Tyr Leu Arg Val Pro Leu Val Asp Arg Ala Thr Cys Leu
370                 375                 380

Leu Ser Thr Lys Phe Thr Ile Tyr Asn Asn Met Phe Cys Ala Gly Tyr
385                 390                 395                 400

His Glu Gly Gly Lys Asp Ser Cys Gln Gly Asp Ser Gly Gly Pro His
                405                 410                 415

Val Thr Glu Val Glu Gly Thr Ser Phe Leu Thr Gly Ile Ile Ser Trp
            420                 425                 430

Gly Glu Glu Cys Ala Met Lys Gly Lys Tyr Gly Ile Tyr Thr Lys Val
        435                 440                 445

Ser Arg Tyr Val Asn Trp Ile Lys Glu Lys Thr Lys Leu Thr
    450                 455                 460

<210> SEQ ID NO 2
<211> LENGTH: 461
<212> TYPE: PRT
<213> ORGANISM: Artificial sequence
<220> FEATURE:
<223> OTHER INFORMATION: recombinant clotting factor sequence

<400> SEQUENCE: 2

Met Gln Cys Leu Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Arg Gly Asn Leu Glu Arg Glu Cys
    50                  55                  60

Ile Glu Glu Lys Cys Ser Phe Glu Glu Ala Arg Glu Val Phe Glu Asn
65                  70                  75                  80

Thr Glu Lys Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Arg Phe Gly Phe Glu Gly Lys Asn Cys
        115                 120                 125

Glu Leu Asp Ala Thr Cys Ser Ile Lys Asn Gly Arg Cys Lys Gln Phe
    130                 135                 140

Cys Lys Lys Ser Ala Asp Asn Lys Val Val Cys Ser Cys Thr Glu Gly
145                 150                 155                 160

Tyr Arg Leu Ala Glu Asp Gln Lys Ser Cys Glu Pro Ala Val Pro Phe
                165                 170                 175

Pro Cys Gly Arg Val Ser Val Ser His Thr Ser Lys Leu Thr Arg Ala
            180                 185                 190

Glu Thr Ile Phe Ser Asn Met Asp Tyr Glu Asn Ser Thr Glu Ala Glu
        195                 200                 205

Thr Ile Leu Asp Asn Val Thr Gln Ser Thr Gln Ser Phe Asn Asp Phe
            210                 215                 220

Thr Arg Val Val Gly Gly Glu Asn Ala Lys Pro Gly Gln Phe Pro Trp
225                 230                 235                 240

Gln Val Leu Leu Asn Gly Lys Ile Asp Ala Phe Cys Gly Gly Ser Ile
            245                 250                 255

Ile Asn Glu Lys Trp Val Val Thr Ala Ala His Cys Ile Glu Pro Gly
            260                 265                 270

Val Lys Ile Thr Val Val Ala Gly Glu His Asn Ile Glu Lys Thr Glu
            275                 280                 285

Pro Thr Glu Gln Lys Arg Asn Val Ile Arg Val Ile Pro His His Asn
290                 295                 300

Tyr Asn Ala Thr Ile Asn Lys Tyr Ser His Asp Ile Ala Leu Leu Glu
305                 310                 315                 320

Leu Asp Lys Pro Leu Thr Leu Asn Ser Tyr Val Thr Pro Ile Cys Ile
            325                 330                 335

Ala Asp Arg Glu Tyr Thr Asn Ile Phe Leu Lys Phe Gly Ser Gly Tyr
            340                 345                 350

Val Ser Gly Trp Gly Arg Val Phe Asn Arg Gly Arg Ser Ala Ser Ile
            355                 360                 365

Leu Gln Tyr Leu Arg Val Pro Leu Val Asp Arg Ala Thr Cys Leu Leu
370                 375                 380

Ser Thr Lys Phe Thr Ile Tyr Asn Asn Met Phe Cys Ala Gly Tyr His
385                 390                 395                 400

Glu Gly Gly Lys Asp Ser Cys Gln Gly Asp Ser Gly Gly Pro His Val
            405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
            435                 440                 445

Arg Tyr Val Asn Trp Ile Lys Glu Lys Thr Lys Leu Thr
            450                 455                 460

<210> SEQ ID NO 3
<211> LENGTH: 1458
<212> TYPE: PRT
<213> ORGANISM: Artificial sequence
<220> FEATURE:
<223> OTHER INFORMATION: recombinant clotting factor sequence

<400> SEQUENCE: 3

Met Gln Ile Glu Leu Ser Thr Cys Phe Phe Leu Cys Leu Leu Arg Phe
1               5                   10                  15

Ser Phe Ser Ala Thr Arg Arg Tyr Tyr Leu Gly Ala Val Glu Leu Ser
            20                  25                  30

Trp Asp Tyr Met Gln Ser Asp Leu Leu Ser Glu Leu His Val Asp Thr
            35                  40                  45

Arg Phe Pro Pro Arg Val Pro Arg Ser Phe Pro Phe Asn Thr Ser Val
50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
            85                  90                  95

Trp Ala Glu Val Tyr Asp Thr Val Val Ile Thr Leu Lys Asn Met Ala
            100                 105                 110

```
Ser His Pro Val Ser Leu His Ala Val Gly Val Ser Tyr Trp Lys Ala
        115                 120                 125

Ser Glu Gly Ala Glu Tyr Asp Asp Gln Thr Ser Gln Arg Glu Lys Glu
    130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
        195                 200                 205

Thr Gln Thr Leu His Glu Phe Val Leu Leu Phe Ala Val Phe Asp Glu
    210                 215                 220

Gly Lys Ser Trp His Ser Glu Thr Lys Asp Ser Leu Thr Gln Ala Met
225                 230                 235                 240

Asp Ser Ala Ser Ala Gln Ala Trp Pro Lys Met His Thr Val Asn Gly
                245                 250                 255

Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
    290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Asp Tyr Asp Asp
        355                 360                 365

Asp Leu Asp Asp Ser Glu Met Asp Val Leu Arg Phe Asp Asp Asp Asn
370                 375                 380

Ser Pro Ser Phe Ile Gln Ile Arg Ser Val Ala Lys Lys His Pro Lys
385                 390                 395                 400

Thr Trp Val His Tyr Ile Ala Ala Glu Glu Glu Asp Trp Asp Tyr Ala
                405                 410                 415

Pro Ser Val Leu Thr Pro Asp Asp Arg Ser Tyr Lys Ser Gln Tyr Leu
            420                 425                 430

Asn Asn Gly Pro Gln Arg Ile Gly Arg Lys Tyr Lys Lys Val Arg Phe
        435                 440                 445

Met Ala Tyr Thr Asp Glu Thr Phe Lys Thr Arg Glu Ala Ile Gln Tyr
    450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Ser Pro Leu His Ser Gly Arg Leu Pro
            500                 505                 510

Lys Gly Val Lys His Leu Lys Asp Leu Pro Ile Leu Pro Gly Glu Ile
        515                 520                 525
```

```
Phe Lys Tyr Lys Trp Thr Val Thr Val Glu Asp Gly Pro Thr Lys Ser
    530                 535                 540

Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Gln Ser Trp Tyr Leu Thr
        595                 600                 605

Glu Asn Met Gln Arg Phe Leu Pro Asn Ala Ala Gly Val Gln Pro Gln
    610                 615                 620

Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
                660                 665                 670

Phe Ser Gly Tyr Thr Phe Lys His Lys Met Val Tyr Glu Asp Thr Leu
        675                 680                 685

Thr Leu Phe Pro Phe Ser Gly Glu Thr Val Phe Met Ser Met Glu Asn
    690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Gly
                725                 730                 735

Asp Tyr Tyr Glu Asp Thr Tyr Glu Asp Ile Pro Thr Tyr Leu Leu Ser
            740                 745                 750

Glu Asn Asn Val Ile Glu Pro Arg Ser Phe Ser Gln Asn Pro Pro Val
        755                 760                 765

Leu Lys Arg His Gln Arg Glu Ile Thr Leu Thr Thr Leu Gln Ser Glu
    770                 775                 780

Gln Glu Glu Ile Asp Tyr Asp Asp Thr Ile Ser Ile Glu Met Lys Arg
785                 790                 795                 800

Glu Asp Phe Asp Ile Tyr Gly Glu Asp Glu Asn Gln Gly Pro Arg Ser
                805                 810                 815

Phe Gln Lys Arg Thr Arg His Tyr Phe Ile Ala Ala Val Glu Arg Leu
                820                 825                 830

Trp Asp Tyr Gly Met Ser Ser Ser Pro His Val Leu Arg Asn Arg Ala
        835                 840                 845

Gln Ser Gly Ser Val Pro Gln Phe Lys Lys Val Val Phe Gln Glu Phe
    850                 855                 860

Thr Asp Gly Ser Phe Thr Gln Pro Leu Tyr Arg Gly Glu Leu Asn Glu
865                 870                 875                 880

His Leu Gly Leu Leu Gly Pro Tyr Ile Arg Ala Glu Val Glu Asp Asn
                885                 890                 895

Ile Met Val Thr Phe Lys Asn Gln Ala Ser Arg Pro Tyr Ser Phe Tyr
                900                 905                 910

Ser Ser Leu Ile Ser Tyr Glu Glu Asp Gln Arg Gln Gly Ala Glu Pro
        915                 920                 925

Arg Lys Asn Phe Val Lys Pro Asn Glu Thr Lys Thr Tyr Phe Trp Lys
    930                 935                 940

Val Gln His His Met Ala Pro Thr Lys Asp Glu Phe Asp Cys Lys Ala
```

```
            945                 950                 955                 960
Trp Ala Tyr Phe Ser Asp Val Asp Leu Glu Lys Asp Met His Ser Gly
                    965                 970                 975
Leu Ile Gly Pro Leu Ile Cys His Thr Asn Thr Leu Asn Pro Ala
                    980                 985                 990
His Gly Arg Gln Val Thr Val Gln Glu Phe Ala Leu Phe Phe Thr Ile
            995                 1000                1005
Phe Asp Glu Thr Lys Ser Trp Tyr Phe Thr Glu Asn Met Glu Arg
            1010                1015                1020
Asn Cys Arg Ala Pro Cys Asn Ile Gln Met Glu Asp Pro Thr Phe
            1025                1030                1035
Lys Glu Asn Tyr Arg Phe His Ala Ile Asn Gly Tyr Val Met Asp
            1040                1045                1050
Thr Leu Pro Gly Leu Val Met Ala Gln Asp Gln Arg Ile Arg Trp
            1055                1060                1065
Tyr Leu Leu Ser Met Gly Ser Asn Glu Asn Ile His Ser Ile His
            1070                1075                1080
Phe Ser Gly His Val Phe Thr Val Arg Lys Lys Glu Glu Tyr Lys
            1085                1090                1095
Met Ala Val Tyr Asn Leu Tyr Pro Gly Val Phe Glu Thr Val Glu
            1100                1105                1110
Met Leu Pro Ser Lys Ala Gly Ile Trp Arg Val Glu Cys Leu Ile
            1115                1120                1125
Gly Glu His Leu His Ala Gly Met Ser Thr Leu Phe Leu Val Tyr
            1130                1135                1140
Ser Lys Gln Cys Gln Thr Pro Leu Gly Met Ala Ser Gly His Ile
            1145                1150                1155
Arg Asp Phe Gln Ile Thr Ala Ser Gly Gln Tyr Gly Gln Trp Ala
            1160                1165                1170
Pro Lys Leu Ala Arg Leu His Tyr Ser Gly Ser Ile Asn Ala Trp
            1175                1180                1185
Ser Thr Lys Glu Pro Phe Ser Trp Ile Lys Val Asp Leu Leu Ala
            1190                1195                1200
Pro Met Ile Ile His Gly Ile Lys Thr Gln Gly Ala Arg Gln Lys
            1205                1210                1215
Phe Ser Ser Leu Tyr Ile Ser Gln Phe Ile Ile Met Tyr Ser Leu
            1220                1225                1230
Asp Gly Lys Lys Trp Gln Thr Tyr Arg Gly Asn Ser Thr Gly Thr
            1235                1240                1245
Leu Met Val Phe Phe Gly Asn Val Asp Ser Ser Gly Ile Lys His
            1250                1255                1260
Asn Ile Phe Asn Pro Pro Ile Ile Ala Arg Tyr Ile Arg Leu His
            1265                1270                1275
Pro Thr His Tyr Ser Ile Arg Ser Thr Leu Arg Met Glu Leu Met
            1280                1285                1290
Gly Cys Asp Leu Asn Ser Cys Ser Met Pro Leu Gly Met Glu Ser
            1295                1300                1305
Lys Ala Ile Ser Asp Ala Gln Ile Thr Ala Ser Ser Tyr Phe Thr
            1310                1315                1320
Asn Met Phe Ala Thr Trp Ser Pro Ser Gln Ala Arg Leu His Leu
            1325                1330                1335
Gln Gly Arg Thr Asn Ala Trp Arg Pro Gln Val Asn Asn Pro Lys
            1340                1345                1350
```

```
Glu Trp Leu Gln Val Asp Phe Gln Lys Thr Met Lys Val Thr Gly
    1355                1360                1365

Ile Thr Thr Gln Gly Val Lys Ser Leu Leu Thr Ser Met Tyr Val
    1370                1375                1380

Lys Glu Phe Leu Ile Ser Ser Gln Asp Gly His His Trp Thr
    1385                1390                1395

Leu Phe Leu Gln Asn Gly Lys Val Lys Val Phe Gln Gly Asn Gln
    1400                1405                1410

Asp Ser Phe Thr Pro Val Val Asn Ser Leu Asp Pro Pro Leu Leu
    1415                1420                1425

Thr Arg Tyr Leu Arg Ile His Pro Gln Ser Trp Val His Gln Ile
    1430                1435                1440

Ala Leu Arg Leu Glu Val Leu Gly Cys Glu Ala Gln Gln Leu Tyr
    1445                1450                1455
```

<210> SEQ ID NO 4
<211> LENGTH: 1458
<212> TYPE: PRT
<213> ORGANISM: Artificial sequence
<220> FEATURE:
<223> OTHER INFORMATION: recombinant clotting factor sequence

<400> SEQUENCE: 4

```
Met Gln Ile Glu Leu Ser Thr Cys Phe Phe Leu Cys Leu Leu Pro Phe
1               5                   10                  15

Ser Phe Ser Ala Thr Arg Arg Tyr Tyr Leu Gly Ala Val Glu Leu Ser
                20                  25                  30

Trp Asp Tyr Met Gln Ser Asp Leu Leu Ser Glu Leu His Val Asp Thr
            35                  40                  45

Arg Phe Pro Pro Arg Val Pro Arg Ser Phe Pro Phe Asn Thr Ser Val
        50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Arg Ala Glu Val Tyr Asp Thr Val Val Ile Thr Leu Lys Asn Met Ala
                100                 105                 110

Ser His Pro Val Ser Leu His Ala Val Gly Val Ser Tyr Trp Lys Ala
            115                 120                 125

Ser Glu Gly Ala Glu Tyr Asp Asp Gln Thr Ser Gln Arg Glu Lys Glu
        130                 135                 140

Asp Asp Lys Val Ile Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
        195                 200                 205

Thr Gln Thr Leu His Glu Phe Val Leu Leu Phe Ala Val Phe Asp Glu
    210                 215                 220

Gly Lys Ser Trp His Ser Glu Ala Asn Glu Ser Leu Thr Gln Ala Met
225                 230                 235                 240

Asp Ser Ala Ser Ala Arg Pro Trp Pro Lys Met His Thr Val Asn Gly
                245                 250                 255
```

```
Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Pro Ser His Gln
                325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Asp Tyr Asp Asp
        355                 360                 365

Asp Leu Tyr Asp Ser Asp Met Asp Val Leu Arg Phe Asp Asp Asp Asn
    370                 375                 380

Ser Pro Pro Phe Ile Gln Ile Arg Ser Val Ala Lys Lys His Pro Lys
385                 390                 395                 400

Thr Trp Ile His Tyr Ile Ala Ala Glu Glu Asp Trp Asp Tyr Ala
                405                 410                 415

Pro Ser Val Leu Thr Pro Thr Asp Arg Ser Tyr Lys Ser Gln Tyr Leu
            420                 425                 430

Asn Asn Gly Pro Gln Arg Ile Gly Arg Lys Tyr Lys Val Arg Phe
        435                 440                 445

Met Ala Tyr Thr Asp Glu Thr Phe Lys Thr Arg Glu Ala Ile Gln Tyr
    450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asn Val Ser Pro Leu His Ser Gly Arg Leu Pro
            500                 505                 510

Lys Gly Val Lys His Leu Lys Asp Met Pro Ile Met Pro Gly Glu Ile
        515                 520                 525

Phe Lys Tyr Lys Trp Thr Val Thr Leu Glu Asp Gly Pro Thr Lys Ser
    530                 535                 540

Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Arg Ser Trp Tyr Leu Thr
        595                 600                 605

Glu Asn Met Gln Arg Phe Leu Pro Asn Ala Ala Gly Val Gln Pro Gln
    610                 615                 620

Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
            660                 665                 670
```

```
Phe Ser Gly Tyr Thr Phe Lys His Lys Met Val Phe Glu Asp Thr Leu
            675                 680                 685

Thr Leu Phe Pro Phe Ser Gly Glu Thr Val Phe Met Ser Met Glu Asn
690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Asp
                725                 730                 735

Asp Tyr Tyr Glu Asp Thr Tyr Glu Asp Ile Pro Thr Tyr Leu Leu Asn
            740                 745                 750

Glu Asn Asn Val Ile Glu Pro Arg Ser Phe Ser Gln Asn Pro Pro Val
        755                 760                 765

Leu Lys His His Gln Arg Glu Ile Thr Leu Thr Thr Leu Gln Pro Glu
    770                 775                 780

Gln Glu Lys Ile Asp Tyr Asp Asp Thr Leu Ser Ile Glu Met Lys Arg
785                 790                 795                 800

Glu Asp Phe Asp Ile Tyr Gly Glu Asp Glu Asn Gln Gly Pro Arg Ser
                805                 810                 815

Phe Gln Lys Arg Thr Arg His Tyr Phe Ile Ala Ala Val Glu Arg Leu
            820                 825                 830

Trp Asp Tyr Gly Met Ser Arg Ser Pro His Ala Leu Arg Asn Arg Ala
        835                 840                 845

Gln Ser Gly Ser Val Pro Gln Phe Lys Lys Val Val Phe Gln Glu Phe
    850                 855                 860

Thr Asp Gly Ser Phe Thr Gln Pro Leu Tyr Arg Gly Glu Leu Asn Glu
865                 870                 875                 880

His Leu Gly Leu Leu Gly Pro Tyr Ile Arg Ala Glu Val Glu Asp Asn
                885                 890                 895

Ile Met Val Thr Phe Lys Asn Gln Ala Ser Arg Pro Tyr Ser Phe Tyr
            900                 905                 910

Ser Ser Leu Ile Ser Tyr Glu Glu Asp Gln Arg Gln Gly Ala Glu Pro
        915                 920                 925

Arg Lys Asn Phe Val Lys Pro Asn Glu Thr Lys Thr Tyr Phe Trp Lys
    930                 935                 940

Val Gln His His Met Ala Pro Thr Lys Asp Glu Phe Asp Cys Lys Ala
945                 950                 955                 960

Trp Ala Tyr Phe Ser Asp Val Asp Leu Glu Lys Asp Leu His Ser Gly
                965                 970                 975

Leu Ile Gly Pro Leu Leu Ile Cys Arg Thr Asn Thr Leu Asn Pro Ala
            980                 985                 990

His Gly Arg Gln Leu Thr Val Gln Glu Phe Ala Leu Phe Phe Thr Ile
        995                 1000                1005

Phe Asp Glu Thr Lys Ser Trp Tyr Phe Thr Glu Asn Met Glu Arg
    1010                1015                1020

Asn Cys Arg Ala Pro Cys Asn Ile Gln Met Glu Asp Pro Thr Phe
    1025                1030                1035

Lys Lys Asn Tyr Arg Phe His Ala Ile Asn Gly Tyr Val Met Asp
    1040                1045                1050

Thr Leu Pro Gly Leu Val Met Ala Gln Asp Gln Arg Ile Arg Trp
    1055                1060                1065

Tyr Leu Leu Ser Met Gly Ser Asn Glu Asn Ile His Ser Ile His
    1070                1075                1080

Phe Ser Gly His Val Phe Thr Val Arg Lys Lys Glu Glu Tyr Lys
```

```
                1085                1090                1095
Met Ala Val Tyr Asn Leu Tyr Pro Gly Val Phe Glu Thr Val Glu
            1100                1105                1110
Met Leu Pro Ser Lys Ala Gly Ile Trp Arg Val Glu Cys Leu Ile
            1115                1120                1125
Gly Glu His Leu Gln Ala Gly Met Ser Thr Leu Phe Leu Val Tyr
            1130                1135                1140
Ser Lys Glu Cys Gln Thr Pro Leu Gly Met Ala Ser Gly Arg Ile
            1145                1150                1155
Arg Asp Ser Gln Ile Thr Ala Ser Gly Gln Tyr Gly Gln Trp Ala
            1160                1165                1170
Pro Lys Leu Ala Arg Leu His Tyr Ser Gly Ser Ile Asn Ala Trp
            1175                1180                1185
Ser Thr Lys Asp Pro Phe Ser Trp Ile Lys Val Asp Leu Leu Ala
            1190                1195                1200
Pro Met Ile Ile His Gly Ile Lys Thr Gln Gly Ala Arg Gln Lys
            1205                1210                1215
Phe Ser Ser Leu Tyr Ile Ser Gln Phe Ile Ile Met Tyr Ser Leu
            1220                1225                1230
Asp Gly Lys Lys Trp Gln Ser Tyr Arg Gly Asn Ser Thr Gly Thr
            1235                1240                1245
Leu Met Val Phe Phe Gly Asn Val Asp Ser Ser Gly Ile Lys His
            1250                1255                1260
Asn Ile Phe Asn Pro Pro Ile Ile Ala Arg Tyr Ile Arg Leu His
            1265                1270                1275
Pro Thr His Tyr Ser Ile Arg Ser Thr Leu Arg Met Glu Leu Met
            1280                1285                1290
Gly Cys Asp Leu Asn Ser Cys Ser Met Pro Leu Gly Met Glu Ser
            1295                1300                1305
Lys Ala Ile Ser Asp Ala Gln Ile Thr Ala Ser Ser Tyr Phe Thr
            1310                1315                1320
Asn Met Phe Ala Thr Trp Ser Pro Ser Gln Ala Arg Leu His Leu
            1325                1330                1335
Gln Gly Arg Thr Asn Ala Trp Arg Pro Gln Val Asn Asn Pro Lys
            1340                1345                1350
Glu Trp Leu Gln Val Asp Phe Gln Lys Thr Met Lys Val Thr Gly
            1355                1360                1365
Ile Thr Thr Gln Gly Ala Lys Ser Leu Leu Thr Ser Met Tyr Val
            1370                1375                1380
Lys Glu Phe Leu Ile Ser Ser Ser Gln Asp Gly His His Trp Thr
            1385                1390                1395
Leu Phe Leu Gln Asn Gly Lys Val Lys Val Phe Gln Gly Asn Gln
            1400                1405                1410
Asp Ser Phe Thr Pro Val Val Asn Ser Leu Asp Pro Pro Leu Leu
            1415                1420                1425
Thr Arg Tyr Leu Arg Ile His Pro Gln Ser Trp Val His His Ile
            1430                1435                1440
Ala Leu Arg Leu Glu Val Leu Gly Cys Glu Ala Gln Gln Leu Tyr
            1445                1450                1455

<210> SEQ ID NO 5
<211> LENGTH: 1458
<212> TYPE: PRT
<213> ORGANISM: Artificial sequence
```

<220> FEATURE:
<223> OTHER INFORMATION: recombinant clotting factor sequence

<400> SEQUENCE: 5

```
Met Gln Ile Glu Leu Ser Thr Cys Phe Phe Leu Cys Leu Leu Arg Phe
1               5                   10                  15

Ser Phe Ser Ala Thr Arg Arg Tyr Tyr Leu Gly Ala Val Glu Leu Ser
            20                  25                  30

Trp Asp Tyr Met Gln Ser Asp Leu Leu Gly Glu Leu His Val Asp Thr
        35                  40                  45

Arg Phe Pro Pro Arg Val Pro Arg Ser Phe Pro Phe Asn Thr Ser Val
    50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Trp Ala Glu Val Tyr Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Asp Asp Gln Thr Ser Gln Arg Glu Lys Glu
    130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
        195                 200                 205

Thr Gln Thr Leu His Glu Phe Val Leu Leu Phe Ala Val Phe Asp Glu
    210                 215                 220

Gly Lys Ser Trp His Ser Glu Thr Lys Asp Ser Leu Thr Gln Ala Met
225                 230                 235                 240

Asp Ser Ala Ser Ala Gln Ala Trp Pro Lys Met His Thr Val Asn Gly
                245                 250                 255

Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
    290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Asp Tyr Asp Asp
    355                 360                 365

Asp Leu Asp Asp Ser Glu Met Asp Val Leu Arg Phe Asp Asp Asp Asn
370                 375                 380

Ser Pro Ser Phe Ile Gln Ile Arg Ser Val Ala Lys Lys His Pro Lys
385                 390                 395                 400
```

Thr Trp Val His Tyr Ile Ala Ala Glu Glu Asp Trp Asp Tyr Ala
            405                 410                 415

Pro Ser Val Leu Thr Pro Asp Asp Arg Ser Tyr Lys Ser Gln Tyr Leu
            420                 425                 430

Asn Asn Gly Pro Gln Arg Ile Gly Arg Lys Tyr Lys Lys Val Arg Phe
            435                 440                 445

Met Ala Tyr Thr Asp Glu Thr Phe Lys Thr Arg Glu Ala Ile Gln Tyr
    450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Ser Pro Leu His Ser Gly Arg Leu Pro
                500                 505                 510

Lys Gly Val Lys His Leu Lys Asp Leu Pro Ile Leu Pro Gly Glu Ile
            515                 520                 525

Phe Lys Tyr Lys Trp Thr Val Thr Val Glu Asp Gly Pro Thr Lys Ser
            530                 535                 540

Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
                580                 585                 590

Val Ile Leu Phe Ser Val Phe Asp Glu Asn Gln Ser Trp Tyr Leu Thr
            595                 600                 605

Glu Asn Met Gln Arg Phe Leu Pro Asn Ala Ala Gly Val Gln Pro Gln
            610                 615                 620

Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
                660                 665                 670

Phe Ser Gly Tyr Thr Phe Lys His Lys Met Val Tyr Glu Asp Thr Leu
            675                 680                 685

Thr Leu Phe Pro Phe Ser Gly Glu Thr Val Phe Met Ser Met Glu Asn
            690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Gly
                725                 730                 735

Asp Tyr Tyr Glu Asp Thr Tyr Glu Asp Ile Pro Thr Tyr Leu Leu Ser
            740                 745                 750

Glu Asn Asn Val Ile Glu Pro Arg Ser Phe Ser Gln Asn Pro Pro Val
            755                 760                 765

Leu Lys Arg His Gln Arg Glu Ile Thr Leu Thr Thr Leu Gln Ser Glu
770                 775                 780

Gln Glu Glu Ile Asp Tyr Asp Asp Thr Ile Ser Ile Glu Met Lys Arg
785                 790                 795                 800

Glu Asp Phe Asp Ile Tyr Gly Glu Asp Glu Asn Gln Gly Pro Arg Ser
                805                 810                 815

-continued

```
Phe Gln Lys Arg Thr Arg His Tyr Phe Ile Ala Ala Val Glu Arg Leu
                820                 825                 830
Trp Asp Tyr Gly Met Ser Ser Pro His Val Leu Arg Asn Arg Ala
        835                 840                 845
Gln Ser Gly Ser Val Pro Gln Phe Lys Lys Val Phe Gln Glu Phe
        850                 855                 860
Thr Asp Gly Ser Phe Thr Gln Pro Leu Tyr Arg Gly Glu Leu Asn Glu
865                 870                 875                 880
His Leu Gly Leu Leu Gly Pro Tyr Ile Arg Ala Glu Val Glu Asp Asn
                885                 890                 895
Ile Met Val Thr Phe Lys Asn Gln Ala Ser Arg Pro Tyr Ser Phe Tyr
                900                 905                 910
Ser Ser Leu Ile Ser Tyr Glu Glu Asp Gln Arg Gln Gly Ala Glu Pro
                915                 920                 925
Arg Lys Asn Phe Val Lys Pro Asn Glu Thr Lys Thr Tyr Phe Trp Lys
        930                 935                 940
Val Gln His His Met Ala Pro Thr Lys Asp Glu Phe Asp Cys Lys Ala
945                 950                 955                 960
Trp Ala Tyr Phe Ser Asp Val Asp Leu Glu Lys Asp Met His Ser Gly
                965                 970                 975
Leu Ile Gly Pro Leu Leu Ile Cys His Thr Asn Thr Leu Asn Pro Ala
                980                 985                 990
His Gly Arg Gln Val Thr Val Gln Glu Phe Ala Leu Phe Phe Thr Ile
                995                1000                1005
Phe Asp Glu Thr Lys Ser Trp Tyr Phe Thr Glu Asn Met Glu Arg
        1010                1015                1020
Asn Cys Arg Ala Pro Cys Asn Ile Gln Met Glu Asp Pro Thr Phe
        1025                1030                1035
Lys Glu Asn Tyr Arg Phe His Ala Ile Asn Gly Tyr Val Met Asp
        1040                1045                1050
Thr Leu Pro Gly Leu Val Met Ala Gln Asp Gln Arg Ile Arg Trp
        1055                1060                1065
Tyr Leu Leu Ser Met Gly Ser Asn Glu Asn Ile His Ser Ile His
        1070                1075                1080
Phe Ser Gly His Val Phe Thr Val Arg Lys Lys Glu Glu Tyr Lys
        1085                1090                1095
Met Ala Val Tyr Asn Leu Tyr Pro Gly Val Phe Glu Thr Val Glu
        1100                1105                1110
Met Leu Pro Ser Lys Ala Gly Ile Trp Arg Val Glu Cys Leu Ile
        1115                1120                1125
Gly Glu His Leu His Ala Gly Met Ser Thr Leu Phe Leu Val Tyr
        1130                1135                1140
Ser Lys Gln Cys Gln Thr Pro Leu Gly Met Ala Ser Gly His Ile
        1145                1150                1155
Arg Asp Phe Gln Ile Thr Ala Ser Gly Gln Tyr Gly Gln Trp Ala
        1160                1165                1170
Pro Lys Leu Ala Arg Leu His Tyr Ser Gly Ser Ile Asn Ala Trp
        1175                1180                1185
Ser Thr Lys Glu Pro Phe Ser Trp Ile Lys Val Asp Leu Leu Ala
        1190                1195                1200
Pro Met Ile Ile His Gly Ile Lys Thr Gln Gly Ala Arg Gln Lys
        1205                1210                1215
Phe Ser Ser Leu Tyr Ile Ser Gln Phe Ile Ile Met Tyr Ser Leu
```

```
              1220                1225                1230

Asp Gly Lys Lys Trp Gln Thr Tyr Arg Gly Asn Ser Thr Gly Thr
              1235                1240                1245

Leu Met Val Phe Phe Gly Asn Val Asp Ser Ser Gly Ile Lys His
              1250                1255                1260

Asn Ile Phe Asn Pro Pro Ile Ala Arg Tyr Ile Arg Leu His
              1265                1270                1275

Pro Thr His Tyr Ser Ile Arg Ser Thr Leu Arg Met Glu Leu Met
              1280                1285                1290

Gly Cys Asp Leu Asn Ser Cys Ser Met Pro Leu Gly Met Glu Ser
              1295                1300                1305

Lys Ala Ile Ser Asp Ala Gln Ile Thr Ala Ser Ser Tyr Phe Thr
              1310                1315                1320

Asn Met Phe Ala Thr Trp Ser Pro Ser Gln Ala Arg Leu His Leu
              1325                1330                1335

Gln Gly Arg Thr Asn Ala Trp Arg Pro Gln Val Asn Asn Pro Lys
              1340                1345                1350

Glu Trp Leu Gln Val Asp Phe Gln Lys Thr Met Lys Val Thr Gly
              1355                1360                1365

Ile Thr Thr Gln Gly Val Lys Ser Leu Leu Thr Ser Met Tyr Val
              1370                1375                1380

Lys Glu Phe Leu Ile Ser Ser Ser Gln Asp Gly His His Trp Thr
              1385                1390                1395

Leu Phe Phe Gln Asn Gly Lys Val Lys Val Phe Gln Gly Asn Gln
              1400                1405                1410

Asp Ser Phe Thr Pro Val Val Asn Ser Leu Asp Pro Pro Leu Leu
              1415                1420                1425

Thr Arg Tyr Leu Arg Ile His Pro Gln Ser Trp Val His Gln Ile
              1430                1435                1440

Ala Leu Arg Leu Glu Val Leu Gly Cys Glu Ala Gln Gln Leu Tyr
              1445                1450                1455

<210> SEQ ID NO 6
<211> LENGTH: 1458
<212> TYPE: PRT
<213> ORGANISM: Artificial sequence
<220> FEATURE:
<223> OTHER INFORMATION: recombinant clotting factor sequence

<400> SEQUENCE: 6

Met Gln Ile Glu Leu Ser Thr Cys Phe Phe Leu Cys Leu Leu Arg Phe
1               5                   10                  15

Ser Phe Ser Ala Thr Arg Arg Tyr Tyr Leu Gly Ala Val Glu Leu Ser
                20                  25                  30

Trp Asp Tyr Met Gln Ser Asp Leu Leu Gly Glu Leu His Val Asp Thr
            35                  40                  45

Arg Phe Pro Pro Arg Val Pro Arg Ser Phe Pro Phe Asn Thr Ser Val
        50                  55                  60

Met Tyr Lys Lys Thr Val Phe Val Glu Phe Asp His Leu Phe Asn
65                  70                  75                  80

Ile Ala Lys Pro Arg Pro Pro Trp Met Gly Leu Leu Gly Pro Thr Ile
                85                  90                  95

Gln Ala Glu Val Tyr Asp Thr Val Val Ile Thr Leu Lys Asn Met Ala
            100                 105                 110

Ser His Pro Val Ser Leu His Ala Val Gly Val Ser Tyr Trp Lys Ala
```

```
            115                 120                 125
Ser Glu Gly Ala Glu Tyr Asp Asp Gln Thr Ser Gln Arg Glu Lys Glu
    130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
        195                 200                 205

Thr Gln Thr Leu His Glu Phe Val Leu Leu Phe Ala Val Phe Asp Glu
    210                 215                 220

Gly Lys Ser Trp His Ser Glu Thr Lys Asp Ser Leu Met Gln Asp Thr
225                 230                 235                 240

Asp Ser Ala Ser Ala Gln Ala Trp Pro Lys Met His Thr Val Asn Gly
                245                 250                 255

Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
    290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Asp Tyr Asp Asn
        355                 360                 365

Asp Leu Asp Asp Ser Glu Met Asp Val Leu Arg Phe Asp Asp Asp Asn
    370                 375                 380

Ser Pro Ser Phe Ile Gln Ile Arg Ser Val Ala Lys Lys His Pro Lys
385                 390                 395                 400

Thr Trp Val His Tyr Ile Ala Ala Glu Glu Asp Trp Asp Tyr Ala
                405                 410                 415

Pro Ser Val Leu Thr Pro Asp Asp Arg Ser Tyr Lys Ser Gln Tyr Leu
            420                 425                 430

Asn Asn Gly Pro Gln Arg Ile Gly Arg Lys Tyr Lys Val Arg Phe
        435                 440                 445

Met Ala Tyr Thr Asp Glu Thr Phe Lys Thr Arg Glu Ala Ile Gln Tyr
    450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Ser Pro Leu His Ser Gly Arg Leu Pro
            500                 505                 510

Lys Gly Val Lys His Leu Lys Asp Leu Pro Ile Leu Pro Gly Glu Ile
        515                 520                 525

Phe Lys Tyr Lys Trp Thr Val Thr Val Glu Asp Gly Pro Thr Lys Ser
    530                 535                 540
```

```
Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
            565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Gln Ser Trp Tyr Leu Thr
            595                 600                 605

Glu Asn Met Gln Arg Phe Leu Pro Asn Ala Ala Gly Val Gln Pro Gln
610                 615                 620

Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
            645                 650                 655

Trp Tyr Ile Leu Ser Ile Gly Ala Gln Thr Asp Phe Leu Ser Val Phe
            660                 665                 670

Phe Ser Gly Tyr Thr Phe Lys His Lys Met Val Tyr Glu Asp Thr Leu
            675                 680                 685

Thr Leu Phe Pro Phe Ser Gly Glu Thr Val Phe Met Ser Met Glu Asn
690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Gly
            725                 730                 735

Asp Tyr Tyr Glu Asp Thr Tyr Glu Asp Ile Ser Thr Tyr Leu Leu Ser
            740                 745                 750

Glu Asn Asn Val Ile Glu Pro Arg Ser Phe Ser Gln Asn Pro Pro Val
            755                 760                 765

Leu Lys Arg His Gln Arg Glu Ile Thr Leu Thr Leu Gln Ser Asp
770                 775                 780

Gln Glu Glu Ile Asp Tyr Asp Asp Thr Ile Ser Thr Glu Met Lys Arg
785                 790                 795                 800

Glu Asp Phe Asp Ile Tyr Gly Glu Asp Asn Gln Gly Pro Arg Ser
            805                 810                 815

Phe Gln Lys Lys Thr Arg His Tyr Phe Ile Ala Ala Val Glu Arg Leu
            820                 825                 830

Trp Asp Tyr Gly Met Ser Ser Pro His Val Leu Arg Asn Arg Ala
            835                 840                 845

Gln Ser Gly Ser Val Pro Gln Phe Lys Lys Val Val Phe Gln Glu Phe
    850                 855                 860

Thr Asp Gly Ser Phe Thr Gln Pro Leu Tyr Arg Gly Glu Leu Asn Glu
865                 870                 875                 880

His Leu Gly Leu Leu Gly Pro Tyr Ile Arg Ala Glu Val Glu Asp Asn
            885                 890                 895

Ile Met Val Thr Phe Lys Asn Gln Ala Ser Arg Pro Tyr Ser Phe Tyr
            900                 905                 910

Ser Ser Leu Ile Ser Tyr Glu Glu Asp Gln Arg Gln Gly Ala Glu Pro
            915                 920                 925

Arg Lys Asn Phe Val Lys Pro Asn Glu Thr Lys Thr Tyr Phe Trp Lys
            930                 935                 940

Val Gln His His Met Ala Pro Thr Lys Asp Glu Phe Asp Cys Lys Ala
945                 950                 955                 960
```

```
Trp Ala Tyr Phe Ser Asp Val Asp Leu Glu Lys Asp Met His Ser Gly
                965             970             975

Leu Ile Gly Pro Leu Leu Ile Cys His Thr Asn Thr Leu Asn Pro Ala
            980             985             990

His Gly Arg Gln Val Thr Val Gln Glu Phe Ala Leu Phe Phe Thr Ile
        995            1000            1005

Phe Asp Glu Thr Lys Ser Trp Tyr Phe Thr Glu Asn Met Glu Arg
   1010            1015            1020

Asn Cys Arg Ala Pro Cys Asn Ile Gln Met Glu Asp Pro Thr Phe
   1025            1030            1035

Lys Glu Asn Tyr Arg Phe His Ala Ile Asn Gly Tyr Val Met Asp
   1040            1045            1050

Thr Leu Pro Gly Leu Val Met Ala Gln Asp Gln Arg Ile Arg Trp
   1055            1060            1065

Tyr Leu Leu Ser Met Gly Ser Asn Glu Asn Ile His Ser Ile His
   1070            1075            1080

Phe Ser Gly His Val Phe Thr Val Arg Lys Lys Glu Glu Tyr Lys
   1085            1090            1095

Met Ala Val Tyr Asn Leu Tyr Pro Gly Val Phe Glu Thr Val Glu
   1100            1105            1110

Met Leu Pro Ser Lys Ala Gly Ile Trp Arg Val Glu Cys Leu Ile
   1115            1120            1125

Gly Glu His Leu His Ala Gly Met Ser Thr Leu Phe Leu Val Tyr
   1130            1135            1140

Ser Lys Gln Cys Gln Thr Pro Leu Gly Met Ala Ser Gly His Ile
   1145            1150            1155

Arg Asp Phe Gln Ile Thr Ala Ser Gly Gln Tyr Gly Gln Trp Ala
   1160            1165            1170

Pro Lys Leu Ala Arg Leu His Tyr Ser Gly Ser Ile Asn Ala Trp
   1175            1180            1185

Ser Thr Lys Glu Pro Phe Ser Trp Ile Lys Val Asp Leu Leu Ala
   1190            1195            1200

Pro Met Ile Ile His Gly Ile Lys Thr Gln Gly Ala Arg Gln Lys
   1205            1210            1215

Phe Ser Ser Leu Tyr Ile Ser Gln Phe Ile Ile Met Tyr Ser Leu
   1220            1225            1230

Asp Gly Lys Lys Trp Gln Thr Tyr Arg Gly Asn Ser Thr Gly Thr
   1235            1240            1245

Leu Met Val Phe Phe Gly Asn Val Asp Ser Ser Gly Ile Lys His
   1250            1255            1260

Asn Ile Phe Asn Pro Pro Ile Ile Ala Arg Tyr Ile Arg Leu His
   1265            1270            1275

Pro Thr His Tyr Ser Ile Arg Ser Thr Leu Arg Met Glu Leu Met
   1280            1285            1290

Gly Cys Asp Leu Asn Ser Cys Ser Met Pro Leu Gly Met Glu Ser
   1295            1300            1305

Lys Ala Ile Ser Asp Ala Gln Ile Thr Ala Ser Ser Tyr Phe Thr
   1310            1315            1320

Asn Met Phe Ala Thr Trp Ser Pro Ser Gln Ala Arg Leu His Leu
   1325            1330            1335

Gln Gly Arg Thr Asn Ala Trp Arg Pro Gln Val Asn Asn Pro Lys
   1340            1345            1350

Glu Trp Leu Gln Val Asp Phe Gln Lys Thr Met Lys Val Thr Gly
```

-continued

```
                1355                1360                1365

Ile Thr Thr Gln Gly Val Lys Ser Leu Leu Thr Ser Met Tyr Val
        1370                1375                1380

Lys Glu Phe Leu Ile Ser Ser Gln Asp Gly His His Trp Thr
1385                1390                1395

Leu Phe Phe Gln Asn Gly Lys Val Lys Val Phe Gln Gly Asn Gln
    1400                1405                1410

Asp Ser Phe Thr Pro Val Val Asn Ser Leu Asp Pro Pro Leu Leu
    1415                1420                1425

Thr Arg Tyr Leu Arg Ile His Pro Gln Ser Trp Val His Gln Ile
    1430                1435                1440

Ala Leu Arg Leu Glu Val Leu Gly Cys Glu Ala Gln Gln Leu Tyr
    1445                1450                1455

<210> SEQ ID NO 7
<211> LENGTH: 444
<212> TYPE: PRT
<213> ORGANISM: Artificial sequence
<220> FEATURE:
<223> OTHER INFORMATION: recombinant clotting factor sequence

<400> SEQUENCE: 7

Met Ala Pro Arg Ala Leu Ala Leu Leu Cys Phe Leu Leu Gly Leu Gln
1               5                   10                  15

Gly Ser Leu Ala Ala Val Phe Ile Thr Gln Glu Glu Ala His Ser Val
            20                  25                  30

Leu His Arg Gln Arg Arg Ala Asn Ser Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Arg Ser Thr Glu Arg Thr Lys Gln Phe Trp Ile
65                  70                  75                  80

Ser Tyr Asn Asp Gly Asp Gln Cys Ala Ser Asn Pro Cys Gln Asn Gly
                85                  90                  95

Gly Ser Cys Glu Asp Gln Leu Gln Ser Tyr Ile Cys Phe Cys Leu Pro
            100                 105                 110

Asp Phe Glu Gly Arg Asn Cys Glu Thr Asn Lys Asn Asp Gln Leu Ile
        115                 120                 125

Cys Met Asn Glu Asn Gly Gly Cys Glu Gln Tyr Cys Ser Asp His Ala
    130                 135                 140

Glu Ala Lys Arg Ser Cys Arg Cys His Glu Gly Tyr Thr Leu Gln Ala
145                 150                 155                 160

Asp Gly Val Ser Cys Thr Pro Thr Val Glu Tyr Pro Cys Gly Lys Ile
                165                 170                 175

Pro Val Leu Glu Lys Arg Asn Ala Ser Asn Pro Gln Gly Arg Ile Val
            180                 185                 190

Gly Gly Lys Val Cys Pro Lys Gly Glu Cys Pro Trp Gln Ala Val Leu
        195                 200                 205

Lys Leu Asn Gly Ala Leu Leu Cys Gly Gly Thr Leu Leu Asp Thr Ser
    210                 215                 220

Trp Val Val Ser Ala Ala His Cys Phe Asp Lys Ile Arg Ser Trp Arg
225                 230                 235                 240

Asn Leu Thr Val Val Leu Gly Glu His Asp Leu Ser Glu Glu Asp Gly
                245                 250                 255

Asp Glu Gln Glu Arg Gln Val Ala Gln Val Ile Ile Pro Asp Lys Tyr
```

```
            260                 265                 270
Val Pro Gly Lys Thr Asp His Asp Ile Ala Leu Leu Arg Leu Arg Arg
            275                 280                 285

Pro Val Ala Leu Thr Asp His Val Val Pro Leu Cys Leu Pro Glu Arg
            290                 295                 300

Ala Phe Ser Glu Arg Thr Leu Ala Tyr Ile Arg Phe Ser Arg Val Ser
305                 310                 315                 320

Gly Trp Gly Gln Leu Leu Asp Arg Gly Ala Thr Ala Leu Glu Leu Met
                325                 330                 335

Ala Ile Asp Val Pro Arg Leu Met Thr Gln Asp Cys Leu Gln Gln Ser
                340                 345                 350

Lys Arg Arg Ala Asp Ser Pro Ala Ile Thr Glu Asn Met Phe Cys Ala
                355                 360                 365

Gly Tyr Leu Asp Gly Ser Lys Asp Ala Cys Lys Gly Asp Ser Gly Gly
                370                 375                 380

Pro His Ala Thr Arg Tyr Arg Gly Thr Trp Tyr Leu Thr Gly Val Val
385                 390                 395                 400

Ser Trp Gly Glu Gly Cys Ala Ala Val Gly His Phe Gly Val Tyr Thr
                405                 410                 415

Arg Val Ser Gln Tyr Thr Glu Trp Leu Ser Arg Leu Met Asp Ser Glu
                420                 425                 430

Pro His Pro Gly Val Leu Leu Arg Ala Pro Phe Pro
                435                 440

<210> SEQ ID NO 8
<211> LENGTH: 444
<212> TYPE: PRT
<213> ORGANISM: Artificial sequence
<220> FEATURE:
<223> OTHER INFORMATION: recombinant clotting factor sequence

<400> SEQUENCE: 8

Met His Ser Arg Arg Leu Ala Phe Leu Cys Phe Leu Leu Gly Leu Gln
1               5                   10                  15

Gln Ser Leu Thr Ala Val Phe Ile Asn Gln Glu Glu Ala Asn Ser Val
                20                  25                  30

Leu His Arg Gln Arg Arg Ala Asn Ser Phe Leu Glu Glu Leu Arg Ser
                35                  40                  45

Gly Ser Leu Glu Arg Glu Cys Lys Glu Glu Gln Cys Ser Phe Glu Glu
            50                  55                  60

Ala Arg Glu Ile Phe Lys Ser Thr Glu Arg Thr Lys Gln Phe Trp Ile
65                  70                  75                  80

Thr Tyr Asn Asp Gly Asn Gln Cys Ala Ser Asn Pro Cys Gln Asn Gly
                85                  90                  95

Gly Ser Cys Val Asp Gln Leu Gln Ser Tyr Ile Cys Phe Cys Leu Glu
                100                 105                 110

Asp Phe Glu Gly Arg Asn Cys Glu Thr Asn Lys Asn Ser Gln Leu Ile
                115                 120                 125

Cys Met Asn Glu Asn Gly Gly Cys Glu Gln Tyr Cys Ser Asp Asn Pro
                130                 135                 140

Glu Thr Lys Arg Ser Cys Arg Cys His Glu Gly Tyr Thr Leu Met Ala
145                 150                 155                 160

Asp Gly Val Ser Cys Thr Pro Thr Val Glu Tyr Pro Cys Gly Lys Ile
                165                 170                 175

Pro Val Leu Glu Lys Arg Asn Asp Ser Asn Pro Gln Gly Arg Ile Val
```

```
                    180                 185                 190
        Gly Gly Lys Val Cys Pro Lys Gly Glu Cys Pro Trp Gln Ala Val Ile
                    195                 200                 205

Lys Leu Asn Gly Glu Leu Leu Cys Gly Gly Thr Leu Leu Asp Ala Thr
                    210                 215                 220

Trp Val Val Ser Ala Ala His Cys Phe Asp Lys Leu Arg Asn Trp Lys
        225                 230                 235                 240

Asn Leu Thr Val Val Leu Gly Glu His Asp Leu Ser Glu Glu Asp Gly
                            245                 250                 255

Asp Glu Gln Glu Arg Gln Val Ala Gln Ile Ile Ile Pro Asp Lys Tyr
                    260                 265                 270

Ile Pro Gly Lys Thr Asp His Asp Ile Ala Leu Leu Arg Leu Arg Thr
                    275                 280                 285

Pro Val Asn Phe Thr Asp Tyr Val Val Pro Leu Cys Leu Pro Glu Lys
                    290                 295                 300

Ala Phe Ser Glu Gln Thr Leu Ala Tyr Ile Arg Phe Ser Ser Val Ser
        305                 310                 315                 320

Gly Trp Gly Gln Leu Leu Asp Arg Gly Ala Thr Ala Leu Glu Leu Met
                            325                 330                 335

Thr Ile Asp Val Pro Arg Leu Met Thr Gln Asp Cys Leu Glu Gln Thr
                            340                 345                 350

Lys Arg Thr Ala Asn Ser Pro Ala Ile Thr Glu Asn Met Phe Cys Ala
                    355                 360                 365

Gly Tyr Leu Asp Gly Thr Lys Asp Ala Cys Lys Gly Asp Ser Gly Gly
                    370                 375                 380

Pro His Ala Thr Lys Tyr Gln Gly Thr Trp Tyr Leu Thr Gly Ile Val
        385                 390                 395                 400

Ser Trp Gly Glu Gly Cys Ala Ala Val Gly His Phe Gly Val Tyr Thr
                            405                 410                 415

Arg Val Ser Gln Tyr Ile Glu Trp Leu Asn Arg Leu Met Asp Ser Lys
                    420                 425                 430

Pro Ser Pro Gly Val Leu Leu Arg Ala Pro Phe Pro
                    435                 440

<210> SEQ ID NO 9
<211> LENGTH: 1389
<212> TYPE: DNA
<213> ORGANISM: Artificial sequence
<220> FEATURE:
<223> OTHER INFORMATION: recombinant clotting factor sequence

<400> SEQUENCE: 9
atgcagtgcc tgaacatgat catggccgag tcccccggcc tgatcaccat ctgcctgctg      60
gggtacctgc tgagcgccga gtgcaccgtg ttcctggacc acgagaacgc caccaagatc     120
ctgaacaggc ccaagagata caactccggc aagctggagg agttcgtgag ggggaacctg     180
gagagagagt gcatcgagga agtgcagc ttcgaggagg ccagggaggt gttcgagaac       240
accgagaaga ccaccgagtt ctggaagcag tacgtggacg cgaccagtg cgagtccaac      300 ccctgcctga cggcgggtc ctgcaaggac gacatcaaca gctacgagtg ctggtgcagg      360
ttcggcttcg aggggaagaa ctgcgagctg gacgccacct gcagcatcaa gaacggcaga     420
tgcaagcagt tctgcaagaa gtccgccgac aacaaggtgg tgtgcagctg caccgaggga     480
tacagactgg ctgaggacca gaagtcctgc gagccagctg tgccattccc atgcgggagg     540
gtgtccgtga gccacaccag caagaagctg accagagccg aaaccatctt ctccaacatg     600
```

```
gactacgaga acagcaccga ggccgaaacc atcctggaca acgtgaccca gtccacccag    660
agcttcaacg acttcacccg ggtggtggga ggagagaacg ctaagccagg acagttccca    720
tggcaggtgc tgctgaacgg gaagatcgac gccttctgcg gcgggtccat catcaacgag    780
aagtgggtgg tgaccgctgc tcactgcatc gagccaggag tgaagatcac cgtggtggct    840
ggggagcaca acatcgagaa gaccgagccc accgagcaga agcgcaacgt gatccgcgtg    900
atcccccacc acaactacaa cgccaccatc aacaagtact cccacgacat cgccctgctg    960
gagctggaca agcccctgac cctgaacagc tacgtgaccc ccatctgcat cgccaacagg   1020
gagtacacca acatcttcct gaagttcgga tccggatacg tgagcggatg ggacgcgtg    1080 ttcaaccgcg gccggtccgc cagcatcctg cagtacctga gagtgccact ggtggacaga   1140
gctacctgcc tgctgtccac caagttcacc atctacaaca acatgttctg cgctggatac   1200
cacgagggag ggaaggactc ctgccagggg gacagcggag gaccacacgt gaccgaggtg   1260
gagggcacct ccttcctgac cggcatcatc agctgggggg aggagtgcgc catgaagggc   1320
aagtacggga tctacaccaa ggtgagcaga tacgtgaact ggatcaagga gaagaccaag   1380
ctgacctga                                                           1389

<210> SEQ ID NO 10
<211> LENGTH: 1386
<212> TYPE: DNA
<213> ORGANISM: Artificial sequence
<220> FEATURE:
<223> OTHER INFORMATION: recombinant clotting factor sequence

<400> SEQUENCE: 10
atgcagtgcc tgaacatgat catggccgag tcccccggcc tgatcaccat ctgcctgctg     60
gggtacctgc tgagcgccga gtgcaccgtg ttcctggacc acgagaacgc caacaagatc    120
ctgaacaggc caagagata caactccggc aagctggagg agttcgtgag ggggaacctg    180
gagagagagt gcatcgagga gaagtgcagc ttcgaggagg ccagggaggt gttcgagaac    240
accgagaaga ccaccgagtt ctggaagcag tacgtggacg cgaccagtg cgagtccaac    300 ccctgcctga acgcgggtc ctgcaaggac gacatcaaca gctacgagtg ctggtgcagg    360
ttcggcttcg aggggaagaa ctgcgagctg gacgccacct gcagcatcaa gaacggcaga    420
tgcaagcagt tctgcaagaa gtccgccgac aacaaggtgg tgtgcagctg caccgaggga    480
tacagactgg ctgaggacca gaagtcctgc gagccagctg tgccattccc atgcgggagg    540
gtgtccgtga gccacaccag caagctgacc agagccgaaa ccatcttctc caacatggac    600
tacgagaaca gcaccgaggc cgaaaccatc ctggacaacg tgacccagtc caccagagc    660 ttcaacgact tcacccgggt ggtgggagga gagaacgcta agccaggaca gttcccatgg    720
caggtgctgc tgaacgggaa gatcgacgcc ttctgcggcg ggtccatcat caacgagaag    780
tgggtggtga ccgctgctca ctgcatcgag ccaggagtga gatcaccgt ggtggctggg    840 gagcacaaca tcgagaagac cgagcccacc gagcagaagc gcaacgtgat ccgcgtgatc    900
ccccaccaca actacaacgc caccatcaac aagtactccc acgacatcgc cctgctggag    960
ctggacaagc ccctgaccct gaacagctac gtgaccccca tctgcatcgc cgacagggag   1020
tacaccaaca tcttcctgaa gttcggatcc ggatacgtga gcggatgggg acgcgtgttc    1080
aaccgcggcc ggtccgccag catcctgcag tacctgagag tgccactggt ggacagagct   1140
acctgcctgc tgtccaccaa gttcaccatc tacaacaaca tgttctgcgc tggataccac   1200
```

-continued

| | |
|---|---|
| gagggaggga aggactcctg ccagggggac agcggaggac cacacgtgac cgaggtggag | 1260 |
| ggcacctcct tcctgaccgg catcatcagc tggggggagg agtgcgccat gaagggcaag | 1320 |
| tacgggatct acaccaaggt gagcagatac gtgaactgga tcaaggagaa gaccaagctg | 1380 |
| acctga | 1386 |

<210> SEQ ID NO 11
<211> LENGTH: 4377
<212> TYPE: DNA
<213> ORGANISM: Artificial sequence
<220> FEATURE:
<223> OTHER INFORMATION: recombinant clotting factor sequence

<400> SEQUENCE: 11

| | |
|---|---|
| atgcagatcg agctgtccac ctgcttcttc ctgtgcctgc tgcgcttctc cttcagcgcc | 60 |
| acccgccggt actacctggg agctgtggag ctgagctggg actacatgca gtccgacctg | 120 |
| ctgagcgagc tgcacgtgga caccagattc ccacccaggg tgccaagatc cttccccttc | 180 |
| aacaccagcg tgatgtacaa gaagaccgtg ttcgtggagt tcaccgacca cctgttcaac | 240 |
| atcgccaagc caggcccccc tggatgggc ctgctgggac aaccatctg gctgaggtg | 300 |
| tacgacaccg tcgtcatcac cctgaagaac atggcctccc accccgtgag cctgcacgct | 360 |
| gtgggcgtgt cctactggaa ggctagcgag ggagctgagt acgacgacca gacctcccag | 420 |
| agagagaagg aggacgacaa ggtgttcccc ggcgagagcc acacctacgt gtggcaggtg | 480 |
| ctgaaggaga acggaccaat ggcttccgac ccaccatgcc tgacctactc ctacctgagc | 540 |
| cacgtggacc tggtgaagga cctgaactcc ggcctgatcg gggcccctgct ggtgtgcaga | 600 |
| gagggcagcc tggctaagga gagaacccag accctgcacg agttcgtgct gctgttcgcc | 660 |
| gtgttcgacg agggaagtc ctggcacagc gaaaccaagg actccctgac ccaggctatg | 720 |
| gactccgcca gcgcccaggc ttggccaaag atgcacaccg tgaacggata cgtgaaccgc | 780 |
| tccctgccag gcctgatcgg atgccacaga aagagcgtgt actggcacgt gatcggaatg | 840 |
| ggaaccaccc cagaggtgca cagcatcttc ctggaggggc acaccttcct ggtgcgcaac | 900 |
| cacagacagg cttccctgga gatcagcccc atcaccttcc tgaccgctca ccctgctg | 960 |
| atggacctgg acagttcct gctgttctgc cacatctcca gccaccagca cgacgggatg | 1020 |
| gaggcctacg tgaaggtgga ctcctgccca gaggagccac agctgcggat gaagaacaac | 1080 |
| gaggaggagg aggactacga cgacgacctg acgactccg agatggacgt gctgcgcttc | 1140 |
| gacgacgaca actcccccag cttcatccag atccggagcg tggccaagaa gcaccccaag | 1200 |
| acctgggtgc actacatcgc tgctgaggag gaggactggg actacgctcc aagcgtgctg | 1260 |
| accccagacg acaggtccta caagagccag tacctgaaca cggccccca gaggatcggg | 1320 |
| agaaagtaca gaaggtgag gttcatggcc tacaccgacg aaaccttcaa gaccagagag | 1380 |
| gccatccagt acgagtccgg aatcctggga ccactgctgt acggagaagt ggggacacc | 1440 |
| ctgctgatca tcttcaagaa ccaggccagc aggcccacaa acatctaccc acacggaatc | 1500 |
| accgacgtgt ccccactgca cagcggcaga ctgccaaagg gggtgaagca cctgaaggac | 1560 |
| ctgcccatcc tgcccggcga gatcttcaag tacaagtgga ccgtgaccgt ggaggacgga | 1620 |
| ccaaccaagt ccgacccacg ctgcctgacc cggtactact ccagcttcat caacctggag | 1680 |
| cgcgacctgg ctagcggcct gatcggaccc ctgctgatct gctacaagga gtccgtggac | 1740 |
| cagggggca accagatgat gagcgacaag agaaacgtga tcctgttctc cgtgttcgac | 1800 |
| gagaaccaga gctggtacct gaccgaaaac atgcagcggt tcctgccaa cgctgctgga | 1860 |

```
gtgcagccac aggacccaga gttccaggct tccaacatca tgcacagcat caacggctac    1920
gtgttcgact ccctgcagct gagcgtgtgc ctgcacgagg tggcctactg gtacatcctg    1980
tccgtgggag ctcaaaccga cttcctgtcc gtgttcttca gcgggtacac cttcaagcac    2040
aagatggtgt acgaggacac cctgaccctg ttccccttct ccggcgaaac cgtgttcatg    2100
agcatggaga acccaggcct gtgggtgctg gatgccaca actccgactt caggaacaga    2160
ggcatgaccg ccctgctgaa ggtgtccagc tgcgaccgca caccgggga ctactacgag    2220 gacacctacg aggacatccc cacctacctg ctgagcgaga caacgtgat cgagccacgg    2280 tccttcagcc agaacccacc cgtgctgaag agacaccaga gagagatcac cctgaccacc    2340
ctgcagtccg agcaggagga gatcgactac gacgacacca tcagcatcga tgaagagg    2400 gaggacttcg acatctacgg cgaggacgag aaccagggc ccagatcctt ccagaagcgc    2460
acccggcact acttcatcgc tgctgtggag cgcctgtggg actacggcat gtccagctcc    2520
ccccacgtgc tgaggaacag agctcagtcc ggaagcgtgc cacagttcaa gaaggtggtg    2580
ttccaggagt tcaccgacgg atccttcacc cagccactgt acagaggaga gctgaacgag    2640
cacctgggcc tgctgggacc atacatcaga gccgaggtgg aggacaacat catggtgacc    2700
ttcaagaacc aggcctcccg gccctacagc ttctacagct ccctgatcag ctacgaggag    2760
gaccagaggc agggagctga gcccagaaag aacttcgtga gcccaacga aaccaagacc    2820 tacttctgga aggtgcagca ccacatggcc cccaccaagg acgagttcga ctgcaaggcc    2880
tgggcctact ctccgacgt ggacctggag aaggacatgc acagcggcct gatcggacca    2940
ctgctgatct gccacaccaa caccctgaac ccagctcacg gcaggcaggt gaccgtgcag    3000
gagttcgccc tgttcttcac catcttcgac gaaaccaagt cctggtactt caccgagaac    3060
atggagagga actgcagagc ccctgcaac atccagatgg aggaccccac cttcaaggag    3120
aactacagat tccacgccat caacggctac gtgatggaca ccctgccagg cctggtcatg    3180
gctcaggacc agcgcatccg gtggtacctg ctgtccatgg gcagcaacga aacatccac    3240 tccatccact tcagcgggca cgtgttcacc gtgaggaaga aggaggagta caagatggcc    3300
gtgtacaacc tgtaccccgg cgtgttcgaa accgtggaga tgctgcccag caaggccggg    3360
atctggagag tggagtgcct gatcggagag cacctgcacg ctggaatgtc caccctgttc    3420
ctggtgtaca gcaagcagtg ccagaccca ctgggaatgg cttccggaca catccgcgac    3480
ttccagatca ccgctagcgg acagtacgga cagtgggctc ccaagctggc ccggctgcac    3540
tactccggca gcatcaacgc ctggtccacc aaggagccct tcagctggat caaggtggac    3600
ctgctggccc ccatgatcat ccacggcatc aagacccagg gggcaggca aagttcagc    3660 tccctgtaca tctcccagtt catcatcatg tacagcctgg acggcaagaa gtggcagacc    3720
tacagaggca actccaccgg gaccctgatg gtgttcttcg gcaacgtgga cagctccggg    3780
atcaagcaca acatcttcaa ccccccatc atcgctagat acatcagact gcacccaacc    3840
cactactcca tcaggagcac cctgagaatg gagctgatgg gctgcgacct gaactcctgc    3900
agcatgcccc tggggatgga gtccaaggcc atcagcgacg cccagatcac cgccagctcc    3960
tacttcacca acatgttcgc tacctggtcc cccagccagc tagactgca cctgcagggc    4020 cgcaccaacg cctggcggcc ccaggtgaac aaccccaagg agtggctgca ggtggacttc    4080
cagaagacca tgaaggtgac cggcatcacc acccagggcg tgaagtccct gctgaccagc    4140
atgtacgtga aggagttcct gatcagctcc agccaggacg gacaccactg gacctgttc    4200
```

```
ctgcagaacg gcaaggtgaa ggtgttccag gggaaccagg actccttcac cccagtggtg    4260
aacagcctgg atccaccact gctgaccagg tacctgagaa tccaccccca gtcctgggtg    4320
caccagatcg ccctgagact ggaggtgctg ggatgcgagg cccagcagct gtactga       4377
```

<210> SEQ ID NO 12
<211> LENGTH: 4388
<212> TYPE: DNA
<213> ORGANISM: Artificial sequence
<220> FEATURE:
<223> OTHER INFORMATION: recombinant clotting factor sequence

<400> SEQUENCE: 12

```
atgcagatcg agctgagcac ctgcttcttc ctgtgcctgc tgcccttcag cttctccgcc      60
acccgccggt actacctggg agctgtggag ctgtcctggg actacatgca gagcgacctg     120
ctgtccgagc tgcacgtgga caccagattc ccaccccgcg tgccacggag cttcccctto     180 aacacctccg tgatgtacaa gaagaccgtg ttcgtggagt tcaccgacca cctgttcaac     240
atcgccaagc ctcgcccgcc ctggatgggc ctgctgggac aaccatccg ggccgaggtg      300 tacgacaccg tcgtcatcac cctgaagaac atggccagcc accccgtgtc cctgcacgct     360
gtgggcgtga gctactggaa ggcttccgag ggagctgagt acgacgacca gaccagccag     420
cgggagaagg aggacgacaa ggtcatcccc ggcgagtccc acacctacgt gtggcaggtg     480
ctgaaggaga cgaccaat ggcttccgac ccaccatgcc tgacctacag ctacctgtcc       540
cacgtggacc tggtgaagga cctgaacagc ggcctgatcg gggccctgct ggtgtgcaga     600
gagggctccc tggctaagga gagaaccag accctgcacg agttcgtgct gctgttcgcc     660
gtgttcgacg aggggaagag ctggcactcc gaggccaacg agagcctgac ccaggctatg     720
gacagcgcct ccgccgcc ctggcccaag atgcacaccg tgaacggcta cgtgaacagg      780
agcctgccag gcctgatcgg atgccacaga aagtccgtgt actggcacgt gatcggaatg     840
ggaaccaccc cagaggtgca ctccatcttc ctggaggggc acaccttcct ggtgaggaac     900
cacagacagg ccagcctgga gatctccccc atcaccttcc tgaccgctca gaccctgctg     960
atggacctgg acagttcct gctgttctgc cacatcccaa gccaccagca cgacggaatg    1020
gaggcctacg tgaaggtgga ctcctgccca gaggagccac agctgaggat gaagaacaac    1080
gaggaggagg aggactacga cgacgacctg tacgacagcg acatggacgt gctgcgcttc    1140
gacgacgaca acagcccccc cttcatccag atccggtccg tggccaagaa gcaccccaag    1200
acctggatcc actacatcgc tgctgaggag gaggactggg actacgctcc atccgtgctg    1260
accccaaccg acagaagcta caagtcccag tacctgaaca cggaccaca gagaatcgga    1320 cggaagtaca agaaggtgag gttcatggcc tacaccgacg aaaccttcaa gaccagagag    1380
gccatccagt acgagagcgg aatcctggga ccactgctgt acggagaagt ggggacacc    1440 ctgctgatca tcttcaagaa ccaggcctcc cgcccctaca acatctaccc ccacggcatc    1500
accaacgtga gcccactgca ctccggccgg ctgcccaagg gggtgaagca cctgaaggac    1560
atgcccatca tgcccggcga gatcttcaag tacaagtgga ccgtgaccct ggaggacgga    1620
ccaaccaaga gcgacccacg ctgcctgacc cggtactact ccagcttcat caacctggag    1680
cgcgacctgg cttccggcct gatcggaccc ctgctgatct gctacaagga gagcgtggac    1740
cagcgcggca accagatgat gtccgacaag cggaacgtga tcctgttcag cgtgttcgac    1800
gagaaccgct cctggtacct gaccgagaac atgcagcggt cctgcccaa cgctgctgga    1860 gtgcagccac aggacccaga gttccaggct agcaacatca tgcactccat caacggctac    1920
```

```
gtgttcgaca gcctgcagct gtccgtgtgc ctgcacgagg tggcctactg gtacatcctg    1980
tccgtgggag ctcagaccga cttcctgagc gtgttcttct ccgggtacac cttcaagcac    2040
aagatggtgt tcgaggacac cctgaccctg ttccccttca gcggcgaaac cgtgttcatg    2100
tccatggaga acccaggcct gtgggtgctg ggatgccaca actccgactt caggaacaga    2160
gggatgaccg ccctgctgaa ggtgtccagc tgcgaccgga acaccgacga ctactacgag    2220
gacacctacg aggacatccc cacctacctg ctgaacgaga caacgtgat cgagcccagg     2280 agcttctccc agaaccccc cgtgctgaag caccaccaga gagagatcac cctgaccacc     2340
ctgcagcccg agcaggagaa gatcgactac gacgacaccc tgagcatcga gatgaagcgc    2400
gaggacttcg acatctacgg agaggacgag aaccagggac cacggtcctt ccagaagaga    2460
acccggcact acttcatcgc tgctgtggag aggctgtggg actacggcat gagcagatcc    2520
ccccacgccc tgaggaacag agctcagagc ggatccgtgc acagttcaa gaaggtggtg     2580 ttccaggagt tcaccgacgg cagcttcacc cagcccctgt acaggggaga gctgaacgag    2640
cacctgggcc tgctgggacc ctacatcaga gccgaggtgg aggacaacat catggtgacc    2700
ttcaagaacc aggccagccg cccctactcc ttctactcca gcctgatctc ctacgaggag    2760
gaccagaggc agggagctga gcccagaaag aacttcgtga gcccaacga aaccaagacc     2820 tacttctgga aggtgcagca ccacatggcc cccaccaagg acgagttcga ctgcaaggcc    2880
tgggcctact tcagcgacgt ggacctggag aaggacctgc actccggcct gatcggacca    2940
ctgctgatct gcaggaccaa cacccctgaac ccagctcacg gcagacagct gaccgtgcag    3000
gagttcgccc tgttcttcac catcttcgac gaaaccaagt cctggtactt caccgagaac    3060
atggagagga actgcagagc ccctgcaac atccagatgg aggaccccac cttcaagaag    3120
aactacaggt tccacgccat caacggctac gtgatggaca ccctgccagg cctggtcatg    3180
gctcaggacc agcgcatccg gtggtacctg ctgagcatgg gctccaacga gaacatccac    3240
agcatccact tctccgggca cgtgttcacc gtgcgcaaga aggaggagta caagatggcc    3300
gtgtacaacc tgtaccccgg cgtgttcgaa accgtggaga tgctgccaag caaggctgga    3360
atctggagag tggagtgcct gatcggagag cacctgcagg ctggaatgag caccctgttc    3420
ctggtgtact ccaaggagtg ccagaccccca ctgggaatgg cttccgggag gatcagagac    3480
agccagatca ccgcttccgg acagtacgga cagtgggctc ccaagctggc ccggctgcac    3540
tacagcggct ccatcaacgc ctggagcacc aaggaccccct ctcctggat caaggtggac    3600 ctgctggccc ccatgatcat ccacggcatc aagacccagg gggccaggca gaagttctcc    3660
agcctgtaca tcagccagtt catcatcatg tactccctgg acggcaagaa gtggcagagc    3720
tacagaggca actccaccgg gaccctgatg gtgttcttcg gcaacgtgga ctccagcggg    3780
atcaagcaca acatcttcaa cccccccatc atcgctagat acatcagact gcacccaacc    3840
cactacagca tcaggtccac cctgagaatg gagctgatgg gctgcgacct gaacagctgc    3900
tccatgcccc tggggatgga gagcaaggcc atctccgacg cccagatcac cgcctccagc    3960
tacttcacca acatgttcgc cacctggagc ccctccaggg ccaggctgca cctgcaggga    4020
agaaccaacg cttggcggcc ccaggtgaac aaccccaagg agtggctgca ggtggacttc    4080
cagaagacca tgaaggtgac cggaatcacc acccagggag ctaagagcct gctgacctcc    4140
atgtacgtga aggagttcct gatctccagc tcccaggacg acaccactg gaccctgttc     4200 ctgcagaacg gcaaggtgaa ggtgttccag gggaaccagg acagcttcac cccagtggtg    4260
```

| | |
|---|---:|
| aactccctgg atccaccact gctgaccagg tacctgagaa tccaccccca gtcctgggtg | 4320 |
| caccacatcg ccctgagact ggaggtgctg ggatgcgagg ctcagcagct gtactgagcg | 4380 |
| gccgctga | 4388 |

<210> SEQ ID NO 13
<211> LENGTH: 4377
<212> TYPE: DNA
<213> ORGANISM: Artificial sequence
<220> FEATURE:
<223> OTHER INFORMATION: recombinant clotting factor sequence

<400> SEQUENCE: 13

| | |
|---|---:|
| atgcagatcg agctgtccac ctgcttcttc ctgtgcctgc tgcgcttctc cttcagcgcc | 60 |
| acccgccggt actacctggg agctgtggag ctgtcctggg actacatgca gagcgacctg | 120 |
| ctgggagagc tgcacgtgga caccagattc cacccaggg tgccaagatc cttccccttc | 180 |
| aacaccagcg tgatgtacaa gaagaccgtg ttcgtggagt tcaccgacca cctgttcaac | 240 |
| atcgccaagc ccaggccccc ctggatgggc ctgctgggac aaccatctg gctgaggtg | 300 |
| tacgacaccg tcgtcatcac cctgaagaac atggcctccc accccgtgag cctgcacgct | 360 |
| gtgggcgtgt cctactggaa ggctagcgag ggagctgagt acgacgacca gacctcccag | 420 |
| agagagaagg aggacgacaa ggtgttcccc ggcgagagcc acacctacgt gtggcaggtg | 480 |
| ctgaaggaga cgaccaat ggcttccgac ccaccatgcc tgacctactc ctacctgagc | 540 |
| cacgtggacc tggtgaagga cctgaactcc ggcctgatcg ggccctgct ggtgtgcaga | 600 |
| gagggcagcc tggctaagga gagaacccag accctgcacg agttcgtgct gctgttcgcc | 660 |
| gtgttcgacg aggggaagtc ctggcacagc gaaaccaagg actccctgac ccaggctatg | 720 |
| gactccgcca cgcccaggc ttggccaaag atgcacaccg tgaacggata cgtgaaccgc | 780 |
| tccctgccag gcctgatcgg atgccacaga aagagcgtgt actggcacgt gatcggaatg | 840 |
| ggaaccaccc cagaggtgca cagcatcttc tggaggggc acaccttcct ggtgcgcaac | 900 |
| cacagacagg cttccctgga gatcagcccc atcaccttcc tgaccgctca gaccctgctg | 960 |
| atggacctgg acagttcct gctgttctgc cacatctcca gccaccagca cgacgggatg | 1020 |
| gaggcctacg tgaaggtgga ctcctgccca gaggagccac agctgcggat gaagaacaac | 1080 |
| gaggaggagg aggactacga cgacgacctg gacgactccg agatggacgt gctgcgcttc | 1140 |
| gacgacgaca actcccccag cttcatccag atccggagcg tggccaagaa gcaccccaag | 1200 |
| acctgggtgc actacatcgc tgctgaggag gaggactggg actacgctcc aagcgtgctg | 1260 |
| accccagacg acaggtccta caagagccag tacctgaaca cgcccccca gaggatcggg | 1320 |
| agaaagtaca agaaggtgag gttcatggcc tacaccgacg aaaccttcaa gaccagagag | 1380 |
| gccatccagt acgagtccgg aatcctggga ccactgctgt acggagaagt ggggacacc | 1440 |
| ctgctgatca tcttcaagaa ccaggccagc aggccctaca acatctaccc acacggaatc | 1500 |
| accgacgtgt ccccactgca cagcggcaga ctgccaaagg gggtgaagca cctgaaggac | 1560 |
| ctgcccatcc tgcccggcga gatcttcaag tacaagtgga ccgtgaccgt ggaggacgga | 1620 |
| ccaaccaagt ccgacccacg ctgcctgacc cggtactact ccagcttcat caacctggag | 1680 |
| cgcgacctgg ctagcggcct gatcggaccc ctgctgatct gctacaagga gtccgtggac | 1740 |
| cagaggggca accagatgat gagcgacaag agaaacgtga cctgttctc cgtgttcgac | 1800 |
| gagaaccaga gctggtacct gaccgaaaac atgcagcggg tcctgcccaa cgctgctgga | 1860 |
| gtgcagccac aggacccaga gttccaggct tccaacatca tgcacagcat caacggctac | 1920 |

-continued

```
gtgttcgact ccctgcagct gagcgtgtgc ctgcacgagg tggcctactg gtacatcctg    1980
tccgtgggag ctcaaaccga cttcctgtcc gtgttcttca gcgggtacac cttcaagcac    2040
aagatggtgt acgaggacac cctgaccctg ttccccttct ccggcgaaac cgtgttcatg    2100
agcatggaga acccaggcct gtgggtgctg ggatgccaca actccgactt caggaacaga    2160
ggcatgaccg ccctgctgaa ggtgtccagc tgcgaccgca acaccgggga ctactacgag    2220
gacacctacg aggacatccc cacctacctg ctgagcgaga caacgtgat cgagccacgg     2280
tccttcagcc agaacccacc cgtgctgaag agacaccaga gagagatcac cctgaccacc    2340
ctgcagtccg agcaggagga gatcgactac gacgacacca tcagcatcga gatgaagagg    2400
gaggacttcg acatctacgg cgaggacgag aaccaggggc ccagatcctt ccagaagcgc    2460
acccggcact acttcatcgc tgctgtggag cgcctgtggg actacggcat gtccagctcc    2520
ccccacgtgc tgaggaacag agctcagtcc ggaagcgtgc acagttcaa gaaggtggtg     2580
ttccaggagt tcaccgacgg atccttcacc cagccactgt acagaggaga gctgaacgag    2640
cacctgggcc tgctgggacc atacatcaga gccgaggtgg aggacaacat catggtgacc    2700
ttcaagaacc aggcctcccg gccctacagc ttctacagct ccctgatcag ctacgaggag    2760
gaccagaggc agggagctga gcccagaaag aacttcgtga gcccaacga aaccaagacc     2820
tacttctgga aggtgcagca ccacatggcc cccaccaagg acgagttcga ctgcaaggcc    2880
tgggcctact ctccgacgt ggacctggag aaggacatgc acagcggcct gatcggacca     2940
ctgctgatct gccacaccaa cacccctgaac ccagctcacg gcaggcaggt gaccgtgcag   3000
gagttcgccc tgttcttcac catcttcgac gaaaccaagt cctggtactt caccgagaac    3060
atggagagga actgcagagc ccctgcaac atccagatgg aggacccccac cttcaaggag    3120
aactacagat tccacgccat caacggctac gtgatggaca ccctgccagg cctggtcatg    3180
gctcaggacc agcgcatccg gtggtacctg ctgtccatgg gcagcaacga gaacatccac    3240
tccatccact tcagcgggca cgtgttcacc gtgaggaaga aggaggagta caagatggcc    3300
gtgtacaacc tgtaccccgg cgtgttcgaa accgtggaga tgctgcccag caaggccggg    3360
atctggagag tggagtgcct gatcggagag cacctgcacg ctggaatgtc caccctgttc    3420
ctggtgtaca gcaagcagtg ccagaccccca ctgggaatgg cttccggaca catccgcgac   3480
ttccagatca ccgctagcgg acagtacgga cagtgggctc ccaagctggc ccggctgcac    3540
tactccggca gcatcaacgc ctggtccacc aaggagccct tcagctggat caaggtggac    3600
ctgctggccc ccatgatcat ccacggcatc aagacccagg gggccaggca agttcagc      3660
tccctgtaca tctcccagtt catcatcatg tacagcctgg acggcaagaa gtggcagacc    3720
tacagaggca actccaccgg gaccctgatg gtgttcttcg gcaacgtgga cagctccggg    3780
atcaagcaca acatcttcaa ccccccccatc atcgctagat acatcagact gcacccaacc   3840
cactactcca tcaggagcac cctgagaatg gagctgatgg gctgcgacct gaactcctgc    3900
agcatgcccc tggggatgga gtccaaggcc atcagcgacg cccagatcac cgccagctcc    3960
tacttcacca acatgttcgc tacctggtcc cccagccagg ctagactgca cctgcagggc    4020
cgcaccaacg cctggcggcc ccaggtgaac aaccccaagg agtggctgca ggtggacttc    4080
cagaagacca tgaaggtgac cggcatcacc acccagggcg tgaagtccct gctgaccagc    4140
atgtacgtga aggagttcct gatcagctcc agccaggacg gacaccactg gacccctgttc   4200
ttccagaacg gcaaggtgaa ggtgttccag gggaaccagg actccttcac cccagtggtg    4260
```

```
aacagcctgg atccaccact gctgaccagg tacctgagaa tccaccccca gtcctgggtg    4320
caccagatcg ccctgagact ggaggtgctg ggatgcgagg cccagcagct gtactga      4377

<210> SEQ ID NO 14
<211> LENGTH: 4388
<212> TYPE: DNA
<213> ORGANISM: Artificial sequence
<220> FEATURE:
<223> OTHER INFORMATION: recombinant clotting factor sequence

<400> SEQUENCE: 14
atgcagatcg agctgtccac ctgcttcttc ctgtgcctgc tgcgcttctc cttcagcgcc      60
acccgccggt actacctggg agctgtggag ctgtcctggg actacatgca gagcgacctg     120 ctggagagc tgcacgtgga caccagattc ccaccccgcg tgccacggtc cttcccttc       180 aacaccagcg tgatgtacaa gaagaccgtg ttcgtggagt tcaccgacca cctgttcaac     240
atcgccaagc ccaggccccc ctggatgggc ctgctgggac aaccatcca ggctgaggtg      300 tacgacaccg tcgtcatcac cctgaagaac atggcctccc accccgtgag cctgcacgct    360
gtgggcgtgt cctactggaa ggctagcgag ggagctgagt acgacgacca gacctcccag     420
cgcgagaagg aggacgacaa ggtgttcccc ggcgagagcc acacctacgt gtggcaggtg     480
ctgaaggaga acggaccaat ggcttccgac ccaccatgcc tgacctactc ctacctgagc    540 cacgtgacc tggtgaagga cctgaactcc ggcctgatcg gggccctgct ggtgtgcaga      600
gagggcagcc tggctaagga gagaacccag accctgcacg agttcgtgct gctgttcgcc    660
gtgttcgacg aggggaagtc ctggcacagc gaaaccaagg actccctgat gcaggatacc    720
gactccgcca gcgcccaggc ttggccaaag atgcacaccg tgaacggata cgtgaaccgc    780
tccctgccag gcctgatcgg atgccacaga agagcgtgt actggcacgt gatcggaatg     840
ggaaccaccc cagaggtgca cagcatcttc ctgggagggc acaccttcct ggtgaggaac    900
cacagacagg cctccctgga gatcagcccc atcaccttcc tgaccgctca gaccctgctg     960
atggacctgg acagttcct gctgttctgc cacatctcca gccaccagca cgacgggatg    1020
gaggcctacg tgaaggtgga ctcctgccca gaggagccac agctgcggat gaagaacaac    1080
gaggaggagg aggactacga caacgacctg gacgactccg agatggacgt gctgcgcttc    1140
gacgacgaca actccccag cttcatccag atccggagcg tggccaagaa gcaccccaag    1200
acctgggtgc actacatcgc tgctgaggag gaggactggg actacgctcc aagcgtgctg    1260
accccagacg acaggtccta caagagccag tacctgaaca cggaccaca gagaatcgga    1320 cggaagtaca agaaggtgag gttcatggcc tacaccgacg aaaccttcaa gaccagagag    1380
gccatccagt acgagtccgg aatcctggga ccactgctgt acgagagaagt ggggacacc   1440 ctgctgatca tcttcaagaa ccaggccagc cgccctaca acatctaccc acacggaatc    1500
accgacgtgt ccccactgca cagcggccgg ctgcccaagg gggtgaagca cctgaaggac   1560
ctgcccatcc tgcccggcga gatcttcaag tacaagtgga ccgtgaccgt ggaggacgga    1620
ccaaccaagt ccgacccaag gtgcctgacc agatactact ccagcttcat caacctggag    1680
cgcgacctgg ctagcggcct gatcggaccc ctgctgatct gctacaagga gtccgtggac    1740
cagaggggca accagatgat gagcgacaag agaaacgtga tcctgttctc cgtgttcgac    1800
gagaaccaga gctggtacct gaccgaaaac atgcagcggt tcctgccaa cgctgctgga    1860 gtgcagccac aggacccaga gttccaggct tccaacatca tgcacagcat caacggctac    1920
gtgttcgact ccctgcagct gagcgtgtgc ctgcacgagg tggcctactg gtacatcctg    1980
```

```
tccatcggcg cccagaccga cttcctgtcc gtgttcttca gcgggtacac cttcaagcac   2040
aagatggtgt acgaggacac cctgaccctg ttccccttct ccggcgaaac cgtgttcatg   2100
agcatggaga acccaggcct gtgggtgctg ggatgccaca acagcgactt caggaacaga   2160
ggcatgaccg ccctgctgaa ggtgtccagc tgcgacagga acaccgggga ctactacgag   2220
gacacctacg aggacatctc cacctacctg ctgagcgaga caacgtgat cgagcccaga    2280 tccttcagcc agaatccccc cgtgctgaag aggcaccaga gagagatcac cctgaccacc   2340
ctgcagtccg atcaggagga gatcgactac gacgacacca tcagcaccga tgaagcgc    2400 gaggacttcg acatctacgg agaggacgag aaccagggac caaggtcctt ccagaagaag   2460
accagacact acttcatcgc tgctgtggag cggctgtggg actacggaat gtccagctcc   2520
ccacacgtgc tgagaaacag agctcagtcc gggagcgtgc cccagttcaa gaaggtggtg   2580
ttccaggagt tcaccgacgg ctccttcacc cagcccctgt acggggaga gctgaacgag   2640 cacctgggcc tgctgggacc ctacatcaga gccgaggtgg aggacaacat catggtgacc   2700
ttcaagaacc aggcctcccg cccctacagc ttctacagct ccctgatcag ctacgaggag   2760
gaccagagac agggagctga gccacggaag aacttcgtga gcccaacga aaccaagacc   2820 tacttctgga aggtgcagca ccacatggcc cccaccaagg acgagttcga ctgcaaggcc   2880
tgggcctact ctccgacgt ggacctggag aaggacatgc acagcggcct gatcggacca   2940
ctgctgatct gccacaccaa caccctgaac ccagctcacg gcaggcaggt gaccgtgcag   3000
gagttcgccc tgttcttcac catcttcgac gaaaccaagt cctggtactt caccgagaac   3060
atggagcgca actgccgggc ccctgcaac atccagatgg aggaccccac cttcaaggag    3120
aactacagat tccacgccat caacggctac gtgatggaca ccctgccagg cctggtcatg   3180
gctcaggacc agaggatcag atggtacctg ctgtccatgg gcagcaacga aacatccac    3240 tccatccact tcagcgggca cgtgttcacc gtgaggaaga aggaggagta caagatggcc   3300
gtgtacaacc tgtaccccgg cgtgttcgaa accgtggaga tgctgcccag caaggccggg   3360
atctggagag tggagtgcct gatcggagag cacctgcacg ctggaatgtc caccctgttc   3420
ctggtgtaca gcaagcagtg ccagacccca ctgggaatgg cttccggaca catcagggac   3480
ttccagatca ccgctagcgg acagtacgga cagtgggctc caaagctggc tagactgcac   3540
tactccggca gcatcaacgc ctggtccacc aaggagccct tcagctggat caaggtggac   3600
ctgctggccc ccatgatcat ccacggcatc aagacccagg agctagaca aagttcagc     3660 tccctgtaca tctcccagtt catcatcatg tacagcctgg acggcaagaa gtggcagacc   3720
taccggggca actccaccgg gaccctgatg gtgttcttcg gcaacgtgga cagctccggg   3780
atcaagcaca acatcttcaa ccccccatc atcgccaggt acatcagact gcaccccacc    3840
cactactcca tccgcagcac cctgcggatg gagctgatgg gctgcgacct gaactcctgc   3900
agcatgcccc tggggatgga gtccaaggcc atcagcgacg cccagatcac cgccagctcc   3960
tacttcacca acatgttcgc tacctggtcc cccagccagg ctagactgca cctgcaggga   4020
aggaccaacg cttggcgccc ccaggtgaac aaccccaagg agtggctgca ggtggacttc   4080
cagaagacca tgaaggtgac cggcatcacc acccaggggcg tgaagtccct gctgaccagc   4140
atgtacgtga aggagttcct gatcagctcc agccaggacg gacaccactg gaccctgttc   4200
ttccagaacg gcaaggtgaa ggtgttccag gggaaccagg actccttcac cccagtggtg   4260
aacagcctgg atccaccact gctgaccaga tacctgcgga tccaccccca gtcctgggtg   4320
```

```
caccagatcg ccctgagact ggaggtgctg ggatgcgagg cccagcagct gtactgagcg    4380
gccgctga                                                             4388
```

<210> SEQ ID NO 15
<211> LENGTH: 1335
<212> TYPE: DNA
<213> ORGANISM: Artificial sequence
<220> FEATURE:
<223> OTHER INFORMATION: recombinant clotting factor sequence

<400> SEQUENCE: 15

```
atggctcccc gggccctggc cctgctgtgc ttcctgctgg gcctgcaggg gtccctggct     60
gccgtgttca tcacccagga ggaggctcac agcgtgctgc acaggcagag aagagctaac    120
tccttcctgg aggagctgcg ccccggcagc ctggagcgcg agtgcaagga ggagcagtgc    180
tccttcgagg aggccaggga gatcttcaga agcaccgagc gcaccaagca gttctggatc    240
tcctacaacg acggcgacca gtgcgctagc aacccatgcc agaacggagg atcctgcgag    300
gaccagctgc agagctacat ctgcttctgc ctgccagact cgagggaag aaactgcgaa    360 accaacaaga cgaccagct gatctgcatg aacgagaacg gcgggtgcga gcagtactgc    420
tccgaccacg ctgaggctaa gcagcagctg agatgccacg agggatacac cctgcaggct    480
gacggggtgt cctgcacccc aaccgtggag tacccatgcg gcaagatccc cgtgctggag    540
aagcggaacg ctagcaaccc acagggaagg atcgtgggag gaaggtgtg cccaaaggga    600 gagtgcccat ggcaggccgt gctgaagctg aacgggccc tgctgtgcgg agggaccctg    660
ctggacacct cctgggtggt gagcgccgct cactgcttcg acaagatcag gtcctggaga    720
aacctgaccg tggtgctggg agagcacgac ctgagcgagg aggacgggga cgagcaggag    780
agacaggtgg cccaggtcat catccccgac aagtacgtgc ccggcaagac cgaccacgac    840
atcgccctgc tgagactgcg caggcccgtg gccctgaccg accacgtggt gccactgtgc    900
ctgccagaga gagccttctc cgagaggacc ctggcctaca tccgcttctc ccgggtgagc    960
ggatggggac agctgctgga cagaggagcc accgccctgg agctgatggc catcgacgtg   1020
cccaggctga tgaccagga ctgcctggag cagtccaaga aagagctga cagcccagcc   1080 atcaccgaga acatgttctg cgctggatac ctggacggat ccaaggacgc ctgcaagggc   1140
gacagcggag gaccacacgc taccaggtac agaggcacct ggtacctgac cggagtggtg   1200
tcctggggag agggatgcgc tgctgtggga cacttcgggg tgtacaccag agtgagccag   1260
tacaccgagt ggctgtcccg cctgatggac agcgagccac accccggcgt gctgctgcgc   1320 gccccttcc cctga                                                    1335
```

<210> SEQ ID NO 16
<211> LENGTH: 1335
<212> TYPE: DNA
<213> ORGANISM: Artificial sequence
<220> FEATURE:
<223> OTHER INFORMATION: recombinant clotting factor sequence

<400> SEQUENCE: 16

```
atgcactccc gccggctggc cttcctgtgc ttcctgctgg cctgcagca gagcctgacc     60 gccgtgttca tcaaccagga ggaggccaac tccgtgctgc acaggcagag agagagccaac   120 agcttcctgg aggagctgcg ctccggagc ctggagagag agtgcaagga ggagcagtgc    180
tccttcgagg aggccaggga gatcttcaag agcaccgaga gaaccaagca gttctggatc    240
acctacaacg acggcaacca gtgcgcttcc aacccatgcc agaacggagg atcctgcgtg    300
```

```
gaccagctgc agagctacat ctgcttctgc ctggaggact tcgaggggag aaactgcgaa    360
accaacaaga acagccagct gatctgcatg aacgagaacg gcgggtgcga gcagtactgc    420
tccgacaacc ccgaaaccaa gaggagctgc agatgccacg agggctacac cctgatggct    480
gacggggtgt cctgcacccc aaccgtggag tacccatgcg gcaagatccc cgtgctggag    540
aagcgcaacg acagcaaccc acagggaaga atcgtgggag ggaaggtgtg cccaaaggga    600
gagtgcccat ggcaggccgt gatcaagctg aacggggagc tgctgtgcgg agggaccctg    660
ctggacgcta cctgggtggt gtccgccgct cactgcttcg acaagctgcg caactggaag    720
aacctgaccg tggtgctggg agagcacgac ctgagcgagg aggacgggga cgagcaggag    780
agacaggtgg cccagatcat catccccgac aagtacatcc ccggcaagac cgaccacgac    840
atcgccctgc tgagactgag aacccccgtg aacttcaccg actacgtggt gcccactgtg    900
ctgccagaga aggccttctc cgagcagacc ctggcctaca tcaggttctc cagcgtgagc    960
ggatggggac agctgctgga cagaggagcc accgccctgg agctgatgac catcgacgtg   1020
ccccgcctga tgacccagga ctgcctggag cagaccaaga gaaccgctaa ctccccagct   1080
atcaccgaga acatgttctg cgctggatac ctggacggaa ccaaggacgc ttgcaagggc   1140
gacagcggag gaccccacgc caccaagtac cagggcacct ggtacctgac cggaatcgtg   1200
tcctggggag agggatgcgc tgctgtggga cacttcgggg tgtacaccag ggtgagccag   1260
tacatcgagt ggctgaacag actgatggac tccaagccca gccccggcgt gctgctgcgc   1320 gccccttcc cctga                                                      1335
```

```
<210> SEQ ID NO 17
<211> LENGTH: 462
<212> TYPE: PRT
<213> ORGANISM: Artificial sequence
<220> FEATURE:
<223> OTHER INFORMATION: recombinant clotting factor sequence

<400> SEQUENCE: 17

Met Gln Cys Leu Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Thr Lys Ile Leu Asn Arg Pro Lys Arg Tyr Asn
            35                  40                  45

Ser Gly Lys Leu Glu Glu Phe Val Gln Gly Asn Leu Glu Arg Glu Cys
        50                  55                  60

Ile Glu Glu Lys Cys Ser Phe Glu Glu Ala Arg Glu Val Phe Glu Asn
65                  70                  75                  80

Thr Glu Lys Thr Thr Glu Phe Trp Lys Gln Tyr Val Asp Gly Asp Gln
                85                  90                  95

Cys Glu Ser Asn Pro Cys Leu Asn Gly Gly Met Cys Lys Asp Asp Ile
            100                 105                 110

Asn Ser Tyr Glu Cys Trp Cys Gln Val Gly Phe Glu Gly Lys Asn Cys
        115                 120                 125

Glu Leu Asp Ala Thr Cys Ser Ile Lys Asn Gly Arg Cys Lys Gln Phe
    130                 135                 140

Cys Lys Lys Gly Ala Asp Asn Lys Val Val Cys Ser Cys Thr Thr Gly
145                 150                 155                 160

Tyr Arg Leu Ala Glu Asp Gln Lys Ser Cys Glu Pro Ala Val Pro Phe
                165                 170                 175
```

-continued

Pro Cys Gly Arg Val Ser Val Ser His Thr Ser Lys Lys Leu Thr Arg
              180                 185                 190

Ala Glu Thr Ile Phe Ser Asn Met Asp Tyr Glu Asn Ser Thr Glu Ala
              195                 200                 205

Glu Thr Ile Leu Asp Asn Val Thr Gln Ser Thr Gln Ser Phe Asn Asp
210                 215                 220

Phe Thr Arg Val Val Gly Gly Glu Asn Ala Lys Pro Gly Gln Phe Pro
225                 230                 235                 240

Trp Gln Val Leu Leu Asn Gly Lys Ile Asp Ala Phe Cys Gly Gly Ser
              245                 250                 255

Ile Ile Asn Glu Lys Trp Val Val Thr Ala Ala His Cys Ile Glu Pro
              260                 265                 270

Gly Val Lys Ile Thr Val Val Ala Gly Glu His Asn Thr Glu Glu Thr
              275                 280                 285

Glu His Thr Glu Gln Lys Arg Asn Val Ile Arg Val Ile Pro His His
290                 295                 300

Ser Tyr Asn Ala Thr Ile Asn Lys Tyr Ser His Asp Ile Ala Leu Leu
305                 310                 315                 320

Glu Leu Asp Lys Pro Leu Thr Leu Asn Ser Tyr Val Thr Pro Ile Cys
              325                 330                 335

Ile Ala Asn Arg Glu Tyr Thr Asn Ile Phe Leu Lys Phe Gly Ser Gly
              340                 345                 350

Tyr Val Ser Gly Trp Gly Lys Val Phe Asn Arg Gly Arg Ser Ala Ser
              355                 360                 365

Ile Leu Gln Tyr Leu Lys Val Pro Leu Val Asp Arg Ala Thr Cys Leu
              370                 375                 380

Arg Ser Thr Lys Phe Thr Ile Tyr Asn Asn Met Phe Cys Ala Gly Tyr
385                 390                 395                 400

His Glu Gly Gly Lys Asp Ser Cys Gln Gly Asp Ser Gly Gly Pro His
              405                 410                 415

Val Thr Glu Val Glu Gly Thr Ser Phe Leu Thr Gly Ile Ile Ser Trp
              420                 425                 430

Gly Glu Glu Cys Ala Met Lys Gly Lys Tyr Gly Ile Tyr Thr Lys Val
              435                 440                 445

Ser Arg Tyr Val Asn Trp Ile Lys Glu Lys Thr Lys Leu Thr
              450                 455                 460

<210> SEQ ID NO 18
<211> LENGTH: 462
<212> TYPE: PRT
<213> ORGANISM: Artificial sequence
<220> FEATURE:
<223> OTHER INFORMATION: recombinant clotting factor sequence

<400> SEQUENCE: 18

Met Gln Cys Leu Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
              20                  25                  30

Asp His Glu Asn Ala Thr Lys Ile Leu Asn Arg Pro Lys Arg Tyr Asn
              35                  40                  45

Ser Gly Lys Leu Glu Glu Phe Val Gln Gly Asn Leu Glu Arg Glu Cys
        50                  55                  60

Ile Glu Glu Lys Cys Ser Phe Glu Glu Ala Arg Glu Val Phe Glu Asn
65                  70                  75                  80

Thr Glu Lys Thr Thr Glu Phe Trp Lys Gln Tyr Val Asp Gly Asp Gln
                85                  90                  95

Cys Glu Ser Asn Pro Cys Leu Asn Gly Leu Cys Lys Asp Asp Ile
            100                 105                 110

Asn Ser Tyr Glu Cys Trp Cys Gln Val Gly Phe Glu Gly Lys Asn Cys
        115                 120                 125

Glu Leu Asp Ala Thr Cys Ser Ile Lys Asn Gly Arg Cys Lys Gln Phe
130                 135                 140

Cys Lys Lys Gly Ala Asp Asn Lys Val Val Cys Ser Cys Thr Thr Gly
145                 150                 155                 160

Tyr Arg Leu Ala Glu Asp Gln Lys Ser Cys Glu Pro Ala Val Pro Phe
                165                 170                 175

Pro Cys Gly Arg Val Ser Val Ser His Thr Ser Thr Lys Leu Thr Arg
            180                 185                 190

Ala Glu Thr Ile Phe Ser Asn Met Asp Tyr Glu Asn Ser Thr Glu Ala
        195                 200                 205

Glu Thr Ile Leu Asp Asn Val Thr Gln Ser Thr Gln Ser Phe Asn Asp
210                 215                 220

Phe Thr Arg Val Val Gly Gly Glu Asn Ala Lys Pro Gly Gln Phe Pro
225                 230                 235                 240

Trp Gln Val Leu Leu Asn Gly Lys Ile Asp Ala Phe Cys Gly Gly Ser
                245                 250                 255

Ile Ile Asn Glu Lys Trp Val Val Thr Ala Ala His Cys Ile Glu Pro
            260                 265                 270

Gly Val Lys Ile Thr Val Val Ala Gly Glu His Asn Thr Glu Glu Thr
        275                 280                 285

Glu His Thr Glu Gln Lys Arg Asn Val Ile Arg Val Ile Pro His His
290                 295                 300

Ser Tyr Asn Ala Thr Ile Asn Lys Tyr Ser His Asp Ile Ala Leu Leu
305                 310                 315                 320

Glu Leu Asp Lys Pro Leu Thr Leu Asn Ser Tyr Val Thr Pro Ile Cys
                325                 330                 335

Ile Ala Asp Arg Glu Tyr Thr Asn Ile Phe Leu Lys Phe Gly Ser Gly
            340                 345                 350

Tyr Val Ser Gly Trp Gly Lys Val Phe Asn Arg Gly Arg Ser Ala Ser
        355                 360                 365

Ile Leu Gln Tyr Leu Lys Val Pro Leu Val Asp Arg Ala Thr Cys Leu
370                 375                 380

Arg Ser Thr Lys Phe Thr Ile Tyr Asn Asn Met Phe Cys Ala Gly Phe
385                 390                 395                 400

His Glu Gly Gly Lys Asp Ser Cys Gln Gly Asp Ser Gly Gly Pro His
                405                 410                 415

Val Thr Glu Val Glu Gly Thr Ser Phe Leu Thr Gly Ile Ile Ser Trp
            420                 425                 430

Gly Glu Glu Cys Ala Met Lys Gly Lys Tyr Gly Ile Tyr Thr Lys Val
        435                 440                 445

Ser Arg Tyr Val Asn Trp Ile Lys Glu Lys Thr Lys Leu Thr
450                 455                 460

<210> SEQ ID NO 19
<211> LENGTH: 462
<212> TYPE: PRT
<213> ORGANISM: Artificial sequence
<220> FEATURE:

<223> OTHER INFORMATION: recombinant clotting factor sequence

<400> SEQUENCE: 19

```
Met Gln Cys Leu Asn Met Ile Met Ala Glu Ser Pro Gly Leu Val Thr
1               5                   10                  15

Ile Cys Leu Leu Gly Tyr Leu Leu Ser Ala Glu Cys Thr Val Phe Leu
            20                  25                  30

Asp Arg Glu Asn Ala Thr Lys Ile Leu Asn Arg Pro Lys Arg Tyr Asn
        35                  40                  45

Ser Gly Lys Leu Glu Glu Phe Val Arg Gly Asn Leu Glu Arg Glu Cys
    50                  55                  60

Ile Glu Glu Lys Cys Ser Phe Glu Glu Ala Arg Glu Val Phe Glu Asn
65                  70                  75                  80

Thr Glu Lys Thr Thr Glu Phe Trp Lys Gln Tyr Val Asp Gly Asp Gln
                85                  90                  95

Cys Glu Ser Asn Pro Cys Leu Asn Gly Gly Leu Cys Lys Asp Asp Ile
            100                 105                 110

Asn Ser Tyr Glu Cys Trp Cys Gln Val Gly Phe Glu Gly Lys Asn Cys
        115                 120                 125

Glu Leu Asp Ala Thr Cys Ser Ile Lys Asn Gly Arg Cys Lys Gln Phe
    130                 135                 140

Cys Lys Lys Gly Ala Asp Asn Lys Val Val Cys Ser Cys Thr Thr Gly
145                 150                 155                 160

Tyr Arg Leu Ala Glu Asp Gln Lys Ser Cys Glu Pro Ala Val Pro Phe
                165                 170                 175

Pro Cys Gly Arg Val Ser Val Ser His Thr Ser Thr Lys Leu Thr Arg
            180                 185                 190

Ala Glu Thr Ile Phe Ser Asn Met Asp Tyr Glu Asn Ser Thr Glu Ala
        195                 200                 205

Glu Ile Ile Leu Asp Asn Val Thr Gln Ser Asn Gln Ser Phe Asn Asp
    210                 215                 220

Phe Thr Arg Ile Val Gly Gly Glu Asn Ala Lys Pro Gly Gln Phe Pro
225                 230                 235                 240

Trp Gln Val Leu Leu Asn Gly Lys Ile Asp Ala Phe Cys Gly Gly Ser
                245                 250                 255

Ile Ile Asn Glu Lys Trp Val Val Thr Ala Ala His Cys Ile Glu Pro
            260                 265                 270

Gly Val Lys Ile Thr Val Val Ala Gly Glu His Asn Thr Glu Glu Thr
        275                 280                 285

Glu Pro Thr Glu Gln Lys Arg Asn Val Ile Arg Ala Ile Pro His His
    290                 295                 300

Ser Tyr Asn Ala Thr Val Asn Lys Tyr Ser His Asp Ile Ala Leu Leu
305                 310                 315                 320

Glu Leu Asp Glu Pro Leu Thr Leu Asn Ser Tyr Val Thr Pro Ile Cys
                325                 330                 335

Ile Ala Asp Arg Glu Tyr Thr Asn Ile Phe Leu Lys Phe Gly Ser Gly
            340                 345                 350

Tyr Val Ser Gly Trp Gly Lys Val Phe Asn Arg Gly Arg Ser Ala Ser
        355                 360                 365

Ile Leu Gln Tyr Leu Lys Val Pro Leu Val Asp Arg Ala Thr Cys Leu
    370                 375                 380

Arg Ser Thr Lys Phe Thr Ile Tyr Asn Asn Met Phe Cys Ala Gly Phe
385                 390                 395                 400
```

```
His Glu Gly Gly Lys Asp Ser Cys Gln Gly Asp Ser Gly Gly Pro His
            405                 410                 415

Val Thr Glu Val Glu Gly Thr Ser Phe Leu Thr Gly Ile Ile Ser Trp
        420                 425                 430

Gly Glu Glu Cys Ala Val Lys Gly Lys Tyr Gly Ile Tyr Thr Lys Val
            435                 440                 445

Ser Arg Tyr Val Asn Trp Ile Lys Glu Lys Thr Lys Leu Thr
        450                 455                 460

<210> SEQ ID NO 20
<211> LENGTH: 462
<212> TYPE: PRT
<213> ORGANISM: Artificial sequence
<220> FEATURE:
<223> OTHER INFORMATION: recombinant clotting factor sequence

<400> SEQUENCE: 20

Met Gln Cys Leu Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Thr Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Ile Glu Glu Lys Cys Ser Phe Glu Glu Ala Arg Glu Val Phe Glu Asn
65                  70                  75                  80

Thr Glu Lys Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Gln Val Gly Phe Glu Gly Lys Asn Cys
        115                 120                 125

Glu Leu Asp Ala Thr Cys Ser Ile Lys Asn Gly Arg Cys Lys Gln Phe
    130                 135                 140

Cys Lys Lys Gly Ala Asp Asn Lys Val Val Cys Ser Cys Thr Glu Gly
145                 150                 155                 160

Tyr Arg Leu Ala Glu Asp Gln Lys Ser Cys Glu Pro Ala Val Pro Phe
                165                 170                 175

Pro Cys Gly Arg Val Ser Val Ser His Thr Ser Lys Lys Leu Thr Arg
            180                 185                 190

Ala Glu Thr Ile Phe Ser Asn Met Asp Tyr Glu Asn Ser Thr Glu Ala
        195                 200                 205

Glu Thr Ile Leu Asp Asn Val Thr Gln Ser Thr Gln Ser Phe Asn Asp
    210                 215                 220

Phe Thr Arg Val Val Gly Gly Glu Asn Ala Lys Pro Gly Gln Phe Pro
225                 230                 235                 240

Trp Gln Val Leu Leu Asn Gly Lys Ile Asp Ala Phe Cys Gly Gly Ser
                245                 250                 255

Ile Ile Asn Glu Lys Trp Val Val Thr Ala Ala His Cys Ile Glu Pro
            260                 265                 270

Gly Val Lys Ile Thr Val Val Ala Gly Glu His Asn Ile Glu Glu Thr
        275                 280                 285

Glu His Thr Glu Gln Lys Arg Asn Val Ile Arg Val Ile Pro His His
    290                 295                 300
```

```
Asn Tyr Asn Ala Thr Ile Asn Lys Tyr Ser His Asp Ile Ala Leu Leu
305                 310                 315                 320

Glu Leu Asp Lys Pro Leu Thr Leu Asn Ser Tyr Val Thr Pro Ile Cys
            325                 330                 335

Ile Ala Asn Arg Glu Tyr Thr Asn Ile Phe Leu Lys Phe Gly Ser Gly
            340                 345                 350

Tyr Val Ser Gly Trp Gly Arg Val Phe Asn Arg Gly Arg Ser Ala Ser
        355                 360                 365

Ile Leu Gln Tyr Leu Arg Val Pro Leu Val Asp Arg Ala Thr Cys Leu
    370                 375                 380

Arg Ser Thr Lys Phe Thr Ile Tyr Asn Asn Met Phe Cys Ala Gly Tyr
385                 390                 395                 400

His Glu Gly Gly Lys Asp Ser Cys Gln Gly Asp Ser Gly Gly Pro His
            405                 410                 415

Val Thr Glu Val Glu Gly Thr Ser Phe Leu Thr Gly Ile Ile Ser Trp
        420                 425                 430

Gly Glu Glu Cys Ala Met Lys Gly Lys Tyr Gly Ile Tyr Thr Lys Val
            435                 440                 445

Ser Arg Tyr Val Asn Trp Ile Lys Glu Lys Thr Lys Leu Thr
450                 455                 460

<210> SEQ ID NO 21
<211> LENGTH: 462
<212> TYPE: PRT
<213> ORGANISM: Artificial sequence
<220> FEATURE:
<223> OTHER INFORMATION: recombinant clotting factor sequence

<400> SEQUENCE: 21

Met Gln His Leu Asn Thr Ile Met Ala Glu Ser Pro Gly Leu Ile Thr
1               5                   10                  15

Ile Phe Leu Leu Gly Tyr Leu Leu Ser Ala Glu Cys Ala Val Phe Leu
            20                  25                  30

Asp Arg Glu Asn Ala Thr Lys Ile Leu Thr Arg Pro Lys Arg Tyr Asn
        35                  40                  45

Ser Gly Lys Leu Glu Glu Phe Val Gln Gly Asn Leu Glu Arg Glu Cys
    50                  55                  60

Ile Glu Glu Arg Cys Ser Phe Glu Glu Ala Arg Glu Val Phe Glu Asn
65                  70                  75                  80

Thr Glu Lys Thr Thr Glu Phe Trp Lys Gln Tyr Val Asp Gly Asp Gln
                85                  90                  95

Cys Glu Ser Asn Pro Cys Leu Asn Gly Gly Lys Cys Lys Asp Asp Ile
            100                 105                 110

Asn Ser Tyr Glu Cys Trp Cys Gln Val Gly Phe Glu Gly Arg Asn Cys
        115                 120                 125

Glu Leu Asp Ala Thr Cys Asn Ile Lys Asn Gly Arg Cys Lys Gln Phe
    130                 135                 140

Cys Lys Asn Gly Ala Asp Asn Lys Val Ile Cys Ser Cys Thr Glu Gly
145                 150                 155                 160

Tyr Gln Leu Ala Glu Asp Gln Lys Ser Cys Glu Pro Ala Val Pro Phe
                165                 170                 175

Pro Cys Gly Arg Val Ser Val Ser Tyr Ser Ser Lys Lys Leu Thr Arg
            180                 185                 190

Ala Glu Thr Ile Phe Ser Asn Met Asp Tyr Glu Asn Ser Thr Glu Ala
        195                 200                 205
```

```
Glu Thr Ile Leu Asp Asn Val Thr Glu Asn Ser Glu Ser Leu Asn Asp
            210                 215                 220
Phe Thr Arg Val Val Gly Gly Glu Asn Ala Lys Pro Gly Gln Ile Pro
225                 230                 235                 240
Trp Gln Val Ile Leu Asn Gly Glu Ile Glu Ala Phe Cys Gly Gly Ala
                    245                 250                 255
Ile Ile Asn Glu Lys Trp Val Val Thr Ala Ala His Cys Leu Lys Pro
                260                 265                 270
Gly Asp Lys Ile Glu Val Val Ala Gly Glu Tyr Asn Ile Asp Glu Lys
            275                 280                 285
Glu Asp Thr Glu Gln Arg Arg Asn Val Ile Arg Thr Ile Pro His His
290                 295                 300
His Tyr Asn Ala Thr Ile Asn Lys Tyr Ser His Asp Ile Ala Leu Leu
305                 310                 315                 320
Glu Leu Asp Lys Pro Leu Ile Leu Asn Ser Tyr Val Thr Pro Ile Cys
                    325                 330                 335
Val Ala Asn Arg Glu Tyr Thr Asn Ile Phe Leu Lys Phe Gly Ser Gly
                340                 345                 350
Tyr Val Ser Gly Trp Gly Lys Val Phe Asn Lys Gly Arg Gln Ala Ser
            355                 360                 365
Ile Leu Gln Tyr Leu Arg Val Pro Leu Val Asp Arg Ala Thr Cys Leu
370                 375                 380
Arg Ser Thr Thr Phe Thr Ile Tyr Asn Asn Met Phe Cys Ala Gly Tyr
385                 390                 395                 400
Arg Glu Gly Gly Lys Asp Ser Cys Glu Gly Asp Ser Gly Gly Pro His
                    405                 410                 415
Val Thr Glu Val Glu Gly Thr Ser Phe Leu Thr Gly Ile Ile Ser Trp
                420                 425                 430
Gly Glu Glu Cys Ala Met Lys Gly Lys Tyr Gly Ile Tyr Thr Lys Val
            435                 440                 445
Ser Arg Tyr Val Asn Trp Ile Lys Glu Lys Thr Lys Leu Thr
450                 455                 460
```

<210> SEQ ID NO 22
<211> LENGTH: 462
<212> TYPE: PRT
<213> ORGANISM: Artificial sequence
<220> FEATURE:
<223> OTHER INFORMATION: recombinant clotting factor sequence

<400> SEQUENCE: 22

```
Met Gln Cys Leu Asn Met Ile Met Ala Glu Ser Pro Gly Leu Ile Thr
1               5                   10                  15
Ile Cys Leu Leu Gly Tyr Leu Leu Ser Ala Glu Cys Thr Val Phe Leu
                20                  25                  30
Asp His Glu Asn Ala Thr Lys Ile Leu Asn Arg Pro Lys Arg Tyr Asn
            35                  40                  45
Ser Gly Lys Leu Glu Glu Phe Val Gln Gly Asn Leu Glu Arg Glu Cys
        50                  55                  60
Ile Glu Glu Lys Cys Ser Phe Glu Glu Ala Arg Glu Val Phe Glu Asn
65                  70                  75                  80
Thr Glu Lys Thr Thr Glu Phe Trp Lys Gln Tyr Val Asp Gly Asp Gln
                85                  90                  95
Cys Glu Ser Asn Pro Cys Leu Asn Gly Gly Ser Cys Lys Asp Asp Ile
                100                 105                 110
```

-continued

```
Asn Ser Tyr Glu Cys Trp Cys Gln Val Gly Phe Glu Gly Lys Asn Cys
            115                 120                 125

Glu Leu Asp Ala Thr Cys Ser Ile Lys Asn Gly Arg Cys Lys Gln Phe
        130                 135                 140

Cys Lys Lys Gly Ala Asp Asn Lys Val Val Cys Ser Cys Thr Glu Gly
145                 150                 155                 160

Tyr Arg Leu Ala Glu Asp Gln Lys Ser Cys Glu Pro Ala Val Pro Phe
                165                 170                 175

Pro Cys Gly Arg Val Ser Val Ser His Thr Ser Lys Lys Leu Thr Arg
            180                 185                 190

Ala Glu Thr Ile Phe Ser Asn Met Asp Tyr Glu Asn Ser Thr Glu Ala
        195                 200                 205

Glu Thr Ile Leu Asp Asn Val Thr Gln Ser Thr Gln Ser Phe Asn Asp
    210                 215                 220

Phe Thr Arg Val Val Gly Gly Glu Asn Ala Lys Pro Gly Gln Phe Pro
225                 230                 235                 240

Trp Gln Val Leu Leu Asn Gly Lys Ile Asp Ala Phe Cys Gly Gly Ser
                245                 250                 255

Ile Ile Asn Glu Lys Trp Val Val Thr Ala Ala His Cys Ile Glu Pro
            260                 265                 270

Gly Val Lys Ile Thr Val Val Ala Gly Glu His Asn Ile Glu Glu Thr
        275                 280                 285

Glu His Thr Glu Gln Lys Arg Asn Val Ile Arg Val Ile Pro His His
    290                 295                 300

Asn Tyr Asn Ala Thr Ile Asn Lys Tyr Ser His Asp Ile Ala Leu Leu
305                 310                 315                 320

Glu Leu Asp Lys Pro Leu Thr Leu Asn Ser Tyr Val Thr Pro Ile Cys
                325                 330                 335

Ile Ala Asn Arg Glu Tyr Thr Asn Ile Phe Leu Lys Phe Gly Ser Gly
            340                 345                 350

Tyr Val Ser Gly Trp Gly Arg Val Phe Asn Arg Gly Arg Ser Ala Ser
        355                 360                 365

Ile Leu Gln Tyr Leu Arg Val Pro Leu Val Asp Arg Ala Thr Cys Leu
    370                 375                 380

Arg Ser Thr Lys Phe Thr Ile Tyr Asn Asn Met Phe Cys Ala Gly Tyr
385                 390                 395                 400

His Glu Gly Gly Lys Asp Ser Cys Gln Gly Asp Ser Gly Gly Pro His
                405                 410                 415

Val Thr Glu Val Glu Gly Thr Ser Phe Leu Thr Gly Ile Ile Ser Trp
            420                 425                 430

Gly Glu Glu Cys Ala Met Lys Gly Lys Tyr Gly Ile Tyr Thr Lys Val
        435                 440                 445

Ser Arg Tyr Val Asn Trp Ile Lys Glu Lys Thr Lys Leu Thr
    450                 455                 460

<210> SEQ ID NO 23
<211> LENGTH: 462
<212> TYPE: PRT
<213> ORGANISM: Artificial sequence
<220> FEATURE:
<223> OTHER INFORMATION: recombinant clotting factor sequence

<400> SEQUENCE: 23

Met Gln Cys Leu Asn Met Ile Met Ala Glu Ser Pro Gly Leu Ile Thr
1               5                   10                  15
```

-continued

```
Ile Cys Leu Leu Gly Tyr Leu Leu Ser Ala Glu Cys Thr Val Phe Leu
             20                  25                  30

Asp His Glu Asn Ala Thr Lys Ile Leu Asn Arg Pro Lys Arg Tyr Asn
         35                  40                  45

Ser Gly Lys Leu Glu Glu Phe Val Arg Gly Asn Leu Glu Arg Glu Cys
     50                  55                  60

Ile Glu Glu Lys Cys Ser Phe Glu Glu Ala Arg Glu Val Phe Glu Asn
 65                  70                  75                  80

Thr Glu Lys Thr Thr Glu Phe Trp Lys Gln Tyr Val Asp Gly Asp Gln
                 85                  90                  95

Cys Glu Ser Asn Pro Cys Leu Asn Gly Gly Ser Cys Lys Asp Asp Ile
            100                 105                 110

Asn Ser Tyr Glu Cys Trp Cys Arg Phe Gly Phe Glu Gly Lys Asn Cys
        115                 120                 125

Glu Leu Asp Ala Thr Cys Ser Ile Lys Asn Gly Arg Cys Lys Gln Phe
    130                 135                 140

Cys Lys Lys Ser Ala Asp Asn Lys Val Val Cys Ser Cys Thr Glu Gly
145                 150                 155                 160

Tyr Arg Leu Ala Glu Asp Gln Lys Ser Cys Glu Pro Ala Val Pro Phe
                165                 170                 175

Pro Cys Gly Arg Val Ser Val Ser His Thr Ser Lys Lys Leu Thr Arg
            180                 185                 190

Ala Glu Thr Ile Phe Ser Asn Met Asp Tyr Glu Asn Ser Thr Glu Ala
        195                 200                 205

Glu Thr Ile Leu Asp Asn Val Thr Gln Ser Thr Gln Ser Phe Asn Asp
    210                 215                 220

Phe Thr Arg Val Val Gly Gly Glu Asn Ala Lys Pro Gly Gln Phe Pro
225                 230                 235                 240

Trp Gln Val Leu Leu Asn Gly Lys Ile Asp Ala Phe Cys Gly Gly Ser
                245                 250                 255

Ile Ile Asn Glu Lys Trp Val Val Thr Ala Ala His Cys Ile Glu Pro
            260                 265                 270

Gly Val Lys Ile Thr Val Val Ala Gly Glu His Asn Ile Glu Lys Thr
        275                 280                 285

Glu Pro Thr Glu Gln Lys Arg Asn Val Ile Arg Val Ile Pro His His
    290                 295                 300

Asn Tyr Asn Ala Thr Ile Asn Lys Tyr Ser His Asp Ile Ala Leu Leu
305                 310                 315                 320

Glu Leu Asp Lys Pro Leu Thr Leu Asn Ser Tyr Val Thr Pro Ile Cys
                325                 330                 335

Ile Ala Asn Arg Glu Tyr Thr Asn Ile Phe Leu Lys Phe Gly Ser Gly
            340                 345                 350

Tyr Val Ser Gly Trp Gly Arg Val Phe Asn Arg Gly Arg Ser Ala Ser
        355                 360                 365

Ile Leu Gln Tyr Leu Arg Val Pro Leu Val Asp Arg Ala Thr Cys Leu
    370                 375                 380

Arg Ser Thr Lys Phe Thr Ile Tyr Asn Asn Met Phe Cys Ala Gly Tyr
385                 390                 395                 400

His Glu Gly Gly Lys Asp Ser Cys Gln Gly Asp Ser Gly Gly Pro His
                405                 410                 415

Val Thr Glu Val Glu Gly Thr Ser Phe Leu Thr Gly Ile Ile Ser Trp
            420                 425                 430

Gly Glu Glu Cys Ala Met Lys Gly Lys Tyr Gly Ile Tyr Thr Lys Val
```

```
            435                 440                 445
Ser Arg Tyr Val Asn Trp Ile Lys Glu Lys Thr Lys Leu Thr
    450                 455                 460

<210> SEQ ID NO 24
<211> LENGTH: 461
<212> TYPE: PRT
<213> ORGANISM: Artificial sequence
<220> FEATURE:
<223> OTHER INFORMATION: recombinant clotting factor sequence

<400> SEQUENCE: 24

Met Gln Cys Leu Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Arg Gly Asn Leu Glu Arg Glu Cys
        50                  55                  60

Ile Glu Glu Lys Cys Ser Phe Glu Glu Ala Arg Glu Val Phe Glu Asn
65                  70                  75                  80

Thr Glu Lys Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Arg Phe Gly Phe Glu Gly Lys Asn Cys
        115                 120                 125

Glu Leu Asp Ala Thr Cys Ser Ile Lys Asn Gly Arg Cys Lys Gln Phe
    130                 135                 140

Cys Lys Lys Ser Ala Asp Asn Lys Val Val Cys Ser Cys Thr Glu Gly
145                 150                 155                 160

Tyr Arg Leu Ala Glu Asp Gln Lys Ser Cys Glu Pro Ala Val Pro Phe
                165                 170                 175

Pro Cys Gly Arg Val Ser Val Ser His Thr Ser Lys Leu Thr Arg Ala
            180                 185                 190

Glu Thr Ile Phe Ser Asn Met Asp Tyr Glu Asn Ser Thr Glu Ala Glu
        195                 200                 205

Thr Ile Leu Asp Asn Val Thr Gln Ser Thr Gln Ser Phe Asn Asp Phe
    210                 215                 220

Thr Arg Val Val Gly Gly Glu Asn Ala Lys Pro Gly Gln Phe Pro Trp
225                 230                 235                 240

Gln Val Leu Leu Asn Gly Lys Ile Asp Ala Phe Cys Gly Gly Ser Ile
                245                 250                 255

Ile Asn Glu Lys Trp Val Val Thr Ala Ala His Cys Ile Glu Pro Gly
            260                 265                 270

Val Lys Ile Thr Val Val Ala Gly Glu His Asn Ile Glu Lys Thr Glu
        275                 280                 285

Pro Thr Glu Gln Lys Arg Asn Val Ile Arg Val Ile Pro His His Asn
    290                 295                 300

Tyr Asn Ala Thr Ile Asn Lys Tyr Ser His Asp Ile Ala Leu Leu Glu
305                 310                 315                 320

Leu Asp Lys Pro Leu Thr Leu Asn Ser Tyr Val Thr Pro Ile Cys Ile
                325                 330                 335

Ala Asp Arg Glu Tyr Thr Asn Ile Phe Leu Lys Phe Gly Ser Gly Tyr
```

```
                340             345             350
Val Ser Gly Trp Gly Arg Val Phe Asn Arg Gly Arg Ser Ala Ser Ile
            355                 360                 365

Leu Gln Tyr Leu Arg Val Pro Leu Val Asp Arg Ala Thr Cys Leu Arg
        370                 375                 380

Ser Thr Lys Phe Thr Ile Tyr Asn Asn Met Phe Cys Ala Gly Tyr His
385                 390                 395                 400

Glu Gly Gly Lys Asp Ser Cys Gln Gly Asp Ser Gly Gly Pro His Val
            405                 410                 415

Thr Glu Val Glu Gly Thr Ser Phe Leu Thr Gly Ile Ile Ser Trp Gly
        420                 425                 430

Glu Glu Cys Ala Met Lys Gly Lys Tyr Gly Ile Tyr Thr Lys Val Ser
            435                 440                 445

Arg Tyr Val Asn Trp Ile Lys Glu Lys Thr Lys Leu Thr
        450                 455                 460

<210> SEQ ID NO 25
<211> LENGTH: 461
<212> TYPE: PRT
<213> ORGANISM: Artificial sequence
<220> FEATURE:
<223> OTHER INFORMATION: recombinant clotting factor sequence

<400> SEQUENCE: 25

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Lys Thr Thr Glu Phe Trp Lys Gln Tyr Val Asp Gly Asp Gln
            85                  90                  95

Cys Glu Ser Asn Pro Cys Leu Asn Gly Gly Ser Cys Lys Asp Asp Ile
        100                 105                 110

Asn Ser Tyr Glu Cys Trp Cys Pro Phe Gly Phe Glu Gly Lys Asn Cys
    115                 120                 125

Glu Leu Asp Val Thr Cys Asn Ile Lys Asn Gly Arg Cys Lys Gln Phe
130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
            165                 170                 175

Pro Cys Gly Arg Val Ser Val Ser Gln Thr Ser Lys Leu Thr Arg Ala
        180                 185                 190

Glu Thr Val Phe Pro Asp Val Asp Tyr Val Asn Ser Thr Glu Ala Glu
    195                 200                 205

Thr Ile Leu Asp Asn Ile Thr Gln Ser Thr Gln Ser Phe Asn Asp Phe
210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
```

```
                245                 250                 255
Val Asn Glu Lys Trp Val Val Thr Ala Ala His Cys Ile Glu Thr Gly
                260                 265                 270

Val Lys Ile Thr Val Val Ala Gly Glu His Asn Ile Glu Glu Thr Glu
                275                 280                 285

His Thr Glu Gln Lys Arg Asn Val Ile Arg Ile Ile Pro His His Asn
                290                 295                 300

Tyr Asn Ala Thr Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
                340                 345                 350

Val Ser Gly Trp Gly Arg Val Phe Asn Lys Gly Arg Ser Ala Ser Val
                355                 360                 365

Leu Gln Tyr Leu Arg Val Pro Leu Val Asp Arg Ala Thr Cys Leu Arg
                370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Pro His Val
                405                 410                 415

Thr Glu Val Glu Gly Thr Ser Phe Leu Thr Gly Ile Ile Ser Trp Gly
                420                 425                 430

Glu Glu Cys Ala Met Lys Gly Lys Tyr Gly Ile Tyr Thr Lys Val Ser
                435                 440                 445

Arg Tyr Val Asn Trp Ile Lys Glu Lys Thr Lys Leu Thr
                450                 455                 460

<210> SEQ ID NO 26
<211> LENGTH: 2359
<212> TYPE: PRT
<213> ORGANISM: Artificial sequence
<220> FEATURE:
<223> OTHER INFORMATION: recombinant clotting factor sequence

<400> SEQUENCE: 26

Met Gln Ile Glu Leu Ser Thr Cys Phe Phe Leu Cys Leu Leu Pro Phe
1               5                   10                  15

Ser Phe Ser Ala Thr Arg Arg Tyr Tyr Leu Gly Ala Val Glu Leu Ser
                20                  25                  30

Trp Asp Tyr Met Gln Ser Asp Leu Leu Ser Glu Leu His Val Asp Thr
            35                  40                  45

Arg Phe Pro Pro Arg Val Pro Arg Ser Phe Pro Phe Asn Thr Ser Val
        50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Arg Ala Glu Val Tyr Asp Thr Val Val Ile Thr Leu Lys Asn Met Ala
                100                 105                 110

Ser His Pro Val Ser Leu His Ala Val Gly Val Ser Tyr Trp Lys Ala
            115                 120                 125

Ser Glu Gly Ala Glu Tyr Asp Asp Gln Thr Ser Gln Arg Glu Lys Glu
        130                 135                 140

Asp Asp Lys Val Ile Pro Gly Glu Ser His Thr Tyr Val Trp Gln Val
```

```
            145                 150                 155                 160
Leu Lys Glu Asn Gly Pro Met Ala Ser Asp Pro Pro Cys Leu Thr Tyr
                    165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
                195                 200                 205

Thr Gln Thr Leu His Glu Phe Val Leu Leu Phe Ala Val Phe Asp Glu
        210                 215                 220

Gly Lys Ser Trp His Ser Glu Ala Asn Glu Ser Leu Thr Gln Ala Met
225                 230                 235                 240

Asp Ser Ala Ser Ala Arg Pro Trp Pro Lys Met His Thr Val Asn Gly
                245                 250                 255

Tyr Val Asn Arg Ser Leu Pro Gly Leu Ile Gly Cys His Arg Lys Ser
                260                 265                 270

Val Tyr Trp His Val Ile Gly Met Gly Thr Thr Pro Glu Val His Ser
            275                 280                 285

Ile Phe Leu Glu Gly His Thr Phe Leu Val Arg Asn His Arg Gln Ala
        290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Pro Ser His Gln
                325                 330                 335

His Asp Gly Met Glu Ala Tyr Val Lys Val Asp Ser Cys Pro Glu Glu
                340                 345                 350

Pro Gln Leu Arg Met Lys Asn Asn Glu Glu Glu Asp Tyr Asp Asp
                355                 360                 365

Asp Leu Tyr Asp Ser Asp Met Asp Val Leu Arg Phe Asp Asp Asp Asn
        370                 375                 380

Ser Pro Pro Phe Ile Gln Ile Arg Ser Val Ala Lys Lys His Pro Lys
385                 390                 395                 400

Thr Trp Ile His Tyr Ile Ala Ala Glu Glu Glu Asp Trp Asp Tyr Ala
                405                 410                 415

Pro Ser Val Leu Thr Pro Thr Asp Arg Ser Tyr Lys Ser Gln Tyr Leu
                420                 425                 430

Asn Asn Gly Pro Gln Arg Ile Gly Arg Lys Tyr Lys Lys Val Arg Phe
            435                 440                 445

Met Ala Tyr Thr Asp Glu Thr Phe Lys Thr Arg Glu Ala Ile Gln Tyr
450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asn Val Ser Pro Leu His Ser Gly Arg Leu Pro
                500                 505                 510

Lys Gly Val Lys His Leu Lys Asp Met Pro Ile Met Pro Gly Glu Ile
            515                 520                 525

Phe Lys Tyr Lys Trp Thr Val Thr Leu Glu Asp Gly Pro Thr Lys Ser
            530                 535                 540

Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
                565                 570                 575
```

-continued

```
Glu Ser Val Asp Gln Arg Gly Asn Gln Met Met Ser Asp Lys Arg Asn
            580                 585                 590

Val Ile Leu Phe Ser Val Phe Asp Glu Asn Arg Ser Trp Tyr Leu Thr
        595                 600                 605

Glu Asn Met Gln Arg Phe Leu Pro Asn Ala Ala Gly Val Gln Pro Gln
610                 615                 620

Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
            660                 665                 670

Phe Ser Gly Tyr Thr Phe Lys His Lys Met Val Phe Glu Asp Thr Leu
        675                 680                 685

Thr Leu Phe Pro Phe Ser Gly Glu Thr Val Phe Met Ser Met Glu Asn
    690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Asp
                725                 730                 735

Asp Tyr Tyr Glu Asp Thr Tyr Glu Asp Ile Pro Thr Tyr Leu Leu Asn
            740                 745                 750

Glu Asn Asn Val Ile Glu Pro Arg Ser Phe Ser Gln Asn Ser Arg His
        755                 760                 765

Pro Ser Pro Arg Gln Lys Gln Phe Lys Ala Thr Thr Thr Pro Glu Asn
    770                 775                 780

Asp Ile Glu Lys Ile Asp Pro Gln Phe Gly Glu Arg Thr Gln Leu Leu
785                 790                 795                 800

Lys Ala Gln Ser Val Ser Ser Asp Leu Leu Met Leu Leu Gly Gln
                805                 810                 815

Ser Pro Thr Pro His Gly Leu Ser Leu Ser Asp Leu Gln Glu Ala Thr
            820                 825                 830

Tyr Glu Ala Ile Pro Asp Asp His Ser Pro Gly Ala Ile Glu Ser Asn
        835                 840                 845

Glu Gly Pro Ser Glu Val Ala His Leu Arg Pro Glu Leu His His Ser
    850                 855                 860

Gly Asp Thr Val Phe Thr Pro Glu Pro Gly Leu Gln Leu Arg Leu Asn
865                 870                 875                 880

Glu Asn Leu Glu Thr Thr Ile Thr Val Glu Leu Lys Lys Leu Asp Leu
                885                 890                 895

Lys Val Ser Ser Ser Asn Asn Val Met Thr Ser Pro Thr Ile Pro
            900                 905                 910

Ser Asp Asn Leu Ala Ala Gly Thr Glu Lys Thr Gly Ser Leu Gly Pro
        915                 920                 925

Leu Asn Met Pro Val His Phe Ser Ser Gln Leu Gly Thr Ile Leu Phe
    930                 935                 940

Gly Lys Lys Ser Ser Pro Leu Ile Gly Ser Gly Val Pro Leu His Leu
945                 950                 955                 960

Ser Glu Arg Asp Asn Asp Ser Lys Leu Leu Glu Ala Ala Leu Met Asn
                965                 970                 975

Ser Gln Glu Ser Ser Leu Gly Glu Asn Val Ser Ser Met Glu Ser Asp
            980                 985                 990
```

```
Arg Leu Phe Lys Glu Lys Arg Val His Gly Pro Ala Ser Leu Thr Lys
            995                 1000                1005

Asp Asn Ala Leu Phe Lys Val Asn Ile Ser Leu Val Lys Thr Asn
    1010                1015                1020

Lys Ala Pro Asn Asn Ser Thr Thr Asn Gly Lys Thr His Ile Asp
    1025                1030                1035

Gly Pro Thr Leu Leu Asn Glu Asn Ser Thr Ser Val Trp Gln Asp
    1040                1045                1050

Ile Ile Leu Glu Asn Asp Thr Glu Phe Gln Glu Val Thr Ser Leu
    1055                1060                1065

Ile His Asn Glu Met Phe Met Asp Lys Asn Thr Thr Ala Leu Gly
    1070                1075                1080

Leu Asn His Val Ser Asn Lys Thr Thr Ser Ser Lys Asn Met Glu
    1085                1090                1095

Met Val His Gln Lys Lys Glu Asp Pro Val Pro Leu Asp Ala Glu
    1100                1105                1110

Asn Pro Asp Met Ser Phe Phe Lys Met Leu Phe Leu Pro Asp Ser
    1115                1120                1125

Ala Asn Trp Ile Lys Arg Thr His Gly Lys Asn Ser Leu Ser Ser
    1130                1135                1140

Glu Gln Gly Pro Ser Pro Lys Gln Leu Ile Ser Leu Gly Ser Glu
    1145                1150                1155

Lys Ser Val Lys Asp Gln Asn Phe Leu Ser Glu Lys Ser Lys Val
    1160                1165                1170

Ala Val Gly Glu Asp Glu Phe Thr Lys Asp Thr Gly Leu Lys Glu
    1175                1180                1185

Met Ile Phe Pro Asn Ser Lys Ser Ile Phe Leu Thr Asn Leu Ala
    1190                1195                1200

Asn Val Gln Glu Asn Asp Thr His Asn Gln Glu Lys Lys Phe Gln
    1205                1210                1215

Glu Glu Ile Glu Arg Lys Thr Leu Ile Gln Glu Asn Val Val
    1220                1225                1230

Leu Pro Gln Val Tyr Thr Val Thr Gly Thr Lys Asn Phe Leu Lys
    1235                1240                1245

Asn Leu Phe Leu Leu Ser Thr Arg Gln Asn Val Glu Gly Leu Asp
    1250                1255                1260

Glu Gly Thr Tyr Ala Pro Val Leu Gln Asp Thr Arg Ser Leu Asn
    1265                1270                1275

Asp Ser Ala Asn Arg Ala Gly Ile His Met Ala His Phe Ser Lys
    1280                1285                1290

Arg Arg Glu Glu Ala Asn Leu Glu Gly Leu Arg Asn Gln Thr Lys
    1295                1300                1305

Gln Met Val Glu Lys Tyr Pro Ser Thr Thr Arg Met Ser Phe Asn
    1310                1315                1320

Pro Ser Gln Gln Asn Val Ile Thr Gln Arg Gly Lys Arg Ala Leu
    1325                1330                1335

Lys Gln Phe Gly Leu Pro Leu Glu Glu Ile Glu Leu Glu Arg Gly
    1340                1345                1350

Leu Ile Val Asn Asp Thr Ser Thr Gln Trp Ser Lys Asn Met Lys
    1355                1360                1365

Tyr Leu Thr Gln Gly Thr Leu Thr Gln Ile Asp Tyr Asn Glu Lys
    1370                1375                1380

Glu Lys Arg Ala Ile Thr Gln Ser Pro Leu Ser Asp Cys Ser Met
```

```
            1385                1390                1395

Arg Asn His Gly Ile Thr Gln Thr Asn Asp Ser Ala Leu Pro Ile
            1400                1405                1410

Ala Lys Val Ser Ala Phe Pro Ser Ile Arg Pro Thr Asp Leu Thr
            1415                1420                1425

Lys Ile Pro Ser Gln Asp Asn Ser Ser His Leu Leu Ala Ser Ala
            1430                1435                1440

Cys Asn Tyr Thr Phe Arg Glu Arg Ser Ser Gly Val Gln Glu Ser
            1445                1450                1455

Ser His Phe Leu Gln Gly Ala Lys Arg Asn Asn Leu Ser Ser Ala
            1460                1465                1470

Ile Leu Thr Leu Glu Met Ile Arg Gly Gln Glu Lys Val Gly Ser
            1475                1480                1485

Leu Gly Thr Ser Ala Thr Asn Ser Leu Met Tyr Lys Lys Leu Glu
            1490                1495                1500

Asn Thr Val Leu Leu Lys Pro Gly Leu Pro Glu Ala Ser Gly Lys
            1505                1510                1515

Val Glu Leu Leu Pro Lys Val His Val His Gln Glu Asp Ser Phe
            1520                1525                1530

Pro Thr Glu Thr Ser Asn Gly Ser Pro Gly His Leu Asp Leu Met
            1535                1540                1545

Glu Glu Ile Leu Leu Gln Lys Thr Gln Gly Ala Ile Lys Leu Asn
            1550                1555                1560

Lys Val Asn Arg Pro Gly Lys Val Pro Phe Leu Lys Gly Ala Thr
            1565                1570                1575

Glu Ser Ser Glu Lys Thr Leu Pro Lys Leu Leu Gly Pro Leu Ala
            1580                1585                1590

Trp Asp Asn Gln Tyr Ala Thr Gln Ile Pro Arg Glu Glu Trp Lys
            1595                1600                1605

Ser Gln Glu Lys Ser Pro Lys Asn Thr Ala Phe Lys Thr Lys Asp
            1610                1615                1620

Thr Ile Leu Pro Leu Asn Pro Cys Glu Ser Asn His Ala Ile Ala
            1625                1630                1635

Ala Ile Asn Glu Gly Gln Asp Arg Pro Gln Arg Glu Ala Thr Trp
            1640                1645                1650

Ala Lys Gln Gly Gly Thr Gly Arg Leu Cys Ser Gln Asn Pro Pro
            1655                1660                1665

Val Leu Lys His His Gln Arg Glu Ile Thr Leu Thr Thr Leu Gln
            1670                1675                1680

Pro Glu Gln Glu Lys Ile Asp Tyr Asp Asp Thr Leu Ser Ile Glu
            1685                1690                1695

Met Lys Arg Glu Asp Phe Asp Ile Tyr Gly Glu Asp Glu Asn Gln
            1700                1705                1710

Gly Pro Arg Ser Phe Gln Lys Arg Thr Arg His Tyr Phe Ile Ala
            1715                1720                1725

Ala Val Glu Arg Leu Trp Asp Tyr Gly Met Ser Arg Ser Pro His
            1730                1735                1740

Ala Leu Arg Asn Arg Ala Gln Ser Gly Ser Val Pro Gln Phe Lys
            1745                1750                1755

Lys Val Val Phe Gln Glu Phe Thr Asp Gly Ser Phe Thr Gln Pro
            1760                1765                1770

Leu Tyr Arg Gly Glu Leu Asn Glu His Leu Gly Leu Leu Gly Pro
            1775                1780                1785
```

```
Tyr Ile Arg Ala Glu Val Glu Asp Asn Ile Met Val Thr Phe Lys
    1790            1795                1800
Asn Gln Ala Ser Arg Pro Tyr Ser Phe Tyr Ser Ser Leu Ile Ser
    1805            1810                1815
Tyr Glu Glu Asp Gln Arg Gln Gly Ala Glu Pro Arg Lys Asn Phe
    1820            1825                1830
Val Lys Pro Asn Glu Thr Lys Thr Tyr Phe Trp Lys Val Gln His
    1835            1840                1845
His Met Ala Pro Thr Lys Asp Glu Phe Asp Cys Lys Ala Trp Ala
    1850            1855                1860
Tyr Phe Ser Asp Val Asp Leu Glu Lys Asp Leu His Ser Gly Leu
    1865            1870                1875
Ile Gly Pro Leu Leu Ile Cys Arg Thr Asn Thr Leu Asn Pro Ala
    1880            1885                1890
His Gly Arg Gln Leu Thr Val Gln Glu Phe Ala Leu Phe Phe Thr
    1895            1900                1905
Ile Phe Asp Glu Thr Lys Ser Trp Tyr Phe Thr Glu Asn Met Glu
    1910            1915                1920
Arg Asn Cys Arg Ala Pro Cys Asn Ile Gln Met Glu Asp Pro Thr
    1925            1930                1935
Phe Lys Lys Asn Tyr Arg Phe His Ala Ile Asn Gly Tyr Val Met
    1940            1945                1950
Asp Thr Leu Pro Gly Leu Val Met Ala Gln Asp Gln Arg Ile Arg
    1955            1960                1965
Trp Tyr Leu Leu Ser Met Gly Ser Asn Glu Asn Ile His Ser Ile
    1970            1975                1980
His Phe Ser Gly His Val Phe Thr Val Arg Lys Lys Glu Glu Tyr
    1985            1990                1995
Lys Met Ala Val Tyr Asn Leu Tyr Pro Gly Val Phe Glu Thr Val
    2000            2005                2010
Glu Met Leu Pro Ser Lys Ala Gly Ile Trp Arg Val Glu Cys Leu
    2015            2020                2025
Ile Gly Glu His Leu Gln Ala Gly Met Ser Thr Leu Phe Leu Val
    2030            2035                2040
Tyr Ser Lys Glu Cys Gln Thr Pro Leu Gly Met Ala Ser Gly Arg
    2045            2050                2055
Ile Arg Asp Ser Gln Ile Thr Ala Ser Gly Gln Tyr Gly Gln Trp
    2060            2065                2070
Ala Pro Lys Leu Ala Arg Leu His Tyr Ser Gly Ser Ile Asn Ala
    2075            2080                2085
Trp Ser Thr Lys Asp Pro Phe Ser Trp Ile Lys Val Asp Leu Leu
    2090            2095                2100
Ala Pro Met Ile Ile His Gly Ile Lys Thr Gln Gly Ala Arg Gln
    2105            2110                2115
Lys Phe Ser Ser Leu Tyr Ile Ser Gln Phe Ile Ile Met Tyr Ser
    2120            2125                2130
Leu Asp Gly Lys Lys Trp Gln Ser Tyr Arg Gly Asn Ser Thr Gly
    2135            2140                2145
Thr Leu Met Val Phe Phe Gly Asn Val Asp Ser Ser Gly Ile Lys
    2150            2155                2160
His Asn Ile Phe Asn Pro Pro Ile Ile Ala Arg Tyr Ile Arg Leu
    2165            2170                2175
```

-continued

```
His Pro Thr His Tyr Ser Ile Arg Ser Thr Leu Arg Met Glu Leu
    2180                2185                2190

Met Gly Cys Asp Leu Asn Ser Cys Ser Met Pro Leu Gly Met Glu
2195                2200                2205

Ser Lys Ala Ile Ser Asp Ala Gln Ile Thr Ala Ser Ser Tyr Phe
    2210                2215                2220

Thr Asn Met Phe Ala Thr Trp Ser Pro Ser Gln Ala Arg Leu His
2225                2230                2235

Leu Gln Gly Arg Thr Asn Ala Trp Arg Pro Gln Val Asn Asn Pro
    2240                2245                2250

Lys Glu Trp Leu Gln Val Asp Phe Gln Lys Thr Met Lys Val Thr
2255                2260                2265

Gly Ile Thr Thr Gln Gly Ala Lys Ser Leu Leu Thr Ser Met Tyr
    2270                2275                2280

Val Lys Glu Phe Leu Ile Ser Ser Ser Gln Asp Gly His His Trp
2285                2290                2295

Thr Leu Phe Leu Gln Asn Gly Lys Val Lys Val Phe Gln Gly Asn
    2300                2305                2310

Gln Asp Ser Phe Thr Pro Val Val Asn Ser Leu Asp Pro Pro Leu
2315                2320                2325

Leu Thr Arg Tyr Leu Arg Ile His Pro Gln Ser Trp Val His His
    2330                2335                2340

Ile Ala Leu Arg Leu Glu Val Leu Gly Cys Glu Ala Gln Gln Leu
2345                2350                2355

Tyr

<210> SEQ ID NO 27
<211> LENGTH: 2359
<212> TYPE: PRT
<213> ORGANISM: Artificial sequence
<220> FEATURE:
<223> OTHER INFORMATION: recombinant clotting factor sequence

<400> SEQUENCE: 27

Met Gln Ile Glu Leu Ser Thr Cys Phe Phe Leu Cys Leu Leu Pro Phe
1               5                   10                  15

Ser Phe Ser Ala Thr Arg Arg Tyr Tyr Leu Gly Ala Val Glu Leu Ser
                20                  25                  30

Trp Asp Tyr Met Gln Ser Glu Leu Leu Ser Glu Leu His Val Asp Thr
            35                  40                  45

Arg Phe Pro Pro Arg Val Pro Arg Ser Phe Pro Phe Asn Thr Ser Val
        50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Arg Ala Glu Val Tyr Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Glu Asp Gln Thr Ser Gln Arg Glu Lys Glu
    130                 135                 140

Asp Asp Lys Val Ile Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
```

```
            165                 170                 175
Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
            195                 200                 205

Thr Gln Thr Leu His Glu Phe Val Leu Leu Phe Ala Val Phe Asp Glu
        210                 215                 220

Gly Lys Ser Trp His Ser Glu Thr Asn Glu Ser Leu Thr Gln Ala Met
225                 230                 235                 240

Asp Pro Ala Ser Ala Gln Ala Gln Pro Glu Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Thr Pro Glu Val His Ser
            275                 280                 285

Ile Phe Leu Glu Gly His Thr Phe Leu Val Arg Asn His Arg Gln Ala
        290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Glu Asp Tyr Asp Asp
            355                 360                 365

Asp Leu Tyr Asp Ser Asp Met Asp Val Val Arg Phe Asp Asp Asp Asn
        370                 375                 380

Ser Pro Pro Phe Ile Gln Ile Arg Ser Val Ala Lys Lys His Pro Lys
385                 390                 395                 400

Thr Trp Val His Tyr Ile Ala Ala Glu Glu Glu Asp Trp Asp Tyr Ala
                405                 410                 415

Pro Ser Val Leu Thr Pro Asn Asp Arg Ser Tyr Lys Ser Leu Tyr Leu
            420                 425                 430

Asn Asn Gly Pro Gln Arg Ile Gly Arg Lys Tyr Lys Lys Val Arg Phe
        435                 440                 445

Met Ala Tyr Thr Asp Glu Thr Phe Lys Thr Arg Glu Ala Ile Gln Tyr
    450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Ser Pro Leu His Ser Gly Arg Leu Pro
            500                 505                 510

Lys Gly Val Lys His Leu Lys Asp Met Pro Ile Leu Pro Gly Glu Ile
        515                 520                 525

Phe Lys Tyr Lys Trp Thr Val Thr Val Glu Asp Gly Pro Thr Lys Ser
    530                 535                 540

Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
            580                 585                 590
```

```
Val Ile Leu Phe Ser Val Phe Asp Glu Asn Arg Ser Trp Tyr Leu Thr
            595                 600                 605

Glu Asn Met Gln Arg Phe Leu Pro Asn Ala Asp Gly Val Gln Pro Gln
610                 615                 620

Asp Pro Glu Phe Gln Val Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
                660                 665                 670

Phe Ser Gly Tyr Thr Phe Lys His Lys Met Val Tyr Glu Asp Thr Leu
            675                 680                 685

Thr Leu Phe Pro Phe Ser Gly Glu Thr Val Phe Met Ser Met Glu Asn
690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asn Arg Asn Thr Gly
                725                 730                 735

Asp Tyr Tyr Glu Asp Thr Tyr Glu Asp Ile Pro Thr Ser Leu Leu Asn
            740                 745                 750

Glu Asn Asn Val Ile Glu Pro Arg Ser Phe Ser Gln Asn Ser Arg His
755                 760                 765

Pro Ser Thr Arg Gln Lys Gln Phe Lys Ala Thr Thr Thr Pro Glu Asn
770                 775                 780

Asp Ile Glu Lys Ile Asp Pro Gln Ser Gly Glu Arg Thr Gln Leu Leu
785                 790                 795                 800

Lys Val Gln Ser Val Ser Ser Asp Leu Leu Met Leu Leu Gly Gln
                805                 810                 815

Asn Pro Thr Pro His Gly Leu Ser Leu Ser Asp Leu Gln Glu Ala Thr
            820                 825                 830

Tyr Glu Ala Ile Pro Asp Asp His Leu Pro Gly Ala Ile Glu Arg Asn
            835                 840                 845

Lys Gly Pro Ser Glu Val Ala His Leu Arg Pro Glu Leu His His Ser
            850                 855                 860

Gly Asp Arg Val Phe Thr Pro Glu Pro Glu Leu Gln Leu Arg Leu Asn
865                 870                 875                 880

Glu Asn Leu Gly Thr Thr Ile Thr Val Glu Leu Lys Lys Leu Asp Leu
                885                 890                 895

Lys Ile Ser Ser Ser Ser Asn Asn Leu Met Thr Ser Pro Thr Ile Pro
                900                 905                 910

Ser Asp Lys Leu Ala Ala Gly Thr Glu Lys Thr Gly Ser Leu Gly Pro
            915                 920                 925

Pro Asn Met Pro Val His Phe Ser Ser Gln Leu Gly Thr Ile Val Phe
            930                 935                 940

Gly Lys Asn Ser Ser His Leu Ile Gly Ser Gly Val Pro Leu Gly Leu
945                 950                 955                 960

Ser Glu Gly Asp Asn Asp Ser Lys Leu Leu Glu Ala Ala Leu Met Asn
                965                 970                 975

Ser Gln Glu Ser Ser Leu Gly Glu Asn Val Leu Ser Met Glu Ser Asp
            980                 985                 990

Arg Leu Phe Lys Glu Glu Arg Val  His Gly Pro Ala Ser  Leu Thr Lys
            995                 1000                 1005
```

-continued

```
Asp Asn Ala Leu Phe Lys Val Asn Ile Ser Leu Val Lys Thr Asn
1010                1015                1020

Lys Ala Pro Ile Asn Ser Thr Thr Asn Arg Lys Thr His Ile Asp
1025                1030                1035

Gly Pro Thr Leu Leu Ile Glu Asn Ser Thr Ser Val Trp Gln Asp
1040                1045                1050

Ile Ile Leu Glu Ser Asn Thr Glu Phe Gln Glu Val Thr Ser Leu
1055                1060                1065

Ile His Asp Glu Thr Phe Met Asp Lys Asn Thr Thr Ala Leu Gly
1070                1075                1080

Leu Asn His Val Ser Asn Lys Thr Thr Ser Ser Lys Asn Met Glu
1085                1090                1095

Met Val His Gln Lys Lys Glu Gly Pro Val Pro Leu Gly Ala Glu
1100                1105                1110

Asn Pro Asp Met Ser Phe Phe Lys Met Leu Phe Leu Pro Asp Ser
1115                1120                1125

Ala Asn Trp Ile Lys Arg Thr His Gly Lys Asn Ser Leu Ser Ser
1130                1135                1140

Gly Gln Arg Pro Ser Pro Lys Gln Leu Thr Ser Leu Gly Ser Glu
1145                1150                1155

Lys Ser Val Lys Asp Gln Asn Phe Leu Ser Glu Lys Asn Lys Val
1160                1165                1170

Val Val Gly Glu Asp Glu Phe Thr Lys Asp Thr Gly Leu Lys Glu
1175                1180                1185

Met Ile Phe Pro Asn Ser Lys Ser Ile Phe Leu Thr Asn Leu Ala
1190                1195                1200

Asn Val Gln Glu Asn Asp Thr His Asn Gln Glu Lys Lys Ser Gln
1205                1210                1215

Glu Glu Ile Glu Arg Lys Glu Lys Leu Ile Gln Glu Asn Val Val
1220                1225                1230

Leu Pro Gln Val Tyr Thr Val Thr Gly Thr Lys Asn Phe Leu Lys
1235                1240                1245

Asn Leu Phe Leu Leu Ser Thr Lys Gln Asn Val Glu Gly Leu Asp
1250                1255                1260

Glu Gly Thr Tyr Thr Pro Ile Leu Gln Asp Thr Arg Ser Leu Asn
1265                1270                1275

Asp Ser Ala Asn Arg Ala Gly Ile His Met Ala His Phe Ser Lys
1280                1285                1290

Ile Arg Glu Glu Ala Asn Leu Glu Gly Leu Gly Asn Gln Thr Lys
1295                1300                1305

Gln Met Val Glu Lys Tyr Pro Ser Thr Thr Arg Met Ser Pro Asn
1310                1315                1320

Pro Ser Gln Gln Asn Val Ile Thr Gln Arg Gly Lys Arg Ala Leu
1325                1330                1335

Lys Gln Phe Arg Leu Pro Leu Glu Glu Ile Lys Leu Glu Arg Gly
1340                1345                1350

Val Ile Leu Asn Asp Thr Ser Thr Gln Trp Ser Lys Asn Met Lys
1355                1360                1365

Tyr Leu Thr Gln Gly Thr Leu Thr Gln Ile Glu Tyr Asn Glu Lys
1370                1375                1380

Glu Lys Arg Ala Ile Thr Gln Ser Leu Leu Ser Asp Cys Ser Met
1385                1390                1395

Arg Asn His Gly Ile Ile Gln Thr Asn Asp Ser Ala Leu Pro Ile
```

-continued

```
              1400              1405              1410
Ala Lys Val Ser Ala Phe Pro Ser Ile Arg Pro Thr Asp Leu Thr
    1415              1420              1425
Lys Ile Pro Ser Gln Asp Asn Ser Ser His Leu Leu Ala Ser Ala
    1430              1435              1440
Cys Asn Tyr Thr Phe Arg Glu Arg Ser Ser Gly Val Gln Glu Ser
    1445              1450              1455
Ser His Phe Leu Gln Gly Ala Lys Arg Asn Asn Leu Ser Leu Ala
    1460              1465              1470
Phe Leu Thr Leu Glu Met Ile Arg Gly Gln Gly Lys Ile Ser Ser
    1475              1480              1485
Leu Gly Lys Ser Ala Thr Asn Ser Leu Met Tyr Lys Lys Leu Glu
    1490              1495              1500
Asn Thr Val Leu Leu Lys Pro Gly Leu Ser Glu Ala Ser Gly Lys
    1505              1510              1515
Val Glu Leu Leu Pro Lys Val His Val His Gln Glu Asp Ser Phe
    1520              1525              1530
Pro Thr Lys Thr Ser Asn Gly Ser Pro Gly His Leu Asp Leu Met
    1535              1540              1545
Glu Glu Ile Phe Leu Gln Lys Thr Gln Gly Pro Val Lys Leu Asn
    1550              1555              1560
Lys Val Asn Arg Pro Gly Lys Val Pro Phe Leu Lys Trp Ala Thr
    1565              1570              1575
Glu Ser Ser Glu Lys Thr Pro Ser Lys Leu Leu Gly Pro Leu Ala
    1580              1585              1590
Trp Asp Asn Gln Tyr Ala Thr Gln Ile Pro Arg Glu Glu Trp Lys
    1595              1600              1605
Ser Gln Glu Lys Ser Gln Lys Asn Thr Ala Phe Lys Thr Lys Asp
    1610              1615              1620
Thr Ile Leu Pro Leu Asp Pro Cys Glu Asn Asn His Ser Ile Ala
    1625              1630              1635
Ala Ile Asn Glu Gly Gln Asp Lys Pro Gln Arg Glu Ala Thr Trp
    1640              1645              1650
Ala Lys Gln Gly Gly Thr Gly Arg Leu Cys Ser Gln Asn Pro Pro
    1655              1660              1665
Val Leu Lys Arg His Gln Arg Glu Ile Thr Leu Thr Thr Leu Gln
    1670              1675              1680
Pro Glu Glu Asp Lys Ile Asp Tyr Asp Asp Thr Phe Ser Ile Glu
    1685              1690              1695
Met Lys Arg Glu Asp Phe Asp Ile Tyr Gly Glu Asp Glu Asn Gln
    1700              1705              1710
Gly Pro Arg Ser Phe Gln Lys Arg Thr Arg His Tyr Phe Ile Ala
    1715              1720              1725
Ala Val Glu Arg Leu Trp Asp Tyr Gly Met Ser Arg Ser Pro His
    1730              1735              1740
Ala Leu Arg Asn Arg Ala Gln Ser Gly Asp Val Pro Gln Phe Lys
    1745              1750              1755
Lys Val Val Phe Gln Glu Phe Thr Asp Gly Ser Phe Thr Gln Pro
    1760              1765              1770
Leu Tyr Arg Gly Glu Leu Asn Glu His Leu Gly Leu Leu Gly Pro
    1775              1780              1785
Tyr Ile Arg Ala Glu Val Glu Asp Asn Ile Met Val Thr Phe Lys
    1790              1795              1800
```

-continued

Asn Gln Ala Ser Arg Pro Tyr Ser Phe Tyr Ser Ser Leu Ile Ser
1805                1810                1815

Tyr Glu Glu Asp Gln Arg Gln Gly Ala Glu Pro Arg Lys Lys Phe
1820                1825                1830

Val Lys Pro Asn Glu Thr Lys Ile Tyr Phe Trp Lys Val Gln His
1835                1840                1845

His Met Ala Pro Thr Lys Asp Glu Phe Asp Cys Lys Ala Trp Ala
1850                1855                1860

Tyr Phe Ser Asp Val Asp Leu Glu Lys Asp Val His Ser Gly Leu
1865                1870                1875

Ile Gly Pro Leu Leu Ile Cys Arg Ala Asn Thr Leu Asn Pro Ala
1880                1885                1890

His Gly Arg Gln Val Thr Val Gln Glu Phe Ala Leu Phe Phe Thr
1895                1900                1905

Ile Phe Asp Glu Thr Lys Ser Trp Tyr Phe Thr Glu Asn Met Glu
1910                1915                1920

Arg Asn Cys Arg Ala Pro Cys Asn Ile Gln Met Glu Asp Pro Thr
1925                1930                1935

Phe Lys Glu Asn Tyr Arg Phe His Ala Ile Asn Gly Tyr Val Met
1940                1945                1950

Asp Thr Leu Pro Gly Leu Val Met Ala Gln Asp Gln Arg Ile Arg
1955                1960                1965

Trp Tyr Leu Leu Ser Met Gly Ser Asn Glu Asn Ile His Ser Ile
1970                1975                1980

His Phe Ser Gly His Val Phe Thr Val Arg Lys Lys Glu Glu Tyr
1985                1990                1995

Lys Met Ala Val Tyr Asn Leu Tyr Pro Gly Val Phe Glu Thr Val
2000                2005                2010

Glu Met Leu Pro Ser Lys Val Gly Ile Trp Arg Ile Glu Cys Leu
2015                2020                2025

Ile Gly Glu His Leu Gln Ala Gly Met Ser Thr Leu Phe Leu Val
2030                2035                2040

Tyr Ser Lys Gln Cys Gln Thr Pro Leu Gly Met Ala Ser Gly Arg
2045                2050                2055

Ile Arg Asp Phe Gln Ile Thr Ala Ser Gly Gln Tyr Gly Gln Trp
2060                2065                2070

Ala Pro Lys Leu Ala Arg Leu His Tyr Ser Gly Ser Ile Asn Ala
2075                2080                2085

Trp Ser Thr Lys Asp Pro Phe Ser Trp Ile Lys Val Asp Leu Leu
2090                2095                2100

Ala Pro Met Ile Ile His Ser Ile Met Thr Gln Gly Ala Arg Gln
2105                2110                2115

Lys Phe Ser Ser Leu Tyr Ile Ser Gln Phe Ile Ile Met Tyr Ser
2120                2125                2130

Leu Asp Gly Lys Lys Trp Gln Ser Tyr Arg Gly Asn Ser Thr Gly
2135                2140                2145

Thr Leu Met Val Phe Phe Gly Asn Val Asp Ser Ser Gly Ile Lys
2150                2155                2160

His Asn Ile Phe Asn Pro Pro Ile Ile Ala Arg Tyr Ile Arg Leu
2165                2170                2175

His Pro Thr His Tyr Ser Ile Arg Ser Thr Leu Arg Met Glu Leu
2180                2185                2190

-continued

```
Met Gly Cys Asp Leu Asn Ser Cys Ser Met Pro Leu Gly Met Glu
    2195                2200                2205

Ser Lys Ala Ile Ser Asp Ala Gln Ile Thr Ala Ser Ser Tyr Leu
    2210                2215                2220

Asn Asn Met Phe Ala Thr Trp Ser Pro Ser Gln Ala Arg Leu His
    2225                2230                2235

Leu Gln Gly Arg Thr Asn Ala Trp Arg Pro Gln Val Asn Asn Pro
    2240                2245                2250

Lys Glu Trp Leu Gln Val Asp Phe Gln Lys Thr Met Lys Val Thr
    2255                2260                2265

Gly Ile Thr Thr Gln Gly Val Lys Ser Leu Leu Thr Ser Met Tyr
    2270                2275                2280

Val Lys Glu Phe Leu Ile Ser Ser Ser Gln Asp Gly His Asn Trp
    2285                2290                2295

Thr Leu Phe Leu Gln Asn Gly Lys Val Lys Val Phe Gln Gly Asn
    2300                2305                2310

Gln Asp Ser Phe Thr Pro Val Val Asn Ser Leu Asp Pro Pro Leu
    2315                2320                2325

Leu Thr Arg Tyr Leu Arg Ile His Pro Gln Ser Trp Ala His His
    2330                2335                2340

Ile Ala Leu Arg Leu Glu Val Leu Gly Cys Glu Ala Gln Gln Leu
    2345                2350                2355

Tyr

<210> SEQ ID NO 28
<211> LENGTH: 2359
<212> TYPE: PRT
<213> ORGANISM: Artificial sequence
<220> FEATURE:
<223> OTHER INFORMATION: recombinant clotting factor sequence

<400> SEQUENCE: 28

Met Gln Ile Glu Leu Ser Thr Cys Phe Phe Leu Cys Leu Leu Pro Phe
1               5                   10                  15

Ser Phe Ser Ala Ile Arg Arg Tyr Tyr Leu Gly Ala Val Glu Leu Ser
                20                  25                  30

Trp Asp Tyr Met Gln Ser Glu Leu Leu Ser Glu Leu His Val Asp Thr
            35                  40                  45

Arg Phe Pro Pro Arg Val Pro Arg Ser Phe Pro Phe Asn Thr Ser Val
    50                  55                  60

Met Tyr Lys Lys Thr Val Phe Val Glu Phe Thr Asp Gln Leu Phe Asn
65                  70                  75                  80

Ile Ala Lys Pro Arg Pro Pro Trp Met Gly Leu Leu Gly Pro Thr Ile
                85                  90                  95

Gln Ala Glu Val Tyr Asp Thr Val Val Ile Thr Leu Lys Asn Met Ala
                100                 105                 110

Ser His Pro Val Ser Leu His Ala Val Gly Val Ser Tyr Trp Lys Ser
            115                 120                 125

Ser Glu Gly Ala Glu Tyr Glu Asp Gln Thr Ser Gln Arg Glu Lys Glu
    130                 135                 140

Asp Asp Lys Val Ile Pro Gly Lys Ser His Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
```

-continued

```
                180                 185                 190
Ile Gly Ala Leu Leu Val Cys Arg Glu Gly Ser Leu Thr Lys Glu Arg
            195                 200                 205
Thr Gln Thr Leu His Glu Phe Val Leu Leu Phe Ala Val Phe Asp Glu
        210                 215                 220
Gly Lys Ser Trp His Ser Gly Lys Asn Glu Ser Leu Thr Gln Ala Met
225                 230                 235                 240
Asp Pro Ala Ser Ala Arg Ala Gln Pro Ala Met His Thr Ile Asn Gly
                245                 250                 255
Tyr Ile Asn Arg Ser Leu Pro Gly Leu Ile Gly Cys His Lys Lys Ser
            260                 265                 270
Val Tyr Trp His Val Ile Gly Met Gly Thr Thr Pro Glu Val His Ser
        275                 280                 285
Ile Phe Leu Glu Gly His Thr Phe Leu Val Arg Asn His Arg Gln Ala
    290                 295                 300
Ser Leu Glu Ile Ser Pro Ile Thr Phe Leu Thr Ala Gln Thr Leu Leu
305                 310                 315                 320
Met Asp Leu Gly Gln Phe Leu Leu Phe Cys His Ile Ser Ser His Gln
                325                 330                 335
His Asp Gly Met Glu Ala Tyr Val Lys Val Asp Ser Cys Pro Glu Glu
            340                 345                 350
Pro Gln Leu Arg Met Lys Asn Asn Glu Glu Glu Asp Tyr Asp Asp
        355                 360                 365
Asp Leu Tyr Asp Ser Asp Met Asp Val Val Arg Phe Asp Gly Asp Asn
    370                 375                 380
Ala Pro Pro Phe Ile Gln Ile Arg Ser Val Ala Lys Lys His Pro Lys
385                 390                 395                 400
Thr Trp Val His Tyr Ile Ala Ala Glu Glu Asp Trp Asp Tyr Ala
                405                 410                 415
Pro Ser Val Leu Thr Ser Asn Asp Arg Ser Tyr Lys Ser Leu Tyr Leu
            420                 425                 430
Asn Asn Gly Pro Gln Arg Ile Gly Arg Lys Tyr Lys Val Arg Phe
        435                 440                 445
Ile Ala Tyr Thr Asp Glu Thr Phe Lys Thr Arg Glu Ala Ile Gln Tyr
    450                 455                 460
Glu Ser Gly Ile Leu Gly Pro Leu Leu Tyr Gly Glu Val Gly Asp Thr
465                 470                 475                 480
Leu Leu Ile Ile Phe Lys Asn Gln Ala Ser Arg Pro Tyr Asn Ile Tyr
                485                 490                 495
Pro His Gly Ile Thr Asp Val Ser Pro Leu His Ser Gly Arg Phe Pro
            500                 505                 510
Lys Gly Val Lys His Leu Lys Asp Met Pro Ile Leu Pro Gly Glu Ile
        515                 520                 525
Phe Lys Tyr Lys Trp Thr Val Thr Val Glu Asp Gly Pro Thr Lys Ser
    530                 535                 540
Asp Pro Arg Cys Leu Thr Arg Tyr Tyr Ser Ser Phe Val Asn Leu Glu
545                 550                 555                 560
Arg Asp Leu Ala Ser Gly Leu Ile Gly Pro Leu Leu Ile Cys Tyr Lys
                565                 570                 575
Glu Ser Val Asp Gln Arg Gly Asn Gln Met Met Ser Asp Lys Arg Asn
            580                 585                 590
Val Ile Leu Phe Ser Val Phe Asp Glu Asn Gln Ser Trp Tyr Leu Thr
        595                 600                 605
```

-continued

Glu Asn Ile Gln Arg Phe Leu Pro Asn Ala Asp Gly Val Gln Pro Gln
    610                 615                 620

Asp Pro Glu Phe Gln Val Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
            660                 665                 670

Phe Ser Gly Tyr Thr Phe Lys His Lys Met Val Tyr Glu Asp Thr Leu
        675                 680                 685

Thr Leu Phe Pro Phe Ser Glu Thr Val Phe Met Ser Met Glu Asn
    690                 695                 700

Pro Gly Leu Trp Val Leu Gly Cys His Asn Ser Asp Phe Arg Asn Arg
705                 710                 715                 720

Gly Met Thr Ala Leu Leu Lys Val Tyr Ser Cys Asp Arg Asn Thr Gly
                725                 730                 735

Asp Tyr Tyr Glu Asp Thr Tyr Glu Asp Ile Pro Thr Phe Leu Leu Asn
            740                 745                 750

Glu Asn Asn Val Ile Glu Pro Arg Ser Phe Ser Gln Asn Ser Arg His
        755                 760                 765

Pro Ser Thr Arg Gln Lys Gln Phe Lys Ala Thr Thr Pro Glu Asn
    770                 775                 780

Asp Ile Glu Lys Ile Asp Pro Gln Ser Gly Glu Arg Thr Gln Leu Leu
785                 790                 795                 800

Lys Glu Gln Ser Val Ser Ser Asp Leu Leu Met Leu Leu Gly Gln
                805                 810                 815

Asn Pro Thr Pro His Gly Leu Ser Leu Ser Asp Leu Gln Glu Ala Arg
            820                 825                 830

Asn Glu Ala Ile Pro Asp Asp His Leu Pro Gly Ala Ile Glu Arg Asn
        835                 840                 845

Lys Gly Pro Ser Glu Val Ala His Leu Arg Pro Glu Leu His His Ser
    850                 855                 860

Gly Glu Arg Val Phe Thr Pro Glu Pro Glu Leu Pro Leu Arg Leu Asn
865                 870                 875                 880

Glu Asn Leu Gly Thr Thr Ile Thr Val Glu Leu Lys Lys Leu Asp Phe
                885                 890                 895

Lys Ile Ser Ser Ser Asn Asn Leu Met Thr Ser Pro Thr Ile Pro
            900                 905                 910

Ser Asp Lys Leu Ser Ala Gly Thr Glu Lys Thr Gly Ser Leu Gly Pro
        915                 920                 925

Pro Asn Met Pro Val Asn Phe Ser Ser Gln Leu Gly Thr Ile Val Phe
    930                 935                 940

Gly Lys Asn Ser Ser His Phe Ile Gly Ser Gly Val Pro Leu Gly Leu
945                 950                 955                 960

Ser Glu Glu Asp Asn Asp Ser Lys Leu Leu Glu Ala Ala Leu Met Asn
                965                 970                 975

Ser Gln Glu Ser Ser Leu Gly Glu Asn Val Leu Ser Met Glu Ser Asp
            980                 985                 990

Arg Leu Phe Lys Glu Glu Arg Val His Gly Pro Ala Ser Leu Thr Lys
        995                 1000                1005

Asp Asp Ala Leu Phe Lys Val Asn Ile Ser Leu Val Lys Thr Asn
    1010                1015                1020

```
Lys Ala Pro Ile Asn Ser Thr Thr Asn Arg Lys Thr His Ile Asp
    1025                1030                1035

Asp Pro Thr Leu Leu Ile Glu Asn Ser Thr Ser Val Trp Gln Asp
    1040                1045                1050

Ile Ile Leu Glu Ser Asn Thr Glu Phe Gln Val Thr Ser Leu
    1055                1060                1065

Ile His Asp Glu Thr Phe Met Asp Lys Asn Thr Thr Ala Leu Gly
    1070                1075                1080

Leu Asn His Val Ser Asn Lys Thr Thr Ser Ser Lys Asn Met Glu
    1085                1090                1095

Met Val His Gln Lys Lys Glu Gly Pro Val Pro Leu Asp Ala Glu
    1100                1105                1110

Tyr Pro Asp Thr Ser Phe Phe Lys Thr Leu Phe Leu Pro Asp Ser
    1115                1120                1125

Thr Asn Trp Ile Lys Arg Thr His Gly Lys Asn Ser Leu Ser Ser
    1130                1135                1140

Gly Gln Arg Pro Ser Pro Lys Gln Leu Thr Ser Ser Gly Ser Glu
    1145                1150                1155

Lys Ser Val Lys Asp Gln Asn Phe Leu Ser Glu Lys Asn Lys Val
    1160                1165                1170

Val Val Gly Glu Asp Glu Phe Ser Lys Asp Thr Gly Leu Lys Glu
    1175                1180                1185

Met Ile Phe Pro Asn Ser Lys Ser Ile Phe Leu Thr Asn Leu Ala
    1190                1195                1200

Asn Val Gln Glu Asn Asp Thr His Asn Gln Glu Lys Lys Ser Gln
    1205                1210                1215

Glu Glu Ile Glu Arg Lys Glu Lys Leu Ile Gln Glu Asn Val Val
    1220                1225                1230

Leu Pro Gln Val Tyr Thr Val Thr Gly Thr Lys Asn Phe Leu Lys
    1235                1240                1245

Asn Leu Phe Leu Leu Ser Thr Lys Gln Asn Val Glu Gly Leu Asp
    1250                1255                1260

Glu Gly Thr Tyr Thr Pro Val Leu Gln Asp Thr Arg Ser Leu Asn
    1265                1270                1275

Asp Ser Ala Lys Arg Ala Gly Ile His Met Ala His Phe Ser Lys
    1280                1285                1290

Ile Arg Glu Glu Ala Asn Leu Glu Gly Leu Gly Asn Gln Thr Lys
    1295                1300                1305

Gln Met Val Glu Lys Tyr Pro Ser Thr Thr Arg Met Ser Pro Asn
    1310                1315                1320

Pro Ser Gln Gln Asn Val Ile Pro Gln Arg Gly Lys Arg Asp Leu
    1325                1330                1335

Lys Gln Phe Arg Leu Pro Leu Glu Glu Ile Lys Leu Glu Arg Gly
    1340                1345                1350

Val Ile Leu Asn Asp Thr Ser Thr Gln Trp Ser Lys Asn Met Lys
    1355                1360                1365

Tyr Leu Thr Gln Gly Thr Phe Thr Gln Ile Glu Tyr Asn Lys Lys
    1370                1375                1380

Glu Lys Arg Ala Ile Thr Gln Ser Phe Leu Ser Asp Cys Ser Met
    1385                1390                1395

Arg Ser His Gly Ile Ile Gln Thr Asn Gly Ser Ala Leu Pro Ile
    1400                1405                1410

Ala Lys Val Ser Ala Phe Pro Ser Ile Arg Pro Thr Asp Leu Thr
```

```
              1415                1420                1425

Lys Ile Pro Ser Gln Asp Asn Ser Ser His Leu Pro Ala Ser Ala
    1430                1435                1440

Cys Ser Tyr Thr Phe Gly Glu Arg Ser Ser Gly Val Gln Glu Ser
    1445                1450                1455

Ser His Phe Leu Gln Gly Ala Lys Arg Asn Asn Leu Ser Leu Ala
    1460                1465                1470

Phe Leu Thr Leu Glu Met Ile Arg Gly Gln Gly Lys Ile Ser Thr
    1475                1480                1485

Leu Gly Lys Ser Ala Thr Asn Pro Leu Met Tyr Lys Lys Leu Glu
    1490                1495                1500

Asn Thr Val Leu Leu Lys Pro Gly Leu Ser Glu Ala Ser Gly Lys
    1505                1510                1515

Val Glu Phe Leu Pro Lys Val His Val His Gln Glu Asp Phe Phe
    1520                1525                1530

Pro Thr Lys Thr Ser Asn Gly Ser Pro Ala His Leu Asp Leu Arg
    1535                1540                1545

Glu Glu Ile Phe Leu Gln Lys Thr Gln Gly Leu Val Lys Leu Asn
    1550                1555                1560

Lys Val Asn Arg Pro Gly Lys Val Pro Phe Leu Lys Trp Ala Thr
    1565                1570                1575

Glu Ser Ser Glu Lys Thr Pro Ser Lys Leu Leu Gly Pro Leu Ala
    1580                1585                1590

Trp Asp Asn Gln Tyr Ala Thr Leu Ile Pro Arg Glu Glu Trp Lys
    1595                1600                1605

Ser Leu Glu Lys Ser Gln Lys Ser Thr Ala Leu Lys Thr Lys Asp
    1610                1615                1620

Thr Ile Leu Pro Leu Asp Pro Cys Glu Asn Asn His Ser Ile Ala
    1625                1630                1635

Ala Ile Asn Glu Gly Gln Asp Lys Pro Gln Arg Glu Ala Thr Trp
    1640                1645                1650

Val Lys Gln Gly Gly Thr Gly Arg Leu Cys Ser Gln Asn Pro Pro
    1655                1660                1665

Val Leu Lys Arg His Gln Arg Glu Ile Thr Leu Thr Thr Phe Gln
    1670                1675                1680

Pro Glu Glu Asp Lys Ile Asp Tyr Asp Asp Thr Phe Ser Ile Glu
    1685                1690                1695

Thr Lys Arg Glu Asp Phe Asp Ile Tyr Gly Glu Asp Glu Asn Gln
    1700                1705                1710

Asp Pro Arg Ser Phe Gln Lys Arg Thr Arg His Tyr Phe Ile Ala
    1715                1720                1725

Ala Val Glu Arg Leu Trp Asp Tyr Gly Met Ser Arg Ser Pro His
    1730                1735                1740

Ala Leu Arg Asn Arg Ala Gln Asn Gly Asp Val Pro Gln Phe Lys
    1745                1750                1755

Lys Val Val Phe Gln Glu Phe Thr Asp Gly Ser Phe Thr Gln Pro
    1760                1765                1770

Leu Tyr Arg Gly Glu Leu Asn Glu His Leu Gly Leu Leu Gly Pro
    1775                1780                1785

Tyr Ile Arg Ala Glu Val Glu Asp Asn Ile Met Val Thr Phe Lys
    1790                1795                1800

Asn Gln Ala Ser Arg Pro Tyr Ser Phe Tyr Ser Ser Leu Ile Ser
    1805                1810                1815
```

```
Tyr Glu Glu Asp Gln Arg Gln Gly Ala Glu Pro Arg Lys Lys Phe
    1820            1825                1830

Val Lys Pro Asn Glu Thr Lys Ile Tyr Phe Trp Lys Val Gln His
    1835            1840                1845

His Met Ala Pro Thr Lys Asp Glu Phe Asp Cys Lys Ala Trp Ala
    1850            1855                1860

Tyr Phe Ser Asp Val Asp Leu Glu Lys Asp Val His Ser Gly Leu
    1865            1870                1875

Ile Gly Pro Leu Leu Ile Cys Arg Thr Asn Thr Leu Asn Ala Ala
    1880            1885                1890

His Gly Arg Gln Val Thr Val Gln Glu Phe Ala Leu Phe Phe Thr
    1895            1900                1905

Ile Phe Asp Glu Thr Lys Ser Trp Tyr Phe Thr Glu Asn Met Glu
    1910            1915                1920

Arg Asn Cys Arg Ala Pro Cys Asn Ile Gln Met Glu Asp Pro Thr
    1925            1930                1935

Phe Lys Glu Asn Tyr Arg Phe His Ala Ile Asn Gly Tyr Val Met
    1940            1945                1950

Asp Thr Leu Pro Gly Leu Val Met Ala Gln Asp Gln Arg Ile Arg
    1955            1960                1965

Trp Tyr Leu Leu Ser Met Gly Ser Asn Glu Asn Ile His Ser Ile
    1970            1975                1980

His Phe Ser Gly His Val Phe Thr Val Arg Lys Lys Glu Glu Tyr
    1985            1990                1995

Lys Met Ala Val Tyr Asn Leu Tyr Pro Gly Val Phe Glu Thr Val
    2000            2005                2010

Glu Met Leu Pro Ser Lys Val Gly Ile Trp Arg Ile Glu Cys Leu
    2015            2020                2025

Ile Gly Glu His Leu Gln Ala Gly Met Ser Thr Leu Phe Leu Val
    2030            2035                2040

Tyr Ser Lys Gln Cys Gln Thr Pro Leu Gly Met Ala Ser Gly Arg
    2045            2050                2055

Ile Arg Asp Phe Gln Ile Thr Ala Ser Gly Gln Tyr Gly Gln Trp
    2060            2065                2070

Ala Pro Lys Leu Ala Arg Leu His Tyr Ser Gly Ser Ile Asn Ala
    2075            2080                2085

Trp Ser Thr Lys Asp Pro Phe Ser Trp Ile Lys Val Asp Leu Leu
    2090            2095                2100

Ala Pro Met Ile Ile His Ser Ile Met Thr Gln Gly Ala Arg Gln
    2105            2110                2115

Lys Phe Ser Ser Leu Tyr Ile Ser Gln Phe Ile Ile Met Tyr Ser
    2120            2125                2130

Leu Asp Gly Lys Lys Trp Gln Ser Tyr Arg Gly Asn Ser Thr Gly
    2135            2140                2145

Thr Leu Met Val Phe Phe Gly Asn Val Asp Ser Ser Gly Ile Lys
    2150            2155                2160

His Asn Ile Phe Asn Pro Pro Ile Ile Ala Arg Tyr Ile Arg Leu
    2165            2170                2175

His Pro Thr His Tyr Ser Ile Arg Ser Thr Leu Arg Met Glu Leu
    2180            2185                2190

Met Gly Cys Asp Leu Asn Ser Cys Ser Met Pro Leu Gly Met Glu
    2195            2200                2205
```

```
Asn Lys Ala Ile Ser Asp Ala Gln Ile Thr Ala Ser Ser His Leu
    2210            2215                2220
Ser Asn Met Phe Ala Thr Trp Ser Pro Ser Gln Ala Arg Leu His
    2225            2230                2235
Leu Gln Gly Arg Thr Asn Ala Trp Arg Pro Gln Val Asn Asn Pro
    2240            2245                2250
Lys Glu Trp Leu Gln Val Asp Phe Gln Lys Thr Met Lys Val Thr
    2255            2260                2265
Gly Ile Thr Thr Gln Gly Val Lys Ser Leu Leu Thr Ser Met Tyr
    2270            2275                2280
Val Lys Glu Phe Leu Ile Ser Ser Ser Gln Asp Gly His Asn Trp
    2285            2290                2295
Thr Leu Phe Leu Gln Asn Gly Lys Val Lys Val Phe Gln Gly Asn
    2300            2305                2310
Gln Asp Ser Phe Thr Pro Val Val Asn Ala Leu Asp Pro Pro Leu
    2315            2320                2325
Phe Thr Arg Tyr Leu Arg Ile His Pro Gln Ser Trp Ala His His
    2330            2335                2340
Ile Ala Leu Arg Leu Glu Leu Leu Gly Cys Glu Ala Gln Gln Leu
    2345            2350                2355
Tyr

<210> SEQ ID NO 29
<211> LENGTH: 2359
<212> TYPE: PRT
<213> ORGANISM: Artificial sequence
<220> FEATURE:
<223> OTHER INFORMATION: recombinant clotting factor sequence

<400> SEQUENCE: 29

Met Gln Ile Glu Leu Ser Thr Cys Phe Phe Leu Cys Leu Leu Arg Phe
1               5                   10                  15
Ser Phe Ser Ala Thr Arg Arg Tyr Tyr Leu Gly Ala Val Glu Leu Ser
            20                  25                  30
Trp Asp Tyr Met Gln Ser Asp Leu Leu Ser Glu Leu His Val Asp Thr
        35                  40                  45
Arg Phe Pro Pro Arg Val Pro Arg Ser Phe Pro Phe Asn Thr Ser Val
    50                  55                  60
Met Tyr Lys Lys Thr Val Phe Val Glu Phe Thr Asp His Leu Phe Asn
65              70                  75                  80
Ile Ala Lys Pro Arg Pro Pro Trp Met Gly Leu Leu Gly Pro Thr Ile
            85                  90                  95
Trp Ala Glu Val Tyr Asp Thr Val Val Ile Thr Leu Lys Asn Met Ala
        100                 105                 110
Ser His Pro Val Ser Leu His Ala Val Gly Val Ser Tyr Trp Lys Ala
    115                 120                 125
Ser Glu Gly Ala Glu Tyr Asp Asp Gln Thr Ser Gln Arg Glu Lys Glu
130                 135                 140
Asp Asp Lys Val Phe Pro Gly Glu Ser His Thr Tyr Val Trp Gln Val
145                 150                 155                 160
Leu Lys Glu Asn Gly Pro Met Ala Ser Asp Pro Pro Cys Leu Thr Tyr
                165                 170                 175
Ser Tyr Leu Ser His Val Asp Leu Val Lys Asp Leu Asn Ser Gly Leu
            180                 185                 190
Ile Gly Ala Leu Leu Val Cys Arg Glu Gly Ser Leu Ala Lys Glu Arg
```

```
              195                 200                 205
Thr Gln Thr Leu His Glu Phe Val Leu Phe Ala Val Phe Asp Glu
210                 215                 220
Gly Lys Ser Trp His Ser Glu Thr Lys Asp Ser Leu Thr Gln Ala Met
225                 230                 235                 240
Asp Ser Ala Ser Ala Gln Ala Trp Pro Lys Met His Thr Val Asn Gly
                245                 250                 255
Tyr Val Asn Arg Ser Leu Pro Gly Leu Ile Gly Cys His Arg Lys Ser
            260                 265                 270
Val Tyr Trp His Val Ile Gly Met Gly Thr Thr Pro Glu Val His Ser
        275                 280                 285
Ile Phe Leu Glu Gly His Thr Phe Leu Val Arg Asn His Arg Gln Ala
    290                 295                 300
Ser Leu Glu Ile Ser Pro Ile Thr Phe Leu Thr Ala Gln Thr Leu Leu
305                 310                 315                 320
Met Asp Leu Gly Gln Phe Leu Leu Phe Cys His Ile Ser Ser His Gln
                325                 330                 335
His Asp Gly Met Glu Ala Tyr Val Lys Val Asp Ser Cys Pro Glu Glu
            340                 345                 350
Pro Gln Leu Arg Met Lys Asn Asn Glu Glu Glu Asp Tyr Asp Asp
        355                 360                 365
Asp Leu Asp Asp Ser Glu Met Asp Val Leu Arg Phe Asp Asp Asn
370                 375                 380
Ser Pro Ser Phe Ile Gln Ile Arg Ser Val Ala Lys Lys His Pro Lys
385                 390                 395                 400
Thr Trp Val His Tyr Ile Ala Ala Glu Glu Glu Asp Trp Asp Tyr Ala
                405                 410                 415
Pro Ser Val Leu Thr Pro Asp Asp Arg Ser Tyr Lys Ser Gln Tyr Leu
            420                 425                 430
Asn Asn Gly Pro Gln Arg Ile Gly Arg Lys Tyr Lys Lys Val Arg Phe
        435                 440                 445
Met Ala Tyr Thr Asp Glu Thr Phe Lys Thr Arg Glu Ala Ile Gln Tyr
    450                 455                 460
Glu Ser Gly Ile Leu Gly Pro Leu Leu Tyr Gly Glu Val Gly Asp Thr
465                 470                 475                 480
Leu Leu Ile Ile Phe Lys Asn Gln Ala Ser Arg Pro Tyr Asn Ile Tyr
                485                 490                 495
Pro His Gly Ile Thr Asp Val Ser Pro Leu His Ser Gly Arg Leu Pro
            500                 505                 510
Lys Gly Val Lys His Leu Lys Asp Leu Pro Ile Leu Pro Gly Glu Ile
        515                 520                 525
Phe Lys Tyr Lys Trp Thr Val Thr Val Glu Asp Gly Pro Thr Lys Ser
    530                 535                 540
Asp Pro Arg Cys Leu Thr Arg Tyr Tyr Ser Ser Phe Ile Asn Leu Glu
545                 550                 555                 560
Arg Asp Leu Ala Ser Gly Leu Ile Gly Pro Leu Leu Ile Cys Tyr Lys
                565                 570                 575
Glu Ser Val Asp Gln Arg Gly Asn Gln Met Met Ser Asp Lys Arg Asn
            580                 585                 590
Val Ile Leu Phe Ser Val Phe Asp Glu Asn Gln Ser Trp Tyr Leu Thr
        595                 600                 605
Glu Asn Met Gln Arg Phe Leu Pro Asn Ala Ala Gly Val Gln Pro Gln
    610                 615                 620
```

-continued

```
Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
        645                 650                 655

Trp Tyr Ile Leu Ser Val Gly Ala Gln Thr Asp Phe Leu Ser Val Phe
            660                 665                 670

Phe Ser Gly Tyr Thr Phe Lys His Lys Met Val Tyr Glu Asp Thr Leu
        675                 680                 685

Thr Leu Phe Pro Phe Ser Gly Glu Thr Val Phe Met Ser Met Glu Asn
690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Gly
                725                 730                 735

Asp Tyr Tyr Glu Asp Thr Tyr Glu Asp Ile Pro Thr Tyr Leu Leu Ser
                740                 745                 750

Glu Asn Asn Val Ile Glu Pro Arg Ser Phe Ser Gln Asn Ser Arg His
            755                 760                 765

Pro Ser Thr Arg Gln Lys Gln Phe Lys Ala Thr Thr Ile Pro Glu Asn
770                 775                 780

Asp Ile Glu Lys Ile Asp Pro Gln Phe Gly Glu Arg Thr Gln Met Leu
785                 790                 795                 800

Lys Val Gln Ser Val Ser Ser Asp Leu Leu Met Leu Leu Gly Gln
                805                 810                 815

Ser Pro Thr Pro His Gly Leu Ser Leu Ser Asp Leu Gln Glu Ala Thr
                820                 825                 830

Tyr Glu Ala Ile Pro Asp Asp His Ser Pro Gly Ala Ile Asp Ser Asn
            835                 840                 845

Glu Gly Pro Ser Glu Val Ala His Leu Arg Pro Glu Leu His His Ser
850                 855                 860

Gly Asp Ile Val Phe Thr Pro Glu Pro Gly Leu Gln Leu Arg Leu Asn
865                 870                 875                 880

Glu Asn Leu Gly Thr Thr Ile Ala Val Glu Leu Lys Lys Leu Asp Leu
                885                 890                 895

Lys Val Ser Ser Ser Ser Asn Asn Leu Met Thr Ser Pro Thr Ile Pro
                900                 905                 910

Ser Asp Asn Leu Ala Ala Gly Thr Glu Lys Thr Gly Ser Leu Gly Pro
            915                 920                 925

Pro Asn Met Pro Val His Phe Ser Ser Gln Leu Gly Thr Thr Val Phe
930                 935                 940

Gly Lys Lys Ser Ser Pro Leu Ile Gly Ser Gly Val Pro Leu Ser Leu
945                 950                 955                 960

Ser Glu Arg Asn Asn Asp Ser Lys Leu Leu Glu Ala Ala Leu Met Asn
            965                 970                 975

Ser Gln Glu Ser Ser Leu Gly Lys Asn Val Ser Ser Met Glu Ser Asp
                980                 985                 990

Arg Leu Phe Lys Glu Lys Arg Val His Gly Pro Ala Leu Leu Thr Lys
            995                 1000                1005

Asp Asn Ala Leu Phe Lys Val Asn Ile Ser Leu Val Lys Thr Asn
        1010                1015                1020

Lys Ala Ser Asn Asn Ser Thr Thr Asn Gly Lys Thr His Ile Asp
        1025                1030                1035
```

```
Gly Pro Thr Leu Leu Ile Glu Asn Ser Thr Ser Val Trp Gln Asp
    1040                1045                1050

Ile Ile Leu Glu Ser Asp Thr Glu Phe Gln Glu Val Thr Ser Leu
    1055                1060                1065

Ile His Asp Glu Met Phe Met Asp Lys Asn Thr Thr Ala Leu Arg
    1070                1075                1080

Leu Asn His Val Ser Asn Lys Thr Thr Ser Ser Lys Asn Met Glu
    1085                1090                1095

Met Val His Gln Lys Lys Glu Gly Pro Val Pro Pro Asp Ala Glu
    1100                1105                1110

Asn Pro Asp Met Ser Phe Phe Lys Met Leu Phe Leu Pro Glu Ser
    1115                1120                1125

Ala Asn Trp Ile Lys Arg Thr His Gly Lys Asn Ser Leu Asn Ser
    1130                1135                1140

Gly Gln Gly Pro Ser Pro Lys Gln Leu Ile Ser Leu Gly Ser Glu
    1145                1150                1155

Lys Ser Val Lys Asp Gln Asn Phe Leu Ser Glu Lys Asn Lys Val
    1160                1165                1170

Val Val Gly Glu Asp Glu Phe Thr Lys Asp Thr Gly Leu Lys Glu
    1175                1180                1185

Met Ile Phe Pro Ser Ser Arg Ser Ile Phe Leu Thr Asn Leu Ala
    1190                1195                1200

Asn Val Gln Glu Asn Asp Thr His Asn Gln Glu Lys Lys Phe Gln
    1205                1210                1215

Glu Glu Ile Glu Arg Lys Glu Thr Leu Ile Gln Glu Asn Val Val
    1220                1225                1230

Leu Pro Gln Val Tyr Thr Val Thr Gly Thr Lys Asn Phe Leu Lys
    1235                1240                1245

Asn Leu Phe Leu Leu Ser Thr Arg Gln Asn Val Glu Gly Leu Asp
    1250                1255                1260

Glu Gly Thr Tyr Ala Pro Val Leu Gln Asp Thr Arg Ser Leu Asn
    1265                1270                1275

Asp Ser Ala Asn Arg Ala Glu Ile His Met Ala His Phe Ser Lys
    1280                1285                1290

Arg Arg Glu Glu Glu Asn Leu Glu Gly Leu Arg Asn Gln Thr Lys
    1295                1300                1305

Gln Met Val Glu Lys Tyr Pro Ser Thr Thr Arg Met Ser Pro Asn
    1310                1315                1320

Pro Ser Gln Gln Asn Val Ile Thr Gln Arg Gly Lys Arg Ala Leu
    1325                1330                1335

Lys Gln Phe Arg Leu Pro Leu Glu Glu Ile Glu Leu Glu Arg Gly
    1340                1345                1350

Leu Ile Val Asp Asp Thr Ser Thr Gln Trp Ser Lys Asn Met Lys
    1355                1360                1365

Tyr Leu Thr Gln Gly Thr Leu Thr Gln Ile Asp Tyr Asn Glu Lys
    1370                1375                1380

Glu Lys Lys Ala Ile Thr Gln Ser Pro Leu Ser Asp Cys Pro Met
    1385                1390                1395

Arg Asn His Gly Ile Thr Gln Met Asn Ser Ser Ala Leu Pro Ile
    1400                1405                1410

Ala Lys Val Ser Ala Phe Pro Ser Ile Arg Pro Thr Asp Leu Thr
    1415                1420                1425

Lys Ile Pro Ser Gln Asp Asn Ser Ser His Leu Leu Ala Ser Ala
```

Cys Asn Tyr Thr Phe Arg Glu Arg Ser Ser Gly Val Gln Glu Ser
1445                1450                1455

Ser His Phe Leu Gln Gly Ala Lys Arg Asn Asn Leu Ser Leu Ala
1460                1465                1470

Ile Leu Thr Leu Glu Met Ile Arg Asn Gln Gly Lys Val Gly Ser
1475                1480                1485

Leu Gly Thr Ser Ala Thr Asn Ser Val Met Tyr Lys Lys Leu Glu
1490                1495                1500

Asn Thr Val Leu Leu Lys Pro Gly Leu Pro Ala Ser Gly Lys
1505                1510                1515

Val Glu Leu Leu Pro Lys Val His Ile His Gln Glu Asp Leu Phe
1520                1525                1530

Pro Thr Glu Thr Ser Asn Gly Ser Pro Gly His Leu Asp Leu Met
1535                1540                1545

Glu Glu Ile Leu Leu Gln Lys Thr Gln Gly Ala Ile Lys Trp Asn
1550                1555                1560

Lys Ala Asn Arg Pro Gly Lys Val Pro Phe Leu Lys Gly Ala Thr
1565                1570                1575

Glu Ser Ser Glu Lys Thr Pro Ser Lys Leu Leu Gly Pro Leu Ala
1580                1585                1590

Trp Asp Asn Gln Tyr Ala Thr Gln Ile Pro Lys Glu Glu Trp Lys
1595                1600                1605

Ser Gln Glu Lys Ser Pro Lys Asn Thr Ala Phe Lys Thr Lys Asp
1610                1615                1620

Thr Ile Leu Ser Leu Asn Pro Cys Glu Ser Asn His Ala Ile Ala
1625                1630                1635

Ala Ile Asn Glu Gly Gln Asn Arg Pro Gln Arg Glu Ala Thr Trp
1640                1645                1650

Ala Lys Gln Gly Gly Thr Gly Arg Leu Cys Ser Gln Asn Pro Pro
1655                1660                1665

Val Leu Lys Arg His Gln Arg Glu Ile Thr Leu Thr Thr Leu Gln
1670                1675                1680

Ser Glu Gln Glu Glu Ile Asp Tyr Asp Asp Thr Ile Ser Ile Glu
1685                1690                1695

Met Lys Arg Glu Asp Phe Asp Ile Tyr Gly Glu Asp Glu Asn Gln
1700                1705                1710

Gly Pro Arg Ser Phe Gln Lys Arg Thr Arg His Tyr Phe Ile Ala
1715                1720                1725

Ala Val Glu Arg Leu Trp Asp Tyr Gly Met Ser Ser Ser Pro His
1730                1735                1740

Val Leu Arg Asn Arg Ala Gln Ser Gly Ser Val Pro Gln Phe Lys
1745                1750                1755

Lys Val Val Phe Gln Glu Phe Thr Asp Gly Ser Phe Thr Gln Pro
1760                1765                1770

Leu Tyr Arg Gly Glu Leu Asn Glu His Leu Gly Leu Leu Gly Pro
1775                1780                1785

Tyr Ile Arg Ala Glu Val Glu Asp Asn Ile Met Val Thr Phe Lys
1790                1795                1800

Asn Gln Ala Ser Arg Pro Tyr Ser Phe Tyr Ser Ser Leu Ile Ser
1805                1810                1815

Tyr Glu Glu Asp Gln Arg Gln Gly Ala Glu Pro Arg Lys Asn Phe
1820                1825                1830

```
Val Lys Pro Asn Glu Thr Lys Thr Tyr Phe Trp Lys Val Gln His
1835                1840                1845

His Met Ala Pro Thr Lys Asp Glu Phe Asp Cys Lys Ala Trp Ala
    1850                1855                1860

Tyr Phe Ser Asp Val Asp Leu Glu Lys Asp Met His Ser Gly Leu
    1865                1870                1875

Ile Gly Pro Leu Leu Ile Cys His Thr Asn Thr Leu Asn Pro Ala
    1880                1885                1890

His Gly Arg Gln Val Thr Val Gln Glu Phe Ala Leu Phe Phe Thr
    1895                1900                1905

Ile Phe Asp Glu Thr Lys Ser Trp Tyr Phe Thr Glu Asn Met Glu
    1910                1915                1920

Arg Asn Cys Arg Ala Pro Cys Asn Ile Gln Met Glu Asp Pro Thr
    1925                1930                1935

Phe Lys Glu Asn Tyr Arg Phe His Ala Ile Asn Gly Tyr Val Met
    1940                1945                1950

Asp Thr Leu Pro Gly Leu Val Met Ala Gln Asp Gln Arg Ile Arg
    1955                1960                1965

Trp Tyr Leu Leu Ser Met Gly Ser Asn Glu Asn Ile His Ser Ile
    1970                1975                1980

His Phe Ser Gly His Val Phe Thr Val Arg Lys Lys Glu Glu Tyr
    1985                1990                1995

Lys Met Ala Val Tyr Asn Leu Tyr Pro Gly Val Phe Glu Thr Val
    2000                2005                2010

Glu Met Leu Pro Ser Lys Ala Gly Ile Trp Arg Val Glu Cys Leu
    2015                2020                2025

Ile Gly Glu His Leu His Ala Gly Met Ser Thr Leu Phe Leu Val
    2030                2035                2040

Tyr Ser Lys Gln Cys Gln Thr Pro Leu Gly Met Ala Ser Gly His
    2045                2050                2055

Ile Arg Asp Phe Gln Ile Thr Ala Ser Gly Gln Tyr Gly Gln Trp
    2060                2065                2070

Ala Pro Lys Leu Ala Arg Leu His Tyr Ser Gly Ser Ile Asn Ala
    2075                2080                2085

Trp Ser Thr Lys Glu Pro Phe Ser Trp Ile Lys Val Asp Leu Leu
    2090                2095                2100

Ala Pro Met Ile Ile His Gly Ile Lys Thr Gln Gly Ala Arg Gln
    2105                2110                2115

Lys Phe Ser Ser Leu Tyr Ile Ser Gln Phe Ile Ile Met Tyr Ser
    2120                2125                2130

Leu Asp Gly Lys Lys Trp Gln Thr Tyr Arg Gly Asn Ser Thr Gly
    2135                2140                2145

Thr Leu Met Val Phe Phe Gly Asn Val Asp Ser Ser Gly Ile Lys
    2150                2155                2160

His Asn Ile Phe Asn Pro Pro Ile Ile Ala Arg Tyr Ile Arg Leu
    2165                2170                2175

His Pro Thr His Tyr Ser Ile Arg Ser Thr Leu Arg Met Glu Leu
    2180                2185                2190

Met Gly Cys Asp Leu Asn Ser Cys Ser Met Pro Leu Gly Met Glu
    2195                2200                2205

Ser Lys Ala Ile Ser Asp Ala Gln Ile Thr Ala Ser Ser Tyr Phe
    2210                2215                2220
```

```
Thr Asn Met Phe Ala Thr Trp Ser Pro Ser Gln Ala Arg Leu His
    2225                2230                2235

Leu Gln Gly Arg Thr Asn Ala Trp Arg Pro Gln Val Asn Asn Pro
    2240                2245                2250

Lys Glu Trp Leu Gln Val Asp Phe Gln Lys Thr Met Lys Val Thr
    2255                2260                2265

Gly Ile Thr Thr Gln Gly Val Lys Ser Leu Leu Thr Ser Met Tyr
    2270                2275                2280

Val Lys Glu Phe Leu Ile Ser Ser Ser Gln Asp Gly His His Trp
    2285                2290                2295

Thr Leu Phe Leu Gln Asn Gly Lys Val Lys Val Phe Gln Gly Asn
    2300                2305                2310

Gln Asp Ser Phe Thr Pro Val Val Asn Ser Leu Asp Pro Pro Leu
    2315                2320                2325

Leu Thr Arg Tyr Leu Arg Ile His Pro Gln Ser Trp Val His Gln
    2330                2335                2340

Ile Ala Leu Arg Leu Glu Val Leu Gly Cys Glu Ala Gln Gln Leu
    2345                2350                2355

Tyr

<210> SEQ ID NO 30
<211> LENGTH: 2356
<212> TYPE: PRT
<213> ORGANISM: Artificial sequence
<220> FEATURE:
<223> OTHER INFORMATION: recombinant clotting factor sequence

<400> SEQUENCE: 30

Met Gln Ile Ala Leu Phe Thr Cys Phe Phe Leu Ser Leu Phe Asn Phe
1               5                   10                  15

Cys Ser Ser Ala Thr Arg Arg Tyr Tyr Leu Gly Ala Val Glu Leu Ser
                20                  25                  30

Trp Asn Tyr Met Gln Ser Asp Leu Leu Ser Val Leu His Thr Asp Thr
            35                  40                  45

Arg Phe Leu Pro Arg Met Pro Thr Ser Phe Pro Phe Asn Thr Ser Ile
    50                  55                  60

Met Tyr Lys Lys Thr Val Phe Val Glu Tyr Met Asp His Leu Phe Asn
65                  70                  75                  80

Ile Ala Lys Pro Arg Pro Pro Trp Met Gly Leu Leu Gly Pro Thr Ile
                85                  90                  95

Trp Thr Glu Val His Asp Thr Val Ile Thr Leu Lys Asn Met Ala
            100                 105                 110

Ser His Pro Val Ser Leu His Ala Val Gly Val Ser Tyr Trp Lys Ala
    115                 120                 125

Ser Glu Gly Ala Glu Tyr Glu Asp Gln Thr Ser Gln Arg Glu Lys Glu
130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Lys Glu Gly Ser Leu Ser Lys Glu Arg
    195                 200                 205

Thr Gln Met Leu His Gln Phe Val Leu Leu Phe Ala Val Phe Asp Glu
```

```
            210                 215                 220
Gly Lys Ser Trp His Ser Glu Thr Lys Asp Ser Phe Thr Gln Ala Met
225                 230                 235                 240

Asp Ser Ala Ser Thr Arg Ala Trp Pro Lys Met His Thr Val Asn Gly
                245                 250                 255

Tyr Val Asn Arg Ser Leu Pro Gly Leu Ile Gly Cys His Arg Lys Ser
                260                 265                 270

Val Tyr Trp His Val Ile Gly Met Gly Thr Thr Pro Glu Val His Ser
                275                 280                 285

Ile Phe Leu Glu Gly His Thr Phe Leu Val Arg Asn His Arg Gln Ala
                290                 295                 300

Ser Leu Glu Ile Ser Pro Ile Thr Phe Leu Thr Ala Gln Thr Leu Leu
305                 310                 315                 320

Ile Asp Leu Gly Gln Phe Leu Leu Phe Cys His Ile Ser Ser His Lys
                325                 330                 335

His Asp Gly Met Glu Ala Tyr Val Lys Val Asp Ser Cys Pro Glu Glu
                340                 345                 350

Pro Gln Trp Gln Lys Lys Asn Asn Glu Glu Met Glu Asp Tyr Asp Asp
                355                 360                 365

Asp Leu Leu Asp Ser Glu Met Asp Met Phe Thr Leu Asp Asp Asp Asn
                370                 375                 380

Ser Pro Ser Phe Ile Gln Ile Arg Ser Val Ala Lys Lys Tyr Pro Lys
385                 390                 395                 400

Thr Trp Ile His Tyr Ile Ser Ala Glu Glu Asp Trp Asp Tyr Ala
                405                 410                 415

Pro Ser Val Leu Thr Ser Asp Asp Gly Ser Tyr Lys Ser Gln Tyr Leu
                420                 425                 430

Ser Asn Gly Pro His Arg Ile Gly Arg Lys Tyr Lys Val Arg Phe
                435                 440                 445

Ile Ala Tyr Thr Asp Glu Thr Phe Lys Thr Arg Glu Thr Ile Gln His
                450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Ser Pro Leu His Ser Arg Arg Leu Pro
                500                 505                 510

Arg Gly Ile Lys His Val Lys Asp Leu Pro Ile Arg Pro Gly Glu Ile
                515                 520                 525

Phe Lys Tyr Lys Trp Thr Val Thr Val Glu Asp Gly Pro Thr Lys Ser
                530                 535                 540

Asp Pro Arg Cys Leu Thr Arg Tyr Tyr Ser Ser Phe Ile Asn Pro Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
                580                 585                 590

Val Ile Leu Phe Ser Val Phe Asp Glu Asn Gln Ser Trp Tyr Ile Thr
                595                 600                 605

Glu Asn Met Gln Arg Phe Leu Pro Asn Ala Ala Asp Thr Gln Pro Gln
                610                 615                 620

Asp Pro Glu Phe Gln Ala Ser Asn Ile Met His Ser Ile Asn Gly Tyr
625                 630                 635                 640
```

```
Val Phe Asp Ser Leu Gln Leu Thr Val Cys Leu His Glu Val Ala Tyr
                645                 650                 655

Trp Tyr Ile Leu Ser Val Gly Ala Gln Thr Asp Phe Leu Ser Ile Phe
                660                 665                 670

Phe Ser Gly Tyr Thr Phe Lys His Lys Met Val Tyr Glu Asp Thr Leu
                675                 680                 685

Thr Leu Phe Pro Phe Ser Gly Glu Thr Val Phe Met Ser Met Glu Asn
                690                 695                 700

Pro Gly Leu Trp Val Leu Gly Cys His Asn Ser Asp Phe Arg Lys Arg
705                 710                 715                 720

Gly Met Thr Ala Leu Leu Lys Val Ser Ser Cys Asp Lys Ser Thr Ser
                725                 730                 735

Asp Tyr Tyr Glu Glu Ile Tyr Glu Asp Ile Pro Thr Gln Leu Val Asn
                740                 745                 750

Asp Asn Asn Val Ile Glu Pro Arg Ser Phe Phe Gln Asn Ser Asn His
                755                 760                 765

Pro Asn Thr Arg Lys Lys Lys Phe Lys Ala Thr Thr Ile Pro Glu Asn
770                 775                 780

Asp Ile Glu Lys Ile Glu Pro Gln Phe Gly Thr Ala Glu Met Leu
785                 790                 795                 800

Lys Val Gln Ser Val Ser Ser Ser Asp Leu Leu Met Leu Leu Gly Gln
                805                 810                 815

Ser Pro Thr Pro His Gly Leu Ser Leu Ser Asp Asn Gln Glu Ala Ile
                820                 825                 830

Tyr Glu Ala Ile Pro Asp Asp His Ser Pro Asp Ala Ile Asp Ser Asn
                835                 840                 845

Glu Gly Pro Ser Lys Val Thr Gln Leu Arg Pro Glu Leu His His Ser
850                 855                 860

Gly Lys Ile Val Phe Thr Pro Glu Pro Gly Leu Gln Leu Arg Ser Asn
865                 870                 875                 880

Lys Asn Leu Glu Thr Thr Ile Glu Val Lys Trp Lys Lys Leu Asp Leu
                885                 890                 895

Gln Val Ser Ser Leu Pro Asn Asn Leu Met Thr Thr Pro Thr Ile Leu
                900                 905                 910

Ser Asp Asn Leu Thr Ala Thr Ser Glu Lys Thr Asp Ser Ser Gly Ser
                915                 920                 925

Pro Asp Met Pro Val His Phe Ser Ser Lys Leu Ser Thr Thr Ala Phe
930                 935                 940

Gly Lys Lys Ser Tyr Pro Leu Ile Gly Ser His Val Pro Leu Ser Ile
945                 950                 955                 960

Ser Glu Arg Asn Ser Asp Ser Asn Leu Leu Asp Ala Thr Leu Met Asn
                965                 970                 975

Ser Gln Glu Ser Ser Leu Gly Asp Asn Ile Ser Ser Met Glu Asn Asp
                980                 985                 990

Arg Leu Leu Lys Glu Lys Arg Phe His Gly Ile Ala Leu Leu Thr Lys
                995                 1000                1005

Asp Asn Thr Leu Phe Lys Asp Asn Ile Ser Leu Met Lys Thr Asn
            1010                1015                1020

Lys Thr Tyr Asn His Ser Thr Thr Asn Gly Lys Ala His Ile Asp
            1025                1030                1035

Ser Pro Thr Ser Leu Ile Glu Asn Ser Thr Ala Val Leu Gln Asp
            1040                1045                1050
```

-continued

| | | | | | | | | | | | |
|---|---|---|---|---|---|---|---|---|---|---|---|
| Thr | Ile | Leu | Lys | Ile | Asn | Ser | Glu | Ile | Gln | Glu | Val | Thr | Ser | Leu |
| | 1055 | | | | 1060 | | | | 1065 | | |

Thr Ile Leu Lys Ile Asn Ser Glu Ile Gln Glu Val Thr Ser Leu
    1055                1060                1065

Ile His Asp Gly Thr Leu Ser Gly Lys Asn Thr Thr Tyr Leu Arg
    1070                1075                1080

Leu Asn His Met Leu Asn Arg Thr Thr Ser Ser Lys Asn Lys Glu
    1085                1090                1095

Ile Phe His Gln Lys Asp Glu Asp Pro Val Pro Gln Asp Ala Glu
    1100                1105                1110

Asn Thr Ile Met Pro Phe Lys Met Leu Phe Leu Pro Glu Ser
    1115                1120                1125

Ala Asn Trp Met Lys Arg Thr Asn Gly Asn Asn Ser Leu Asn Ser
    1130                1135                1140

Glu Gln Gly Pro Ser Pro Lys Gln Leu Val Tyr Leu Met Leu Glu
    1145                1150                1155

Lys Ser Val Lys Asn Gln Asn Phe Leu Ser Glu Lys Asn Lys Val
    1160                1165                1170

Ile Val Glu Gln Asp Glu Phe Thr Lys Asp Thr Gly Leu Lys Asp
    1175                1180                1185

Met Val Phe Pro Ser Asn Met Ser Ile Phe Leu Thr Thr Leu Ala
    1190                1195                1200

Asn Val Gln Glu Asn Asp Met His Asn Gln Lys Asn Ile Gln
    1205                1210                1215

Glu Glu Ile Glu Lys Lys Glu Ala Leu Ile Glu Glu Lys Val Val
    1220                1225                1230

Leu Pro Gln Val His Ile Ala Thr Gly Ser Lys Asn Phe Leu Lys
    1235                1240                1245

Asp Ile Phe Phe Leu Gly Thr Arg Gln Asn Val Val Ser Leu Asp
    1250                1255                1260

Glu Glu Ile Tyr Val Pro Val Leu Gln Asp Ile Arg Ser Ile Asn
    1265                1270                1275

Asn Ser Thr Asn Thr Val Glu Ile His Met Ala His Phe Phe Lys
    1280                1285                1290

Arg Arg Glu Asp Glu Asn Ser Glu Gly Leu Val Asn Lys Thr Arg
    1295                1300                1305

Glu Met Val Lys Asn Tyr Pro Ser Thr Thr Arg Met Ser Pro Asn
    1310                1315                1320

Pro Ser Gln Lys Asn Ile Ile Thr Gln Arg Ser Lys Arg Ala Leu
    1325                1330                1335

Gly Gln Phe Arg Leu Pro Leu Glu Glu Thr Glu Leu Glu Lys Gln
    1340                1345                1350

Gln Ile Val Asn Asn Ala Ser Thr Gln Trp Pro Gln Thr Met Asn
    1355                1360                1365

Tyr Leu Thr Gln Ser Ile Ile Thr Gln Ile Asp His Ser Lys Glu
    1370                1375                1380

Gly Glu Lys Ser Ile Thr Gln Ser Ser Leu Ser Asp Ser Ser Met
    1385                1390                1395

Ile Lys Lys Ser Thr Thr Gln Thr Asn Ser Ser Gly Leu His Ile
    1400                1405                1410

Val Lys Thr Ser Ala Phe Pro Pro Ile Arg Pro Thr Asp Leu Lys
    1415                1420                1425

Arg Ile Pro Phe Gln Asp Lys Phe Phe His Val Leu Ala Ser Ser
    1430                1435                1440

Tyr Thr Tyr Asp Phe Lys Thr Lys Ser Ser Arg Ile Gln Glu Ser

-continued

```
            1445                1450                1455

Ser His Phe Leu Lys Glu Thr Lys Ile Asn Asn Ser Ser Leu Ala
    1460                1465                1470

Ile Leu Pro Trp Glu Met Ile Ile Asn Gln Gly Lys Phe Ala Ser
    1475                1480                1485

Pro Gly Thr Ser Asn Thr Asn Ser Val Thr Tyr Lys Lys Leu Glu
    1490                1495                1500

Asn Ile Val Leu Leu Lys Pro Val Leu Pro Glu Glu Ser Gly Lys
    1505                1510                1515

Val Glu Leu Leu Pro Gln Val Ser Ile His Glu Glu Leu Leu
    1520                1525                1530

Pro Thr Glu Thr Ser His Glu Ser Pro Gly His Leu Asp Leu Met
    1535                1540                1545

Lys Glu Val Phe Leu Gln Lys Thr Gln Gly Pro Ile Lys Trp Asn
    1550                1555                1560

Lys Ala Lys Arg His Gly Glu Ser Pro Phe Leu Lys Gly Thr Thr
    1565                1570                1575

Glu Ser Ser Glu Lys Thr Pro Ser Lys Leu Leu Asp Pro Leu Ala
    1580                1585                1590

Trp Asp Asn His Tyr Ala Ala Gln Ile Pro Lys Asp Lys Trp Lys
    1595                1600                1605

Ser Lys Glu Lys Ser Pro Glu Ile Thr Ser Ile Lys Arg Glu Asp
    1610                1615                1620

Thr Ile Leu Ser Leu Asn Pro His Glu Asn Asn His Ser Ile Val
    1625                1630                1635

Ala Ile Asn Glu Lys Gln Asn Trp Pro Gln Arg Glu Ala Thr Trp
    1640                1645                1650

Val Lys Gln Gly Gln Thr Gln Arg Leu Cys Ser Gln Asn Pro Pro
    1655                1660                1665

Val Leu Lys Arg His Gln Arg Glu Leu Ser Ala Leu Gln Ser Glu
    1670                1675                1680

Gln Glu Ala Thr Asp Tyr Asp Asp Ala Ile Thr Ile Glu Thr Asn
    1685                1690                1695

Glu Asp Phe Asp Ile Tyr Gly Glu Asp Ile Lys Gln Gly Pro Arg
    1700                1705                1710

Ser Phe Gln Gln Lys Thr Arg His Tyr Phe Ile Ala Ala Val Glu
    1715                1720                1725

Arg Leu Trp Asp Tyr Gly Met Ser Thr Ser Pro His Val Leu Arg
    1730                1735                1740

Asn Arg Asp Gln Ser Gly Asn Ala Pro Gln Phe Lys Lys Val Val
    1745                1750                1755

Phe Gln Glu Phe Thr Asp Gly Ser Phe Ser Gln Pro Leu Tyr Arg
    1760                1765                1770

Gly Glu Leu Asn Glu His Leu Gly Leu Leu Gly Pro Tyr Ile Arg
    1775                1780                1785

Ala Glu Val Glu Asp Asn Ile Met Val Thr Phe Lys Asn Gln Ala
    1790                1795                1800

Ser Arg Pro Tyr Ser Phe Tyr Ser Ser Leu Ile Ser Tyr Lys Glu
    1805                1810                1815

Asp Gln Arg Gln Gly Glu Glu Pro Arg Arg Asn Phe Val Lys Pro
    1820                1825                1830

Asn Glu Thr Lys Ile Tyr Phe Trp Lys Val Gln His His Met Ala
    1835                1840                1845
```

```
Pro Thr Glu Asp Glu Phe Asp Cys Lys Ala Trp Ala Tyr Phe Ser
    1850            1855                1860

Asp Val Asp Leu Glu Arg Asp Met His Ser Gly Leu Ile Gly Pro
    1865            1870                1875

Leu Leu Ile Cys His Thr Asn Thr Leu Asn Pro Ala His Gly Arg
    1880            1885                1890

Gln Val Ala Val Gln Glu Phe Ala Leu Phe Phe Thr Ile Phe Asp
    1895            1900                1905

Glu Thr Lys Ser Trp Tyr Phe Thr Glu Asn Val Glu Arg Asn Cys
    1910            1915                1920

Lys Thr Pro Cys Asn Ile Gln Met Glu Asp Pro Thr Leu Lys Glu
    1925            1930                1935

Asn Tyr Arg Phe His Ala Ile Asn Gly Tyr Val Met Asp Thr Leu
    1940            1945                1950

Pro Gly Leu Val Met Ala Gln Asp Gln Arg Ile Arg Trp Tyr Leu
    1955            1960                1965

Leu Ser Met Gly Ser Asn Glu Asn Ile Gln Ser Ile His Phe Ser
    1970            1975                1980

Gly His Val Phe Thr Val Arg Lys Lys Glu Glu Tyr Lys Met Ala
    1985            1990                1995

Val Tyr Asn Leu Tyr Pro Gly Val Phe Glu Thr Val Glu Met Leu
    2000            2005                2010

Pro Ser Arg Ala Gly Ile Trp Arg Val Glu Cys Leu Ile Gly Glu
    2015            2020                2025

His Leu Gln Ala Gly Met Ser Thr Leu Phe Leu Val Tyr Ser Lys
    2030            2035                2040

Gln Cys Gln Ile Pro Leu Gly Met Ala Ser Gly Ser Ile Arg Asp
    2045            2050                2055

Phe Gln Ile Thr Ala Ser Gly His Tyr Gly Gln Trp Ala Pro Asn
    2060            2065                2070

Leu Ala Arg Leu His His Ser Gly Ser Ile Asn Ala Trp Ser Thr
    2075            2080                2085

Lys Glu Pro Phe Ser Trp Ile Lys Val Asp Leu Leu Thr Pro Met
    2090            2095                2100

Ile Ile His Gly Ile Lys Thr Gln Gly Ala Arg Gln Lys Phe Ser
    2105            2110                2115

Ser Leu Tyr Ile Ser Gln Phe Ile Ile Met Tyr Ser Leu Asp Gly
    2120            2125                2130

Lys Lys Trp Leu Ser Tyr Arg Gly Asn Ser Thr Gly Thr Leu Met
    2135            2140                2145

Val Phe Phe Gly Asn Val Asp Ser Ser Gly Ile Lys His Asn Ser
    2150            2155                2160

Phe Asn Pro Pro Ile Ile Ala Arg Tyr Ile Arg Leu His Pro Thr
    2165            2170                2175

His Ser Ser Ile Arg Ser Thr Leu Arg Met Glu Leu Met Gly Cys
    2180            2185                2190

Asp Leu Asn Ser Cys Ser Ile Pro Leu Gly Met Glu Asn Lys Val
    2195            2200                2205

Ile Ser Asp Thr Gln Ile Thr Ala Ser Ser Tyr Phe Thr Asn Met
    2210            2215                2220

Phe Ala Thr Trp Ser Pro Ser Gln Ala Arg Leu His Leu Gln Gly
    2225            2230                2235
```

-continued

```
Arg Thr Asn Ala Trp Arg Pro Gln Val Asn Asp Pro Lys Glu Trp
2240                2245                2250
Leu Gln Val Asp Leu Gln Lys Thr Met Lys Val Thr Gly Ile Ile
    2255                2260                2265
Thr Gln Gly Val Lys Ser Leu Phe Thr Ser Met Phe Val Lys Glu
2270                2275                2280
Phe Leu Ile Ser Ser Ser Gln Asp Gly His His Trp Thr His Ile
    2285                2290                2295
Leu His Asn Gly Lys Val Lys Val Phe Gln Gly Asn Gln Asp Ser
    2300                2305                2310
Ser Thr Pro Met Val Asn Ser Leu Asp Pro Pro Leu Leu Thr Arg
    2315                2320                2325
Tyr Leu Arg Ile His Pro Gln Ile Trp Glu His Gln Ile Ala Leu
    2330                2335                2340
Arg Leu Glu Ile Leu Gly Cys Glu Ala Gln Gln Leu Tyr
    2345                2350                2355
```

<210> SEQ ID NO 31
<211> LENGTH: 2359
<212> TYPE: PRT
<213> ORGANISM: Artificial sequence
<220> FEATURE:
<223> OTHER INFORMATION: recombinant clotting factor sequence

<400> SEQUENCE: 31

```
Met Gln Ile Glu Leu Ser Thr Cys Phe Phe Leu Cys Leu Leu Arg Phe
1               5                   10                  15
Ser Phe Ser Ala Thr Arg Arg Tyr Tyr Leu Gly Ala Val Glu Leu Ser
            20                  25                  30
Trp Asp Tyr Met Gln Ser Asp Leu Leu Gly Glu Leu His Val Asp Thr
        35                  40                  45
Arg Phe Pro Pro Arg Val Pro Arg Ser Phe Pro Phe Asn Thr Ser Val
    50                  55                  60
Met Tyr Lys Lys Thr Val Phe Val Glu Phe Thr Asp His Leu Phe Asn
65                  70                  75                  80
Ile Ala Lys Pro Arg Pro Pro Trp Met Gly Leu Leu Gly Pro Thr Ile
                85                  90                  95
Trp Ala Glu Val Tyr Asp Thr Val Val Ile Thr Leu Lys Asn Met Ala
            100                 105                 110
Ser His Pro Val Ser Leu His Ala Val Gly Val Ser Tyr Trp Lys Ala
        115                 120                 125
Ser Glu Gly Ala Glu Tyr Asp Asp Gln Thr Ser Gln Arg Glu Lys Glu
    130                 135                 140
Asp Asp Lys Val Phe Pro Gly Glu Ser His Thr Tyr Val Trp Gln Val
145                 150                 155                 160
Leu Lys Glu Asn Gly Pro Met Ala Ser Asp Pro Pro Cys Leu Thr Tyr
                165                 170                 175
Ser Tyr Leu Ser His Val Asp Leu Val Lys Asp Leu Asn Ser Gly Leu
            180                 185                 190
Ile Gly Ala Leu Leu Val Cys Arg Glu Gly Ser Leu Ala Lys Glu Arg
        195                 200                 205
Thr Gln Thr Leu His Glu Phe Val Leu Leu Phe Ala Val Phe Asp Glu
    210                 215                 220
Gly Lys Ser Trp His Ser Glu Thr Lys Asp Ser Leu Thr Gln Ala Met
225                 230                 235                 240
```

```
Asp Ser Ala Ser Ala Gln Ala Trp Pro Lys Met His Thr Val Asn Gly
                245                 250                 255

Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
    290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Asp Tyr Asp Asp
        355                 360                 365

Asp Leu Asp Asp Ser Glu Met Asp Val Leu Arg Phe Asp Asp Asn
    370                 375                 380

Ser Pro Ser Phe Ile Gln Ile Arg Ser Val Ala Lys Lys His Pro Lys
385                 390                 395                 400

Thr Trp Val His Tyr Ile Ala Ala Glu Glu Glu Asp Trp Asp Tyr Ala
                405                 410                 415

Pro Ser Val Leu Thr Pro Asp Asp Arg Ser Tyr Lys Ser Gln Tyr Leu
            420                 425                 430

Asn Asn Gly Pro Gln Arg Ile Gly Arg Lys Tyr Lys Lys Val Arg Phe
        435                 440                 445

Met Ala Tyr Thr Asp Glu Thr Phe Lys Thr Arg Glu Ala Ile Gln Tyr
    450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Ser Pro Leu His Ser Gly Arg Leu Pro
            500                 505                 510

Lys Gly Val Lys His Leu Lys Asp Leu Pro Ile Leu Pro Gly Glu Ile
        515                 520                 525

Phe Lys Tyr Lys Trp Thr Val Thr Val Glu Asp Gly Pro Thr Lys Ser
    530                 535                 540

Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Gln Ser Trp Tyr Leu Thr
        595                 600                 605

Glu Asn Met Gln Arg Phe Leu Pro Asn Ala Ala Gly Val Gln Pro Gln
    610                 615                 620

Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
```

```
              660                 665                 670
Phe Ser Gly Tyr Thr Phe Lys His Lys Met Val Tyr Glu Asp Thr Leu
            675                 680                 685
Thr Leu Phe Pro Phe Ser Gly Glu Thr Val Phe Met Ser Met Glu Asn
            690                 695                 700
Pro Gly Leu Trp Val Leu Gly Cys His Asn Ser Asp Phe Arg Asn Arg
705                 710                 715                 720
Gly Met Thr Ala Leu Leu Lys Val Ser Ser Cys Asp Arg Asn Thr Gly
                725                 730                 735
Asp Tyr Tyr Glu Asp Thr Tyr Glu Asp Ile Pro Thr Tyr Leu Leu Ser
                740                 745                 750
Glu Asn Asn Val Ile Glu Pro Arg Ser Phe Ser Gln Asn Ser Arg His
                755                 760                 765
Pro Ser Thr Arg Gln Lys Gln Phe Lys Ala Thr Thr Ile Pro Glu Asn
                770                 775                 780
Asp Ile Glu Lys Ile Asp Pro Gln Phe Gly Glu Arg Thr Gln Met Leu
785                 790                 795                 800
Lys Val Gln Ser Val Ser Ser Asp Leu Leu Met Leu Leu Gly Gln
                805                 810                 815
Ser Pro Thr Pro His Gly Leu Ser Leu Ser Asp Leu Gln Glu Ala Thr
                820                 825                 830
Tyr Glu Ala Ile Pro Asp Asp His Ser Pro Gly Ala Ile Asp Ser Asn
                835                 840                 845
Glu Gly Pro Ser Glu Val Ala His Leu Arg Pro Glu Leu His His Ser
                850                 855                 860
Gly Asp Ile Val Phe Thr Pro Glu Pro Gly Leu Gln Leu Arg Leu Asn
865                 870                 875                 880
Glu Asn Leu Gly Thr Thr Ile Ala Val Glu Leu Lys Lys Leu Asp Leu
                885                 890                 895
Lys Val Ser Ser Ser Ser Asn Asn Leu Met Thr Ser Pro Thr Ile Pro
                900                 905                 910
Ser Asp Asn Leu Ala Ala Gly Thr Glu Lys Thr Gly Ser Leu Gly Pro
                915                 920                 925
Pro Asn Met Pro Val His Phe Ser Ser Gln Leu Gly Thr Thr Val Phe
                930                 935                 940
Gly Lys Lys Ser Ser Pro Leu Ile Gly Ser Gly Val Pro Leu Ser Leu
945                 950                 955                 960
Ser Glu Arg Asn Asn Asp Ser Lys Leu Leu Glu Ala Ala Leu Met Asn
                965                 970                 975
Ser Gln Glu Ser Ser Leu Gly Lys Asn Val Ser Ser Met Glu Ser Asp
                980                 985                 990
Arg Leu Phe Lys Glu Lys Arg Val His Gly Pro Ala Leu Leu Thr Lys
                995                1000                1005
Asp Asn Ala Leu Phe Lys Val Asn Ile Ser Leu Val Lys Thr Asn
            1010                1015                1020
Lys Ala Ser Asn Asn Ser Thr Thr Asn Gly Lys Thr His Ile Asp
            1025                1030                1035
Gly Pro Thr Leu Leu Ile Glu Asn Ser Thr Ser Val Trp Gln Asp
            1040                1045                1050
Ile Ile Leu Glu Ser Asp Thr Glu Phe Gln Glu Val Thr Ser Leu
            1055                1060                1065
Ile His Asp Glu Met Phe Met Asp Lys Asn Thr Thr Ala Leu Arg
            1070                1075                1080
```

-continued

```
Leu Asn His Val Ser Asn Lys Thr Thr Ser Ser Lys Asn Met Glu
    1085            1090                1095

Met Val His Gln Lys Lys Glu Gly Pro Val Pro Pro Asp Ala Glu
    1100            1105                1110

Asn Pro Asp Met Ser Phe Phe Lys Met Leu Phe Leu Pro Glu Ser
    1115            1120                1125

Ala Asn Trp Ile Lys Arg Thr His Gly Lys Asn Ser Leu Asn Ser
    1130            1135                1140

Gly Gln Gly Pro Ser Pro Lys Gln Leu Ile Ser Leu Gly Ser Glu
    1145            1150                1155

Lys Ser Val Lys Asp Gln Asn Phe Leu Ser Glu Lys Asn Lys Val
    1160            1165                1170

Val Val Gly Glu Asp Glu Phe Thr Lys Asp Thr Gly Leu Lys Glu
    1175            1180                1185

Met Ile Phe Pro Ser Ser Arg Ser Ile Phe Leu Thr Asn Leu Ala
    1190            1195                1200

Asn Val Gln Glu Asn Asp Thr His Asn Gln Glu Lys Lys Phe Gln
    1205            1210                1215

Glu Glu Ile Glu Arg Lys Glu Thr Leu Ile Gln Glu Asn Val Val
    1220            1225                1230

Leu Pro Gln Val Tyr Thr Val Thr Gly Thr Lys Asn Phe Leu Lys
    1235            1240                1245

Asn Leu Phe Leu Leu Ser Thr Arg Gln Asn Val Glu Gly Leu Asp
    1250            1255                1260

Glu Gly Ala Tyr Ala Pro Val Leu Gln Asp Thr Arg Ser Leu Asn
    1265            1270                1275

Asp Ser Ala Asn Arg Ala Glu Ile His Met Ala His Phe Ser Lys
    1280            1285                1290

Arg Arg Glu Glu Glu Asn Leu Glu Gly Leu Arg Asn Gln Thr Lys
    1295            1300                1305

Gln Met Val Glu Lys Tyr Pro Ser Thr Thr Arg Met Ser Pro Asn
    1310            1315                1320

Pro Ser Gln Gln Asn Val Ile Thr Gln Arg Gly Lys Arg Ala Leu
    1325            1330                1335

Lys Gln Phe Arg Leu Pro Leu Glu Glu Ile Glu Leu Glu Arg Gly
    1340            1345                1350

Leu Ile Val Asp Asp Thr Ser Thr Gln Trp Ser Lys Asn Met Lys
    1355            1360                1365

Tyr Leu Thr Gln Gly Thr Leu Thr Gln Ile Asp Tyr Asn Lys Lys
    1370            1375                1380

Glu Lys Lys Ala Ile Thr Gln Ser Pro Leu Ser Asp Cys Pro Met
    1385            1390                1395

Arg Asn His Gly Ile Thr Gln Met Asn Ser Ser Ala Leu Pro Ile
    1400            1405                1410

Ala Lys Val Ser Ala Phe Pro Ser Ile Arg Pro Thr Asp Leu Thr
    1415            1420                1425

Arg Ile Pro Ser Gln Asp Asn Ser Ser His Leu Leu Ala Ser Ala
    1430            1435                1440

Cys Asn Tyr Thr Phe Arg Glu Arg Ser Ser Gly Val Gln Glu Ser
    1445            1450                1455

Ser His Phe Leu Gln Gly Ala Lys Arg Asn Asn Leu Ser Leu Ala
    1460            1465                1470
```

-continued

| | | | | | | | | | | | |
|---|---|---|---|---|---|---|---|---|---|---|---|
|Ile|Leu|Thr|Leu|Glu|Met|Ile|Arg|Asn|Gln|Gly|Lys|Val|Gly|Ser|
| |1475| | | |1480| | | |1485| | | | | |

Ile Leu Thr Leu Glu Met Ile Arg Asn Gln Gly Lys Val Gly Ser
      1475                1480                1485

Leu Gly Thr Ser Ala Thr Asn Ser Val Met Tyr Lys Lys Leu Glu
      1490                1495                1500

Asn Thr Val Leu Leu Lys Pro Gly Leu Pro Glu Ala Ser Gly Lys
      1505                1510                1515

Val Glu Leu Leu Pro Lys Val His Ile His Gln Glu Asp Leu Phe
      1520                1525                1530

Pro Thr Glu Thr Ser Asn Gly Ser Pro Gly His Leu Asp Leu Met
      1535                1540                1545

Glu Glu Ile Leu Leu Gln Lys Thr Gln Gly Ala Ile Lys Trp Asn
      1550                1555                1560

Lys Ala Asn Arg Pro Gly Lys Val Pro Phe Leu Lys Gly Ala Thr
      1565                1570                1575

Glu Ser Ser Glu Lys Thr Pro Ser Lys Leu Leu Gly Pro Leu Ala
      1580                1585                1590

Trp Asp Asn Gln Tyr Ala Thr Gln Ile Pro Lys Glu Glu Trp Lys
      1595                1600                1605

Ser Gln Glu Lys Ser Pro Lys Asn Thr Ala Phe Lys Thr Lys Asp
      1610                1615                1620

Thr Ile Leu Ser Leu Asn Pro Cys Glu Ser Asn His Ala Ile Ala
      1625                1630                1635

Ala Ile Asn Glu Gly Gln Asp Arg Pro Gln Arg Glu Ala Thr Trp
      1640                1645                1650

Ala Lys Gln Gly Gly Thr Gly Arg Leu Cys Ser Gln Asn Pro Pro
      1655                1660                1665

Val Leu Lys Arg His Gln Arg Glu Ile Thr Leu Thr Thr Leu Gln
      1670                1675                1680

Ser Glu Gln Glu Glu Ile Asp Tyr Asp Asp Thr Ile Ser Ile Glu
      1685                1690                1695

Met Lys Arg Glu Asp Phe Asp Ile Tyr Gly Glu Asp Glu Asn Gln
      1700                1705                1710

Gly Pro Arg Ser Phe Gln Lys Arg Thr Arg His Tyr Phe Ile Ala
      1715                1720                1725

Ala Val Glu Arg Leu Trp Asp Tyr Gly Met Ser Ser Ser Pro His
      1730                1735                1740

Val Leu Arg Asn Arg Ala Gln Ser Gly Ser Val Pro Gln Phe Lys
      1745                1750                1755

Lys Val Val Phe Gln Glu Phe Thr Asp Gly Ser Phe Thr Gln Pro
      1760                1765                1770

Leu Tyr Arg Gly Glu Leu Asn Glu His Leu Gly Leu Leu Gly Pro
      1775                1780                1785

Tyr Ile Arg Ala Glu Val Glu Asp Asn Ile Met Val Thr Phe Lys
      1790                1795                1800

Asn Gln Ala Ser Arg Pro Tyr Ser Phe Tyr Ser Ser Leu Ile Ser
      1805                1810                1815

Tyr Glu Glu Asp Gln Arg Gln Gly Ala Glu Pro Arg Lys Asn Phe
      1820                1825                1830

Val Lys Pro Asn Glu Thr Lys Thr Tyr Phe Trp Lys Val Gln His
      1835                1840                1845

His Met Ala Pro Thr Lys Asp Glu Phe Asp Cys Lys Ala Trp Ala
      1850                1855                1860

Tyr Phe Ser Asp Val Asp Leu Glu Lys Asp Met His Ser Gly Leu

```
              1865                1870                1875

Ile Gly Pro Leu Leu Ile Cys His Thr Asn Thr Leu Asn Pro Ala
        1880                1885                1890

His Gly Arg Gln Val Thr Val Gln Glu Phe Ala Leu Phe Phe Thr
        1895                1900                1905

Ile Phe Asp Glu Thr Lys Ser Trp Tyr Phe Thr Glu Asn Met Glu
        1910                1915                1920

Arg Asn Cys Arg Ala Pro Cys Asn Ile Gln Met Glu Asp Pro Thr
        1925                1930                1935

Phe Lys Glu Asn Tyr Arg Phe His Ala Ile Asn Gly Tyr Val Met
        1940                1945                1950

Asp Thr Leu Pro Gly Leu Val Met Ala Gln Asp Gln Arg Ile Arg
        1955                1960                1965

Trp Tyr Leu Leu Ser Met Gly Ser Asn Glu Asn Ile His Ser Ile
        1970                1975                1980

His Phe Ser Gly His Val Phe Thr Val Arg Lys Lys Glu Glu Tyr
        1985                1990                1995

Lys Met Ala Val Tyr Asn Leu Tyr Pro Gly Val Phe Glu Thr Val
        2000                2005                2010

Glu Met Leu Pro Ser Lys Ala Gly Ile Trp Arg Val Glu Cys Leu
        2015                2020                2025

Ile Gly Glu His Leu His Ala Gly Met Ser Thr Leu Phe Leu Val
        2030                2035                2040

Tyr Ser Lys Gln Cys Gln Thr Pro Leu Gly Met Ala Ser Gly His
        2045                2050                2055

Ile Arg Asp Phe Gln Ile Thr Ala Ser Gly Gln Tyr Gly Gln Trp
        2060                2065                2070

Ala Pro Lys Leu Ala Arg Leu His Tyr Ser Gly Ser Ile Asn Ala
        2075                2080                2085

Trp Ser Thr Lys Glu Pro Phe Ser Trp Ile Lys Val Asp Leu Leu
        2090                2095                2100

Ala Pro Met Ile Ile His Gly Ile Lys Thr Gln Gly Ala Arg Gln
        2105                2110                2115

Lys Phe Ser Ser Leu Tyr Ile Ser Gln Phe Ile Ile Met Tyr Ser
        2120                2125                2130

Leu Asp Gly Lys Lys Trp Gln Thr Tyr Arg Gly Asn Ser Thr Gly
        2135                2140                2145

Thr Leu Met Val Phe Phe Gly Asn Val Asp Ser Ser Gly Ile Lys
        2150                2155                2160

His Asn Ile Phe Asn Pro Pro Ile Ile Ala Arg Tyr Ile Arg Leu
        2165                2170                2175

His Pro Thr His Tyr Ser Ile Arg Ser Thr Leu Arg Met Glu Leu
        2180                2185                2190

Met Gly Cys Asp Leu Asn Ser Cys Ser Met Pro Leu Gly Met Glu
        2195                2200                2205

Ser Lys Ala Ile Ser Asp Ala Gln Ile Thr Ala Ser Ser Tyr Phe
        2210                2215                2220

Thr Asn Met Phe Ala Thr Trp Ser Pro Ser Gln Ala Arg Leu His
        2225                2230                2235

Leu Gln Gly Arg Thr Asn Ala Trp Arg Pro Gln Val Asn Asn Pro
        2240                2245                2250

Lys Glu Trp Leu Gln Val Asp Phe Gln Lys Thr Met Lys Val Thr
        2255                2260                2265
```

```
Gly Ile Thr Thr Gln Gly Val Lys Ser Leu Leu Thr Ser Met Tyr
    2270            2275                2280

Val Lys Glu Phe Leu Ile Ser Ser Ser Gln Asp Gly His His Trp
    2285            2290                2295

Thr Leu Phe Phe Gln Asn Gly Lys Val Lys Val Phe Gln Gly Asn
    2300            2305                2310

Gln Asp Ser Phe Thr Pro Val Val Asn Ser Leu Asp Pro Pro Leu
    2315            2320                2325

Leu Thr Arg Tyr Leu Arg Ile His Pro Gln Ser Trp Val His Gln
    2330            2335                2340

Ile Ala Leu Arg Leu Glu Val Leu Gly Cys Glu Ala Gln Gln Leu
    2345            2350                2355

Tyr

<210> SEQ ID NO 32
<211> LENGTH: 2359
<212> TYPE: PRT
<213> ORGANISM: Artificial sequence
<220> FEATURE:
<223> OTHER INFORMATION: recombinant clotting factor sequence

<400> SEQUENCE: 32

Met Gln Ile Glu Leu Ser Thr Cys Phe Phe Leu Cys Leu Leu Arg Phe
1               5                   10                  15

Ser Phe Ser Ala Thr Arg Arg Tyr Tyr Leu Gly Ala Val Glu Leu Ser
                20                  25                  30

Trp Asp Tyr Met Gln Ser Asp Leu Gly Glu Leu His Val Asp Thr
                35                  40                  45

Arg Phe Pro Pro Arg Val Pro Arg Ser Phe Pro Phe Asn Thr Ser Val
    50                  55                  60

Met Tyr Lys Lys Thr Val Phe Val Glu Phe Asp His Leu Phe Asn
65                  70                  75                  80

Ile Ala Lys Pro Arg Pro Pro Trp Met Gly Leu Leu Gly Pro Thr Ile
                85                  90                  95

Trp Ala Glu Val Tyr Asp Thr Val Val Ile Thr Leu Lys Asn Met Ala
                100                 105                 110

Ser His Pro Val Ser Leu His Ala Val Gly Val Ser Tyr Trp Lys Ala
            115                 120                 125

Ser Glu Gly Ala Glu Tyr Asp Asp Gln Thr Ser Gln Arg Glu Lys Glu
    130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
        195                 200                 205

Thr Gln Thr Leu His Glu Phe Val Leu Leu Phe Ala Val Phe Asp Glu
    210                 215                 220

Gly Lys Ser Trp His Ser Glu Thr Lys Asp Ser Leu Thr Gln Ala Met
225                 230                 235                 240

Asp Ser Ala Ser Ala Gln Ala Trp Pro Lys Met His Thr Val Asn Gly
                245                 250                 255
```

Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
    290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Asp Tyr Asp Asp
        355                 360                 365

Asp Leu Asp Asp Ser Glu Met Asp Val Leu Arg Phe Asp Asp Asn
    370                 375                 380

Ser Pro Ser Phe Ile Gln Ile Arg Ser Val Ala Lys Lys His Pro Lys
385                 390                 395                 400

Thr Trp Val His Tyr Ile Ala Ala Glu Glu Asp Trp Asp Tyr Ala
                405                 410                 415

Pro Ser Val Leu Thr Pro Asp Asp Arg Ser Tyr Lys Ser Gln Tyr Leu
            420                 425                 430

Asn Asn Gly Pro Gln Arg Ile Gly Arg Lys Tyr Lys Lys Val Arg Phe
        435                 440                 445

Met Ala Tyr Thr Asp Glu Thr Phe Lys Thr Arg Glu Ala Ile Gln Tyr
    450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Ser Pro Leu His Ser Gly Arg Leu Pro
            500                 505                 510

Lys Gly Val Lys His Leu Lys Asp Leu Pro Ile Leu Pro Gly Glu Ile
        515                 520                 525

Phe Lys Tyr Lys Trp Thr Val Thr Val Glu Asp Gly Pro Thr Lys Ser
    530                 535                 540

Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Gln Ser Trp Tyr Leu Thr
        595                 600                 605

Glu Asn Met Gln Arg Phe Leu Pro Asn Ala Ala Gly Val Gln Pro Gln
    610                 615                 620

Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
            660                 665                 670

Phe Ser Gly Tyr Thr Phe Lys His Lys Met Val Tyr Glu Asp Thr Leu

```
                675                 680                 685
Thr Leu Phe Pro Phe Ser Gly Glu Thr Val Phe Met Ser Met Glu Asn
690                     695                 700

Pro Gly Leu Trp Val Leu Gly Cys His Asn Ser Asp Phe Arg Asn Arg
705                     710                 715                 720

Gly Met Thr Ala Leu Leu Lys Val Ser Ser Cys Asp Arg Asn Thr Gly
                    725                 730                 735

Asp Tyr Tyr Glu Asp Thr Tyr Glu Asp Ile Pro Thr Tyr Leu Leu Ser
                740                 745                 750

Glu Asn Asn Val Ile Glu Pro Arg Ser Phe Ser Gln Asn Ser Arg His
            755                 760                 765

Pro Ser Thr Arg Gln Lys Gln Phe Lys Ala Thr Thr Ile Pro Glu Asn
770                     775                 780

Asp Ile Glu Lys Ile Asp Pro Gln Phe Gly Arg Thr Gln Met Leu
785                     790                 795                 800

Lys Val Gln Ser Val Ser Ser Asp Leu Leu Met Leu Leu Gly Gln
                    805                 810                 815

Ser Pro Thr Pro His Gly Leu Ser Leu Ser Asp Leu Gln Glu Ala Thr
                820                 825                 830

Tyr Glu Ala Ile Pro Asp Asp His Ser Pro Gly Ala Ile Asp Ser Asn
                835                 840                 845

Glu Gly Pro Ser Glu Val Ala His Leu Arg Pro Glu Leu His His Ser
850                     855                 860

Gly Asp Ile Val Phe Thr Pro Glu Pro Gly Leu Gln Leu Arg Leu Asn
865                     870                 875                 880

Glu Asn Leu Gly Thr Thr Ile Ala Val Glu Leu Lys Lys Leu Asp Leu
                    885                 890                 895

Lys Val Ser Ser Ser Asn Asn Leu Met Thr Ser Pro Thr Ile Pro
                    900                 905                 910

Ser Asp Asn Leu Ala Ala Gly Thr Glu Lys Thr Gly Ser Leu Gly Pro
                915                 920                 925

Pro Asn Met Pro Val His Phe Ser Ser Gln Leu Gly Thr Thr Val Phe
930                     935                 940

Gly Lys Lys Ser Ser Pro Leu Ile Gly Ser Gly Val Pro Leu Ser Leu
945                     950                 955                 960

Ser Glu Arg Asn Asn Asp Ser Lys Leu Leu Glu Ala Ala Leu Met Asn
                    965                 970                 975

Ser Gln Glu Ser Ser Leu Gly Lys Asn Val Ser Ser Met Glu Ser Asp
                980                 985                 990

Arg Leu Phe Lys Glu Lys Arg Ala His Gly Pro Ala Leu Leu Thr Lys
                995                 1000                 1005

Asp Asn Ala Leu Phe Lys Val Asn Ile Ser Leu Val Lys Thr Asn
            1010                1015                1020

Lys Ala Ser Asn Asn Ser Thr Thr Asn Gly Lys Thr His Ile Asp
            1025                1030                1035

Gly Pro Thr Leu Leu Ile Glu Asn Ser Thr Ser Val Trp Gln Asp
            1040                1045                1050

Thr Ile Leu Glu Ser Asp Thr Glu Phe Gln Glu Val Thr Ser Leu
            1055                1060                1065

Ile His Asp Glu Met Phe Met Asp Lys Asn Thr Thr Ala Leu Arg
            1070                1075                1080

Leu Asn His Val Ser Asn Lys Thr Thr Ser Ser Lys Asn Met Glu
            1085                1090                1095
```

```
Met Val His Gln Lys Lys Glu Gly Pro Val Pro Asp Ala Glu
    1100            1105            1110

Asn Pro Asp Met Ser Phe Phe Lys Met Leu Phe Leu Pro Glu Ser
    1115            1120            1125

Ala Asn Trp Ile Lys Arg Thr His Gly Lys Asn Ser Leu Asn Ser
    1130            1135            1140

Gly Gln Gly Pro Ser Pro Lys Gln Leu Ile Ser Leu Gly Ser Glu
    1145            1150            1155

Lys Ser Val Lys Asp Gln Asn Phe Leu Ser Glu Lys Asn Lys Val
    1160            1165            1170

Val Val Gly Glu Asp Glu Phe Thr Lys Asp Thr Gly Leu Lys Glu
    1175            1180            1185

Met Ile Phe Pro Ser Ser Arg Asn Ile Phe Leu Thr Asn Leu Ala
    1190            1195            1200

Asn Val Gln Glu Asn Asp Thr His Asn Gln Glu Lys Lys Phe Gln
    1205            1210            1215

Glu Glu Ile Glu Arg Lys Glu Thr Leu Ile Gln Glu Asn Val Val
    1220            1225            1230

Leu Pro Gln Val Tyr Thr Val Thr Gly Thr Lys Asn Phe Leu Lys
    1235            1240            1245

Asn Leu Phe Leu Leu Ser Thr Arg Gln Asn Val Glu Gly Leu Asp
    1250            1255            1260

Glu Gly Ala Tyr Ala Pro Val Leu Gln Asp Thr Arg Ser Leu Asn
    1265            1270            1275

Asp Ser Ala Asn Arg Ala Glu Ile His Met Ala His Phe Ser Lys
    1280            1285            1290

Arg Arg Glu Glu Glu Asn Leu Glu Gly Leu Arg Asn Gln Thr Lys
    1295            1300            1305

Gln Met Val Glu Lys Tyr Pro Ser Thr Thr Arg Met Ser Pro Asn
    1310            1315            1320

Pro Ser Gln Gln Asn Val Ile Thr Gln Arg Gly Lys Arg Ala Leu
    1325            1330            1335

Lys Gln Phe Arg Leu Pro Leu Glu Glu Ile Glu Leu Glu Lys Gly
    1340            1345            1350

Leu Ile Val Asp Asp Thr Ser Thr Gln Trp Ser Lys Asn Met Lys
    1355            1360            1365

Tyr Leu Thr Gln Gly Thr Leu Thr Gln Ile Asp Tyr Asn Lys Lys
    1370            1375            1380

Glu Lys Lys Ala Ile Thr Gln Ser Pro Leu Ser Asp Cys Pro Met
    1385            1390            1395

Arg Ser His Gly Ile Thr Gln Met Asn Ser Ser Ala Leu Pro Ile
    1400            1405            1410

Ala Lys Val Ser Ala Phe Pro Ser Ile Arg Pro Thr Asp Leu Thr
    1415            1420            1425

Arg Ile Pro Ser Gln Asp Asn Ser Ser His Leu Leu Ala Ser Ala
    1430            1435            1440

Cys Asn Tyr Thr Phe Arg Glu Arg Ser Ser Gly Val Gln Glu Ser
    1445            1450            1455

Ser His Phe Leu Gln Gly Ala Lys Arg Asn Asn Leu Ser Leu Ala
    1460            1465            1470

Ile Leu Thr Leu Glu Met Ile Arg Asn Gln Arg Lys Val Gly Ser
    1475            1480            1485
```

```
Leu Gly Thr Ser Ala Thr Asn Ser Val Met Tyr Lys Lys Leu Glu
1490                1495                1500

Asn Thr Val Leu Leu Lys Pro Gly Leu Pro Glu Ala Ser Gly Lys
1505                1510                1515

Val Glu Leu Leu Pro Lys Val His Ile His Gln Glu Asp Leu Phe
1520                1525                1530

Pro Thr Glu Thr Ser Asn Gly Ser Pro Gly His Leu Asp Leu Met
1535                1540                1545

Glu Glu Ile Leu Leu Gln Lys Thr Gln Gly Ala Ile Lys Trp Asn
1550                1555                1560

Lys Ala Asn Arg Pro Gly Lys Val Pro Phe Leu Lys Gly Ala Thr
1565                1570                1575

Glu Ser Ser Glu Lys Thr Pro Ser Lys Leu Leu Gly Pro Leu Ala
1580                1585                1590

Trp Asp Asn Gln Tyr Ala Thr Gln Ile Pro Lys Glu Glu Trp Lys
1595                1600                1605

Ser Gln Glu Lys Ser Pro Lys Asn Thr Ala Phe Lys Thr Lys Asp
1610                1615                1620

Thr Ile Leu Ser Leu Asn Pro Cys Glu Ser Asn His Ala Ile Ala
1625                1630                1635

Ala Ile Asn Glu Gly Gln Asp Arg Pro Gln Arg Glu Ala Thr Trp
1640                1645                1650

Ala Lys Gln Gly Gly Thr Gly Arg Leu Cys Ser Gln Asn Pro Pro
1655                1660                1665

Val Leu Lys Arg His Gln Arg Glu Ile Thr Leu Thr Thr Leu Gln
1670                1675                1680

Ser Glu Gln Glu Glu Ile Asp Tyr Asp Asp Thr Ile Ser Ile Glu
1685                1690                1695

Met Lys Arg Glu Asp Phe Asp Ile Tyr Gly Glu Asp Glu Asn Gln
1700                1705                1710

Gly Pro Arg Ser Phe Gln Lys Arg Thr Arg His Tyr Phe Ile Ala
1715                1720                1725

Ala Val Glu Arg Leu Trp Asp Tyr Gly Met Ser Ser Ser Pro His
1730                1735                1740

Val Leu Arg Asn Arg Ala Gln Ser Gly Ser Val Pro Gln Phe Lys
1745                1750                1755

Lys Val Val Phe Gln Glu Phe Thr Asp Gly Ser Phe Thr Gln Pro
1760                1765                1770

Leu Tyr Arg Gly Glu Leu Asn Glu His Leu Gly Leu Leu Gly Pro
1775                1780                1785

Tyr Ile Arg Ala Glu Val Glu Asp Asn Ile Met Val Thr Phe Lys
1790                1795                1800

Asn Gln Ala Ser Arg Pro Tyr Ser Phe Tyr Ser Ser Leu Ile Ser
1805                1810                1815

Tyr Glu Glu Asp Gln Arg Gln Gly Ala Glu Pro Arg Lys Asn Phe
1820                1825                1830

Val Lys Pro Asn Glu Thr Lys Thr Tyr Phe Trp Lys Val Gln His
1835                1840                1845

His Met Ala Pro Thr Lys Asp Glu Phe Asp Cys Lys Ala Trp Ala
1850                1855                1860

Tyr Phe Ser Asp Val Asp Leu Glu Lys Asp Met His Ser Gly Leu
1865                1870                1875

Ile Gly Pro Leu Leu Ile Cys His Thr Asn Thr Leu Asn Pro Ala
```

-continued

```
              1880                1885                1890
His Gly Arg Gln Val Thr Val Gln Glu Phe Ala Leu Phe Phe Thr
              1895                1900                1905
Ile Phe Asp Glu Thr Lys Ser Trp Tyr Phe Thr Glu Asn Met Glu
              1910                1915                1920
Arg Asn Cys Arg Ala Pro Cys Asn Ile Gln Met Glu Asp Pro Thr
              1925                1930                1935
Phe Lys Glu Asn Tyr Arg Phe His Ala Ile Asn Gly Tyr Val Met
              1940                1945                1950
Asp Thr Leu Pro Gly Leu Val Met Ala Gln Asp Gln Arg Ile Arg
              1955                1960                1965
Trp Tyr Leu Leu Ser Met Gly Ser Asn Glu Asn Ile His Ser Ile
              1970                1975                1980
His Phe Ser Gly His Val Phe Thr Val Arg Lys Lys Glu Glu Tyr
              1985                1990                1995
Lys Met Ala Val Tyr Asn Leu Tyr Pro Gly Val Phe Glu Thr Val
              2000                2005                2010
Glu Met Leu Pro Ser Lys Ala Gly Ile Trp Arg Val Glu Cys Leu
              2015                2020                2025
Ile Gly Glu His Leu His Ala Gly Met Ser Thr Leu Phe Leu Val
              2030                2035                2040
Tyr Ser Lys Gln Cys Gln Thr Pro Leu Gly Met Ala Ser Gly His
              2045                2050                2055
Ile Arg Asp Phe Gln Ile Thr Ala Ser Gly Gln Tyr Gly Gln Trp
              2060                2065                2070
Ala Pro Lys Leu Ala Arg Leu His Tyr Ser Gly Ser Ile Asn Ala
              2075                2080                2085
Trp Ser Thr Lys Glu Pro Phe Ser Trp Ile Lys Val Asp Leu Leu
              2090                2095                2100
Ala Pro Met Ile Ile His Gly Ile Lys Thr Gln Gly Ala Arg Gln
              2105                2110                2115
Lys Phe Ser Ser Leu Tyr Ile Ser Gln Phe Ile Ile Met Tyr Ser
              2120                2125                2130
Leu Asp Gly Lys Lys Trp Gln Thr Tyr Arg Gly Asn Ser Thr Gly
              2135                2140                2145
Thr Leu Met Val Phe Phe Gly Asn Val Asp Ser Ser Gly Ile Lys
              2150                2155                2160
His Asn Ile Phe Asn Pro Pro Ile Ile Ala Arg Tyr Ile Arg Leu
              2165                2170                2175
His Pro Thr His Tyr Ser Ile Arg Ser Thr Leu Arg Met Glu Leu
              2180                2185                2190
Met Gly Cys Asp Leu Asn Ser Cys Ser Met Pro Leu Gly Met Glu
              2195                2200                2205
Ser Lys Ala Ile Ser Asp Ala Gln Ile Thr Ala Ser Ser Tyr Phe
              2210                2215                2220
Thr Asn Met Phe Ala Thr Trp Ser Pro Ser Gln Ala Arg Leu His
              2225                2230                2235
Leu Gln Gly Arg Thr Asn Ala Trp Arg Pro Gln Val Asn Asn Pro
              2240                2245                2250
Lys Glu Trp Leu Gln Val Asp Phe Gln Lys Thr Met Lys Val Thr
              2255                2260                2265
Gly Ile Thr Thr Gln Gly Val Lys Ser Leu Leu Thr Ser Met Tyr
              2270                2275                2280
```

-continued

```
Val Lys Glu Phe Leu Ile Ser Ser Ser Gln Asp Gly His His Trp
    2285                2290                2295

Thr Leu Phe Phe Gln Asn Gly Lys Val Lys Val Phe Gln Gly Asn
    2300                2305                2310

Gln Asp Ser Phe Thr Pro Val Val Asn Ser Leu Asp Pro Pro Leu
    2315                2320                2325

Leu Thr Arg Tyr Leu Arg Ile His Pro Gln Ser Trp Val His Gln
    2330                2335                2340

Ile Ala Leu Arg Leu Glu Val Leu Gly Cys Glu Ala Gln Gln Leu
    2345                2350                2355

Tyr
```

<210> SEQ ID NO 33
<211> LENGTH: 2355
<212> TYPE: PRT
<213> ORGANISM: Artificial sequence
<220> FEATURE:
<223> OTHER INFORMATION: recombinant clotting factor sequence

<400> SEQUENCE: 33

```
Met Gln Ile Glu Leu Ser Thr Cys Phe Phe Leu Cys Leu Leu Arg Phe
1               5                   10                  15

Ser Phe Ser Ala Thr Arg Arg Tyr Tyr Leu Gly Ala Val Glu Leu Ser
                20                  25                  30

Trp Asp Tyr Met Gln Ser Asp Leu Leu Gly Glu Leu His Val Asp Thr
            35                  40                  45

Arg Phe Pro Pro Arg Val Pro Arg Ser Phe Pro Phe Asn Thr Ser Val
    50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Gln Ala Glu Val Tyr Asp Thr Val Val Ile Thr Leu Lys Asn Met Ala
                100                 105                 110

Ser His Pro Val Ser Leu His Ala Val Gly Val Ser Tyr Trp Lys Ala
            115                 120                 125

Ser Glu Gly Ala Glu Tyr Asp Asp Gln Thr Ser Gln Arg Glu Lys Glu
    130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
        195                 200                 205

Thr Gln Thr Leu His Glu Phe Val Leu Leu Phe Ala Val Phe Asp Glu
    210                 215                 220

Gly Lys Ser Trp His Ser Glu Thr Lys Asp Ser Leu Met Gln Asp Thr
225                 230                 235                 240

Asp Ser Ala Ser Ala Gln Ala Trp Pro Lys Met His Thr Val Asn Gly
                245                 250                 255

Tyr Val Asn Arg Ser Leu Pro Gly Leu Ile Gly Cys His Arg Lys Ser
            260                 265                 270
```

```
Val Tyr Trp His Val Ile Gly Met Gly Thr Thr Pro Glu Val His Ser
            275                 280                 285

Ile Phe Leu Glu Gly His Thr Phe Leu Val Arg Asn His Arg Gln Ala
        290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Asp Tyr Asp Asn
        355                 360                 365

Asp Leu Asp Asp Ser Glu Met Asp Val Leu Arg Phe Asp Asp Asp Asn
370                 375                 380

Ser Pro Ser Phe Ile Gln Ile Arg Ser Val Ala Lys Lys His Pro Lys
385                 390                 395                 400

Thr Trp Val His Tyr Ile Ala Ala Glu Glu Asp Trp Asp Tyr Ala
        405                 410                 415

Pro Ser Val Leu Thr Pro Asp Asp Arg Ser Tyr Lys Ser Gln Tyr Leu
                420                 425                 430

Asn Asn Gly Pro Gln Arg Ile Gly Arg Lys Tyr Lys Val Arg Phe
        435                 440                 445

Met Ala Tyr Thr Asp Glu Thr Phe Lys Thr Arg Glu Ala Ile Gln Tyr
    450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Ser Pro Leu His Ser Gly Arg Leu Pro
                500                 505                 510

Lys Gly Val Lys His Leu Lys Asp Leu Pro Ile Leu Pro Gly Glu Ile
            515                 520                 525

Phe Lys Tyr Lys Trp Thr Val Thr Val Glu Asp Gly Pro Thr Lys Ser
        530                 535                 540

Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Gln Ser Trp Tyr Leu Thr
        595                 600                 605

Glu Asn Met Gln Arg Phe Leu Pro Asn Ala Ala Gly Val Gln Pro Gln
    610                 615                 620

Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Ile Gly Ala Gln Thr Asp Phe Leu Ser Val Phe
                660                 665                 670

Phe Ser Gly Tyr Thr Phe Lys His Lys Met Val Tyr Glu Asp Thr Leu
            675                 680                 685

Thr Leu Phe Pro Phe Ser Gly Glu Thr Val Phe Met Ser Met Glu Asn
```

```
                690              695             700
Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Gly
                725                 730                 735

Asp Tyr Tyr Glu Asp Thr Tyr Glu Asp Ile Ser Thr Tyr Leu Leu Ser
                740                 745                 750

Glu Asn Asn Val Ile Glu Pro Arg Ser Phe Ser Gln Asn Ser Arg His
                755                 760                 765

Pro Ser Thr Arg Gln Lys Gln Phe Lys Ala Thr Thr Ile Pro Glu Asn
770                 775                 780

Asp Ile Glu Lys Ile Asp Pro Gln Phe Gly Glu Arg Thr Gln Met Leu
785                 790                 795                 800

Lys Val Gln Ser Val Ser Ser Asp Leu Leu Met Leu Leu Gly Gln
                805                 810                 815

Ser Pro Thr Pro His Gly Leu Ser Leu Ser Asp Leu Gln Glu Ala Thr
                820                 825                 830

Tyr Glu Ala Ile Pro Asp Asp His Ser Pro Gly Ala Ile Asp Ser Asn
                835                 840                 845

Glu Gly Pro Ser Glu Val Ala His Leu Arg Pro Glu Leu His His Ser
850                 855                 860

Gly Asp Ile Val Phe Thr Pro Glu Pro Gly Leu Gln Leu Arg Leu Asn
865                 870                 875                 880

Glu Asn Leu Gly Thr Thr Ile Ala Val Glu Leu Lys Lys Leu Asp Leu
                885                 890                 895

Lys Val Ser Ser Ser Asn Asn Leu Met Thr Ser Pro Thr Ile Pro
                900                 905                 910

Ser Asp Asn Leu Ala Ala Gly Thr Glu Lys Thr Gly Ser Leu Gly Pro
                915                 920                 925

Pro Asn Met Pro Val His Phe Asp Ser Gln Leu Asp Thr Thr Val Phe
930                 935                 940

Gly Lys Lys Ser Ser Pro Leu Ile Gly Ser Gly Val Pro Leu Ser Leu
945                 950                 955                 960

Ser Glu Gly Asn Asn Asp Ser Lys Leu Leu Glu Ala Ala Leu Met Asn
                965                 970                 975

Ser Gln Glu Ser Ser Leu Gly Lys Asn Val Ser Met Glu Ser Asp
                980                 985                 990

Arg Leu Phe Lys Glu Lys Arg Ala His Gly Pro Ala Leu Leu Thr Lys
                995                 1000                1005

Asp Asn Ala Leu Phe Lys Val Asn Ile Ser Leu Val Lys Thr Asn
1010                1015                1020

Lys Ala Ser Asn Asn Ser Thr Thr Asn Arg Lys Thr His Ile Asp
1025                1030                1035

Gly Pro Thr Leu Leu Ile Glu Asn Ser Thr Ser Val Trp Gln Asp
1040                1045                1050

Thr Ile Leu Glu Ser Asp Thr Glu Phe Gln Glu Val Thr Ser Leu
1055                1060                1065

Ile His Asp Lys Met Phe Met Asp Lys Asn Thr Thr Ala Leu Arg
1070                1075                1080

Leu Asn His Val Ser Asn Lys Thr Thr Ser Ser Lys Asn Met Glu
1085                1090                1095

Met Val His Gln Lys Lys Glu Gly Pro Val Pro Pro Asp Ala Glu
1100                1105                1110
```

-continued

Asn Pro Asp Met Ser Phe Phe Lys Met Leu Phe Leu Pro Glu Ser
1115                1120                1125

Ala Asn Trp Ile Lys Arg Thr His Gly Lys Asn Ser Leu Asn Ser
1130                1135                1140

Gly Gln Gly Pro Ser Pro Lys Gln Leu Ile Ser Leu Gly Ser Glu
1145                1150                1155

Lys Ser Val Lys Asp Gln Asn Phe Leu Ser Glu Lys Asn Lys Val
1160                1165                1170

Val Val Gly Glu Asp Glu Phe Thr Lys Asp Thr Gly Leu Lys Glu
1175                1180                1185

Met Ile Phe Pro Ser Ser Arg Asn Ile Phe Leu Thr Asn Leu Ala
1190                1195                1200

Asn Val His Glu Asn Asp Thr His Asn Gln Glu Lys Lys Ile Gln
1205                1210                1215

Glu Glu Ile Glu Arg Lys Glu Thr Leu Ile Gln Glu Asn Val Val
1220                1225                1230

Leu Pro Gln Val Tyr Thr Val Thr Gly Thr Lys Asn Phe Met Lys
1235                1240                1245

Asn Leu Phe Leu Leu Ser Thr Arg Gln Asn Val Glu Gly Leu Asp
1250                1255                1260

Glu Gly Ala Tyr Ala Pro Val Leu Gln Asp Thr Arg Ser Leu Asn
1265                1270                1275

Asp Ser Ala Asn Arg Thr Glu Ile His Met Ala His Phe Ser Lys
1280                1285                1290

Lys Arg Glu Glu Glu Asn Leu Glu Gly Leu Arg Asn Gln Thr Lys
1295                1300                1305

Gln Met Val Glu Lys Tyr Pro Ser Thr Thr Arg Met Ser Pro Asn
1310                1315                1320

Pro Ser Gln Gln Asn Val Ile Thr Gln Arg Gly Lys Arg Ala Leu
1325                1330                1335

Lys Gln Phe Arg Leu Pro Leu Glu Glu Ile Glu Leu Glu Lys Gly
1340                1345                1350

Leu Ile Val Asp Asp Thr Ser Thr Gln Trp Ser Lys Asn Met Lys
1355                1360                1365

Tyr Leu Thr Gln Gly Thr Leu Thr Gln Ile Asp Tyr Asn Lys Lys
1370                1375                1380

Glu Lys Lys Ala Ile Thr Gln Ser Pro Leu Ser Asp Cys Leu Met
1385                1390                1395

Arg Ser His Gly Ile Thr Gln Met Asn Ser Ser Ala Leu Pro Ile
1400                1405                1410

Ala Lys Val Ser Ala Phe Pro Ser Ile Arg Pro Thr Asp Leu Thr
1415                1420                1425

Arg Ile Pro Ser Gln Asp Asn Ser Ser His Leu Leu Ala Ser Ala
1430                1435                1440

Cys Arg Lys Lys Ser Ser Gly Val Gln Glu Ser Ser His Phe Leu
1445                1450                1455

Gln Gly Ala Lys Arg Asn Asn Leu Ser Leu Ala Ile Leu Thr Leu
1460                1465                1470

Glu Met Ile Gly Asn Gln Arg Lys Val Gly Ser Leu Gly Thr Ser
1475                1480                1485

Ala Thr Asn Ser Val Met Tyr Lys Lys Leu Glu Asn Thr Val Leu
1490                1495                1500

```
Leu Lys Pro Gly Leu Pro Glu Ala Ser Gly Lys Val Glu Leu Leu
    1505                1510                1515

Pro Lys Val His Ile His Gln Glu Asp Leu Phe Pro Thr Glu Thr
    1520                1525                1530

Ser Asn Gly Ser Pro Gly His Leu Asp Leu Met Glu Glu Ile Leu
    1535                1540                1545

Leu Gln Lys Thr Gln Gly Ala Ile Lys Trp Asn Lys Ala Asn Arg
    1550                1555                1560

Pro Gly Lys Val Pro Phe Leu Lys Gly Ala Thr Glu Ser Ser Glu
    1565                1570                1575

Lys Thr Pro Ser Lys Leu Leu Gly Pro Leu Ala Trp Asp Asn Gln
    1580                1585                1590

Tyr Ala Thr Gln Ile Pro Lys Glu Glu Trp Lys Ser Gln Glu Lys
    1595                1600                1605

Ser Pro Glu Asn Thr Ala Phe Lys Thr Lys Asp Thr Ile Leu Ser
    1610                1615                1620

Leu Asn Pro Cys Glu Ser Asn His Ala Ile Ala Ala Ile Asn Glu
    1625                1630                1635

Gly Gln Asp Arg Pro Gln Arg Glu Ala Thr Trp Ala Lys Gln Gly
    1640                1645                1650

Gly Thr Gly Arg Leu Cys Ser Gln Asn Pro Pro Val Leu Lys Arg
    1655                1660                1665

His Gln Arg Glu Ile Thr Leu Thr Thr Leu Gln Ser Asp Gln Glu
    1670                1675                1680

Glu Ile Asp Tyr Asp Asp Thr Ile Ser Thr Glu Met Lys Arg Glu
    1685                1690                1695

Asp Phe Asp Ile Tyr Gly Glu Asp Glu Asn Gln Gly Pro Arg Ser
    1700                1705                1710

Phe Gln Lys Lys Thr Arg His Tyr Phe Ile Ala Ala Val Glu Arg
    1715                1720                1725

Leu Trp Asp Tyr Gly Met Ser Ser Ser Pro His Val Leu Arg Asn
    1730                1735                1740

Arg Ala Gln Ser Gly Ser Val Pro Gln Phe Lys Lys Val Val Phe
    1745                1750                1755

Gln Glu Phe Thr Asp Gly Ser Phe Thr Gln Pro Leu Tyr Arg Gly
    1760                1765                1770

Glu Leu Asn Glu His Leu Gly Leu Leu Gly Pro Tyr Ile Arg Ala
    1775                1780                1785

Glu Val Glu Asp Asn Ile Met Val Thr Phe Lys Asn Gln Ala Ser
    1790                1795                1800

Arg Pro Tyr Ser Phe Tyr Ser Ser Leu Ile Ser Tyr Glu Glu Asp
    1805                1810                1815

Gln Arg Gln Gly Ala Glu Pro Arg Lys Asn Phe Val Lys Pro Asn
    1820                1825                1830

Glu Thr Lys Thr Tyr Phe Trp Lys Val Gln His His Met Ala Pro
    1835                1840                1845

Thr Lys Asp Glu Phe Asp Cys Lys Ala Trp Ala Tyr Phe Ser Asp
    1850                1855                1860

Val Asp Leu Glu Lys Asp Met His Ser Gly Leu Ile Gly Pro Leu
    1865                1870                1875

Leu Ile Cys His Thr Asn Thr Leu Asn Pro Ala His Gly Arg Gln
    1880                1885                1890

Val Thr Val Gln Glu Phe Ala Leu Phe Phe Thr Ile Phe Asp Glu
```

-continued

```
                 1895               1900               1905
Thr Lys Ser Trp Tyr Phe Thr Glu Asn Met Glu Arg Asn Cys Arg
        1910               1915               1920
Ala Pro Cys Asn Ile Gln Met Glu Asp Pro Thr Phe Lys Glu Asn
        1925               1930               1935
Tyr Arg Phe His Ala Ile Asn Gly Tyr Val Met Asp Thr Leu Pro
        1940               1945               1950
Gly Leu Val Met Ala Gln Asp Gln Arg Ile Arg Trp Tyr Leu Leu
        1955               1960               1965
Ser Met Gly Ser Asn Glu Asn Ile His Ser Ile His Phe Ser Gly
        1970               1975               1980
His Val Phe Thr Val Arg Lys Lys Glu Glu Tyr Lys Met Ala Val
        1985               1990               1995
Tyr Asn Leu Tyr Pro Gly Val Phe Glu Thr Val Glu Met Leu Pro
        2000               2005               2010
Ser Lys Ala Gly Ile Trp Arg Val Glu Cys Leu Ile Gly Glu His
        2015               2020               2025
Leu His Ala Gly Met Ser Thr Leu Phe Leu Val Tyr Ser Lys Gln
        2030               2035               2040
Cys Gln Thr Pro Leu Gly Met Ala Ser Gly His Ile Arg Asp Phe
        2045               2050               2055
Gln Ile Thr Ala Ser Gly Gln Tyr Gly Gln Trp Ala Pro Lys Leu
        2060               2065               2070
Ala Arg Leu His Tyr Ser Gly Ser Ile Asn Ala Trp Ser Thr Lys
        2075               2080               2085
Glu Pro Phe Ser Trp Ile Lys Val Asp Leu Leu Ala Pro Met Ile
        2090               2095               2100
Ile His Gly Ile Lys Thr Gln Gly Ala Arg Gln Lys Phe Ser Ser
        2105               2110               2115
Leu Tyr Ile Ser Gln Phe Ile Ile Met Tyr Ser Leu Asp Gly Lys
        2120               2125               2130
Lys Trp Gln Thr Tyr Arg Gly Asn Ser Thr Gly Thr Leu Met Val
        2135               2140               2145
Phe Phe Gly Asn Val Asp Ser Ser Gly Ile Lys His Asn Ile Phe
        2150               2155               2160
Asn Pro Pro Ile Ile Ala Arg Tyr Ile Arg Leu His Pro Thr His
        2165               2170               2175
Tyr Ser Ile Arg Ser Thr Leu Arg Met Glu Leu Met Gly Cys Asp
        2180               2185               2190
Leu Asn Ser Cys Ser Met Pro Leu Gly Met Glu Ser Lys Ala Ile
        2195               2200               2205
Ser Asp Ala Gln Ile Thr Ala Ser Ser Tyr Phe Thr Asn Met Phe
        2210               2215               2220
Ala Thr Trp Ser Pro Ser Gln Ala Arg Leu His Leu Gln Gly Arg
        2225               2230               2235
Thr Asn Ala Trp Arg Pro Gln Val Asn Asn Pro Lys Glu Trp Leu
        2240               2245               2250
Gln Val Asp Phe Gln Lys Thr Met Lys Val Thr Gly Ile Thr Thr
        2255               2260               2265
Gln Gly Val Lys Ser Leu Leu Thr Ser Met Tyr Val Lys Glu Phe
        2270               2275               2280
Leu Ile Ser Ser Ser Gln Asp Gly His His Trp Thr Leu Phe Phe
        2285               2290               2295
```

Gln Asn Gly Lys Val Lys Val Phe Gln Gly Asn Gln Asp Ser Phe
    2300            2305            2310

Thr Pro Val Val Asn Ser Leu Asp Pro Pro Leu Leu Thr Arg Tyr
    2315            2320            2325

Leu Arg Ile His Pro Gln Ser Trp Val His Gln Ile Ala Leu Arg
    2330            2335            2340

Leu Glu Val Leu Gly Cys Glu Ala Gln Gln Leu Tyr
    2345            2350            2355

<210> SEQ ID NO 34
<211> LENGTH: 2355
<212> TYPE: PRT
<213> ORGANISM: Artificial sequence
<220> FEATURE:
<223> OTHER INFORMATION: recombinant clotting factor sequence

<400> SEQUENCE: 34

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Thr
        35                  40                  45

Arg Phe Pro Pro Arg Val Pro Arg Ser Phe Pro Phe Asn Thr Ser Val
    50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Gln Ala Glu Val Tyr Asp Thr Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Asp Asp Gln Thr Ser Gln Arg Glu Lys Glu
    130                 135                 140

Asp Asp Lys Val Phe Pro Gly Gly Ser His Thr Tyr Val Trp Gln Val
145                 150                 155                 160

Leu Lys Glu Asn Gly Pro Met Ala Ser Asp Pro Leu Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Lys
        195                 200                 205

Thr Gln Thr Leu His Lys Phe Val Leu Leu Phe Ala Val Phe Asp Glu
    210                 215                 220

Gly Lys Ser Trp His Ser Glu Thr Lys Asn Ser Leu Met Gln Asp Arg
225                 230                 235                 240

Asp Ala Ala Ser Ala Arg Ala Trp Pro Lys Met His Thr Val Asn Gly
                245                 250                 255

Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
    290                 295                 300

```
Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Ala Glu Asp Tyr Asp Asp
                355                 360                 365

Asp Leu Ala Asp Ser Glu Met Asp Val Val Arg Phe Asp Asp Asp Asn
370                 375                 380

Ser Pro Ser Phe Ile Gln Ile Arg Ser Val Ala Lys Lys His Pro Lys
385                 390                 395                 400

Thr Trp Val His Tyr Ile Ala Ala Glu Glu Asp Trp Asp Tyr Ala
                405                 410                 415

Pro Ser Val Leu Ala Pro Asp Asp Arg Ser Tyr Lys Ser Gln Tyr Leu
                420                 425                 430

Asn Asn Gly Pro Gln Arg Ile Gly Arg Lys Tyr Lys Lys Val Arg Phe
            435                 440                 445

Met Ala Tyr Thr Asp Glu Thr Phe Lys Thr Arg Glu Ala Ile Gln Tyr
            450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Arg Pro Leu Tyr Ser Arg Arg Leu Pro
                500                 505                 510

Lys Gly Val Lys His Leu Lys Asp Phe Pro Ile Leu Pro Gly Glu Ile
                515                 520                 525

Phe Lys Tyr Lys Trp Thr Val Thr Val Glu Asp Gly Pro Thr Lys Ser
530                 535                 540

Asp Pro Arg Cys Leu Thr Arg Tyr Tyr Ser Ser Phe Ile Asn Met Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Ile Met Ser Asp Lys Arg Asn
                580                 585                 590

Val Ile Leu Phe Ser Val Phe Asp Glu Asn Gln Ser Trp Tyr Leu Thr
                595                 600                 605

Glu Asn Ile Gln Arg Phe Leu Pro Asn Pro Ala Gly Val Gln Leu Glu
                610                 615                 620

Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Ile Gly Ala Gln Thr Asp Phe Leu Ser Val Phe
                660                 665                 670

Phe Ser Gly Tyr Thr Phe Lys His Lys Met Val Tyr Glu Asp Thr Leu
            675                 680                 685

Thr Leu Phe Pro Phe Ser Gly Glu Thr Val Phe Met Ser Met Glu Asn
            690                 695                 700

Pro Gly Leu Trp Ile Leu Gly Cys His Asn Ser Asp Phe Arg Asn Arg
705                 710                 715                 720
```

```
Gly Met Thr Ala Leu Leu Lys Val Ser Ser Cys Asp Lys Asn Thr Gly
            725                 730                 735

Asp Tyr Tyr Glu Asp Ser Tyr Glu Asp Ile Ser Thr Tyr Leu Leu Ser
            740                 745                 750

Lys Asn Asn Ala Ile Glu Pro Arg Ser Phe Ser Gln Asn Ser Arg His
            755                 760                 765

Pro Ser Thr Arg Gln Lys Gln Phe Asn Ala Thr Thr Ile Pro Glu Asn
            770                 775                 780

Asp Ile Glu Lys Thr Asp Pro Trp Phe Ala His Arg Thr Pro Met Pro
785                 790                 795                 800

Lys Val Gln Asn Val Ser Ser Asp Leu Leu Met Leu Leu Arg Gln
                805                 810                 815

Ser Pro Thr Pro His Gly Leu Ser Leu Ser Asp Leu Gln Glu Ala Lys
            820                 825                 830

Tyr Glu Thr Phe Ser Asp Asp Pro Ser Pro Gly Ala Ile Asp Ser Asn
            835                 840                 845

Asn Ser Leu Ser Glu Met Thr His Leu Arg Pro Gln Leu His His Ser
            850                 855                 860

Gly Asp Met Val Phe Thr Pro Glu Pro Gly Leu Gln Leu Arg Leu Asn
865                 870                 875                 880

Glu Lys Leu Gly Thr Thr Val Ala Thr Glu Leu Lys Lys Leu Asp Phe
                885                 890                 895

Lys Val Ser Ser Ser Asn Asn Leu Ile Ser Ser Pro Thr Ile Pro
                900                 905                 910

Ser Asp Asn Leu Ala Ala Gly Thr Asp Asn Thr Ser Ser Leu Gly Pro
            915                 920                 925

Pro Asn Met Pro Val His Tyr Asp Ser Gln Leu Asp Thr Thr Leu Phe
            930                 935                 940

Gly Lys Lys Ser Ser Pro Leu Ile Glu Ser Gly Gly Pro Leu Ser Leu
945                 950                 955                 960

Ser Glu Glu Asn Asn Asp Ser Lys Leu Leu Glu Ser Gly Leu Met Asn
                965                 970                 975

Ser Gln Glu Ser Ser Trp Gly Lys Asn Val Ser Ser Thr Glu Ser Gly
            980                 985                 990

Arg Leu Phe Lys Glu Lys Arg Ala His Gly Pro Ala Leu Leu Thr Lys
            995                 1000                1005

Asp Asn Ala Leu Phe Lys Val Ser Ile Ser Leu Leu Lys Thr Asn
            1010                1015                1020

Lys Thr Ser Asn Asn Ser Ala Thr Asn Arg Lys Thr His Ile Asp
            1025                1030                1035

Gly Pro Ser Leu Leu Ile Glu Asn Ser Pro Ser Val Trp Gln Asn
            1040                1045                1050

Thr Ile Leu Glu Ser Asp Thr Glu Phe Gln Lys Val Thr Pro Leu
            1055                1060                1065

Ile His Asp Arg Met Leu Met Asp Lys Asn Thr Thr Ala Leu Arg
            1070                1075                1080

Leu Asn His Met Ser Asn Lys Thr Thr Ser Ser Lys Asn Met Glu
            1085                1090                1095

Met Val Gln Gln Lys Lys Glu Gly Pro Ile Pro Pro Asp Ala Glu
            1100                1105                1110

Asn Pro Asp Met Ser Phe Phe Lys Met Leu Phe Leu Pro Glu Ser
            1115                1120                1125

Ala Asn Trp Ile Gln Arg Thr His Gly Lys Asn Ser Leu Asn Ser
```

```
              1130              1135              1140
Gly Gln Gly Pro Ser Pro Lys Gln Leu Val Ser Leu Gly Pro Glu
       1145              1150              1155
Lys Ser Val Glu Gly Gln Asn Phe Leu Ser Glu Lys Asn Lys Val
       1160              1165              1170
Val Val Gly Lys Gly Glu Phe Thr Lys Asp Val Gly Leu Lys Glu
       1175              1180              1185
Met Val Phe Pro Ser Ser Arg Asn Leu Phe Leu Thr Asn Leu Asp
       1190              1195              1200
Asn Leu His Glu Asn Asn Thr His Asn Gln Glu Lys Lys Ile Gln
       1205              1210              1215
Glu Glu Ile Glu Arg Lys Glu Thr Leu Ile Gln Glu Asn Val Val
       1220              1225              1230
Leu Pro Gln Ile His Thr Val Thr Gly Thr Lys Asn Phe Met Lys
       1235              1240              1245
Asn Leu Phe Leu Leu Ser Thr Arg Gln Asn Val Glu Gly Ser Tyr
       1250              1255              1260
Glu Gly Ala Tyr Ala Pro Val Leu Gln Asp Phe Arg Ser Leu Asn
       1265              1270              1275
Asp Ser Thr Asn Arg Thr Lys Lys His Met Ala His Phe Ser Lys
       1280              1285              1290
Lys Gly Glu Glu Glu Asn Leu Glu Gly Leu Gly Asn Gln Thr Lys
       1295              1300              1305
Gln Ile Val Glu Lys Tyr Pro His Thr Thr Arg Ile Ser Pro Asn
       1310              1315              1320
Pro Ser Gln Gln Asn Phe Val Thr Gln Arg Gly Lys Arg Ala Leu
       1325              1330              1335
Lys Gln Phe Arg Leu Pro Leu Glu Glu Thr Glu Leu Glu Lys Arg
       1340              1345              1350
Leu Ile Val Asp Asp Thr Ser Thr Gln Trp Ser Lys Asn Met Lys
       1355              1360              1365
His Leu Thr Pro Ser Thr Leu Thr Gln Ile Asp Tyr Asn Glu Lys
       1370              1375              1380
Glu Lys Gly Ala Ile Thr Gln Ser Pro Leu Ser Asp Cys Leu Thr
       1385              1390              1395
Arg Ser His Ser Ile Thr Gln Ala Asn Arg Ser Pro Leu Pro Ile
       1400              1405              1410
Ala Lys Val Ser Ser Phe Pro Ser Ile Arg Pro Ile Asp Leu Thr
       1415              1420              1425
Arg Val Leu Phe Gln Asp Asn Ser Ser His Leu Pro Ala Pro Ser
       1430              1435              1440
Tyr Arg Lys Lys Asp Ser Gly Val Gln Glu Ser Ser His Phe Leu
       1445              1450              1455
Gln Gly Ala Lys Lys Asn Asn Leu Ser Leu Ala Ile Leu Thr Leu
       1460              1465              1470
Glu Met Ile Gly Asp Gln Arg Glu Val Gly Ser Leu Gly Thr Ser
       1475              1480              1485
Ala Thr Asn Ser Val Thr Tyr Lys Lys Val Glu Asn Thr Val Leu
       1490              1495              1500
Leu Lys Pro Gly Leu Pro Thr Ser Gly Lys Val Glu Leu Leu
       1505              1510              1515
Pro Lys Val His Ile Tyr Gln Lys Asp Leu Phe Pro Thr Glu Thr
       1520              1525              1530
```

```
Ser Asn Gly Ser Pro Gly His Leu Asp Leu Met Glu Gly Ser Leu
    1535            1540            1545

Leu Gln Glu Thr Glu Gly Ala Ile Lys Trp Asn Glu Ala Asn Arg
    1550            1555            1560

Pro Gly Lys Ile Pro Phe Leu Arg Gly Ala Thr Glu Ser Ser Ala
    1565            1570            1575

Lys Thr Pro Ser Lys Leu Leu Gly Pro Leu Ala Trp Asp Asn His
    1580            1585            1590

Tyr Gly Thr Gln Ile Pro Lys Glu Glu Trp Lys Ser Gln Glu Lys
    1595            1600            1605

Ser Pro Glu Asn Thr Ala Phe Lys Lys Lys Asp Thr Ile Leu Ser
    1610            1615            1620

Leu Asn Pro Cys Glu Ser Asn His Ala Ile Ala Ala Ile Asn Glu
    1625            1630            1635

Gly Gln Asn Lys Pro Gln Ile Glu Val Thr Trp Ala Lys Gln Gly
    1640            1645            1650

Gly Thr Glu Arg Leu Cys Ser Gln Asn Pro Pro Val Leu Lys Arg
    1655            1660            1665

His Gln Arg Glu Ile Thr Leu Thr Thr Leu Gln Ser Asp Gln Glu
    1670            1675            1680

Glu Ile Asp Tyr Asp Asp Thr Ile Ser Val Glu Met Lys Lys Glu
    1685            1690            1695

Asp Phe Asp Ile Tyr Gly Glu Asp Glu Asn Gln Ser Pro Arg Ser
    1700            1705            1710

Phe Gln Lys Lys Thr Arg His Tyr Phe Ile Ala Ala Val Glu Arg
    1715            1720            1725

Leu Trp Asp Tyr Gly Met Ser Ser Ser Pro His Val Leu Arg Asn
    1730            1735            1740

Arg Ala Gln Ser Gly Ser Val Pro Gln Phe Lys Lys Val Val Phe
    1745            1750            1755

Gln Glu Phe Thr Asp Gly Ser Phe Thr Gln Pro Leu Tyr Arg Gly
    1760            1765            1770

Glu Leu Asn Glu His Leu Gly Leu Leu Gly Pro Tyr Ile Arg Ala
    1775            1780            1785

Glu Val Glu Asp Asn Ile Met Val Thr Phe Lys Asn Gln Ala Ser
    1790            1795            1800

Arg Pro Tyr Ser Phe Tyr Ser Ser Leu Ile Ser Tyr Glu Glu Asp
    1805            1810            1815

Gln Arg Gln Gly Ala Glu Pro Arg Lys Asn Phe Val Lys Pro Asn
    1820            1825            1830

Glu Thr Lys Thr Tyr Phe Trp Lys Val Gln His His Met Ala Pro
    1835            1840            1845

Thr Lys Asp Glu Phe Asp Cys Lys Ala Trp Ala Tyr Phe Ser Asp
    1850            1855            1860

Val Asp Leu Glu Lys Asp Val His Ser Gly Leu Ile Gly Pro Leu
    1865            1870            1875

Leu Val Cys His Thr Asn Thr Leu Asn Pro Ala His Gly Arg Gln
    1880            1885            1890

Val Thr Val Gln Glu Phe Ala Leu Phe Phe Thr Ile Phe Asp Glu
    1895            1900            1905

Thr Lys Ser Trp Tyr Phe Thr Glu Asn Met Glu Arg Asn Cys Arg
    1910            1915            1920
```

```
Ala Pro Cys Asn Ile Gln Met Glu Asp Pro Thr Phe Lys Glu Asn
1925                1930                1935

Tyr Arg Phe His Ala Ile Asn Gly Tyr Ile Met Asp Thr Leu Pro
1940                1945                1950

Gly Leu Val Met Ala Gln Asp Gln Arg Ile Arg Trp Tyr Leu Leu
1955                1960                1965

Ser Met Gly Ser Asn Glu Asn Ile His Ser Ile His Phe Ser Gly
1970                1975                1980

His Val Phe Thr Val Arg Lys Lys Glu Tyr Lys Met Ala Val
1985                1990                1995

Tyr Asn Leu Tyr Pro Gly Val Phe Glu Thr Val Glu Met Leu Pro
2000                2005                2010

Ser Lys Ala Gly Ile Trp Arg Val Glu Cys Leu Ile Gly Glu His
2015                2020                2025

Leu His Ala Gly Met Ser Thr Leu Phe Leu Val Tyr Ser Asn Lys
2030                2035                2040

Cys Gln Thr Pro Leu Gly Met Ala Ser Gly Arg Ile Arg Asp Phe
2045                2050                2055

Gln Ile Thr Ala Ser Gly Gln Tyr Gly Gln Trp Ala Pro Lys Leu
2060                2065                2070

Ala Arg Leu His Tyr Ser Gly Ser Ile Asn Ala Trp Ser Thr Lys
2075                2080                2085

Glu Pro Phe Ser Trp Ile Lys Val Asp Leu Leu Ala Pro Met Ile
2090                2095                2100

Ile His Gly Ile Lys Thr Gln Gly Ala Arg Gln Lys Phe Ser Ser
2105                2110                2115

Leu Tyr Ile Ser Gln Phe Ile Ile Met Tyr Ser Leu Asp Gly Lys
2120                2125                2130

Lys Trp Gln Thr Tyr Arg Gly Asn Ser Thr Gly Thr Leu Met Val
2135                2140                2145

Phe Phe Gly Asn Val Asp Ser Ser Gly Ile Lys His Asn Ile Phe
2150                2155                2160

Asn Pro Pro Ile Ile Ala Arg Tyr Ile Arg Leu His Pro Thr His
2165                2170                2175

Tyr Ser Ile Arg Ser Thr Leu Arg Met Glu Leu Met Gly Cys Asp
2180                2185                2190

Leu Asn Ser Cys Ser Met Pro Leu Gly Met Glu Ser Lys Ala Ile
2195                2200                2205

Ser Asp Ala Gln Ile Thr Ala Ser Ser Tyr Phe Thr Asn Met Phe
2210                2215                2220

Ala Thr Trp Ser Pro Ser Lys Ala Arg Leu His Leu Gln Gly Arg
2225                2230                2235

Ser Asn Ala Trp Arg Pro Gln Val Asn Asn Pro Lys Glu Trp Leu
2240                2245                2250

Gln Val Asp Phe Gln Lys Thr Met Lys Val Thr Gly Ile Thr Thr
2255                2260                2265

Gln Gly Val Lys Ser Leu Leu Thr Ser Met Tyr Val Lys Glu Phe
2270                2275                2280

Leu Ile Ser Ser Ser Gln Asp Gly His His Trp Thr Leu Phe Phe
2285                2290                2295

Gln Asn Gly Lys Val Lys Val Phe Gln Gly Asn Gln Asp Ser Phe
2300                2305                2310

Thr Pro Val Val Asn Ser Leu Asp Pro Pro Leu Leu Thr Arg Tyr
```

```
                    2315                2320                2325

Leu Arg  Ile His Pro Gln Ser  Trp Val His Gln Ile  Ala Leu Arg
         2330                2335                2340

Met Glu  Val Leu Gly Cys Glu  Ala Gln Glu Leu Tyr
         2345                2350                2355

<210> SEQ ID NO 35
<211> LENGTH: 446
<212> TYPE: PRT
<213> ORGANISM: Artificial sequence
<220> FEATURE:
<223> OTHER INFORMATION: recombinant clotting factor sequence

<400> SEQUENCE: 35

Met Val Ser Gln Pro Arg Gly Leu Ala Leu Leu Cys Phe Leu Leu Gly
1               5                   10                  15

Leu Gln Gly Ser Leu Ala Ala Val Phe Ile Thr Gln Glu Glu Ala His
                20                  25                  30

Ser Val Leu His Arg Gln Arg Arg Ala Asn Ser Phe Leu Glu Glu Leu
            35                  40                  45

Arg Pro Gly Ser Leu Glu Arg Glu Cys Arg Glu Glu Gln Cys Ser Phe
        50                  55                  60

Glu Glu Ala Arg Glu Ile Phe Lys Asn Thr Glu Arg Thr Lys Gln Phe
65                  70                  75                  80

Trp Ile Ser Tyr Asn Asp Gly Asp Gln Cys Ala Ser Asn Pro Cys Gln
                85                  90                  95

Asn Gly Gly Ser Cys Glu Asp Gln Leu Gln Ser Tyr Ile Cys Phe Cys
            100                 105                 110

Pro Glu Asp Phe Glu Gly Arg Asn Cys Glu Thr Asn Lys Asn Asp Gln
        115                 120                 125

Leu Ile Cys Met Asn Glu Asn Gly Gly Cys Glu Gln Tyr Cys Ser Asp
130                 135                 140

His Ala Glu Ala Arg Arg Ser Cys Arg Cys His Glu Gly Tyr Thr Leu
145                 150                 155                 160

Gln Ala Asp Gly Val Ser Cys Thr Pro Thr Val Glu Tyr Pro Cys Gly
                165                 170                 175

Lys Ile Pro Val Leu Glu Lys Arg Asn Asp Ser Asn Pro Gln Gly Arg
            180                 185                 190

Ile Val Gly Gly Lys Val Cys Pro Lys Gly Glu Cys Pro Trp Gln Ala
        195                 200                 205

Ala Leu Lys Leu Asn Gly Glu Leu Leu Cys Gly Gly Thr Leu Leu Asp
210                 215                 220

Thr Thr Trp Val Val Ser Ala Ala His Cys Phe Asp Arg Ile Arg Ser
225                 230                 235                 240

Trp Lys Asn Leu Thr Val Val Leu Gly Glu His Asp Leu Ser Glu
                245                 250                 255

Asp Gly Asp Glu Gln Glu Arg Gln Val Ala Gln Ile Ile Ile Pro Asp
            260                 265                 270

Lys Tyr Val Pro Arg Lys Thr Asp His Asp Ile Ala Leu Leu Arg Leu
        275                 280                 285

Arg Arg Pro Val Ala Phe Thr Asp His Val Val Pro Leu Cys Leu Pro
290                 295                 300

Glu Lys Ala Phe Ser Glu Arg Thr Leu Ala Phe Ile Arg Phe Ser Ser
305                 310                 315                 320

Val Ser Gly Trp Gly Gln Leu Leu Asp Arg Gly Ala Thr Ala Leu Glu
```

```
                  325                 330                 335
Leu Met Ala Ile Asp Val Pro Arg Leu Met Thr Gln Asp Cys Leu Glu
                340                 345                 350

Gln Ser Arg Arg Ala Gly Ser Pro Ala Ile Thr Glu Asn Met Phe
            355                 360                 365

Cys Ala Gly Tyr Leu Asp Gly Ser Lys Asp Ala Cys Lys Gly Asp Ser
        370                 375                 380

Gly Gly Pro His Ala Thr Lys Phe Gln Gly Thr Trp Tyr Leu Thr Gly
385                 390                 395                 400

Val Val Ser Trp Gly Glu Gly Cys Ala Ala Glu Gly His Phe Gly Val
                405                 410                 415

Tyr Thr Arg Val Ser Gln Tyr Ile Glu Trp Leu His Arg Leu Met Ser
            420                 425                 430

Ser Glu Pro His Ser Gly Gly Leu Leu Arg Ala Pro Leu Pro
        435                 440                 445

<210> SEQ ID NO 36
<211> LENGTH: 444
<212> TYPE: PRT
<213> ORGANISM: Artificial sequence
<220> FEATURE:
<223> OTHER INFORMATION: recombinant clotting factor sequence

<400> SEQUENCE: 36

Met Ala Ser Arg Gly Leu Ala Leu Leu Cys Leu Leu Leu Gly Leu Gln
1               5                   10                  15

Gly Ser Leu Ala Ala Val Phe Ile Thr Gln Glu Gln Ala His Ser Val
            20                  25                  30

Leu His Arg Gln Arg Arg Ala Asn Ser Phe Leu Glu Glu Leu Trp Pro
        35                  40                  45

Gly Ser Leu Glu Arg Glu Cys Arg Glu Glu Gln Cys Ser Phe Glu Glu
    50                  55                  60

Ala Arg Glu Ile Phe Lys Asn Glu Glu Arg Thr Lys Gln Phe Trp Ile
65                  70                  75                  80

Ser Tyr Asn Asp Gly Asp Gln Cys Ala Ser Asn Pro Cys Gln Asn Gly
                85                  90                  95

Gly Ser Cys Glu Asp Gln Leu Gln Ser Tyr Ile Cys Phe Cys Pro Glu
            100                 105                 110

Gly Phe Glu Gly Arg Asn Cys Glu Thr Asn Lys Lys Ser Gln Leu Ile
        115                 120                 125

Cys Met Asn Asp Asn Gly Gly Cys Glu Gln Tyr Cys Ser Asp His Ala
    130                 135                 140

Glu Ala Gly Arg Ser Cys Trp Cys His Glu Gly Tyr Ala Leu Gln Ala
145                 150                 155                 160

Asp Gly Val Ser Cys Thr Pro Thr Val Glu Tyr Pro Cys Gly Lys Ile
                165                 170                 175

Pro Val Leu Glu Lys Arg Asn Asp Ser Asn Pro Gln Gly Arg Ile Val
            180                 185                 190

Gly Gly Lys Val Cys Pro Lys Gly Glu Cys Pro Trp Gln Ala Met Leu
        195                 200                 205

Lys Leu Asn Gly Ala Leu Leu Cys Gly Gly Thr Leu Leu Asp Thr Thr
    210                 215                 220

Trp Val Val Ser Ala Ala His Cys Phe Asp Arg Ile Arg Ser Trp Arg
225                 230                 235                 240

Asn Leu Thr Val Val Leu Gly Glu His Asp Leu Ser Gln Asp Glu Gly
```

-continued

```
                245                 250                 255
Asp Glu Gln Glu Arg Gln Val Ala Gln Val Ile Val Pro Asp Lys Tyr
            260                 265                 270

Val Pro Gly Lys Thr Asp His Asp Leu Ala Leu Leu Arg Leu Ala Arg
        275                 280                 285

Pro Val Ala Leu Ser Asp His Val Val Pro Leu Cys Leu Pro Glu Arg
    290                 295                 300

Ala Phe Ser Glu Arg Thr Leu Ala Phe Val Arg Phe Ser Ala Val Ser
305                 310                 315                 320

Gly Trp Gly Gln Leu Leu Asp Arg Gly Ala Thr Ala Arg Val Leu Met
                325                 330                 335

Ala Ile Gln Val Pro Arg Leu Met Thr Gln Asp Cys Leu Glu Gln Ser
            340                 345                 350

Arg Arg Arg Pro Gly Ser Pro Ala Ile Thr Asp Asn Met Phe Cys Ala
        355                 360                 365

Gly Tyr Leu Asp Gly Ser Lys Asp Ala Cys Lys Gly Asp Ser Gly Gly
    370                 375                 380

Pro His Ala Thr Arg Phe Arg Gly Thr Trp Tyr Leu Thr Gly Val Val
385                 390                 395                 400

Ser Trp Gly Glu Gly Cys Ala Ala Ala Gly His Phe Gly Val Tyr Thr
                405                 410                 415

Arg Val Ser Arg Tyr Thr Ala Trp Leu His Arg Leu Met Gly Ser Pro
            420                 425                 430

Pro Ser Ser Gly Gly Leu Leu Arg Ala Pro Leu Pro
        435                 440
```

<210> SEQ ID NO 37
<211> LENGTH: 444
<212> TYPE: PRT
<213> ORGANISM: Artificial sequence
<220> FEATURE:
<223> OTHER INFORMATION: recombinant clotting factor sequence

<400> SEQUENCE: 37

```
Met Gln Ala Arg Gly Leu Leu Leu Leu Cys Phe Leu Leu Gln Leu Gln
1               5                   10                  15

Gly Pro Leu Gly Ala Val Phe Ile Thr Gln Glu Glu Ala His Ser Val
            20                  25                  30

Leu His Arg Gln Arg Arg Ala Asn Ser Phe Leu Glu Glu Leu Trp Pro
        35                  40                  45

Gly Ser Leu Glu Arg Glu Cys Leu Glu Glu Gln Cys Ser Phe Glu Glu
    50                  55                  60

Ala Arg Glu Ile Phe Lys Ser Thr Glu Arg Thr Lys Gln Phe Trp Ile
65                  70                  75                  80

Val Tyr Thr Asp Gly Asp Gln Cys Ala Ser Asn Pro Cys Gln Asn Gly
                85                  90                  95

Gly Thr Cys Gln Asp His Leu Gln Ser Tyr Ile Cys Phe Cys Leu Leu
            100                 105                 110

Asp Phe Glu Gly Arg Asn Cys Glu Lys Asn Lys Asn Glu Gln Leu Ile
        115                 120                 125

Cys Ala Asn Glu Asn Gly Gly Cys Asp Gln Tyr Cys Thr Asp His Pro
    130                 135                 140

Gly Thr Lys Arg Thr Cys Arg Cys His Glu Asp Tyr Val Leu Gln Pro
145                 150                 155                 160

Asp Glu Val Ser Cys Lys Pro Lys Val Glu Tyr Pro Cys Gly Lys Ile
```

```
                165                 170                 175
Pro Val Leu Glu Lys Arg Asn Ser Ser Pro Gln Gly Arg Ile Val
            180                 185                 190

Gly Gly Lys Val Cys Pro Lys Gly Glu Cys Pro Trp Gln Ala Val Leu
        195                 200                 205

Lys Ile Asn Gly Ala Leu Leu Cys Gly Ala Val Leu Leu Asp Thr Thr
    210                 215                 220

Trp Ile Val Ser Ala Ala His Cys Phe Asp Asn Ile Arg Ser Trp Arg
225                 230                 235                 240

Asn Ile Thr Val Val Met Gly Glu His Asp Phe Ser Glu Lys Asp Gly
                245                 250                 255

Thr Glu Gln Val Arg Arg Val Thr Gln Val Ile Ile Pro Asp Lys Tyr
            260                 265                 270

Ile Pro Gly Lys Ile Asp His Asp Ile Ala Leu Leu Arg Leu His Arg
        275                 280                 285

Pro Val Thr Phe Thr Asp Tyr Val Val Pro Leu Cys Leu Pro Glu Arg
    290                 295                 300

Ala Phe Ser Glu Asn Thr Leu Ala Arg Ile Arg Phe Ser Arg Val Ser
305                 310                 315                 320

Gly Trp Gly Gln Leu Leu Asp Arg Gly Ala Thr Ala Leu Glu Leu Met
                325                 330                 335

Ala Ile Glu Val Pro Arg Leu Met Thr Gln Asp Cys Leu Glu His Ala
            340                 345                 350

Lys His Ser Pro Asn Thr Pro Lys Ile Thr Glu Asn Met Phe Cys Ala
        355                 360                 365

Gly Tyr Met Asp Gly Thr Lys Asp Ala Cys Lys Gly Asp Ser Gly Gly
    370                 375                 380

Pro His Ala Thr His Tyr Arg Gly Thr Trp Tyr Leu Thr Gly Val Val
385                 390                 395                 400

Ser Trp Gly Glu Gly Cys Ala Ala Val Gly His Val Gly Val Tyr Thr
                405                 410                 415

Arg Val Ser Gln Tyr Thr Asp Trp Leu Ile Arg Leu Met Asp Ser Lys
            420                 425                 430

Leu Gln Val Gly Val Ile Phe Arg Val Pro Leu Leu
        435                 440

<210> SEQ ID NO 38
<211> LENGTH: 444
<212> TYPE: PRT
<213> ORGANISM: Artificial sequence
<220> FEATURE:
<223> OTHER INFORMATION: recombinant clotting factor sequence

<400> SEQUENCE: 38

Met Ala Pro Arg Ala Leu Ser Leu Cys Leu Leu Leu Gly Leu Gln
1               5                   10                  15

Gly Ser Leu Ala Ala Val Phe Ile Thr Gln Glu Glu Ala His Gly Val
                20                  25                  30

Leu His Arg Gln Arg Arg Ala Asn Ser Phe Leu Glu Glu Leu Arg Pro
            35                  40                  45

Gly Ser Leu Glu Arg Glu Cys Lys Glu Glu Gln Cys Ser Phe Glu Glu
        50                  55                  60

Ala Arg Glu Ile Phe Arg Ser Thr Glu Arg Thr Lys Gln Phe Trp Ile
65                  70                  75                  80

Ser Tyr Asn Asp Gly Asp Gln Cys Ala Ser Asn Pro Cys Gln Asn Gly
```

```
                85                  90                  95
Gly Ser Cys Glu Asp Gln Leu Gln Ser Tyr Ile Cys Phe Cys Leu Pro
            100                 105                 110

Asp Phe Glu Gly Arg Asn Cys Glu Thr Asn Lys Asn Asp Gln Leu Ile
        115                 120                 125

Cys Val Asn Glu Asn Gly Gly Cys Glu Gln Tyr Cys Ser Asp His Ala
    130                 135                 140

Glu Ala Lys Arg Ser Cys Arg Cys His Glu Gly Tyr Thr Leu Leu Ala
145                 150                 155                 160

Asp Gly Val Ser Cys Thr Pro Thr Val Glu Tyr Pro Cys Gly Lys Ile
                165                 170                 175

Pro Val Leu Glu Lys Arg Asn Ala Ser Asn Pro Gln Gly Arg Ile Val
            180                 185                 190

Gly Gly Lys Val Cys Pro Lys Gly Glu Cys Pro Trp Gln Ala Leu Leu
        195                 200                 205

Thr Leu Asn Gly Ala Leu Leu Cys Gly Gly Thr Leu Leu Asp Thr Ser
    210                 215                 220

Trp Val Val Ser Ala Ala His Cys Phe Asp Lys Ile Arg Ser Trp Arg
225                 230                 235                 240

Asn Leu Thr Val Val Leu Gly Glu His Asp Leu Ser Glu Glu Asp Gly
                245                 250                 255

Asp Glu Gln Glu Arg Gln Val Ala Gln Val Ile Ile Pro Asp Lys Tyr
            260                 265                 270

Val Pro Gly Lys Thr Asp His Asp Ile Ala Leu Leu Arg Leu Arg Arg
        275                 280                 285

Pro Val Ala Leu Thr Asp His Val Val Pro Leu Cys Leu Pro Glu Arg
    290                 295                 300

Ala Phe Ser Glu Arg Thr Leu Ala Tyr Ile Arg Phe Ser Arg Val Ser
305                 310                 315                 320

Gly Trp Gly Gln Leu Leu Asp Arg Gly Ala Thr Ala Leu Glu Leu Met
                325                 330                 335

Ala Ile Asp Val Pro Arg Leu Met Thr Gln Asp Cys Leu Glu Gln Ser
            340                 345                 350

Arg Arg Arg Ala Asp Ser Pro Arg Ile Thr Glu Asn Met Phe Cys Ala
        355                 360                 365

Gly Tyr Leu Asp Gly Ser Lys Asp Ala Cys Lys Gly Asp Ser Gly Gly
    370                 375                 380

Pro His Ala Thr Arg Tyr Arg Gly Thr Trp Tyr Leu Thr Gly Val Val
385                 390                 395                 400

Ser Trp Gly Glu Gly Cys Ala Ala Val Gly His Phe Gly Val Tyr Thr
                405                 410                 415

Arg Val Ser Gln Tyr Thr Glu Trp Leu Ser Arg Leu Met His Ser Glu
            420                 425                 430

Pro Arg Pro Gly Val Leu Leu Arg Ala Pro Phe Pro
        435                 440

<210> SEQ ID NO 39
<211> LENGTH: 444
<212> TYPE: PRT
<213> ORGANISM: Artificial sequence
<220> FEATURE:
<223> OTHER INFORMATION: recombinant clotting factor sequence

<400> SEQUENCE: 39

Met Ala Pro Arg Ala Leu Ser Leu Leu Cys Leu Leu Leu Gly Leu Gln
```

-continued

```
1               5                   10                  15
Gly Ser Leu Ala Ala Val Phe Ile Thr Gln Glu Glu Ala His Gly Val
            20                  25                  30

Leu His Arg Gln Arg Ala Asn Ser Phe Leu Glu Glu Leu Arg Pro
            35                  40                  45

Gly Ser Leu Glu Arg Glu Cys Lys Glu Glu Gln Cys Ser Phe Glu Glu
            50                  55                  60

Ala Arg Glu Ile Phe Arg Asn Thr Glu Arg Thr Lys Gln Phe Trp Ile
65                  70                  75                  80

Ser Tyr Asn Asp Gly Asp Gln Cys Ala Ser Asn Pro Cys Gln Asn Gly
                85                  90                  95

Gly Ser Cys Glu Asp Gln Leu Gln Ser Tyr Ile Cys Phe Cys Leu Pro
            100                 105                 110

Asp Phe Glu Gly Arg Asn Cys Glu Thr Asn Lys Asn Asp Gln Leu Ile
            115                 120                 125

Cys Val Asn Glu Asn Gly Gly Cys Glu Gln Tyr Cys Ser Asp His Ala
            130                 135                 140

Glu Ala Lys Arg Ser Cys Arg Cys His Glu Gly Tyr Thr Leu Leu Ala
145                 150                 155                 160

Asp Gly Val Ser Cys Ala Pro Thr Val Glu Tyr Pro Cys Gly Lys Ile
                165                 170                 175

Pro Ile Leu Glu Lys Arg Asn Ala Ser Asn Pro Gln Gly Arg Ile Val
            180                 185                 190

Gly Gly Lys Val Cys Pro Lys Gly Glu Cys Pro Trp Gln Ala Leu Leu
            195                 200                 205

Thr Leu Asn Gly Ala Leu Leu Cys Gly Gly Thr Leu Leu Asp Thr Ser
        210                 215                 220

Trp Val Val Ser Ala Ala His Cys Phe Asp Lys Ile Lys Ser Trp Arg
225                 230                 235                 240

Asn Leu Thr Val Val Leu Gly Glu His Asp Leu Ser Glu Glu Asp Gly
                245                 250                 255

Asp Glu Gln Glu Arg Gln Val Ala Gln Val Ile Ile Pro Asp Lys Tyr
            260                 265                 270

Val Pro Gly Lys Thr Asp His Asp Ile Ala Leu Leu Arg Leu Arg Arg
            275                 280                 285

Pro Val Ala Leu Thr Asp His Val Val Pro Leu Cys Leu Pro Glu Arg
            290                 295                 300

Ala Phe Ser Glu Arg Thr Leu Ala Tyr Ile Arg Phe Ser Arg Val Ser
305                 310                 315                 320

Gly Trp Gly Gln Leu Leu Asp Arg Gly Ala Thr Ala Leu Glu Leu Met
                325                 330                 335

Ala Ile Asp Val Pro Arg Leu Met Thr Gln Asp Cys Leu Glu Gln Ser
            340                 345                 350

Arg Arg Arg Ala Asp Ser Pro Arg Ile Thr Glu Asn Met Phe Cys Ala
            355                 360                 365

Gly Tyr Leu Asp Gly Ser Lys Asp Ala Cys Lys Gly Asp Ser Gly Gly
            370                 375                 380

Pro His Ala Thr Arg Tyr Arg Gly Thr Trp Tyr Leu Thr Gly Val Val
385                 390                 395                 400

Ser Trp Gly Glu Gly Cys Ala Ala Val Gly His Phe Gly Val Tyr Thr
                405                 410                 415

Arg Val Ser Gln Tyr Thr Glu Trp Leu Ser Arg Leu Met His Ser Glu
            420                 425                 430
```

```
Pro Arg Pro Gly Val Leu Leu Arg Ala Pro Phe Pro
        435                 440
```

<210> SEQ ID NO 40
<211> LENGTH: 444
<212> TYPE: PRT
<213> ORGANISM: Artificial sequence
<220> FEATURE:
<223> OTHER INFORMATION: recombinant clotting factor sequence

<400> SEQUENCE: 40

```
Met Ala Ser Gln Ala Leu Arg Leu Leu Cys Leu Leu Leu Gly Leu Gln
1               5                   10                  15

Gly Ser Leu Ala Ala Val Phe Ile Thr Gln Glu Glu Ala His Gly Val
            20                  25                  30

Leu His Arg Gln Arg Arg Ala Asn Ser Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Arg Asn Thr Glu Arg Thr Lys Gln Phe Trp Ile
65                  70                  75                  80

Ser Tyr Asn Asp Gly Asp Gln Cys Ala Ser Asn Pro Cys Gln Asn Gly
                85                  90                  95

Gly Ser Cys Glu Asp Gln Leu Gln Ser Tyr Ile Cys Phe Cys Leu Pro
            100                 105                 110

Asp Phe Glu Gly Arg Asn Cys Glu Thr Asn Lys Asn Asp Gln Leu Ile
        115                 120                 125

Cys Val Asn Glu Asn Gly Gly Cys Glu Gln Tyr Cys Ser Asp His Ala
    130                 135                 140

Glu Ala Lys Arg Ser Cys Arg Cys His Glu Gly Tyr Ser Leu Leu Ala
145                 150                 155                 160

Asp Gly Val Ser Cys Ala Pro Thr Val Glu Tyr Pro Cys Gly Lys Ile
                165                 170                 175

Pro Ile Leu Glu Lys Arg Asn Ala Ser Asn Pro Gln Gly Arg Ile Val
            180                 185                 190

Gly Gly Lys Val Cys Pro Lys Gly Glu Cys Pro Trp Gln Ala Leu Leu
        195                 200                 205

Thr Leu Asn Gly Ala Leu Leu Cys Gly Gly Thr Leu Ile Asp Thr Ser
    210                 215                 220

Trp Val Val Ser Ala Ala His Cys Phe Asp Lys Ile Lys Ser Trp Arg
225                 230                 235                 240

Asn Leu Thr Val Val Leu Gly Glu His Asp Leu Ser Glu Glu Asp Gly
                245                 250                 255

Asp Glu Gln Glu Arg Arg Val Ala Gln Val Ile Ile Pro Asp Thr Tyr
            260                 265                 270

Val Pro Gly Thr Thr Asp His Asp Ile Ala Leu Leu Arg Leu Arg Arg
        275                 280                 285

Pro Val Ala Leu Thr Asp His Val Val Pro Leu Cys Leu Pro Glu Arg
    290                 295                 300

Ala Phe Ser Glu Arg Thr Leu Ala Tyr Val Arg Phe Ser Arg Val Ser
305                 310                 315                 320

Gly Trp Gly Gln Leu Leu Asp Arg Gly Ala Thr Ala Leu Glu Leu Met
                325                 330                 335

Ala Ile Asp Val Pro Arg Leu Met Thr Gln Asp Cys Leu Gln Gln Ser
            340                 345                 350
```

```
Arg Arg Arg Ala Asp Ser Pro Arg Ile Thr Glu Asn Met Phe Cys Ala
        355                 360                 365

Gly Tyr Leu Asp Gly Ser Lys Asp Ala Cys Lys Gly Asp Ser Gly Gly
        370                 375                 380

Pro His Ala Thr Arg Tyr Arg Gly Thr Trp Tyr Leu Thr Gly Val Val
385                 390                 395                 400

Ser Trp Gly Glu Gly Cys Ala Ala Val Gly His Phe Gly Val Tyr Thr
                405                 410                 415

Arg Val Ser Gln Tyr Thr Glu Trp Leu Ser Arg Leu Met His Ser Glu
                420                 425                 430

Pro Arg Pro Gly Val Leu Leu Arg Ala Pro Phe Pro
        435                 440

<210> SEQ ID NO 41
<211> LENGTH: 444
<212> TYPE: PRT
<213> ORGANISM: Artificial sequence
<220> FEATURE:
<223> OTHER INFORMATION: recombinant clotting factor sequence

<400> SEQUENCE: 41

Met Val Ser Gln Ala Leu Arg Leu Leu Cys Leu Leu Leu Gly Leu Gln
1               5                   10                  15

Gly Cys Leu Ala Ala Val Phe Ile Thr Gln Glu Glu Ala His Gly Val
            20                  25                  30

Leu His Arg Gln Arg Arg Ala Asn Ser Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Leu Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr Asn Lys Asp Asp Gln Leu Ile
        115                 120                 125

Cys Val Asn Glu Asn Gly Gly Cys Glu Gln Tyr Cys Ser Asp His Ala
    130                 135                 140

Gly Ala Lys Arg Ser Cys Arg Cys His Glu Gly Tyr Ser Leu Leu Ala
145                 150                 155                 160

Asp Gly Val Ser Cys Met Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Arg Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Thr Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270
```

```
Val Pro Gly Thr Thr Asn His Asp Ile Ala Leu Leu Arg Leu His Arg
            275                 280                 285

Pro Val Val Leu Thr Asp His Val Val Pro Leu Cys Leu Pro Glu Arg
            290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Ala Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
            355                 360                 365

Gly Tyr Ser Asp Gly Ser Lys Asp Ser Cys Lys Gly Asp Ser Gly Gly
            370                 375                 380

Pro His Ala Thr Arg Tyr Arg Gly Thr Trp Tyr Leu Thr Gly Ile Val
385                 390                 395                 400

Ser Trp Gly Gln Gly Cys Ala Ala Val Gly His Phe Gly Val Tyr Thr
                405                 410                 415

Arg Val Ser Gln Tyr Ile Glu Trp Leu Gln Lys Leu Met His Ser Glu
            420                 425                 430

Pro Arg Pro Gly Val Leu Leu Arg Ala Pro Phe Pro
            435                 440

<210> SEQ ID NO 42
<211> LENGTH: 461
<212> TYPE: PRT
<213> ORGANISM: homo sapiens

<400> SEQUENCE: 42

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
            115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
```

```
                195                 200                 205
Thr Ile Leu Asp Asn Ile Thr Gln Ser Thr Gln Ser Phe Asn Asp Phe
            210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
            275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe Asn Lys Gly Arg Ser Ala Ser Val
            355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
            405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
            435                 440                 445

Arg Tyr Val Asn Trp Ile Lys Glu Lys Thr Lys Leu Thr
450                 455                 460
```